US 10,759,751 B2

(12) United States Patent
Brown et al.

(10) Patent No.: US 10,759,751 B2
(45) Date of Patent: Sep. 1, 2020

(54) SUBSTITUTED SPIROCYCLOHEXANES AS MUSCARINIC $M_1$ RECEPTOR AND/OR $M_4$ RECEPTOR AGONISTS

(71) Applicant: Heptares Therapeutics Limited, Cambridge (GB)

(72) Inventors: Giles Albert Brown, Cambridge (GB); Miles Stuart Congreve, Cambridge (GB); Mark Pickworth, Cambridge (GB); Benjamin Gerald Tehan, Cambridge (GB)

(73) Assignee: Heptares Therapeutics Limited, Cambridge (GB)

(*) Notice: Subject to any disclaimer, the term of this patent is extended or adjusted under 35 U.S.C. 154(b) by 0 days.

(21) Appl. No.: 16/295,364

(22) Filed: Mar. 7, 2019

(65) Prior Publication Data

US 2019/0202783 A1     Jul. 4, 2019

Related U.S. Application Data

(63) Continuation of application No. 15/784,560, filed on Oct. 16, 2017, now Pat. No. 10,259,787.

(60) Provisional application No. 62/408,468, filed on Oct. 14, 2016.

(51) Int. Cl.
| | | |
|---|---|---|
| *A61K 31/395* | (2006.01) | |
| *C07D 209/96* | (2006.01) | |
| *C07D 207/14* | (2006.01) | |
| *C07D 401/08* | (2006.01) | |
| *C07D 403/04* | (2006.01) | |
| *C07D 471/10* | (2006.01) | |
| *C07D 243/08* | (2006.01) | |
| *C07D 409/08* | (2006.01) | |
| *C07D 413/14* | (2006.01) | |
| *C07D 471/04* | (2006.01) | |
| *C07D 487/04* | (2006.01) | |
| *C07D 413/12* | (2006.01) | |
| *C07D 271/06* | (2006.01) | |
| *C07D 413/04* | (2006.01) | |
| *C07D 487/10* | (2006.01) | |
| *C07D 295/205* | (2006.01) | |
| *C07D 213/57* | (2006.01) | |

(52) U.S. Cl.
CPC ......... *C07D 207/14* (2013.01); *C07D 209/96* (2013.01); *C07D 213/57* (2013.01); *C07D 243/08* (2013.01); *C07D 271/06* (2013.01); *C07D 295/205* (2013.01); *C07D 401/08* (2013.01); *C07D 403/04* (2013.01); *C07D 409/08* (2013.01); *C07D 413/04* (2013.01); *C07D 413/12* (2013.01); *C07D 413/14* (2013.01); *C07D 471/04* (2013.01); *C07D 471/10* (2013.01); *C07D 487/04* (2013.01); *C07D 487/10* (2013.01)

(58) Field of Classification Search
CPC .......................... A61K 31/395; C07D 209/96
USPC .......................................... 514/409; 548/411
See application file for complete search history.

(56) References Cited

U.S. PATENT DOCUMENTS

| 10,259,787 B2 | 4/2019 | Brown et al. |
| 2003/0225271 A1 | 12/2003 | Emmanuel et al. |

FOREIGN PATENT DOCUMENTS

| EP | 0034415 A1 | 8/1981 |
| EP | 1679069 A1 | 7/2006 |
| JP | 2013-10719 A | 1/2013 |
| WO | 1994/015928 A1 | 7/1994 |
| WO | 1996/13262 A1 | 5/1996 |
| WO | 1997/016187 A1 | 5/1997 |
| WO | 1998/057641 A1 | 12/1998 |
| WO | 2007/079164 A2 | 7/2007 |
| WO | 2008/077597 A1 | 7/2008 |
| WO | 2010/121046 A1 | 10/2010 |
| WO | 2011/143057 A1 | 11/2011 |
| WO | 2011/150183 A1 | 12/2011 |
| WO | 2012/125661 A1 | 9/2012 |

(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Hackam, et al. Jama, 296(14), 2006, 1731-1732.*
STN Accession No. 1797868-91-7, 4-((4-cyano-4-phenylcyclohexyl)amino)-1-piperidinecarboxylic acid methyl ester, Jul. 9, 2015.
STN Accession No. 1829396-16-8, 4-((4-phenylcyclohexyl)amino)-1-piperidine carboxylic acid ethyl ester, Dec. 14, 2015.

(Continued)

*Primary Examiner* — Douglas M Willis
(74) *Attorney, Agent, or Firm* — McCarter & English, LLP; Steven G. Davis; Mei Bai

(57) ABSTRACT

This invention relates to compounds that are agonists of the muscarinic $M_1$ receptor or $M_1$ and $M_4$ receptors and which are useful in the treatment of muscarinic $M_1$ or $M_1/M_4$ receptor mediated diseases. Also provided are pharmaceutical compositions containing the compounds and the therapeutic uses of the compounds. Compounds provided are of formula wherein $Q^4$, $Q^5$, $R^5$, p, V, $Q^1$, $Q^2$, $X^1$, $X^2$ and W are defined herein.

18 Claims, No Drawings

(56) References Cited

FOREIGN PATENT DOCUMENTS

WO     2016/147011 A1     9/2016

OTHER PUBLICATIONS

International Search Report and Written Opinion for Application No. PCT/GB2017/053115, dated Nov. 29, 2017.
United Kingdom Search Report for Application No. 1617454-2, dated Sep. 1, 2017.
United Kingdom Search Report for Application No. 1401478.1, dated Aug. 20, 2014.
U.S. Appl. No. 15/784,560, filed Oct. 16, 2017, now U.S. Pat. No. 10,259,787, Issued.

* cited by examiner

SUBSTITUTED SPIROCYCLOHEXANES AS MUSCARINIC M₁ RECEPTOR AND/OR M₄ RECEPTOR AGONISTS

RELATED APPLICATION INFORMATION

This application is a continuation of U.S. patent application Ser. No. 15/784,560, filed Oct. 16, 2017, which claims the benefit of U.S. Provisional Application No. 62/408,468, filed on Oct. 14, 2016. The entire contents of these applications are incorporated herein by reference in their entirety.

This invention relates to compounds that are agonists of the muscarinic $M_1$ receptor or the $M_1$ and $M_4$ receptors and which are useful in the treatment of muscarinic $M_1$ or $M_1$ and $M_4$ receptor mediated diseases. Also provided are pharmaceutical compositions containing the compounds and the therapeutic uses of the compounds.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 Br J Pharmacol). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 Br J Pharmacol).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 Science). In schizophrenia, which also has cognitive impairment as an important component of the clinical picture, mAChR density is reduced in the pre-frontal cortex, hippocampus and caudate putamen of schizophrenic subjects (Dean et al., 2002 Mol Psychiatry). Furthermore, in animal models, blockade or damage to central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting adverse events resulting from stimulation of peripheral $M_2$ and $M_3$ mAChRs including disturbed gastrointestinal motility, bradycardia, nausea and vomiting (http://www.drugs.com/pro/donepezil.html; http://www.drugs.com/pro/rivastigmine.html).

Further discovery efforts have targeted the identification of direct $M_1$ mAChR agonists with the aim of inducing selective improvements in cognitive function with a favourable adverse effect profile. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain pathologies: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, nonamyloidgenic and amyloidgenic. Cleavage of APP by γ-secretase is common to both pathways, but in the former APP is cleaved by an α-secretase to yield soluble APPα. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3xTgAD transgenic mouse, a model of the different components of Alzheimer's disease (Caccamo et al., 2006 Neuron). The mAChR agonist cevimeline has been shown to give a small, but significant, reduction in cerebrospinal fluid levels of Aβ in Alzheimer's patients, thus demonstrating potential disease modifying efficacy (Nitsch et al., 2000 Neurol).

Preclinical studies have suggested that mAChR agonists display an atypical antipsychotic-like profile in a range of pre-clinical paradigms. The mAChR agonist, xanomeline, reverses a number of dopamine mediated behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 CNS Drug Rev).

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 Arch Neurol). This compound was also assessed in a small Phase II study of schizophrenics and gave a significant reduction in positive and negative symptoms when compared to placebo control (Shekhar et al., 2008 Am J Psych). However, in all clinical studies xanomeline and other related mAChR agonists have displayed an unacceptable safety margin with respect to cholinergic adverse events, including nausea, gastrointestinal pain, diahorrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage; however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the M1 receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 *Bioorg Med Chem Lett*; Johnson et al., 2010 *Bioorg Med Chem Lett*; Budzik et al., 2010 *ACS Med Chem Lett*). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ mAChR over the $M_2$ and $M_3$ receptor subtypes.

THE INVENTION

The present invention provides compounds having activity as muscarinic $M_1$ and/or $M_4$ receptor agonists. More particularly, the invention provides compounds that exhibit selectivity for the $M_1$ receptor relative to the $M_2$, $M_3$ and $M_4$ receptor subtypes. Alternative compounds of the invention exhibit selectivity for the $M_1$ and $M_4$ receptors relative to the $M_2$ and $M_3$ receptor subtypes.

Accordingly, in a first embodiment (Embodiment 1.1), the invention provides a compound of the formula (1):

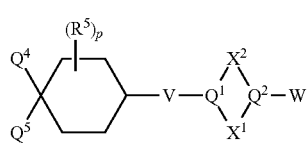

(1)

or a salt thereof, wherein:

p is 0, 1 or 2;

V is selected from a bond, NH, N($C_{1-3}$alkyl), NH—$CH_2$ and N($C_{1-3}$ alkyl)-$CH_2$;

$Q^1$ and $Q^2$ are each nitrogen or carbon; provided that at least one of $Q^1$ or V comprises a nitrogen atom;

W is -$Q^3$C(O)YCH$_2$R$^4$ or an optionally substituted five or six membered aromatic heterocyclic group, wherein when W is an optionally substituted five or six membered aromatic heterocyclic group, $Q^2$ is carbon;

$Q^3$ is a bond or a group -(Alk)$_q$-NR$^6$ where Alk is an alkyl group of 1 to 4 carbon atoms;

q is 0 or 1; and R$^6$ is hydrogen or a saturated $C_{1-4}$ hydrocarbon group; provided that when $Q^2$ is nitrogen and $Q^3$ is a group -(Alk)$_q$-NR$^6$, there are at least two carbon atoms in line between $Q^2$ and NR$^6$ and provided that when $Q^3$ is a bond, $Q^2$ is nitrogen;

$X^1$ and $X^2$ are optionally substituted saturated hydrocarbon groups which together contain a total of one to nine carbon atoms and which link together such that the moiety:

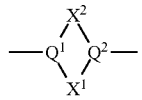

forms a monocyclic or bicyclic ring system;

$Q^4$ is an optionally substituted five or six membered aromatic carbocyclic or heterocyclic group containing 0, 1, 2 or 3 heteroatom ring members selected from O, N and S, or forms an optionally substituted heterocyclic spirocyclic ring with $Q^5$; $Q^5$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof, or forms an optionally substituted heterocyclic spirocyclic ring with $Q^4$;

Y is CH or O;

R$^4$ is hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof; and R$^5$ is fluorine or a $C_{1-4}$ hydrocarbon group.

Particular compounds of the formula (1) are as defined in the Embodiments 1.2 to 1.168 set out below.

1.2 A compound according to Embodiment 1.1 wherein $Q^4$ is an optionally substituted five or six membered aromatic carbocyclic or heterocyclic group selected from optionally substituted phenyl; optionally substituted six membered aromatic heterocyclic rings containing 1, 2 or 3 nitrogen ring members; and optionally substituted five membered aromatic heterocyclic rings containing 1, 2 or 3 heteroatom ring members selected from O, N and S.

1.3 A compound according to Embodiment 1.2 wherein $Q^4$ is an optionally substituted five or six membered aromatic carbocyclic or heterocyclic group selected from optionally substituted phenyl; optionally substituted six membered aromatic heterocyclic rings containing 1 or 2 nitrogen ring members; and optionally substituted five membered aromatic heterocyclic rings containing 1 or 2 heteroatom ring members selected from O, N and S.

1.4 A compound according to Embodiment 1.3 wherein $Q^4$ is an optionally substituted five or six membered aromatic carbocyclic or heterocyclic group selected from optionally substituted phenyl; optionally substituted six membered aromatic heterocyclic rings containing 1 nitrogen ring member; and optionally substituted five membered aromatic heterocyclic rings containing 1 or 2 heteroatom ring members selected from O, N and S.

1.5 A compound according to Embodiment 1.4 wherein $Q^4$ is an optionally substituted five or six membered aromatic carbocyclic or heterocyclic group selected from optionally substituted phenyl; optionally substituted pyridyl; optionally substituted imidazolyl; and optionally substituted thienyl.

1.6 A compound according to Embodiment 1.5 wherein $Q^4$ is an optionally substituted phenyl or pyridyl group.

1.7 A compound according to any one of Embodiments 1.1 to 1.6 wherein the five or six membered aromatic carbocyclic or heterocyclic group $Q^4$ is unsubstituted or is substituted with one or more substituents $Q^6$ selected from halogen; cyano; hydroxy; amino and a $C_{1-10}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof.

1.8 A compound according to Embodiment 1.7 wherein the five or six membered aromatic carbocyclic or heterocyclic group $Q^4$ is unsubstituted or is substituted with one or more substituents $Q^6$ selected from halogen; cyano; hydroxy; amino and a $C_{1-10}$ non-aromatic hydrocarbon group which is optionally substituted with one to six fluorine atoms and wherein one carbon atom of the hydrocarbon group may optionally be replaced by a heteroatom selected from O, N and S or oxidized forms thereof, or two adjacent carbon atoms of the hydrocarbon group may optionally be replaced by a group $X^3C(X^4)$ or $C(X^4)X^3$ where $X^3$ is O, S or N; and $X^4$ is =O, =S or =N.

1.9 A compound according to Embodiment 1.8 wherein the five or six membered aromatic carbocyclic or heterocyclic group $Q^4$ is unsubstituted or is substituted with one or more substituents $Q^6$ selected from halogen; cyano; hydroxy; amino and a $C_{1-10}$ non-aromatic hydrocarbon group which is optionally substituted with one to six fluorine atoms and wherein one carbon atom of the hydrocarbon group may optionally be replaced by a heteroatom selected from O, N and S thereof, or two adjacent carbon atoms of the hydrocarbon group may optionally be replaced by a group OC(=O), C(=O)O, N(C=O) or C(=O)N.

1.10 A compound according to Embodiment 1.9 wherein the five or six membered aromatic carbocyclic or heterocyclic group $Q^4$ is unsubstituted or is substituted with one or more substituents $Q^6$ selected from halogen; cyano; hydroxy; amino and a $C_{1-8}$ non-aromatic hydrocarbon group which is optionally substituted with one to six fluorine atoms and wherein one carbon atom of the hydrocarbon group may optionally be replaced by a heteroatom selected from O, N and S thereof, or two adjacent carbon atoms of the hydrocarbon group may optionally be replaced by a group OC(=O), C(=O)O, N(C=O) or C(=O)N.

1.11 A compound according to Embodiment 1.9 wherein the five or six membered aromatic carbocyclic or heterocyclic group $Q^4$ is unsubstituted or is substituted with one or more substituents $Q^6$ selected from halogen; cyano; hydroxy; amino and a $C_{1-6}$ non-aromatic hydrocarbon group which is optionally substituted with one to six fluorine atoms and wherein one carbon atom of the hydrocarbon group may optionally be replaced by a heteroatom selected from O, N and S thereof, or two adjacent carbon atoms of the hydrocarbon group may optionally be replaced by a group OC(=O), C(=O)O, N(C=O) or C(=O)N.

1.12 A compound according to Embodiment 1.7 wherein the optionally substituted non-aromatic hydrocarbon group is selected from $C_{1-6}$ alkyl; $C_{2-6}$ alkenyl; $C_{2-6}$ alkynyl; $C_{3-6}$ cycloalkyl and $C_{4-6}$ cycloalkenyl groups; and each of the said alkyl, alkenyl, alkynyl, cycloalkyl and cycloalkenyl groups is optionally substituted with one to six fluorine atoms and wherein one or two, but not all, carbon atoms of each of the alkyl, alkenyl, alkynyl, cycloakyl and cycloalkenyl groups may optionally be replaced by a heteroatom selected from O, N and S and oxidised forms thereof.

1.13 A compound according to any one of Embodiments 1.1 to 1.6 wherein $Q^4$ is an unsubstituted five or six membered aromatic carbocyclic or heterocyclic group.

1.14 A compound according to Embodiment 1.13 wherein $Q^4$ is an unsubstituted phenyl or pyridyl group.

1.15 A compound according to any one of Embodiments 1.1 to 1.14 wherein $Q^5$ is selected from hydrogen; fluorine; cyano; hydroxy; amino; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.16 A compound according to Embodiment 1.15 wherein $Q^5$ is selected from hydrogen; fluorine; cyano; hydroxy; amino; and a $C_{1-6}$ non-aromatic hydrocarbon group which is optionally substituted with one to six fluorine atoms and wherein one, but not all, carbon atoms of the hydrocarbon group may optionally be replaced by a heteroatom selected from O, N and S and oxidized forms thereof.

1.17 A compound according to Embodiment 1.16 wherein $Q^5$ is selected from hydrogen; fluorine; cyano; hydroxy; amino; $C_{1-4}$ alkyl and $C_{1-4}$ alkoxy, wherein the $C_{1-4}$ alkyl and $C_{1-4}$ alkoxy are each optionally substituted with one to six fluorine atoms.

1.18 A compound according to Embodiment 1.17 wherein $Q^5$ is selected from hydrogen; fluorine; cyano; hydroxy; amino; methyl, ethyl and methoxy.

1.19 A compound according to Embodiment 1.18 wherein $Q^5$ is cyano.

1.20 A compound according to Embodiment 1.1 wherein W and $Q^5$ form a heterocyclic spirocyclic ring according to formula (1a):

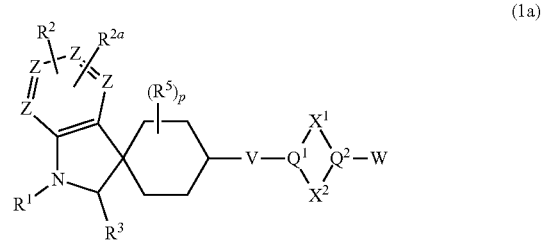

(1a)

wherein Z is C or N;
$R^1$ is H, $COOR^7$, $CONR^7R^8$, $SO_2R^7$ or an optionally substituted $C_{1-6}$ non-aromatic hydrocarbon group where one or more carbon atoms is optionally replaced with a heteroatom selected from O, N or S;
$R^2$ and $R^{2a}$ are independently selected from hydrogen; halogen; cyano; hydroxy; amino; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

$R^3$ is selected from hydrogen or oxo;

$R^7$ and $R^8$ are independently H or a $C_{1-4}$ hydrocarbon group.

1.21 A compound according to Embodiment 1.20 wherein $R^1$ is H, $COOR^7$, $CONR^7R^8$, $SO_2R^7$ or an optionally substituted $C_{1-6}$ alkyl group.

1.22 A compound according to Embodiment 1.21 wherein $R^1$ is an optionally substituted alkyl group selected from $CH_2$—$COOR^7$, $CH_2$—$CONR^7R^7$, $CH_2$—$SO_2R^7$, $CH_2$—$CH_2$—$COOR^7$, $CH_2$—$CH_2$—$CONR^7R^8$ or $CH_2$—$CH_2$—$SO_2R^7$.

1.23 A compound according to Embodiment 1.22 wherein $R^1$ is H, methyl, ethyl, $COOCH_3$, $COOCH_2CH_3$, $SO_2Me$ or $CH_2CONH_2$.

1.24 A compound according to Embodiment 1.23 wherein $R^1$ is H.

1.25 A compound according to Embodiment 1.23 wherein $R^1$ is methyl.

1.26 A compound according to Embodiment 1.23 wherein $R^1$ is $SO_2Me$.

1.27 A compound according to Embodiment 1.23 wherein $R^1$ is $CH_2CONH_2$.

1.28 A compound according to Embodiment 1.23 wherein $R^1$ is $COOCH_2CH_3$.

1.29 A compound according to any one of Embodiments 1.20 to 1.28 wherein $R^2$ and $R^{2a}$ are independently selected from hydrogen; fluorine; chlorine; cyano; hydroxy; amino; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.30 A compound according to Embodiment 1.29 wherein $R^2$ and $R^{2a}$ are independently selected from hydrogen; fluorine; chlorine; cyano; hydroxy; amino; and a $C_{1-4}$ alkyl or $C_{1-4}$ alkoxy group which is optionally substituted with one to six fluorine atoms.

1.31 A compound according to Embodiment 1.30 wherein $R^2$ and $R^{2a}$ are independently selected from hydrogen; fluorine; chlorine; cyano; hydroxy; amino; methyl, ethyl, methoxy trifluoromethoxy or ethoxy.

1.32 A compound according to Embodiment 1.31 wherein $R^2$ and $R^{2a}$ are independently selected from hydrogen; fluorine; chlorine; cyano; methyl or methoxy.

1.33 A compound according to any one of Embodiments 1.20 to 1.32 wherein $R^3$ is H such that the ring position marked $R_3$ is $CH_2$.

1.34 A compound according to any one of Embodiments 1.20 to 1.32 wherein $R^3$ is oxo such that the ring position marked $R_3$ is C=O.

1.35 A compound according to Embodiments 1.34 wherein Z is C.

1.36 A compound according to any one of Embodiments 1.1 to 1.35 wherein p is 0 or 1.

1.37 A compound according to Embodiment 1.36 wherein p is 0.

1.38 A compound according to Embodiment 1.36 wherein p is 1.

1.39 A compound according to any one of Embodiments 1.1 to 1.38 wherein p is 0; or p is 1 and $R^5$ is selected from fluorine and a saturated $C_{1-4}$ hydrocarbon group.

1.40 A compound according to Embodiment 1.39 wherein p is 0; or p is 1 and $R^5$ is selected from fluorine, $C_{1-3}$ alkyl and cyclopropyl.

1.41 A compound according to Embodiment 1.39 wherein p is 0; or p is 1 and $R^5$ is selected from fluorine and methyl.

1.42 A compound according to Embodiment 1.41 wherein p is 0; or p is 1 and $R^5$ is fluorine.

1.43 A compound according to any one of Embodiments 1.1 to 1.42 wherein wherein V is a bond 1.44 A compound according to Embodiment 1.43 wherein V is a bond and $Q^1$ is nitrogen.

1.45 A compound according to any one of Embodiments 1.1 to 1.42 wherein wherein V is selected from NH, N($C_{1-3}$ alkyl), NH—$CH_2$ and N($C_{1-3}$ alkyl)-$CH_2$.

1.46 A compound according to any one of Embodiments 1.1 to 1.42 wherein V is NH.

1.47 A compound according to any one of Embodiments 1.1 to 1.42 wherein V is NH—$CH_2$.

1.48 A compound according to any one of Embodiments 1.1 to 1.42 wherein V is N($C_{1-3}$ alkyl).

1.49 A compound according to any one of Embodiments 1.1 to 1.42 wherein V is N($C_{1-3}$ alkyl)-$CH_2$.

1.50 A compound according to one of Embodiments 1.1 to 1.49 wherein W is an optionally substituted five or six membered heteroaryl group. When W is an optionally substituted five or six membered heteroaryl group, $Q^2$ is carbon.

1.51 A compound according to Embodiment 1.50 wherein W is optionally substituted 1-oxa-2,4-diazole.

1.52 A compound according to Embodiments 1.50 or 1.51 wherein the heteroaryl group W is optionally substituted with $C_{1-4}$ hydrocarbon group which is itself optionally substituted with one to six fluorine atoms.

1.53 A compound according to Embodiment 1.52 wherein the heteroaryl group W is optionally substituted with methyl, ethyl or trifluoromethyl.

1.54 A compound according to Embodiment 1.53 wherein W is selected from groups W1 to W3 shown below:

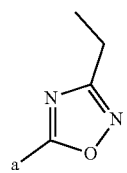

W1

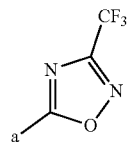

W2

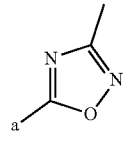

W3 where "a" indicates the point of attachment to $Q^2$.

1.55 A compound according to any Embodiments 1.1 to 1.42 wherein W is -$Q^3C(O)YCH_2R^4$.

1.56 A compound according to Embodiment 1.55 wherein Y is O.

1.57 A compound according to Embodiment 1.55 wherein Y is CH.

1.58 A compound according to Embodiment 1.57 wherein Y is CH and $R^4$ is CH—$CH_3$ such that Y—$R^4$ is CH=CH—$CH_3$.

1.59 A compound according to any one of Embodiments 1.1 to 1.58 wherein $R^4$ is hydrogen or an acyclic $C_{1-6}$ hydrocarbon group.

1.60 A compound according to Embodiment 1.59 wherein $R^4$ is hydrogen or an acyclic $C_{1-3}$ hydrocarbon group.

1.61 A compound according to Embodiment 1.60 wherein $R^4$ is a $C_{1-3}$ alkyl group or a $C_{2-3}$ alkynyl group.

1.62 A compound according to Embodiment 1.61 wherein $R^4$ is selected from H, methyl, ethyl, ethynyl and 1-propynyl.

1.63 A compound according to Embodiment 1.62 wherein Y—$R^4$ is O-ethyl, O-methyl or CH=CH—$CH_3$.

1.64 A compound according to any one of Embodiments 1.1 to 1.63 wherein $X^1$ and $X^2$ together contain one, two, three, four, five, six, seven, eight or nine carbon atoms, which may be optionally substituted with substituents selected from hydrogen, fluorine, hydroxy, methyl, ethyl and methoxy. Where $X^1$ and $X^2$ together contain four carbon atoms, the group may optionally not include 1-4 piperidine, which can be disclaimed from any particular claim if required.

1.65 A compound according to Embodiment 1.64 wherein $X^1$ and $X^2$ together contain five carbon atoms.

1.66 A compound according to Embodiment 1.64 wherein $X^1$ and $X^2$ together contain six carbon atoms.

1.67 A compound according to Embodiment 1.64 wherein $X^1$ and $X^2$ together contain seven carbon atoms.

1.68 A compound according to any one of Embodiments 1.45 to 1.64 wherein V is selected from NH, N($C_{1-3}$alkyl), NH—$CH_2$ and N($C_{1-3}$ alkyl)-$CH_2$ and $Q^1$ and $Q^2$ each represent carbon.

1.69 A compound according to any one of Embodiments 1.45 to 1.64 wherein V is NH or $NHCH_2$ and $Q^1$ and $Q^2$ each represent carbon.

1.70 A compound according to Embodiments 1.43 or 1.44 wherein $Q^1$ and $Q^2$ are both nitrogen and $Q^3$ is a bond; or $Q^1$ is nitrogen, $Q^2$ is carbon and $Q^3$ is a group -(Alk)$_q$-$NR^6$.

1.71 A compound according to Embodiment 1.70 wherein $Q^1$ and $Q^2$ are both nitrogen and $Q^3$ is a bond.

1.72 A compound according to Embodiment 1.70 wherein $Q^1$ is nitrogen, $Q^2$ is carbon and $Q^3$ is a group -(Alk)$_q$-$NR^6$.

1.73 A compound according to Embodiment 1.71 wherein $Q^1$ and $Q^2$ together with $X^1$ and $X^2$ form a bicyclic group, an optionally substituted diazepane group or a diazocane group.

1.74 A compound according to Embodiment 1.73 wherein $Q^1$ and $Q^2$ together with $X^1$ and $X^2$ form a diazocane group.

1.75 A compound according to Embodiment 1.74 wherein the diazocane group is a 1,5-diazocane group.

1.76 A compound according to Embodiment 1.73 wherein $Q^1$ and $Q^2$ together with $X^1$ and $X^2$ form an optionally substituted diazepane group.

1.77 A compound according to Embodiment 1.74 wherein the optionally substituted diazepane group is a 1,4-diazepane group.

1.78 A compound according to any of Embodiments 1.76 or 1.77 wherein the diazepane group is optionally substituted with halogen or hydroxy.

1.79 A compound according to Embodiment 1.73 wherein $Q^1$ and $Q^2$ together with $X^1$ and $X^2$ form a bicyclic group.

1.80 A compound according to Embodiment 1.79 wherein the bicyclic group is a fused bicyclic group.

1.81 A compound according to Embodiment 1.79 wherein the bicyclic group is a spirocyclic bicyclic group.

1.82 A compound according to Embodiment 1.79 wherein the bicyclic group is selected from a [4.2.0] fused bicyclic group, a [4.3.0] fused bicyclic group, a [3.3.0] fused bicyclic group, a [4.5] spirocyclic bicyclic group, a [3.4] spirocyclic bicyclic group and a [3.5] spirocyclic bicyclic group.

1.83 A compound according to Embodiment 1.82 wherein the bicyclic group is selected from a [4.2.0] fused bicyclic group, a [4.3.0] fused bicyclic group and a [3.3.0] fused bicyclic group.

1.84 A compound according to Embodiment 1.83 wherein the bicyclic group is a [4.2.0] fused bicyclic group.

1.85 A compound according to Embodiment 1.84 wherein the [4.2.0] fused bicyclic group is a diazabicyclo[4.2.0]octane group.

1.86 A compound according to Embodiment 1.82 wherein the bicyclic group is a [3.3.0] fused bicyclic group.

1.87 A compound according to Embodiment 1.86 wherein the [3.3.0] fused bicyclic group is a hexahydropyrrolo[3,4-b]pyrrole group.

1.88 A compound according to Embodiment 1.82 wherein the bicyclic group is a [4.3.0] fused bicyclic group.

1.89 A compound according to Embodiment 1.88 wherein the [4.3.0] fused bicyclic group is a octahydro-6H-pyrrolo[3,4-b]pyridine group.

1.90 A compound according to Embodiment 1.82 wherein the spirocyclic bicyclic group is a [3.4] spirocyclic bicyclic group.

1.91 A compound according to Embodiment 1.90 wherein the [3.4] spirocyclic bicyclic group is a 2,6-diazaspiro[3.4]octane group.

1.92 A compound according to Embodiment 1.78 wherein the spirocyclic bicyclic group is a [3.5] spirocyclic bicyclic group.

1.93 A compound according to Embodiment 1.92 wherein the [3.5] spirocyclic bicyclic group is a 2,7-diazaspiro[3.5]nonane group.

1.94 A compound according to Embodiment 1.78 wherein the spirocyclic bicyclic group is a [4.5] spirocyclic bicyclic group.

1.95 A compound according to Embodiment 1.91 wherein the [4.5] spirocyclic bicyclic group is a 2,8-diazaspiro[4.5]decane group.

1.96 A compound according to Embodiment 1.72 wherein $Q^1$ and $Q^2$ together with $X^1$ and $X^2$ form a monocyclic group.

1.97 A compound according to Embodiment 1.96 wherein the monocyclic group is pyrollidine or piperidine or diazepanegroup.

1.98 A compound according to Embodiment 1.97 wherein the piperidine group is a piperidine-1,4-diylgroup.

1.99 A compound according to Embodiment 1.97 wherein the piperidine group is a piperidine-1,3-diylgroup.

1.100 A compound according to Embodiment 1.97 wherein the pyrollidine group is a pyrollidine-1,3-diylgroup.

1.101 A compound according to Embodiment 1.72 wherein $Q^1$ and $Q^2$ together with $X^1$ and $X^2$ form a bicyclic group.

1.102 A compound according to Embodiment 1.101 wherein the bicyclic group is a fused bicyclic group.

1.103 A compound according to Embodiment 1.101 wherein the bicyclic group is a spirocyclic bicyclic group.

1.104 A compound according to Embodiment 1.101 wherein the bicyclic group is a bridged bicyclic group.

1.105 A compound according to Embodiment 1.101 wherein the bicyclic group is selected from a [3.1.0] fused bicyclic group, a [2.2.1] bridged bicyclic group, a [2.2.2]

bridged bicyclic group, a [3.4] spirocyclic bicyclic group, a [3.3] spirocyclic bicyclic group and a [2.3] spirocyclic bicyclic group.

1.106 A compound according to Embodiment 1.105 wherein the bicyclic group is a [3.1.0] fused bicyclic group.

1.107 A compound according to Embodiment 1.106 wherein the [3.1.0] fused bicyclic group is an azabicyclo[3.1.0]hexane group.

1.108 A compound according to Embodiment 1.105 wherein the bicyclic group is selected from a [2.2.1] bridged bicyclic group, a [2.2.2] bridged bicyclic group.

1.109 A compound according to Embodiment 1.108 wherein the bicyclic group is a [2.2.1] bridged bicyclic group.

1.110 A compound according to Embodiment 1.109 wherein the [2.2.1] bridged bicyclic group is an azabicyclo[2.2.1]heptane group.

1.111 A compound according to Embodiment 1.108 wherein the bicyclic group is a [2.2.2] bridged bicyclic group.

1.112 A compound according to Embodiment 1.111 wherein the [2.2.2] bridged bicyclic group is an azabicyclo[2.2.2]octane group.

1.113 A compound according to Embodiment 1.105 wherein the bicyclic group is selected from a [3.4] spirocyclic bicyclic group, a [3.3] spirocyclic bicyclic group and a [2.3] spirocyclic bicyclic group.

1.114 A compound according to Embodiment 1.113 wherein the spirocyclic bicyclic group is a [3.4] spirocyclic bicyclic group.

1.115 A compound according to Embodiment 1.114 wherein the [3.4] spirocyclic bicyclic group is a 7-azaspiro[3.4]octane group.

1.116 A compound according to Embodiment 1.113 wherein the spirocyclic bicyclic group is a [3.3] spirocyclic bicyclic group.

1.117 A compound according to Embodiment 1.116 wherein the [3.3] spirocyclic bicyclic group is a 6-azaspiro[3.3]heptane group.

1.118 A compound according to Embodiment 1.113 wherein the spirocyclic bicyclic group is a [2.3] spirocyclic bicyclic group.

1.119 A compound according to Embodiment 1.118 wherein the [2.3] spirocyclic bicyclic group is a 5-azaspiro[2.3]hexane group.

1.120 A compound according to any one of Embodiments 1.96 to 1.119 wherein q is 1.

1.121 A compound according to Embodiment 1.120 wherein Alk is a $CH_2$ group.

1.122 A compound according to any one of Embodiments 1.96 to 1.119 wherein q is 0.

1.123 A compound according to any one of Embodiments 1.96 to 1.119 wherein $R^6$ is hydrogen or a $C_{1-4}$ alkyl group.

1.124 A compound according to Embodiment 1.123 wherein $R^6$ is hydrogen or a $C_{1-2}$ alkyl group.

1.125 A compound according to Embodiment 1.124 wherein $R^6$ is hydrogen or a methyl group.

1.126 A compound according to Embodiment 1.125 wherein $R^6$ is hydrogen.

1.127 A compound according to Embodiment 1.125 wherein $R^6$ is a methyl group.

1.128 A compound according to Embodiment 1.69 wherein $Q^1$ and $Q^2$ together with $X^1$ and $X^2$ form a monocyclic group.

1.129 A compound according to Embodiment 1.128 wherein the monocyclic group is a cyclopropyl group, a cyclobutyl group, a cyclopentyl group or a cyclohexyl group.

1.130 A compound according to Embodiment 1.129 wherein the monocyclic group is a cyclopropyl group.

1.131 A compound according to Embodiment 1.129 wherein the monocyclic group is a cyclobutyl group.

1.132 A compound according to Embodiment 1.129 wherein the monocyclic group is a cyclopentyl group.

1.133 A compound according to Embodiment 1.129 wherein the monocyclic group is a cyclohexyl group.

1.134 A compound according to any one of Embodiments 1.128 to 1.133 wherein V is NH.

1.135 A compound according to any one of Embodiments 1.128 to 1.133 wherein V is $NHCH_2$.

1.136 A compound according to any one of Embodiments 1.1 to 1.135 wherein the moiety:

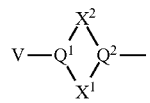

is selected from groups A to GG below:

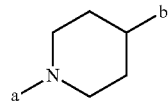
A

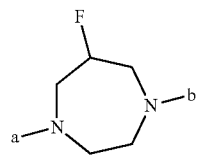
B

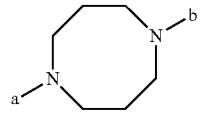
C

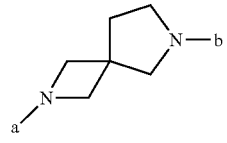
D

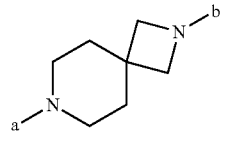
E

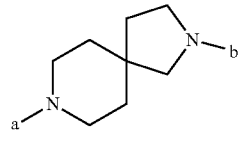
F

-continued
G 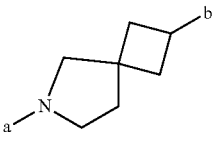
H 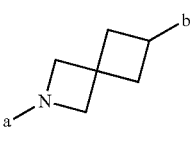
I 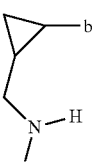
J 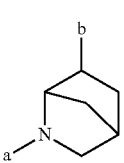
K 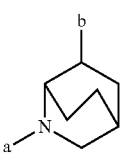
L 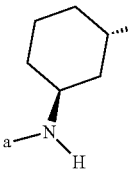
M 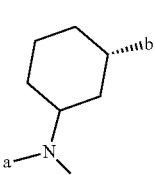
N 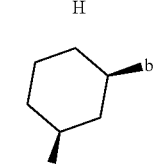
O 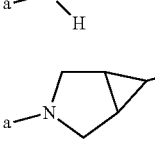
P 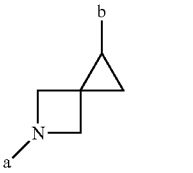
Q 
-continued
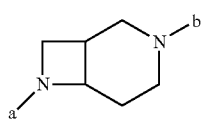
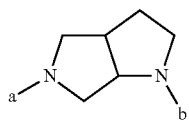
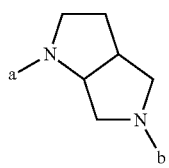
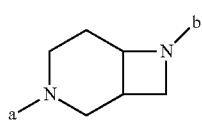
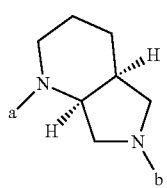
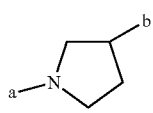
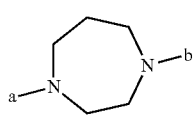
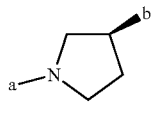
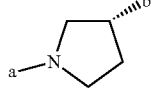
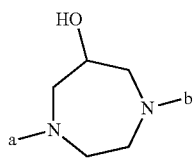
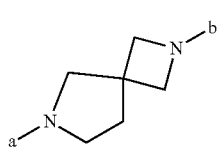
R
S
T
U
V
W
X
Y
Z
AA 

-continued

BB 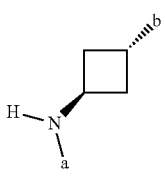

CC 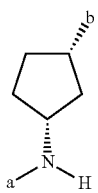

DD 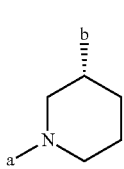

EE 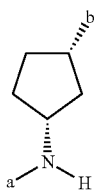

FF 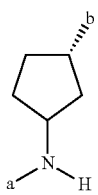

GG 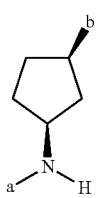

where "a" indicates the point of attachment to the cyclohexane ring and "b" indicates the point of attachment to the W group.

1.137 A compound according to Embodiment 1.1 having the formula (2):

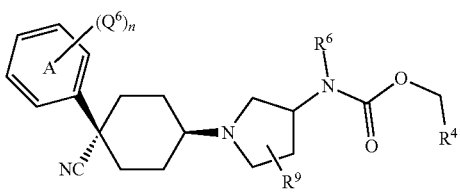

or a salt thereof, wherein the ring A is a phenyl or pyridyl ring; n is 0, 1 or 2;

$Q^6$ is halogen, methyl, cyano or methoxy;
$R^9$ is selected from hydrogen, fluorine, hydroxy, methyl, ethyl and methoxy;
$R^4$ is hydrogen or a $C_{1-6}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidised forms thereof; and
$R^6$ is hydrogen or $C_{1-4}$ alkyl.

1.138 A compound of the formula (3):

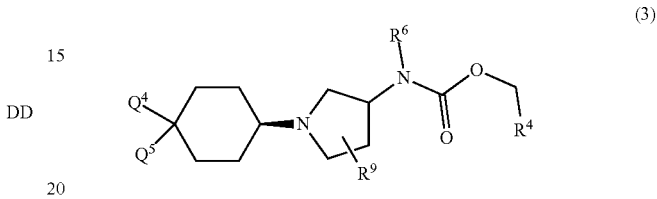

or a salt thereof, wherein:
$Q^4$ is an optionally substituted five or six membered aromatic carbocyclic or heterocyclic group containing 0, 1, 2 or 3 heteroatom ring members selected from O, N and S;
$Q^5$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;
$R^9$ is selected from hydrogen, fluorine, hydroxy, methyl, ethyl and methoxy;
$R^4$ is hydrogen or a $C_{1-6}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidised forms thereof; and
$R^6$ is hydrogen or $C_{1-4}$ alkyl.

1.139 A compound according to formula (3) wherein $Q^4$ and the pyrrolidine ring are in a cis relative orientation.

1.140 A compound according to 1.138 or 1.139 wherein $Q^4$ is an optionally substituted phenyl group or an optionally substituted pyridyl group.

1.141 A compound according to 1.140 wherein $Q^4$ is an optionally substituted phenyl group or an optionally substituted 2-pyridyl group.

1.142 A compound according to 1.138 wherein either $Q^4$ is unsubstituted or is substituted with 1, 2 or 3 substituents $Q^6$ selected from halogen; cyano; and $R^a$—$R^b$; wherein:
$R^a$ is a bond, O, CO, $X^1C(X^2)$, $C(X^2)X^1$, S, SO, $SO_2$ or $NR^c$;
$R^b$ is selected from hydrogen and a $C_{1-9}$ non-aromatic hydrocarbon group which is optionally substituted with one to six fluorine atoms and wherein one or two, but not all, carbon atoms of the hydrocarbon group may optionally be replaced by a heteroatom selected from O, N and S or by a group selected from CO, $X^1C(X^2)$, $C(X^2)X^1$, SO and $SO_2$;
$R^c$ is hydrogen or a $C_{1-4}$ hydrocarbon group;
$X^1$ is O, S or $NR^c$; and
$X^2$ is $=$O, $=$S or $=NR^c$.

1.143 A compound according to 1.138 wherein $Q^4$ is unsubstituted or is substituted with 1 or 2 substituents $Q^6$ selected from fluorine; chlorine; bromine; $C_{1-5}$ alkyl optionally substituted with one to three fluorine atoms; $C_{1-5}$ alkoxy optionally substituted with one to three fluorine atoms; and $C_{1-5}$ alkoxycarbonyl.

1.144 A compound according to 1.143 wherein $Q^4$ is unsubstituted or is substituted with a single substituent $Q^6$ selected from fluorine; chlorine; methyl and methoxy.

1.145 A compound according to any one of 1.138 to 1.144 wherein $Q^5$ is selected from cyano and $C_{1-2}$ alkoxycarbonyl.

1.146 A compound according to any one of 1.138 to 1.145 wherein $R^9$ is selected from hydrogen, hydroxy and fluorine.

1.147 A compound according to any one of 1.138 to 1.146 wherein $R^4$ is selected from hydrogen; $C_{1-4}$ alkyl optionally substituted with one to three fluorine atoms; $C_{1-2}$ alkoxy; $C_{1-3}$ alkyl and $C_{2-3}$ alkynyl.

1.148 A compound according to any one of 1.138 to 1.147 wherein $R^6$ is selected from hydrogen and methyl.

1.149 A compound according to any previous embodiment, wherein the compound is selected from ethyl [(3S)-1-(4-cyano-4-phenylcyclohexyl)pyrrolidin-3-yl] carbamate ethyl [(3R)-1-(4-cyano-4-phenylcyclohexyl)pyrrolidin-3-yl] carbamate ethyl {(3S)-1-[4-cyano-4-(3-fluorophenyl)cyclohexyl]pyrrolidin-3-yl}carbamate ethyl {(3S)-1-[4-cyano-4-(4-fluorophenyl)cyclohexyl]pyrrolidin-3-yl}carbamate ethyl {(3R)-1-[4-cyano-4-(2-fluorophenyl)cyclohexyl]pyrrolidin-3-yl}carbamate ethyl {(3R)-1-[4-cyano-4-(3-fluorophenyl)cyclohexyl]pyrrolidin-3-yl}carbamate ethyl {(3R)-1-[4-cyano-4-(4-fluorophenyl)cyclohexyl]pyrrolidin-3-yl}carbamate ethyl {(3R)-1-[4-cyano-4-(2-methylphenyl)cyclohexyl]pyrrolidin-3-yl}carbamate ethyl {(3S)-1-[4-cyano-4-(3-methylphenyl)cyclohexyl]pyrrolidin-3-yl}carbamate ethyl {(3S)-1-[4-(3-chlorophenyl)-4-cyanocyclohexyl]pyrrolidin-3-yl}carbamate ethyl {(3S)-1-[4-cyano-4-(3-methoxyphenyl)cyclohexyl] pyrrolidin-3-yl}carbamate ethyl {(3S)-1-[4-cyano-4-(pyridin-2-yl)cyclohexyl]pyrrolidin-3-yl}carbamate ethyl {(3R)-1-[4-cyano-4-(pyridin-2-yl)cyclohexyl]pyrrolidin-3-yl}carbamate ethyl {(3S)-1-[4-cyano-4-(5-fluoropyridin-2-yl)cyclohexyl] pyrrolidin-3-yl}carbamate ethyl {(3S)-1-[trans-4-(5-chloropyridin-2-yl)-4-cyanocyclohexyl]pyrrolidin-3-yl}carbamate ethyl {(3R)-1-[4-(5-chloropyridin-2-yl)-4-cyanocyclohexyl] pyrrolidin-3-yl}carbamate ethyl {(3S)-1-[4-cyano-4-(4-methylpyridin-2-yl)cyclohexyl]pyrrolidin-3-yl}carbamate ethyl {(3S)-1-[4-cyano-4-(6-methylpyridin-2-yl)cyclohexyl]pyrrolidin-3-yl}carbamate ethyl {(3R)-1-[4-cyano-4-(4-methylpyridin-2-yl)cyclohexyl]pyrrolidin-3-yl}carbamate ethyl [(3S)-1-(4-cyano-4-phenylcyclohexyl)pyrrolidin-3-yl] methylcarbamate ethyl [(3R)-1-(4-cyano-4-phenylcyclohexyl)pyrrolidin-3-yl] methylcarbamate ethyl {(3R)-1-[4-(5-chloropyridin-2-yl)-4-cyanocyclohexyl] pyrrolidin-3-yl}methylcarbamate.

1.150 A compound of the formula (4):

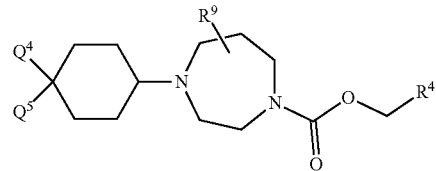

(4)

or a salt thereof, wherein:

$Q^4$ is an optionally substituted five or six membered aromatic carbocyclic or heterocyclic group containing 0, 1, 2 or 3 heteroatom ring members selected from O, N and S;

$Q^5$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^9$ is selected from hydrogen, fluorine, hydroxy and methoxy; and $R^4$ is hydrogen or a $C_{1-6}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidised forms thereof.

1.151 A compound according to formula 4 wherein $Q^4$ is an optionally substituted five or six membered aromatic carbocyclic or heterocyclic group selected from optionally substituted phenyl; optionally substituted pyridyl; optionally substituted imidazolyl; and optionally substituted thienyl.

1.152 A compound according to 1.102 or 1.103 wherein either $Q^4$ is unsubstituted or is substituted with 1, 2 or 3 substituents $Q^6$ selected from halogen; cyano; and $R^a$—$R^b$; wherein:

$R^a$ is a bond, O, CO, $X^1C(X^2)$, $C(X^2)X^1$, S, SO, $SO_2$ or $NR^c$;

$R^b$ is selected from hydrogen and a $C_{1-9}$ non-aromatic hydrocarbon group which is optionally substituted with one to six fluorine atoms and wherein one or two, but not all, carbon atoms of the hydrocarbon group may optionally be replaced by a heteroatom selected from O, N and S or by a group selected from CO, $X^1C(X^2)$, $C(X^2)X^1$, SO and $SO_2$;

$R^c$ is hydrogen or a $C_{1-4}$ hydrocarbon group;

$X^1$ is O, S or $NR^c$; and $X^2$ is =O, =S or =$NR^c$.

1.153 A compound according to 1.104 wherein $Q^4$ is unsubstituted or is substituted with 1 or 2 substituents $Q^6$ selected from fluorine; chlorine; bromine; $C_{1-4}$ alkyl optionally substituted with one to three fluorine atoms; and $C_{1-4}$ alkoxy.

1.154 A compound according to 1.102 wherein $Q^4$ is selected from:

phenyl which is unsubstituted or substituted with one or two substituents selected from fluorine; chlorine; bromine; $C_{1-4}$ alkyl optionally substituted with one to three fluorine atoms; and $C_{1-4}$ alkoxy;

pyridyl which is unsubstituted or substituted with one or two substituents selected from fluorine; chlorine; bromine; $C_{1-4}$ alkyl optionally substituted with one to three fluorine atoms; $C_{1-4}$ alkoxy; and $C_{1-4}$alkoxycarbonyl;

thienyl; and imidazolyl which is unsubstituted or substituted with one or two $C_{1-4}$ alkyl substituents.

1.155 A compound according to any one of embodiments 1.150 to 1.154 wherein $Q^5$ is selected from hydrogen, cyano and $C_{1-2}$ alkoxycarbonyl.

1.156 A compound according to any one of embodiments 1.150 to 1.155 wherein $R^9$ is selected from hydrogen, hydroxy and fluorine.

1.157 A compound according to any one of embodiments 1.149 to 1.155 wherein $R^4$ is selected from hydrogen, $C_{1-4}$ alkyl optionally substituted with one to three fluorine atoms and $C_{2-3}$ alkynyl.

1.158 A compound according to 1.157 wherein $R^4$ is selected from hydrogen, methyl, fluoromethyl, ethynyl and propynyl.

1.159 A compound according to any previous embodiment, wherein the compound is selected from ethyl 4-(4-cyano-4-phenylcyclohexyl)-1,4-diazepane-1-carboxylate
ethyl 4-[4-cyano-4-(3-fluorophenyl)cyclohexyl]-1,4-diazepane-1-carboxylate
ethyl 4-[4-cyano-4-(4-fluorophenyl)cyclohexyl]-1,4-diazepane-1-carboxylate
ethyl 4-[4-cyano-4-(2-chlorophenyl)cyclohexyl]-1,4-diazepane-1-carboxylate
ethyl 4-[4-cyano-4-(3-chlorophenyl)cyclohexyl]-1,4-diazepane-1-carboxylate
ethyl 4-[4-cyano-4-(4-chlorophenyl)cyclohexyl]-1,4-diazepane-1-carboxylate
ethyl 4-[4-cyano-4-(2-methylphenyl)cyclohexyl]-1,4-diazepane-1-carboxylate
ethyl 4-[4-cyano-4-(3-methylphenyl)cyclohexyl]-1,4-diazepane-1-carboxylate
ethyl 4-[4-cyano-4-(4-methoxyphenyl)cyclohexyl]-1,4-diazepane-1-carboxylate
ethyl 4-{4-cyano-4-[2-(trifluoromethyl)phenyl]cyclohexyl}-1,4-diazepane-1-carboxylate
ethyl 4-[4-cyano-4-(pyridin-2-yl)cyclohexyl]-1,4-diazepane-1-carboxylate
ethyl 4-[4-cyano-4-(pyridin-4-yl)cyclohexyl]-1,4-diazepane-1-carboxylate
ethyl 4-[4-(3-chloropyridin-2-yl)-4-cyanocyclohexyl]-1,4-diazepane-1-carboxylate
ethyl 4-[4-(4-methylpyridin-2-yl)-4-cyanocyclohexyl]-1,4-diazepane-1-carboxylate
ethyl 4-[4-(5-fluoropyridin-2-yl)-4-cyanocyclohexyl]-1,4-diazepane-1-carboxylate
ethyl 4-[4-(5-chloropyridin-2-yl)-4-cyanocyclohexyl]-1,4-diazepane-1-carboxylate
ethyl 4-[4-(5-bromopyridin-2-yl)-4-cyanocyclohexyl]-1,4-diazepane-1-carboxylate
ethyl 4-[4-(5-methylpyridin-2-yl)-4-cyanocyclohexyl]-1,4-diazepane-1-carboxylate
ethyl 4-[4-(5-methoxypyridin-2-yl)-4-cyanocyclohexyl]-1,4-diazepane-1-carboxylate
ethyl 4-[4-cyano-4-(5-ethoxypyridin-2-yl)cyclohexyl]-1,4-diazepane-1-carboxylate
ethyl 4-{4-cyano-4-[5-(trifluoromethyl)pyridin-2-yl]cyclohexyl}-1,4-diazepane-1-carboxylate
ethyl 4-[4-(6-methylpyridin-2-yl)-4-cyanocyclohexyl]-1,4-diazepane-1-carboxylate
ethyl 4-{4-cyano-4-[6-(trifluoromethyl)pyridin-2-yl]cyclohexyl}-1,4-diazepane-1-carboxylate
ethyl 4-[4-cyano-4-(thiophen-2-yl)cyclohexyl]-1,4-diazepane-1-carboxylate
ethyl 4-(4-cyano-4-phenylcyclohexyl)-6-fluoro-1,4-diazepane-1-carboxylate
ethyl 4-(4-cyano-4-phenylcyclohexyl)-6-hydroxy-1,4-diazepane-1-carboxylate
ethyl 4-[4-(5-chloropyridin-2-yl)-4-cyanocyclohexyl]-6-fluoro-1,4-diazepane-1-carboxylate
methyl 4-(4-cyano-4-phenylcyclohexyl)-1,4-diazepane-1-carboxylate
2-fluoroethyl 4-(4-cyano-4-phenylcyclohexyl)-1,4-diazepane-1-carboxylate
but-2-yn-1-yl 4-[4-cyano-4-(pyridin-4-yl)cyclohexyl]-1,4-diazepane-1-carboxylate
prop-2-yn-1-yl 4-[4-cyano-4-(5-methoxypyridin-2-yl)cyclohexyl]-1,4-diazepane-1-carboxylate
but-2-yn-1-yl 4-[4-cyano-4-(5-methoxypyridin-2-yl)cyclohexyl]-1,4-diazepane-1-carboxylate
ethyl 4-[4-(methoxycarbonyl)-4-phenylcyclohexyl]-1,4-diazepane-1-carboxylate
ethyl 4-[4-(3-chloropyridin-2-yl)-4-(methoxycarbonyl)cyclohexyl]-1,4-diazepane-1-carboxylate
ethyl 4-[4-(4-ethyl-5-methyl-1H-imidazol-2-yl)cyclohexyl]-1,4-diazepane-1-carboxylate.

1.160 A compound according to any one of Embodiments 1.20 to 1.135 wherein Z is C.

1.161 A compound according to any one of Embodiments 1.20 to 1.135 wherein a single Z is N.

1.162 A compound according to Embodiment 1.112 having the formula (5a), (5b), (5c) or (5d):

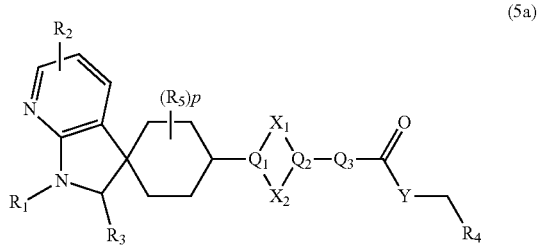

(5a)

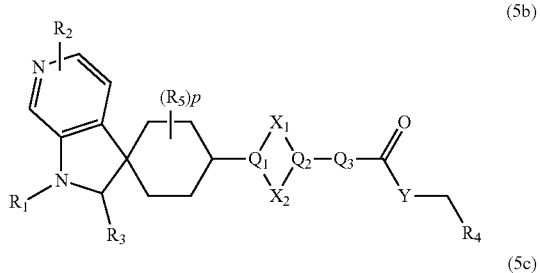

(5b)

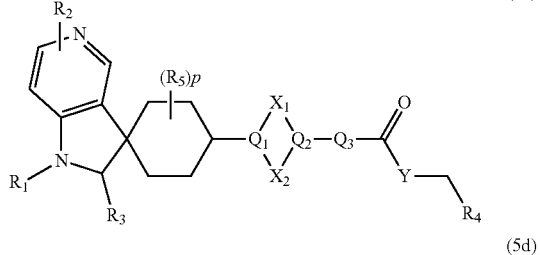

(5c)

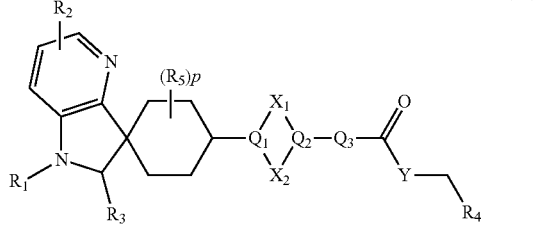

(5d)

or a salt thereof, wherein:

p is 0, 1 or 2;

$Q^1$ and $Q^2$ are each nitrogen or carbon; provided that at least one of $Q^1$ and $Q^2$ is nitrogen;

$Q^3$ is a bond or a group -(Alk)$_q$-NR$^6$ where Alk is an alkyl group of 1 to 4 carbon atoms;

q is 0 or 1; and $R^6$ is hydrogen or a saturated $C_{1-4}$ hydrocarbon group; provided that when $Q^2$ is nitrogen and $Q^3$ is a group -(Alk)$_q$-NR$^6$, there are at least two carbon atoms in line between $Q^2$ and NR$^6$ and provided that when $Q^3$ is a bond, $Q^2$ is nitrogen;

$X^1$ and $X^2$ are optionally substituted saturated hydrocarbon groups which together contain a total of three to nine carbon atoms and which link together such that the moiety:

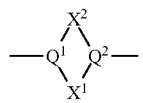

forms a monocyclic or bicyclic ring system;

$R^1$ is H, OH, COOR$^7$, CONR$^7$R$^8$, SO$_2$R$^7$ or an optionally substituted $C_{1-6}$ non-aromatic hydrocarbon group where one or more carbon atoms is optionally replaced with a heteratom selected from O, N or S;

$R^2$ is selected from hydrogen; halogen; cyano; hydroxy; amino; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

$R^3$ is selected from hydrogen or oxo;

Y is CH or O;

$R^4$ is hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$ is fluorine or a $C_{1-4}$ hydrocarbon group; and $R^7$ and $R^8$ are independently H or a $C_{1-4}$ hydrocarbon group.

1.163 A compound having formula (6)

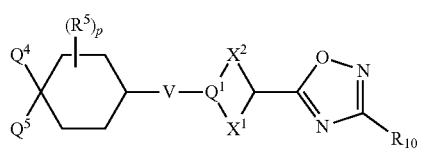

(6)

or a salt thereof, wherein:

p is 0, 1 or 2;

V is selected from a bond, NH, N(C$_{1-3}$ alkyl), NH—CH$_2$ and N(C$_{1-3}$ alkyl)-CH$_2$;

$Q^1$ is nitrogen or carbon; provided that at least one of $Q^1$ or V comprises a nitrogen atom;

$X^1$ and $X^2$ are optionally substituted saturated hydrocarbon groups which together contain a total of one to nine carbon atoms and which link together such that the moiety:

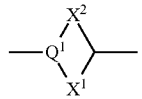

forms a monocyclic or bicyclic ring system;

$Q^4$ is an optionally substituted five or six membered aromatic carbocyclic or heterocyclic group containing 0, 1, 2 or 3 heteroatom ring members selected from O, N and S, or forms an optionally substituted heterocyclic spirocyclic ring with $Q^5$;

$Q^5$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof, or forms an optionally substituted heterocyclic spirocyclic ring with $Q^4$;

$R^{10}$ is hydrogen or a $C_{1-4}$ hydrocarbon group which is optionally substituted with one to six fluorine atoms; and $R^5$ is fluorine or a $C_{1-4}$ hydrocarbon group.

1.164 A compound according to any previous embodiment, wherein the compound is selected from ethyl [(3S)-1-(2'-oxo-1',2'-dihydrospiro[cyclohexane-1,3'-indol]-4-yl)pyrrolidin-3-yl]carbamate ethyl [(3R)-1-(2'-oxo-1',2'-dihydrospiro[cyclohexane-1,3'-indol]-4-yl)pyrrolidin-3-yl]carbamate ethyl [(3S)-1-(7'-methyl-2'-oxo-1',2'-dihydrospiro[cyclohexane-1,3'-indol]-4-yl)pyrrolidin-3-yl]carbamate ethyl [(3S)-1-(6'-methyl-2'-oxo-1',2'-dihydrospiro[cyclohexane-1,3'-indol]-4-yl)pyrrolidin-3-yl]carbamate ethyl [(3S)-1-(5'-methyl-2'-oxo-1',2'-dihydrospiro[cyclohexane-1,3'-indol]-4-yl)pyrrolidin-3-yl]carbamate ethyl [(3S)-1-(4'-methyl-2'-oxo-1',2'-dihydrospiro[cyclohexane-1,3'-indol]-4-yl)pyrrolidin-3-yl]carbamate ethyl [(3S)-1-(6'-fluoro-2'-oxo-1',2'-dihydrospiro[cyclohexane-1,3'-indol]-4-yl)pyrrolidin-3-yl]carbamate ethyl [(3S)-1-(5'-fluoro-2'-oxo-1',2'-dihydrospiro[cyclohexane-1,3'-indol]-4-yl)pyrrolidin-3-yl]carbamate ethyl [(3S)-1-(6'-methoxy-2'-oxo-1',2'-dihydrospiro[cyclohexane-1,3'-indol]-4-yl)pyrrolidin-3-yl]carbamate ethyl [(3S)-1-(5'-methoxy-2'-oxo-1',2'-dihydrospiro[cyclohexane-1,3'-indol]-4-yl)pyrrolidin-3-yl]carbamate ethyl methyl[(3S)-1-(2'-oxo-1',2'-dihydrospiro[cyclohexane-1,3'-indol]-4-yl)pyrrolidin-3-yl]carbamate ethyl methyl[(3R)-1-(2'-oxo-1',2'-dihydrospiro[cyclohexane-1,3'-indol]-4-yl)pyrrolidin-3-yl]carbamate ethyl [(3S)-1-(1'-methyl-2'-oxo-1',2'-dihydrospiro[cyclohexane-1,3'-indol]-4-yl)pyrrolidin-3-yl]carbamate ethyl 4-{(3S)-3-[(ethoxycarbonyl)amino]pyrrolidin-1-yl}-2'-oxospiro[cyclohexane-1,3'-indole]-1'(2'H)-carboxylate ethyl {(3S)-1-[1'-(2-amino-2-oxoethyl)-2'-oxo-1',2'-dihydrospiro[cyclohexane-1,3'-indol]-4-yl]pyrrolidin-3-yl}carbamate ethyl [(3S)-1-(2'-oxo-1',2'-dihydrospiro[cyclohexane-1,3'-pyrrolo[2,3-b]pyridin]-4-yl)pyrrolidin-3-yl]carbamate ethyl [(3S)-1-(5'-chloro-2'-oxo-1',2'-dihydrospiro[cyclohexane-1,3'-pyrrolo[2,3-b]pyridin]-4-yl)pyrrolidin-3-yl]carbamate ethyl methyl[(3R)-1-(2'-oxo-1',2'-dihydrospiro[cyclohexane-1,3'-pyrrolo[2,3-b]pyridin]-4-yl)pyrrolidin-3-yl]carbamate ethyl [(3S)-1-(5'-methoxy-2'-oxo-1',2'-dihydrospiro[cyclohexane-1,3'-pyrrolo[2,3-c]pyridin]-4-yl)pyrrolidin-3-yl]carbamate
ethyl [(3S)-1-(5'-methoxy-2'-oxo-1',2'-dihydrospiro[cyclohexane-1,3'-pyrrolo[3,2-b]pyridin]-4-yl)pyrrolidin-3-yl]carbamate
ethyl methyl[(3R)-1-(2'-oxo-1',2'-dihydrospiro[cyclohexane-1,3'-pyrrolo[3,2-b]pyridin]-4-yl)pyrrolidin-3-yl]carbamate
ethyl [1-(2'-oxo-1',2'-dihydrospiro[cyclohexane-1,3'-indol]-4-yl)piperidin-4-yl]carbamate
ethyl {[1-(2'-oxo-1',2'-dihydrospiro[cyclohexane-1,3'-indol]-4-yl)piperidin-4-yl]methyl}carbamate
methyl 4-(2'-oxo-1',2'-dihydrospiro[cyclohexane-1,3'-indol]-4-yl)-1,4-diazepane-1-carboxylate
ethyl 4-(2'-oxo-1',2'-dihydrospiro[cyclohexane-1,3'-indol]-4-yl)-1,4-diazepane-1-carboxylate
4-(4-butanoyl-1,4-diazepan-1-yl)spiro[cyclohexane-1,3'-indol]-2'(1'H)-one
4-{4-[(2E)-but-2-enoyl]-1,4-diazepan-1-yl}spiro[cyclohexane-1,3'-indol]-2'(1'H)-one
ethyl 4-(7'-methyl-2'-oxo-1',2'-dihydrospiro[cyclohexane-1,3'-indol]-4-yl)-1,4-diazepane-1-carboxylate
ethyl 4-(6'-methyl-2'-oxo-1',2'-dihydrospiro[cyclohexane-1,3'-indol]-4-yl)-1,4-diazepane-1-carboxylate
ethyl 4-(5'-methyl-2'-oxo-1',2'-dihydrospiro[cyclohexane-1,3'-indol]-4-yl)-1,4-diazepane-1-carboxylate
ethyl 4-(4'-methyl-2'-oxo-1',2'-dihydrospiro[cyclohexane-1,3'-indol]-4-yl)-1,4-diazepane-1-carboxylate
ethyl 4-(6'-fluoro-2'-oxo-1',2'-dihydrospiro[cyclohexane-1,3'-indol]-4-yl)-1,4-diazepane-1-carboxylate
ethyl 4-(5'-fluoro-2'-oxo-1',2'-dihydrospiro[cyclohexane-1,3'-indol]-4-yl)-1,4-diazepane-1-carboxylate
ethyl 4-(6'-methoxy-2'-oxo-1',2'-dihydrospiro[cyclohexane-1,3'-indol]-4-yl)-1,4-diazepane-1-carboxylate
ethyl 4-(5'-methoxy-2'-oxo-1',2'-dihydrospiro[cyclohexane-1,3'-indol]-4-yl)-1,4-diazepane-1-carboxylate
ethyl 4-(6'-cyano-2'-oxo-1',2'-dihydrospiro[cyclohexane-1,3'-indol]-4-yl)-1,4-diazepane-1-carboxylate
ethyl 4-(5'-cyano-2'-oxo-1',2'-dihydrospiro[cyclohexane-1,3'-indol]-4-yl)-1,4-diazepane-1-carboxylate
ethyl 4-(2'-oxo-1',2'-dihydrospiro[cyclohexane-1,3'-pyrrolo[2,3-b]pyridin]-4-yl)-1,4-diazepane-1-carboxylate
ethyl 4-(5'-chloro-2'-oxo-1',2'-dihydrospiro[cyclohexane-1,3'-pyrrolo[2,3-b]pyridin]-4-yl)-1,4-diazepane-1-carboxylate
ethyl 4-(5'-methoxy-2'-oxo-1',2'-dihydrospiro[cyclohexane-1,3'-pyrrolo[2,3-b]pyridin]-4-yl)-1,4-diazepane-1-carboxylate
ethyl 4-(1',2'-dihydrospiro[cyclohexane-1,3'-pyrrolo[2,3-b]pyridin]-4-yl)-1,4-diazepane-1-carboxylate
ethyl 4-[1'-(methylsulfonyl)-1',2'-dihydrospiro[cyclohexane-1,3'-pyrrolo[2,3-b]pyridin]-4-yl]-1,4-diazepane-1-carboxylate
ethyl 4-[1'-(methylsulfonyl)-1',2'-dihydrospiro[cyclohexane-1,3'-pyrrolo[2,3-b]pyridin]-4-yl]-1,4-diazepane-1-carboxylate
ethyl 4-(2'-oxo-1',2'-dihydrospiro[cyclohexane-1,3'-pyrrolo[2,3-c]pyridin]-4-yl)-1,4-diazepane-1-carboxylate
ethyl 4-(5'-methoxy-2'-oxo-1',2'-dihydrospiro[cyclohexane-1,3'-pyrrolo[2,3-c]pyridin]-4-yl)-1,4-diazepane-1-carboxylate
ethyl 4-(2'-oxo-1',2'-dihydrospiro[cyclohexane-1,3'-pyrrolo[3,2-b]pyridin]-4-yl)-1,4-diazepane-1-carboxylate
ethyl 4-(5'-methyl-2'-oxo-1',2'-dihydrospiro[cyclohexane-1,3'-pyrrolo[3,2-b]pyridin]-4-yl)-1,4-diazepane-1-carboxylate
ethyl 4-(5'-methoxy-2'-oxo-1',2'-dihydrospiro[cyclohexane-1,3'-pyrrolo[3,2-b]pyridin]-4-yl)-1,4-diazepane-1-carboxylate
ethyl 6-(2'-oxo-1',2'-dihydrospiro[cyclohexane-1,3'-indol]-4-yl)-2,6-diazaspiro[3.4]octane-2-carboxylate
ethyl 8-(2'-oxo-1',2'-dihydrospiro[cyclohexane-1,3'-indol]-4-yl)-2,8-diazaspiro[4.5]decane-2-carboxylate
ethyl 4-[2-(ethoxycarbonyl)-2,8-diazaspiro[4.5]dec-8-yl]-2'-oxospiro[cyclohexane-1,3'-indole]-1'(2'H)-carboxylate
ethyl 8-(4-cyano-4-phenylcyclohexyl)-2,8-diazaspiro[4.5]decane-2-carboxylate
ethyl 7-(4-cyano-4-phenylcyclohexyl)-3,7-diazabicyclo[4.2.0]octane-3-carboxylate
ethyl 5-(4-cyano-4-phenylcyclohexyl)hexahydropyrrolo[3,4-b]pyrrole-1(2H)-carboxylate
ethyl 1-(4-cyano-4-phenylcyclohexyl)hexahydropyrrolo[3,4-b]pyrrole-5(1H)-carboxylate
ethyl 3-(4-cyano-4-phenylcyclohexyl)-3,7-diazabicyclo[4.2.0]octane-7-carboxylate
ethyl (4aS,7aS)-1-(4-cyano-4-phenylcyclohexyl)octahydro-6H-pyrrolo[3,4-b]pyridine-6-carboxylate
4-{[(1R,3S)-3-(3-methyl-1,2,4-oxadiazol-5-yl)cyclopentyl]amino}-1-(pyridin-2-yl)cyclohexanecarbonitrile
4-{[(1R,3S)-3-(3-ethyl-1,2,4-oxadiazol-5-yl)cyclopentyl]amino}-1-phenylcyclohexanecarbonitrile
1-phenyl-4-{6-[3-(trifluoromethyl)-1,2,4-oxadiazol-5-yl]-2-azaspiro[3.3]hept-2-yl}cyclohexanecarbonitrile
4-[2-(3-methyl-1,2,4-oxadiazol-5-yl)-6-azaspiro[3.4]oct-6-yl]-1-phenylcyclohexanecarbonitrile
1-(2-fluorophenyl)-4-[2-(3-methyl-1,2,4-oxadiazol-5-yl)-6-azaspiro[3.4]oct-6-yl]cyclohexanecarbonitrile
1-(5-fluoropyridin-2-yl)-4-[2-(3-methyl-1,2,4-oxadiazol-5-yl)-6-azaspiro[3.4]oct-6-yl]cyclohexanecarbonitrile
1-(5-methoxypyridin-2-yl)-4-[2-(3-methyl-1,2,4-oxadiazol-5-yl)-6-azaspiro[3.4]oct-6-yl]cyclohexanecarbonitrile
4-[2-(3-methyl-1,2,4-oxadiazol-5-yl)-6-azaspiro[3.4]oct-6-yl]-1-(5-methylpyridin-2-yl)cyclohexanecarbonitrile
4-[(3R)-3-(3-methyl-1,2,4-oxadiazol-5-yl)piperidin-1-yl]spiro[cyclohexane-1,3'-indol]-2'(1'H)-one
5'-methoxy-4-[(3R)-3-(3-methyl-1,2,4-oxadiazol-5-yl)piperidin-1-yl]spiro[cyclohexane-1,3'-indol]-2'(1'H)-one
5'-methyl-4-[(3R)-3-(3-methyl-1,2,4-oxadiazol-5-yl)piperidin-1-yl]spiro[cyclohexane-1,3'-indol]-2'(1'H)-one
6'-methyl-4-[(3R)-3-(3-methyl-1,2,4-oxadiazol-5-yl)piperidin-1-yl]spiro[cyclohexane-1,3'-indol]-2'(1'H)-one
4-({[2-(3-methyl-1,2,4-oxadiazol-5-yl)cyclopropyl]methyl}amino)spiro[cyclohexane-1,3'-indol]-2'(1'H)-one
4-({(1R,3S)-3-[3-(trifluoromethyl)-1,2,4-oxadiazol-5-yl]cyclopentyl}amino)spiro[cyclohexane-1,3'-indol]-2'(1'H)-one
5'-methyl-4-({(1R,3S)-3-[3-(trifluoromethyl)-1,2,4-oxadiazol-5-yl]cyclopentyl}amino)spiro[cyclohexane-1,3'-indol]-2'(1'H)-one
6'-methyl-4-{[(1R,3S)-3-(3-methyl-1,2,4-oxadiazol-5-yl)cyclopentyl]amino}spiro[cyclohexane-1,3'-indol]-2'(1'H)-one
4-[6-(3-ethyl-1,2,4-oxadiazol-5-yl)-2-azaspiro[3.3]hept-2-yl]spiro[cyclohexane-1,3'-indol]-2'(1'H)-one
5'-methyl-4-[2-(3-methyl-1,2,4-oxadiazol-5-yl)-6-azaspiro[3.4]oct-6-yl]spiro[cyclohexane-1,3'-indol]-2'(1'H)-one
5'-methoxy-4-[2-(3-methyl-1,2,4-oxadiazol-5-yl)-6-azaspiro[3.4]oct-6-yl]spiro[cyclohexane-1,3'-indol]-2'(1'H)-one
4-[2-(3-ethyl-1,2,4-oxadiazol-5-yl)-6-azaspiro[3.4]oct-6-yl]spiro[cyclohexane-1,3'-indol]-2'(1'H)-one
4-({[2-(3-ethyl-1,2,4-oxadiazol-5-yl)cyclopropyl]methyl}amino)-1-phenylcyclohexanecarbonitrile 1-(5-fluoropyridin-2-yl)-4-({(1R,3S)-3-[3-(trifluoromethyl)-1,2,4-oxadiazol-5-yl]cyclopentyl}amino)cyclohexanecarbonitrile 1-(5-methylpyridin-2-yl)-4-({(1R,3S)-3-[3-(trifluoromethyl)-1,2,4-oxadiazol-5-yl]cyclopentyl}amino)cyclohexanecarbonitrile 1.165 A compound according to any one of Embodiments 1.1 to 1.164 having a molecular weight of less than 550, for example less than 500, or less than 450.

1.166 A compound according to any one of Embodiments 1.1 to 1.165 which is in the form of a salt.

1.167 A compound according to Embodiment 1.166 wherein the salt is an acid addition salt.

1.168 A compound according to Embodiment 1.166 or Embodiment 1.167 wherein the salt is a pharmaceutically acceptable salt.

Definitions

In this application, the following definitions apply, unless indicated otherwise.

The term "treatment", in relation to the uses of the compounds of the formula (1), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

In formula (1), $X^1$ and $X^2$ are saturated hydrocarbon groups which together contain a total of four to nine carbon atoms and which link together such that the moiety:

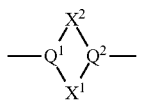

forms a monocyclic or bicyclic ring system. The term "bicyclic ring system as used herein in the context of $X^1$ and $X^2$ includes fused bicyclic systems, bridged bicyclic systems and spirocyclic systems containing two linked rings.

Bicyclic ring systems may be characterized herein according to the number of atoms in each ring. For example, the term "4.5 spirocyclic ring system" may be used to define a spirocyclic ring system in which one ring contains 4 ring members and the other ring contains 5 ring members, e.g. a ring system such as:

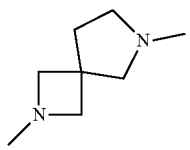

Similarly the term "4.6 fused bicyclic group" may be used to define a fused ring system in which one ring contains 4 ring members and the other ring contains 6 ring members, e.g. a ring system such as:

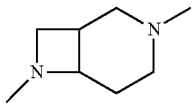

The term "non-aromatic hydrocarbon group" (as in "$C_{1-10}$ non-aromatic hydrocarbon group" or "acyclic $C_{1-5}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The terms "alkyl", "alkenyl", "alkynyl", "cycloalkyl" and "cycloalkenyl" are used in their conventional sense (e.g. as defined in the IUPAC Gold Book) unless indicated otherwise.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of R groups above, where stated, one or two but not all, carbon atoms of the non-aromatic hydrocarbon group may optionally be replaced by a heteroatom selected from O, N and S and oxidised forms thereof. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—S(O)$_2$—$CH_2$—, replacement of a carbon atom in a —$CH_2$—$CH_2$—$CH_2$-chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —CH$_2$—CH$_2$—C(O)—O—. In each such replacement, at least one carbon atom of the hydrocarbon group must remain.

Salts

Many compounds of the formula (1) can exist in the form of salts, for example acid addition salts or, in certain cases salts of organic and inorganic bases such as carboxylate, sulfonate and phosphate salts. All such salts are within the scope of this invention, and references to compounds of the formula (1) include the salt forms of the compounds as defined in Embodiments 1.166 to 1.168.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.167) may be formed with a wide variety of acids, both inorganic and organic. Examples of acid addition salts falling within Embodiment 1.167 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1 S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1) contain an amine function, these may form quaternary ammonium salts, for example by reaction with an alkylating agent according to methods well known to the skilled person. Such quaternary ammonium compounds are within the scope of formula (1).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Zand E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.200), the invention provides a geometric isomer of a compound according to any one of Embodiments 1.1 to 1.168.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.201) the invention provides a compound according to any one of Embodiments 1.1 to 1.168 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry by Jerry March*, 4$^{th}$ Edition, John Wiley & Sons, New York, 1992, pages 109-114, and see also Cahn, Ingold & Prelog, *Angew. Chem. Int. Ed. Engl.*, 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.202), the invention provides compositions containing a compound according to Embodiment 1.201 having one or more chiral centres, wherein at least 55% (e.g. at least 60%, 65%, 70%, 75%, 80%, 85%, 90% or 95%) of the compound of Embodiment 1.201 is present as a single optical isomer (e.g. enantiomer or diastereoisomer).

In one general embodiment (Embodiment 1.203), 99% or more (e.g. substantially all) of the total amount of the compound (or compound for use) of Embodiment 1.201 is present as a single optical isomer.

For example, in one embodiment (Embodiment 1.204 the compound is present as a single enantiomer.

In another embodiment (Embodiment 1.205), the compound is present as a single diastereoisomer.

The invention also provides mixtures of optical isomers, which may be racemic or non-racemic. Thus, the invention provides:

1.206 A compound according to Embodiment 1.131 which is in the form of a racemic mixture of optical isomers.

1.207 A compound according to Embodiment 1.131 which is in the form of a non-racemic mixture of optical isomers.

Isotopes

The compounds of the invention as defined in any one of Embodiments 1.1 to 1.207 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.208), the compound of any one of Embodiments 1.1 to 1.207 contains no radioactive isotopes. Such compounds are preferred for therapeutic use. In another embodiment (Embodiment 1.209), however, the compound of any one of Embodiments 1.1 to 1.207 may contain one or more radioisotopes. Compounds containing such radioisotopes may be useful in a diagnostic context.

Solvates

Compounds of the formula (1) as defined in any one of Embodiments 1.1 to 1.209 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.301 and 1.302, the invention provides:

1.301 A compound according to any one of Embodiments 1.1 to 1.209 in the form of a solvate.

1.302 A compound according to Embodiment 1.301 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.303), the invention provides a compound as defined in any one of Embodiments 1.1 to 1.209 in an anhydrous form (e.g. anhydrous crystalline form).

Crystalline and Amorphous Forms

The compounds of any one of Embodiments 1.1 to 1.303 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.401 A compound according to any one of Embodiments 1.1 to 1.303 in a crystalline form.

1.402 A compound according to any one of Embodiments 1.1 to 1.303 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.403 A compound according to any one of Embodiments 1.1 to 1.303 which is in an amorphous form.

Prodrugs

The compounds of the formula (1) or (1a) as defined in any one of Embodiments 1.1 to 1.168 may be presented in the form of a pro-drug. By "prodrugs" is meant for example any compound that is converted in vivo into a biologically active compound of the formula (1), as defined in any one of Embodiments 1.1 to 1.168.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.500), the invention provides a pro-drug of a compound as defined in any one of Embodiments 1.1 to 1.168 wherein the compound contains a functional group which is convertable under physiological conditions to form a hydroxyl group or amino group.

Complexes and Clathrates

Also encompassed by formula (1) in Embodiments 1.1 to 1.168 are complexes (e.g. inclusion complexes or clathrates with compounds such as cyclodextrins, or complexes with metals) of the compounds of Embodiments 1.1 to 1.168.

Accordingly, in another embodiment (Embodiment 1.600), the invention provides a compound according to any one of Embodiments 1.1 to 1.168 in the form of a complex or clathrate.

Biological Activity and Therapeutic Uses

The compounds of the present invention have activity as muscarinic $M_1$ receptor agonists. The muscarinic activity of the compounds can be determined using the Phospho-ERK1/2 assay described in Example A below.

A significant advantage of compounds of the invention is that they are highly selective for the $M_1$ receptor relative to the $M_2$ and $M_3$ receptor subtypes. Compounds of the invention are neither agonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 100) against the $M_1$ receptor in the functional assay described in Example A, they may have $pEC_{50}$ values of less than 5 and $E_{max}$ values of less than 20% when tested against the $M_2$ and $M_3$ subtypes in the functional assay of Example A.

Some compounds of the invention are also highly selective for the $M_1$ receptor relative to the $M_4$ receptor. Examples of such compounds include 1-1, 1-3, 1-4, 1-9, 1-10, 2-1, 2-3, 2-4, 2-5, 2-7, 2-8, 2-10, 2-17, 3-19, 3-20, 3-31, 3-32, 4-7, 4-12 and 5-1.

Other compounds of the invention have activity at both the $M_1$ and $M_4$ receptors.

Examples of such compounds include 3-2, 3-3, 3-6, 3-8, 3-16, 3-17, 4-6, 6-2, 12-1, 12-2 and 13-1.

Accordingly, in Embodiments 2.1 to 2.17, the invention provides:

2.1 A compound according to any one of Embodiments 1.1 to 1.600 for use in medicine.

2.2 A compound according to any one of Embodiments 1.1 to 1.600 for use as a muscarinic $M_1$ receptor agonist.

2.3 A compound according to any one of Embodiments 1.1 to 1.600 which is a muscarinic $M_1$ receptor agonist having a $pEC_{50}$ in the range from 6.0 to 10.0 and an $E_{max}$ of at least 90 against the $M_1$ receptor in the assay of Example A herein or an assay substantially similar thereto.

2.4 A compound according to Embodiment 2.3 which is a muscarinic $M_1$ receptor agonist having a $pEC_{50}$ in the range from 6.5 to 10.0.

2.5 A compound according to Embodiment 2.3 which is a muscarinic $M_1$ receptor agonist having a $pEC_{50}$ in the range from 6.8 to 7.9.

2.6 A compound according to Embodiment 2.3 which is a muscarinic $M_1$ receptor agonist having a $pEC_{50}$ in the range from 7.1 to 7.9.

2.7 A compound according to Embodiments 2.3 to 2.6 having an $E_{max}$ of at least 95 against the $M_1$ receptor.

2.8 A compound according to any one of Embodiments 1.1 to 1.600 which is a muscarinic $M_4$ receptor agonist having a $pEC_{50}$ in the range from 6.0 to 9.0 and an $E_{max}$ of at least 90 against the $M_4$ receptor in the assay of Example A herein or an assay substantially similar thereto.

2.9 A compound according to Embodiment 2.8 which is a muscarinic $M_4$ receptor agonist having a $pEC_{50}$ in the range from 6.5 to 9.0.

2.10 A compound according to Embodiment 2.8 or Embodiment 2.9 having an $E_{max}$ of at least 95 against the $M_4$ receptor.

2.11 A compound according to any one of Embodiments 2.3 to 2.7 which is selective for the $M_1$ receptor compared to the muscarinic $M_2$ and $M_3$ receptors.

2.12 A compound according to any one of Embodiments 2.3 to 2.11 which has a $pEC_{50}$ of less than 5 and an $E_{max}$ of less than 50 against the muscarinic $M_2$ and $M_3$ receptor subtypes.

2.13 A compound according to Embodiment 2.12 which has a $pEC_{50}$ of less than 4.5 and/or an $E_{max}$ of less than 30 against the muscarinic $M_2$ and $M_3$ receptor subtypes.

2.14 A compound according to any one of Embodiments 1.1 to 1.600 and Embodiments 2.3 to 2.13 for use in the treatment of a disease or condition mediated by the muscarinic $M_1$ receptor.

2.15 A compound according to any one of Embodiments 1.1 to 1.600 which is selective for the $M_1$ receptor compared to the muscarinic $M_2$, $M_3$ and $M_4$ receptors.

2.16 A compound according to Embodiment 2.15 which has a $pEC_{50}$ of less than 5 and an $E_{max}$ of less than 50 against each of the muscarinic $M_2$, $M_3$ and $M_4$ receptor subtypes.

2.17 A compound according to Embodiment 2.16 which has a $pEC_{50}$ of less than 4.5 and/or an $E_{max}$ of less than 30 against the each of the muscarinic $M_2$, $M_3$ and $M_4$ receptor subtypes.

2.18 A compound according to any one of Embodiments 1.1 to 1.600 which is selective for the $M_1$ and $M_4$ receptors compared to the muscarinic $M_2$ and $M_3$ receptors.

2.19 A compound according to Embodiment 2.18 which has a $pEC_{50}$ of less than 5 and an $E_{max}$ of less than 50 against each of the muscarinic $M_2$ and $M_3$ receptor subtypes.

2.20 A compound according to Embodiment 2.19 which has a $pEC_{50}$ of less than 4.5 and/or an $E_{max}$ of less than 30 against the each of the muscarinic $M_2$ and $M_3$ receptor subtypes.

By virtue of their muscarinic $M_1$ and/or $M_4$ receptor agonist activity, compounds of the invention can be used in the treatment of Alzheimer's disease, schizophrenia and other psychotic disorders, cognitive disorders and other diseases mediated by the muscarinic $M_1$ and/or $M_4$ receptor, and can also be used in the treatment of various types of pain.

Accordingly, in Embodiments 2.21 to 2.42, the invention provides:

2.21 A compound according to any one of Embodiments 1.1 to 1.600 for use in the treatment of a cognitive disorder or psychotic disorder.

2.22 A compound for use in according to Embodiment 2.21 wherein the cognitive disorder or psychotic disorder comprises, arises from or is associated with a condition selected from cognitive impairment, Mild Cognitive Impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders, epilepsy and schizo-affective disorder.

2.23 A compound according to any one of Embodiments 1.1 to 1.600 for use in the treatment of Alzheimer's disease.

2.24 A compound according to any one of Embodiments 1.1 to 1.600 for use in the treatment of Schizophrenia.

2.25 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.600.

2.26 A method according to Embodiment 2.25 wherein the cognitive disorder comprises, arises from or is associated with a condition as defined in Embodiment 2.22.

2.27 A method according to Embodiment 2.26 wherein the cognitive disorder arises from or is associated with Alzheimer's disease.

2.28 A method according to Embodiment 2.27 wherein the cognitive disorder is Schizophrenia.

2.29 The use of a compound according to any one of Embodiments 1.1 to 1.600 for the manufacture of a medicament for the treatment of a cognitive disorder.

2.30 The use according to Embodiment 2.29 wherein the cognitive disorder comprises, arises from or is associated with a condition as defined in Embodiment 2.22.

2.31 The use according to Embodiment 2.30 wherein the cognitive disorder arises from or is associated with Alzheimer's disease.

2.32 The use according to Embodiment 2.30 wherein the cognitive disorder is Schizophrenia.

2.33 A compound according to any one of Embodiments 1.1 to 1.600 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.34 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.600.

2.35 A compound according to any one of Embodiments 1.1 to 1.600 for the treatment of peripheral disorders such as reduction of intra ocular pressure in Glaucoma and treatment of dry eyes and dry mouth including Sjogren's Syndrome.

2.36 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.600.

2.37 The use of a compound according to any one of Embodiments 1.1 to 1.600 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.38 The use of a compound according to any one of Embodiments 1.1 to 1.600 for the use in the treatment of skin lesions for example due to pemphigus vulgaris, dermatitis herpetiformis, pemphigoid and other blistering skin conditions.

2.39 The use of a compound according to any one of Embodiments 1.1 to 1.600 for the use in treating, preventing, ameliorating or reversing conditions associated with altered gastro-intestinal function and motility such as functional dyspepsia, irritable bowel syndrome, gastroesophageal acid reflux (GER) and esophageal dysmotility, symptoms of gastroparesis and chronic diarrhea.

2.40 The use of a compound according to any one of Embodiments 1.1 to 1.600 for the use in in the treatment of olfactory dysfunction such as Bosma-Henkin-Christiansen syndrome, chemical poisoning (e.g. selenium and silver), hypopituitarism, Kallmann Syndrome, skull fractures, tumour therapy and underactive thyroid gland.

2.41 The use of a compound according to any one of Embodiments 1.1 to 1.600 for the treatment of addiction.

2.42 The use of a compound according to any one of Embodiments 1.1 to 1.600 for the treatment of movement disorders such as Parkinson's disease, ADHD, Huntingdon's disease, tourette's syndrome and other syndromes associated with dopaminergic dysfunction as an underlying pathogenetic factor driving disease.

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.168, which process comprises:

(A) when it is required to prepare a compound of formula (1) wherein $Q^1$ is nitrogen, the reaction of a compound of the formula (10):

with a compound of the formula (11):

under reductive amination conditions; wherein p, $Q^1$, $Q^2$, $Q^4$, $Q^5$, $R^5$, V, W, $X^1$ and $X^2$ are as defined in any one of Embodiments 1.1 to 1.168; or (B) when it is required to prepare a compound of formula (1) wherein $Q^2$ is nitrogen, W is -$Q^3$C(O)YCH$_2$R$^4$ and $Q^3$ is a bond, the reaction of a compound of the formula (12):

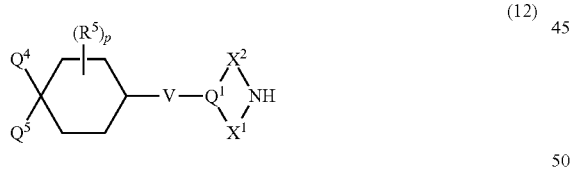

with a compound of the formula Cl—C(=O)—O—CH$_2$—R$^4$; wherein p, $Q^1$, $Q^4$, $Q^5$, $R^4$, $R^5$, V, $X^1$ and $X^2$ are as defined in any one of Embodiments 1.1 to 1.168; or (C) when it is required to prepare a compound of formula (1) wherein $Q^2$ is nitrogen, W is -$Q^3$C(O)YCH$_2$R$^4$ and $Q^3$ is a group -(Alk)$_q$-NR$^6$, the reaction of a compound of a compound of the formula (13):

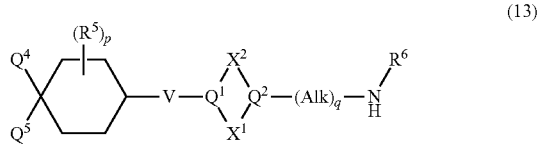

with a compound of the formula Cl—C(=O)—O—CH$_2$—R$^4$; wherein p, $Q^1$, $Q^2$, $Q^4$, $Q^5$, $R^4$, $R^5$, $R^6$, V, $X^1$ and $X^2$ are as defined in any one of Embodiments 1.1 to 1.168;

and optionally:

(D) converting one compound of the formula (1) to another compound of the formula (1).

In process variant (A), the mono-protected diamine (11) is reacted with the substituted cyclohexanone (10) under reductive amination conditions. The reductive amination reaction is typically carried out at ambient temperature to mild heating (e.g. to a temperature of about 20° C. to about 70° C.) using either a borohydride reducing agent such as sodium triacetoxy-borohydride in a solvent such as dichloromethane or dichloroethane containing acetic acid, or sodium cyanoborohydride in combination with zinc chloride, or sodium triacetoxy-borohydride in combination with titanium isopropoxide.

Substituted cyclohexanones of the formula (10) can be prepared by the sequence of reactions shown in Scheme 1 below. Thus, a protected substituted cyclohexanone (14) is deprotonated using a suitable base such as lithium diisopropylamide (LDA), sodium hexamethyldisilazide (NaHMDS) or potassium hexamethyldisilazide (KHMDS) and then reacting the anion with a suitable reactive organohalide (15) to give the protected substituted cyclohexanones (16). This is then deprotected by removal of the cyclic acetal group using an organic acid such as trifluoroacetic acid in dichloromethane or an inorganic acid such as HCl in dioxane to give the substituted cyclohexanones (10), as shown in Scheme 1.

Scheme 1

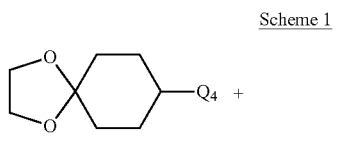

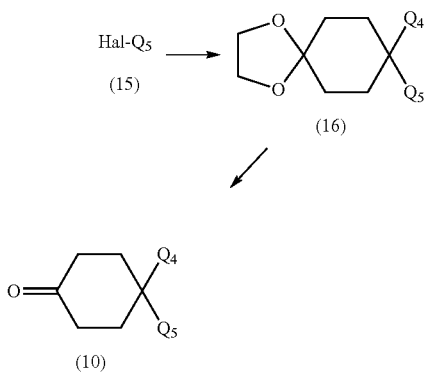

An alternate route to substituted cyclohexanones of the formula (10) is shown in Scheme 2. Alkyl compounds of the formula (17) can deprotonated using a suitable base such as tBuOK, NaHMDS or KHMDS and then reacting the anion with methyl acrylate to give the protected substituted cyclohexanone (18). These can be decarboxylated by treating with a suitable base such as tBuOK, LiOH or NaOH followed by heating to give the substituted cyclohexanones (10).

Scheme 2

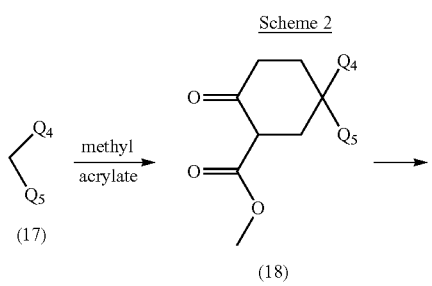

Once formed, one compound of the formula (1), or a protected derivative thereof, can be converted into another compound of the formula (1) by methods well known to the skilled person. Examples of synthetic procedures for converting one functional group into another functional group are set out in standard texts such as *Advanced Organic Chemistry* and *Organic Syntheses* (see references above) or *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Once formed, one compound of the formula (1), or a protected derivative thereof, can be converted into another compound of the formula (1) by methods well known to the skilled person. Examples of synthetic procedures for converting one functional group into another functional group are set out in standard texts such as *Advanced Organic Chemistry* and *Organic Syntheses* (see references above) or *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Methods for the Preparation of Compounds of the Formula (1a)

Compounds of the formula (1a) can be prepared in accordance with synthetic methods well known to the skilled person and as described herein.

Accordingly, in another embodiment (Embodiment 3.2), the invention provides a process for the preparation of a compound as defined in any one of Embodiments 1.20 to 1.168, which process comprises:

(A) when it is required to prepare a compound of formula (1a) wherein $Q^1$ is nitrogen, the reaction of a compound of the formula (10a):

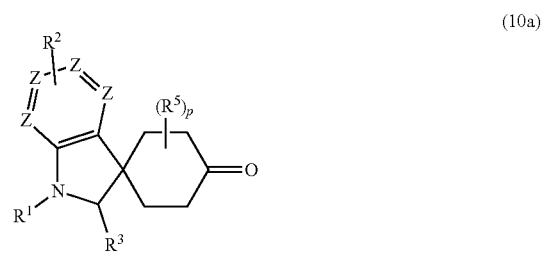

with a compound of the formula (11a):

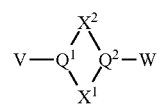

under reductive amination conditions; wherein p, Z, $Q^1$, $Q^2$, $Q^3$, $R^1$, $R^2$, $R^3$, $R^5$, V, W, $X^1$ and $X^2$ are as defined in any one of Embodiments 1.20 to 1.168; or (B) when it is required to prepare a compound of formula (1a) wherein $Q^2$ is nitrogen, W is -$Q^3$C(O)YCH$_2$R$^4$ and $Q^3$ is a bond, the reaction of a compound of the formula (12a):

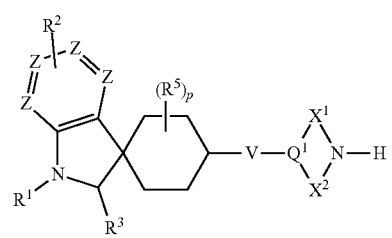

with a compound of the formula Cl—C(=O)—O—CH$_2$—R$^4$; wherein p, Z, $Q^1$, $R^1$, $R^2$, $R^3$, $R^4$, $R^5$, V, $X^1$ and $X^2$ are as defined in any one of Embodiments 1.20 to 1.168; or (C) when it is required to prepare a compound of formula (1a) wherein $Q^2$ is nitrogen, W is -$Q^3$C(O)YCH$_2$R$^4$ and $Q^3$ is a group -(Alk)$_q$-NR$^6$, the reaction of a compound of a compound of the formula (13a):

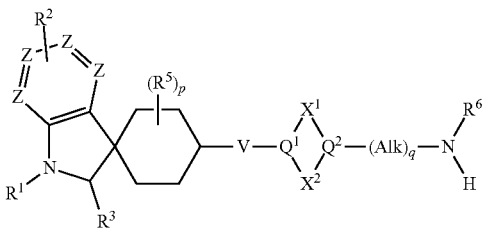

(13a)

with a compound of the formula Cl—C(=O)—O—CH$_2$—R$^4$; wherein p, q, Z, Q$^1$, Q$^2$, R$^1$, R$^2$, R$^3$, R$^4$, R$^5$, R$^6$, V, X$^1$ and X$^2$ are as defined in any one of Embodiments 1.1 to 1.168;

and optionally:

(D) converting one compound of the formula (1a) to another compound of the formula (1a).

In process variant (A), the mono-protected diamine (11a) is reacted with the substituted cyclohexanone (10a) under reductive amination conditions. The reductive amination reaction is typically carried out at ambient temperature to mild heating (e.g. to a temperature of about 20° C. to about 70° C.) using either a borohydride reducing agent such as sodium triacetoxy-borohydride in a solvent such as dichloromethane or dichloroethane containing acetic acid, or sodium cyanoborohydride in combination with zinc chloride, or sodium triacetoxy-borohydride in combination with titanium isopropoxide.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Once formed, one compound of the formula (1a), or a protected derivative thereof, can be converted into another compound of the formula (1a) by methods well known to the skilled person. Examples of synthetic procedures for converting one functional group into another functional group are set out in standard texts such as *Advanced Organic Chemistry and Organic Syntheses* (see references above) or *Fiesers' Reagents for Organic Synthesis*, Volumes 1-17, John Wiley, edited by Mary Fieser (ISBN: 0-471-58283-2).

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.600 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 25-1

The compounds of Examples 1-1 to 25-1 shown in Table 1 below have been prepared. Starting materials and intermediates are described in Table 2. The NMR and LCMS properties of the compounds of Examples 1-1 to 25-1 and the methods used to prepare them are set out in Table 3.

TABLE 1

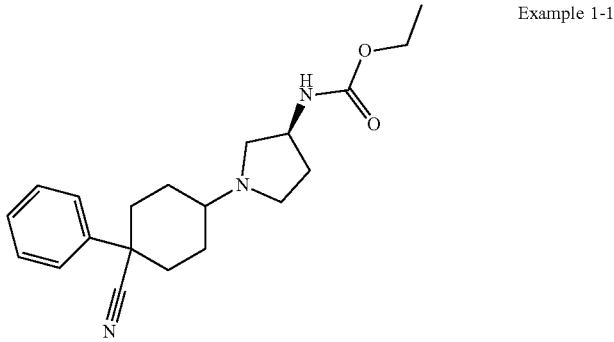

Example 1-1

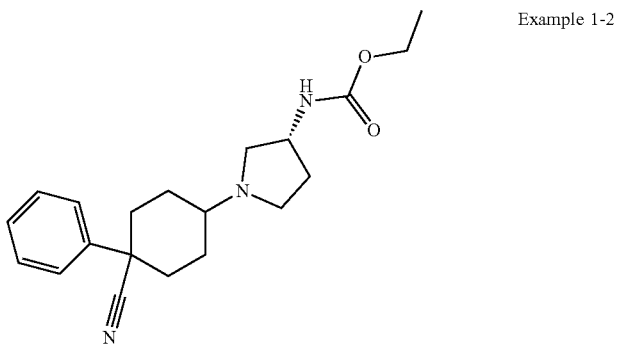

Example 1-2

TABLE 1-continued
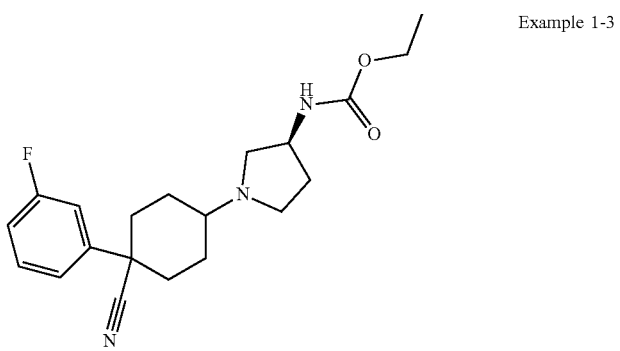
Example 1-3
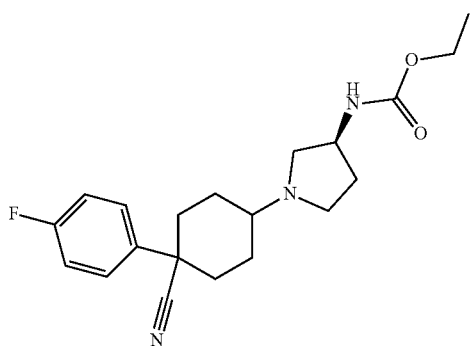 [SMILES: CCOC(=O)N[C@H]1CCN(C2CCC(C#N)(c3ccc(F)cc3)CC2)C1]
Example 1-4
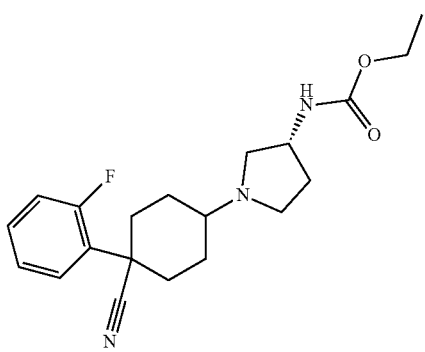 [SMILES: CCOC(=O)N[C@@H]1CCN(C2CCC(C#N)(c3ccccc3F)CC2)C1]
Example 1-5
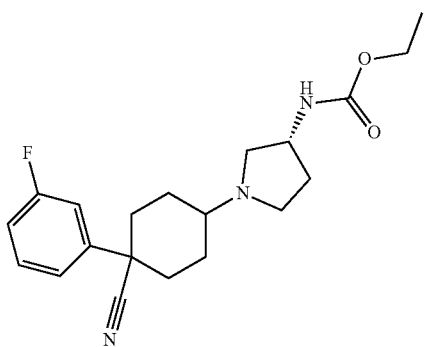 [SMILES: CCOC(=O)N[C@@H]1CCN(C2CCC(C#N)(c3cccc(F)c3)CC2)C1]
Example 1-6

TABLE 1-continued
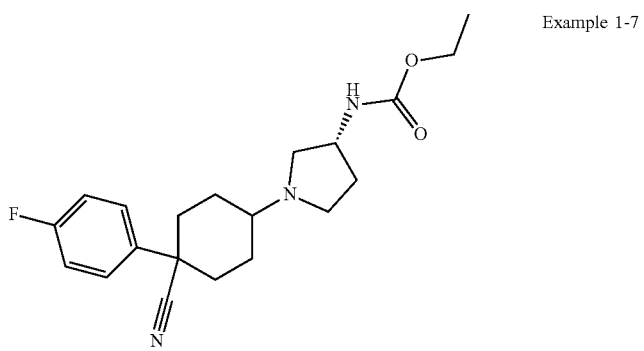
Example 1-7
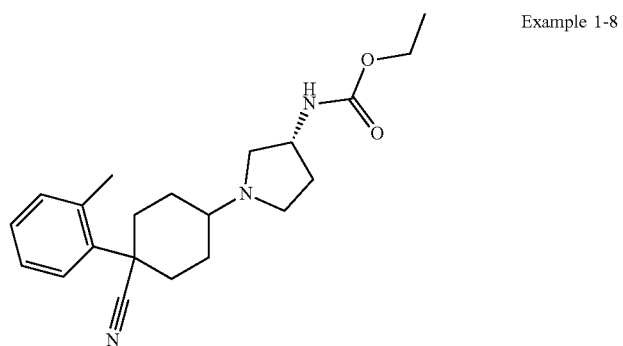
Example 1-8
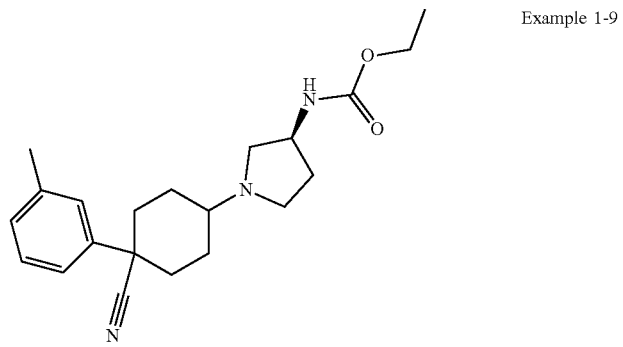
Example 1-9
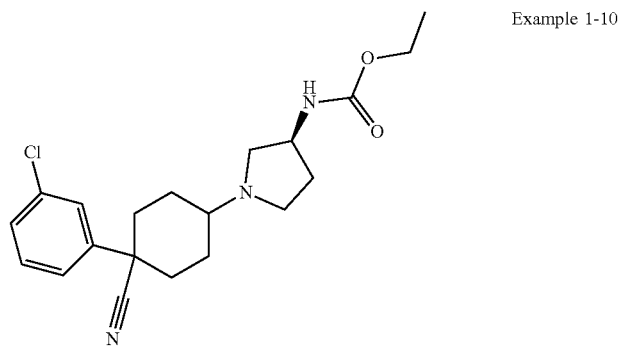
Example 1-10

TABLE 1-continued
| | |
|---|---|
| 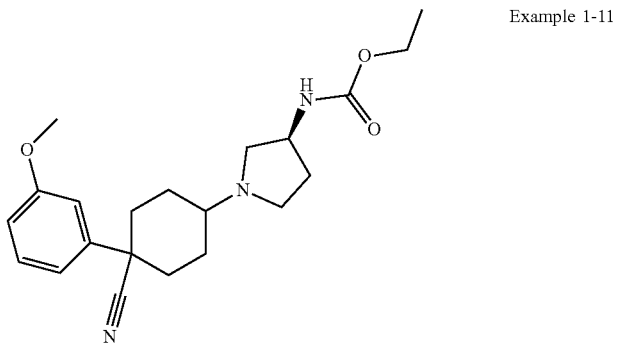 | Example 1-11 |
| 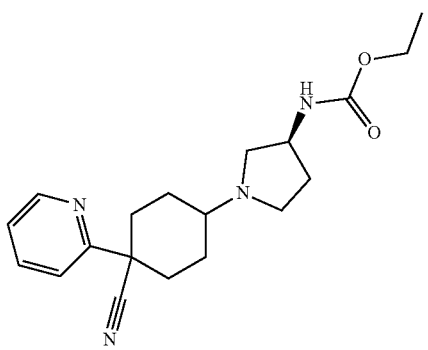 [SMILES: CCOC(=O)N[C@H]1CCN(C2CCC(C#N)(c3ccccn3)CC2)C1] | Example 1-12 |
| 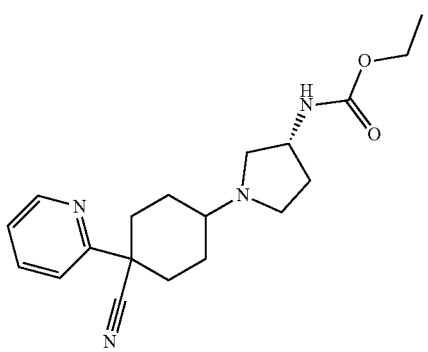 [SMILES: CCOC(=O)N[C@@H]1CCN(C2CCC(C#N)(c3ccccn3)CC2)C1] | Example 1-13 |
| 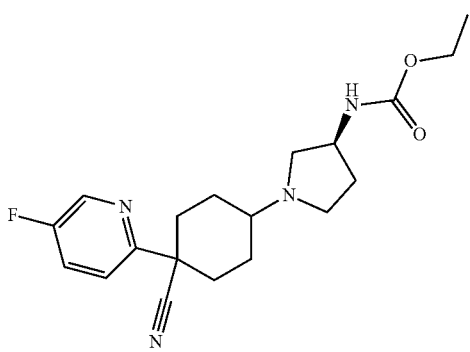 [SMILES: CCOC(=O)N[C@H]1CCN(C2CCC(C#N)(c3ccc(F)cn3)CC2)C1] | Example 1-14 |

TABLE 1-continued
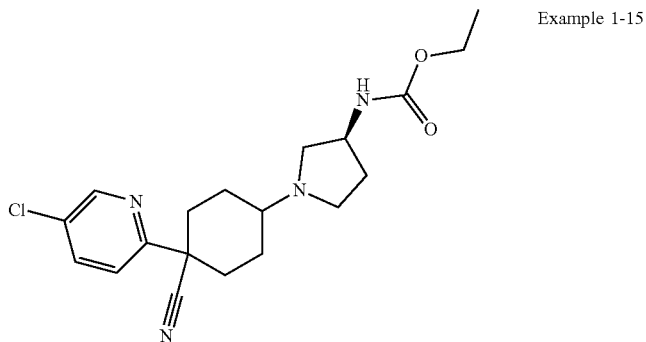
Example 1-15
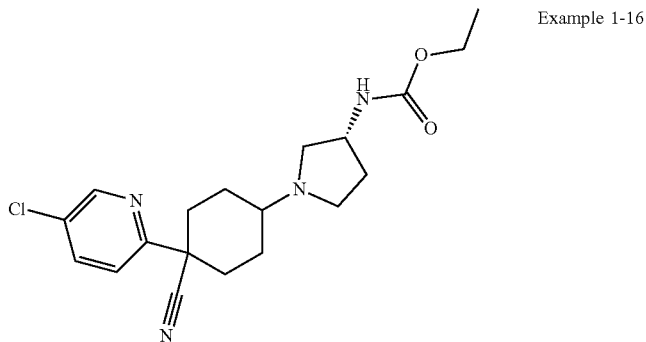
Example 1-16
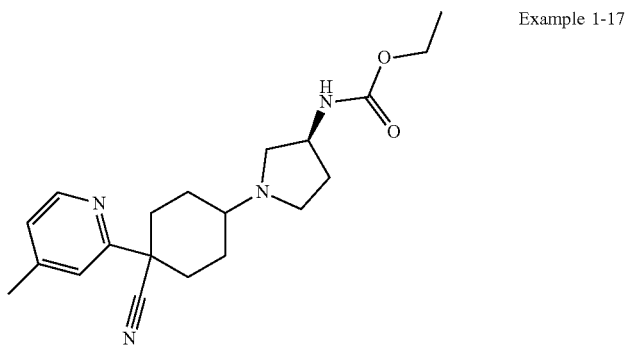
Example 1-17
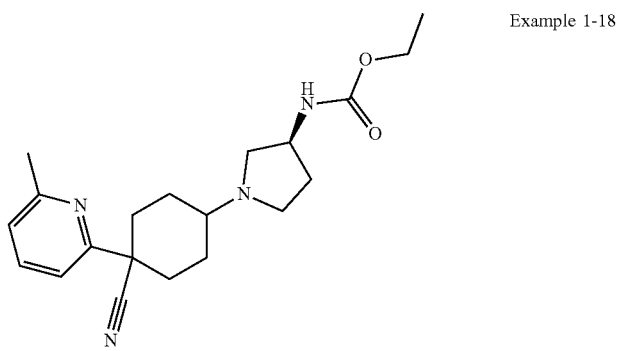
Example 1-18

TABLE 1-continued
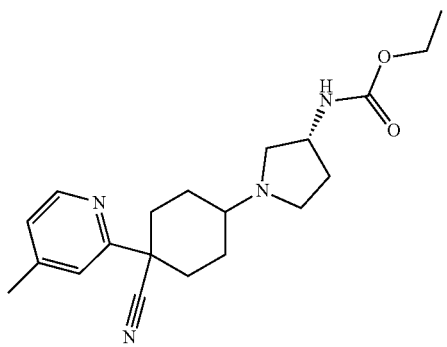 [SMILES: CCOC(=O)N[C@@H]1CCN(C2CCC(C#N)(c3cc(C)ccn3)CC2)C1]
Example 1-19
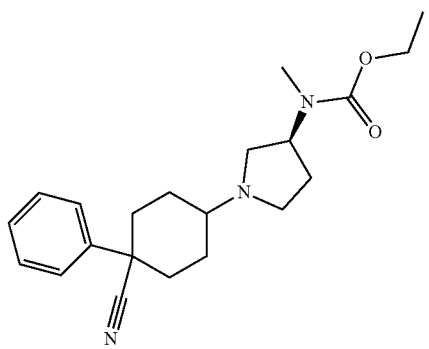 [SMILES: CCOC(=O)N(C)[C@H]1CCN(C2CCC(C#N)(c3ccccc3)CC2)C1]
Example 1-20
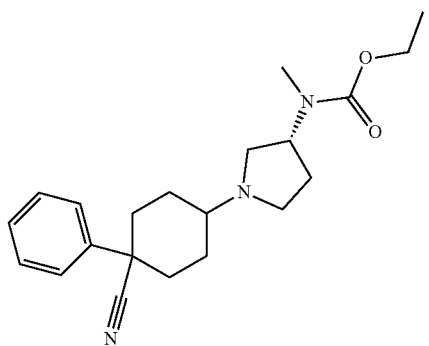 [SMILES: CCOC(=O)N(C)[C@@H]1CCN(C2CCC(C#N)(c3ccccc3)CC2)C1]
Example 1-21
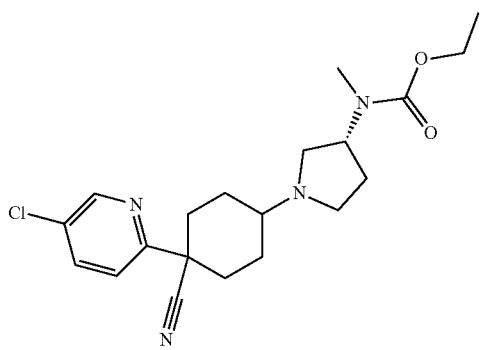 [SMILES: CCOC(=O)N(C)[C@@H]1CCN(C2CCC(C#N)(c3ccc(Cl)cn3)CC2)C1]
Example 1-22
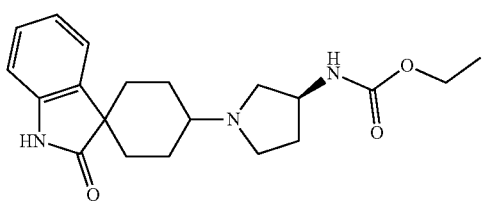 [SMILES: CCOC(=O)N[C@H]1CCN(C2CCC3(CC2)C(=O)Nc2ccccc23)C1]
Example 2-1

TABLE 1-continued
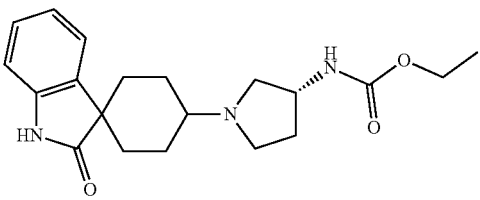 [SMILES: CCOC(=O)N[C@@H]1CCN(C2CCC3(CC2)C(=O)Nc2ccccc23)C1]
Example 2-2
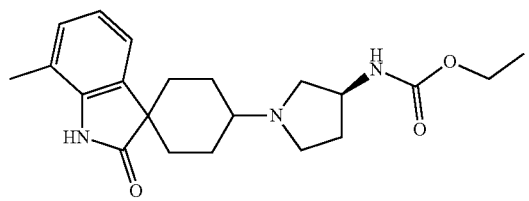 [SMILES: CCOC(=O)N[C@H]1CCN(C2CCC3(CC2)C(=O)Nc2c(C)cccc23)C1]
Example 2-3
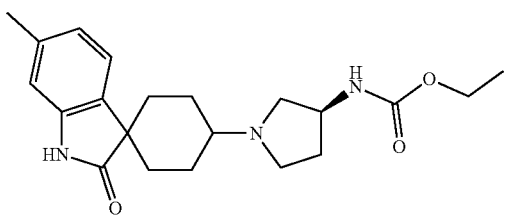 [SMILES: CCOC(=O)N[C@H]1CCN(C2CCC3(CC2)C(=O)Nc2cc(C)ccc23)C1]
Example 2-4
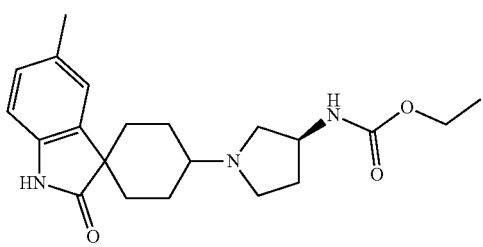 [SMILES: CCOC(=O)N[C@H]1CCN(C2CCC3(CC2)C(=O)Nc2ccc(C)cc23)C1]
Example 2-5
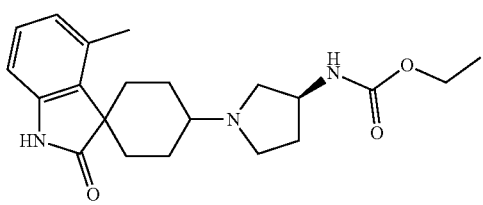 [SMILES: CCOC(=O)N[C@H]1CCN(C2CCC3(CC2)C(=O)Nc2cccc(C)c23)C1]
Example 2-6
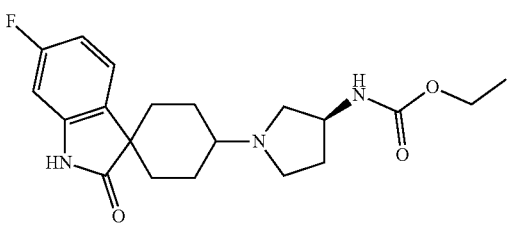 [SMILES: CCOC(=O)N[C@H]1CCN(C2CCC3(CC2)C(=O)Nc2cc(F)ccc23)C1]
Example 2-7
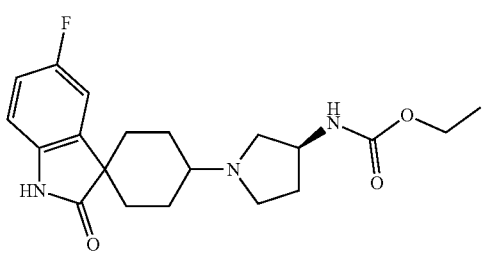 [SMILES: CCOC(=O)N[C@H]1CCN(C2CCC3(CC2)C(=O)Nc2ccc(F)cc23)C1]
Example 2-8

TABLE 1-continued
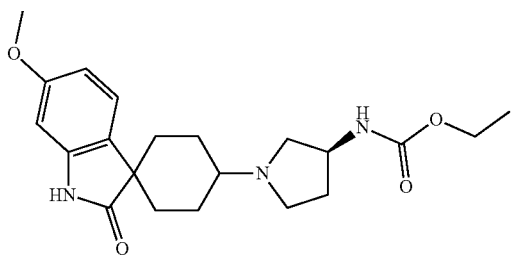 [SMILES: CCOC(=O)N[C@H]1CCN(C2CCC3(CC2)C(=O)Nc2cc(OC)ccc23)C1]
Example 2-9
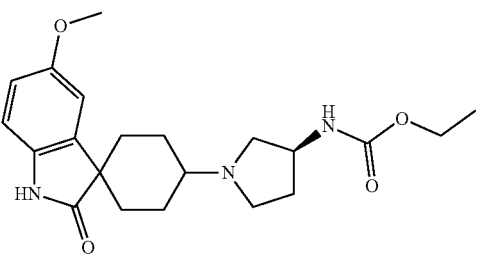 [SMILES: CCOC(=O)N[C@H]1CCN(C2CCC3(CC2)C(=O)Nc2ccc(OC)cc23)C1]
Example 2-10
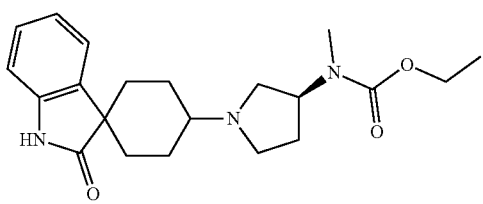 [SMILES: CCOC(=O)N(C)[C@H]1CCN(C2CCC3(CC2)C(=O)Nc2ccccc23)C1]
Example 2-11
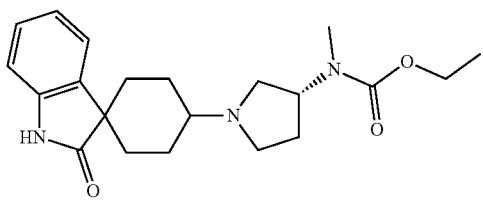 [SMILES: CCOC(=O)N(C)[C@@H]1CCN(C2CCC3(CC2)C(=O)Nc2ccccc23)C1]
Example 2-12
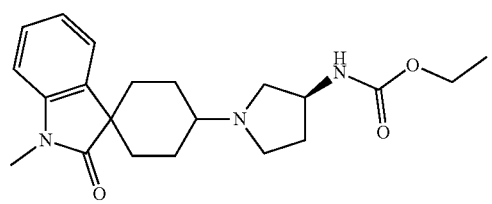 [SMILES: CCOC(=O)N[C@H]1CCN(C2CCC3(CC2)C(=O)N(C)c2ccccc23)C1]
Example 2-13
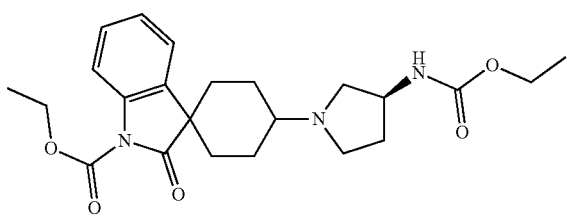 [SMILES: CCOC(=O)N[C@H]1CCN(C2CCC3(CC2)C(=O)N(C(=O)OCC)c2ccccc23)C1]
Example 2-14
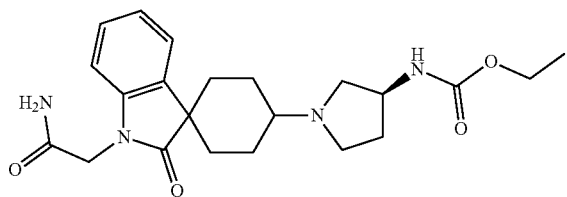 [SMILES: CCOC(=O)N[C@H]1CCN(C2CCC3(CC2)C(=O)N(CC(N)=O)c2ccccc23)C1]
Example 2-15

TABLE 1-continued
| | |
|---|---|
| 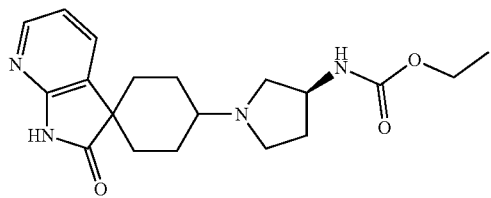 [SMILES: CCOC(=O)N[C@H]1CCN(C2CCC3(CC2)C(=O)Nc2ncccc23)C1] | Example 2-16 |
| 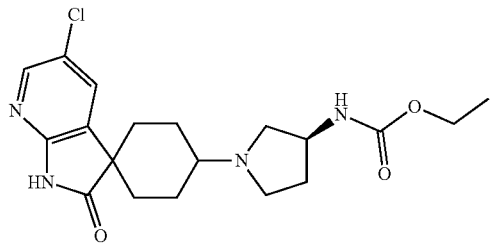 [SMILES: CCOC(=O)N[C@H]1CCN(C2CCC3(CC2)C(=O)Nc2ncc(Cl)cc23)C1] | Example 2-17 |
| 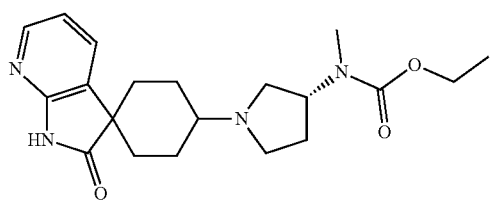 [SMILES: CCOC(=O)N(C)[C@@H]1CCN(C2CCC3(CC2)C(=O)Nc2ncccc23)C1] | Example 2-18 |
| 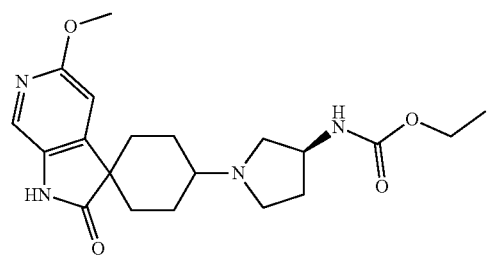 | Example 2-19 |
| 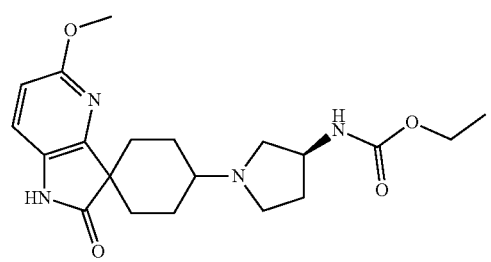 [SMILES: CCOC(=O)N[C@H]1CCN(C2CCC3(CC2)C(=O)Nc2ccc(OC)nc23)C1] | Example 2-20 |
| 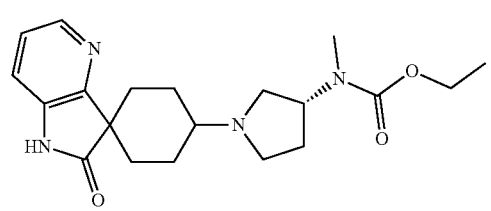 | Example 2-21 |
| 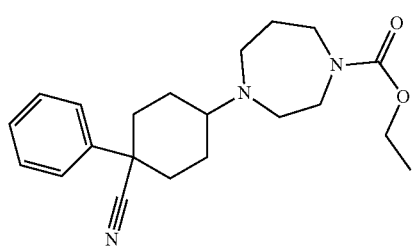 [SMILES: CCOC(=O)N1CCCN(C2CCC(C#N)(c3ccccc3)CC2)CC1] | Example 3-1 |

TABLE 1-continued
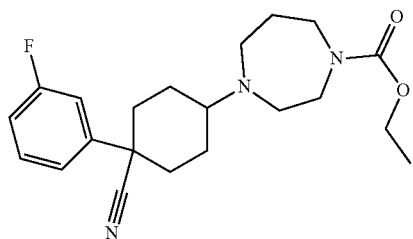 [SMILES: CCOC(=O)N1CCCN(C2CCC(C#N)(c3cccc(F)c3)CC2)CC1] Example 3-2
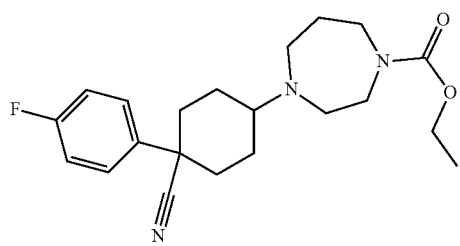 [SMILES: CCOC(=O)N1CCCN(C2CCC(C#N)(c3ccc(F)cc3)CC2)CC1] Example 3-3
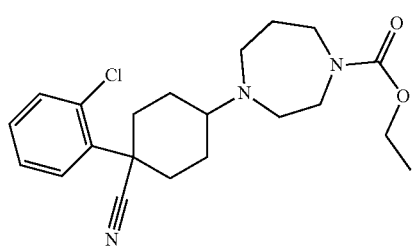 [SMILES: CCOC(=O)N1CCCN(C2CCC(C#N)(c3ccccc3Cl)CC2)CC1] Example 3-4
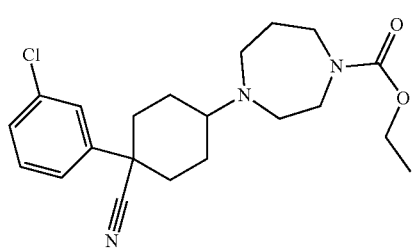 Example 3-5
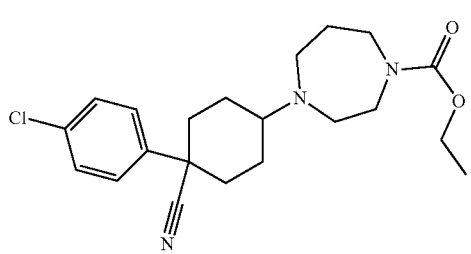 [SMILES: CCOC(=O)N1CCCN(C2CCC(C#N)(c3ccc(Cl)cc3)CC2)CC1] Example 3-6
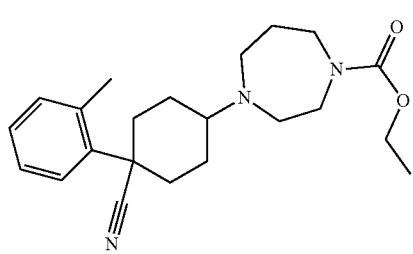 [SMILES: CCOC(=O)N1CCCN(C2CCC(C#N)(c3ccccc3C)CC2)CC1] Example 3-7

TABLE 1-continued
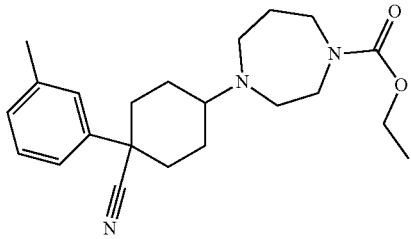 [SMILES: CCOC(=O)N1CCCN(C2CCC(C#N)(c3cccc(C)c3)CC2)CC1]
Example 3-8
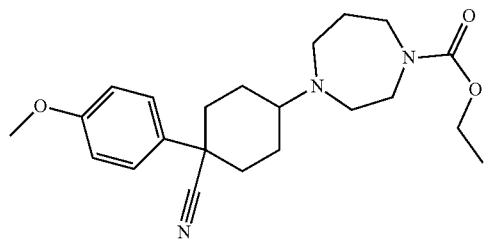 [SMILES: CCOC(=O)N1CCCN(C2CCC(C#N)(c3ccc(OC)cc3)CC2)CC1]
Example 3-9
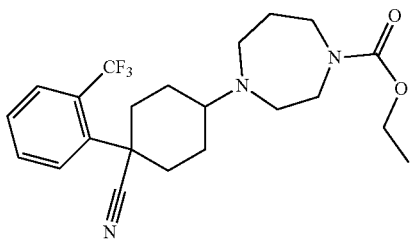 [SMILES: CCOC(=O)N1CCCN(C2CCC(C#N)(c3ccccc3C(F)(F)F)CC2)CC1]
Example 3-10
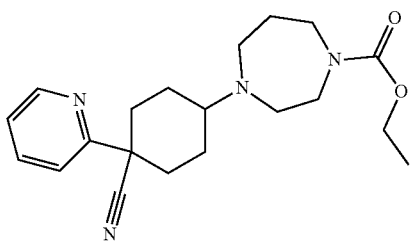 [SMILES: CCOC(=O)N1CCCN(C2CCC(C#N)(c3ccccn3)CC2)CC1]
Example 3-11
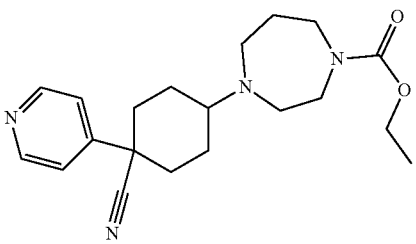 [SMILES: CCOC(=O)N1CCCN(C2CCC(C#N)(c3ccncc3)CC2)CC1]
Example 3-12
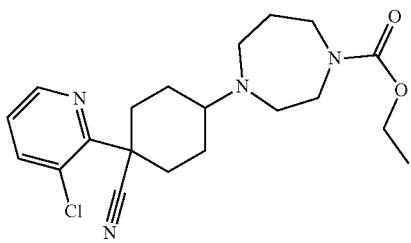 [SMILES: CCOC(=O)N1CCCN(C2CCC(C#N)(c3ncccc3Cl)CC2)CC1]
Example 3-13

TABLE 1-continued
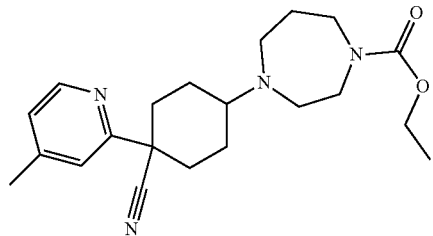 [SMILES: CCOC(=O)N1CCCN(C2CCC(C#N)(c3cc(C)ccn3)CC2)CC1]
Example 3-14
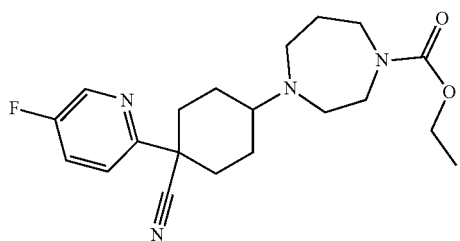 [SMILES: CCOC(=O)N1CCCN(C2CCC(C#N)(c3ccc(F)cn3)CC2)CC1]
Example 3-15
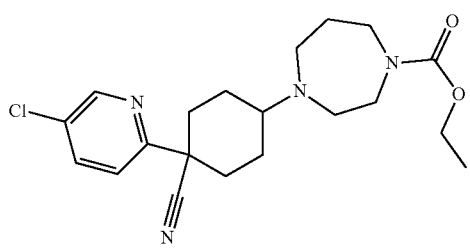 [SMILES: CCOC(=O)N1CCCN(C2CCC(C#N)(c3ccc(Cl)cn3)CC2)CC1]
Example 3-16
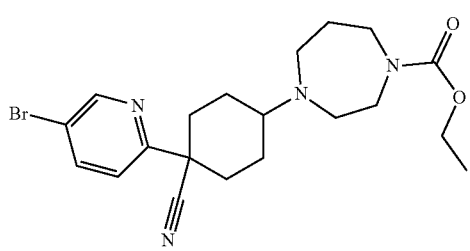
Example 3-17
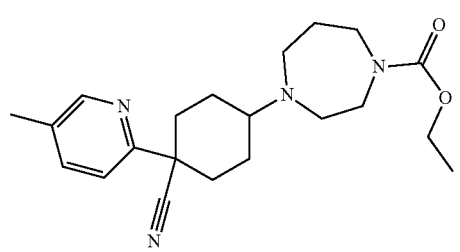 [SMILES: CCOC(=O)N1CCCN(C2CCC(C#N)(c3ccc(C)cn3)CC2)CC1]
Example 3-18
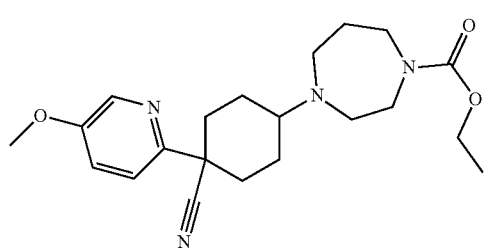 [SMILES: CCOC(=O)N1CCCN(C2CCC(C#N)(c3ccc(OC)cn3)CC2)CC1]
Example 3-19

TABLE 1-continued
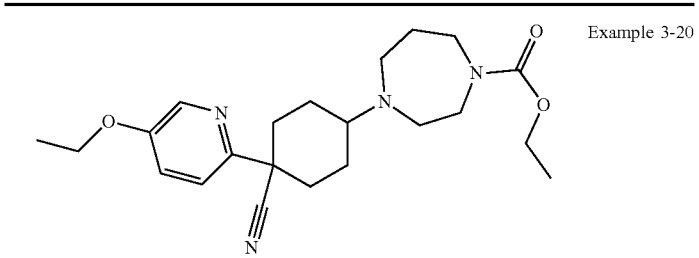 Example 3-20
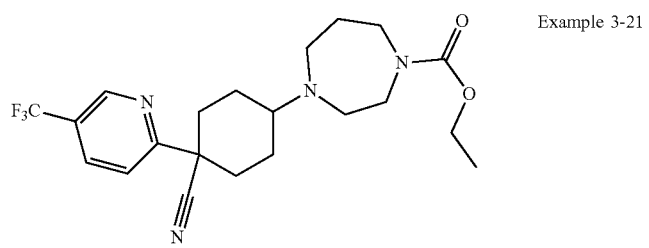 Example 3-21
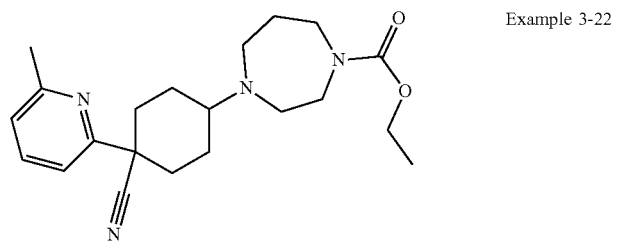 Example 3-22
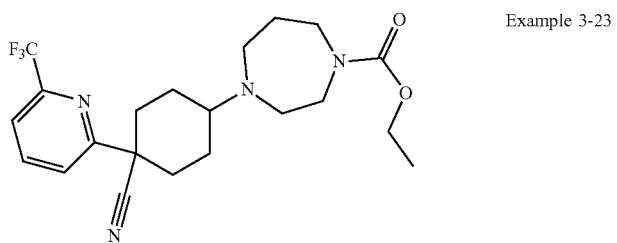 Example 3-23
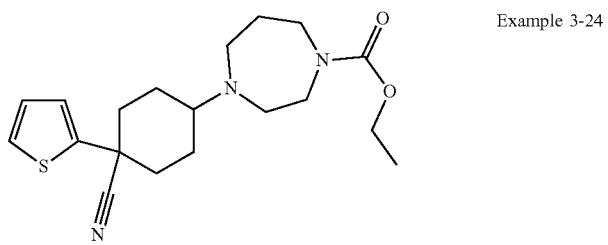 Example 3-24
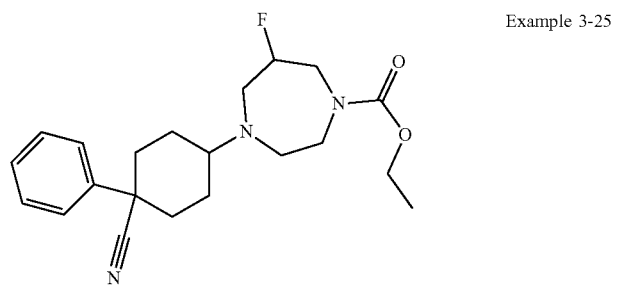 Example 3-25

TABLE 1-continued
| | |
|---|---|
| 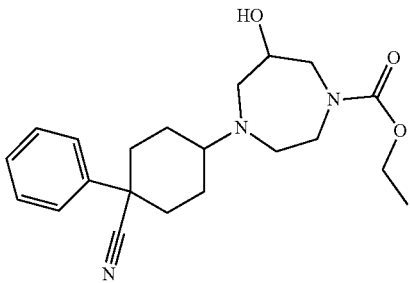 [SMILES: CCOC(=O)N1CCN(C2CCC(C#N)(c3ccccc3)CC2)CC(O)C1] | Example 3-26 |
| 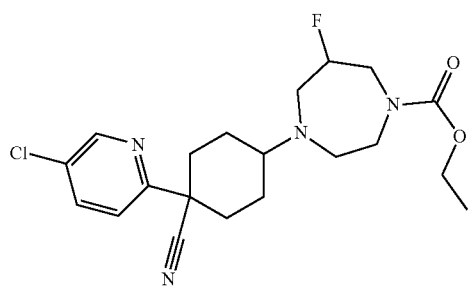 [SMILES: CCOC(=O)N1CCN(C2CCC(C#N)(c3ccc(Cl)cn3)CC2)CC(F)C1] | Example 3-27 |
| 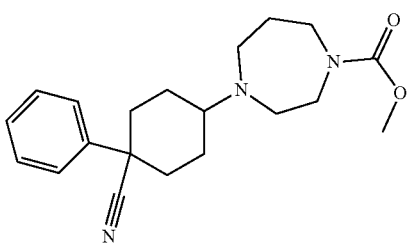 [SMILES: COC(=O)N1CCCN(C2CCC(C#N)(c3ccccc3)CC2)CC1] | Example 3-28 |
| 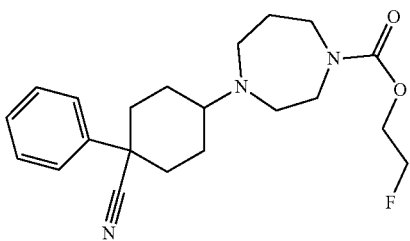 [SMILES: N#CC1(c2ccccc2)CCC(N2CCCN(C(=O)OCCF)CC2)CC1] | Example 3-29 |
| 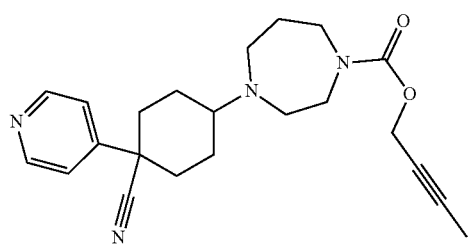 [SMILES: CC#CCOC(=O)N1CCCN(C2CCC(C#N)(c3ccncc3)CC2)CC1] | Example 3-30 |
| 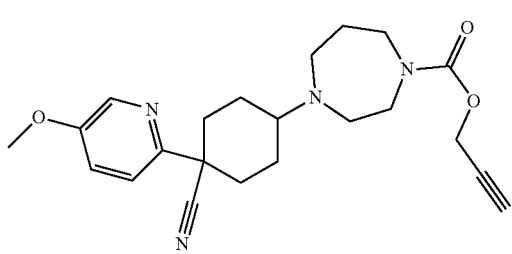 [SMILES: C#CCOC(=O)N1CCCN(C2CCC(C#N)(c3ccc(OC)cn3)CC2)CC1] | Example 3-31 |

TABLE 1-continued
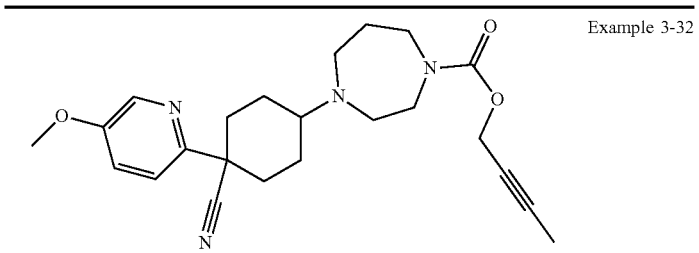 Example 3-32
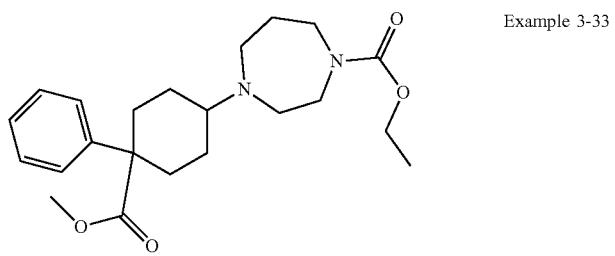 Example 3-33
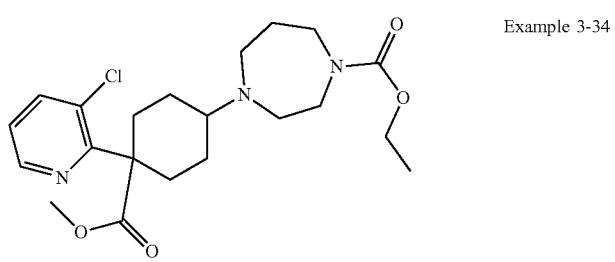 Example 3-34
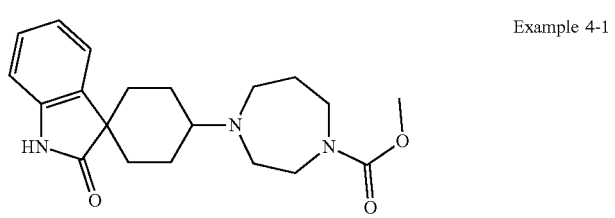 Example 4-1
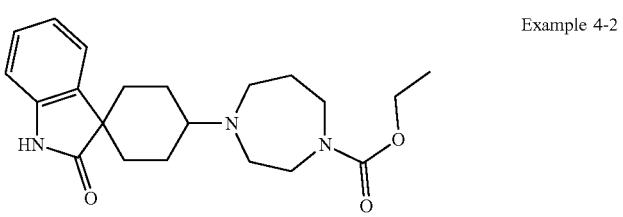 Example 4-2
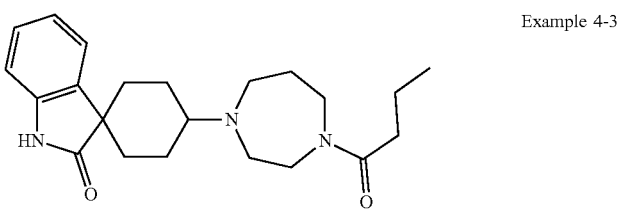 Example 4-3
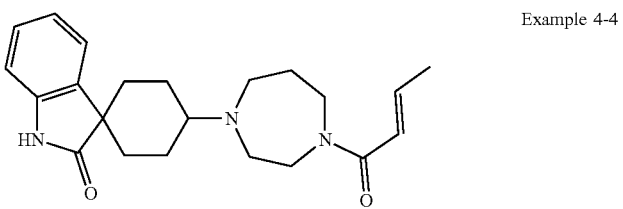 Example 4-4

TABLE 1-continued
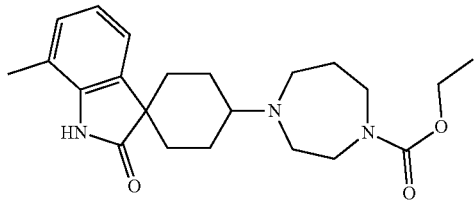 [SMILES: CCOC(=O)N1CCCN(C2CCC3(CC2)C(=O)Nc2c(C)cccc23)CC1]
Example 4-5
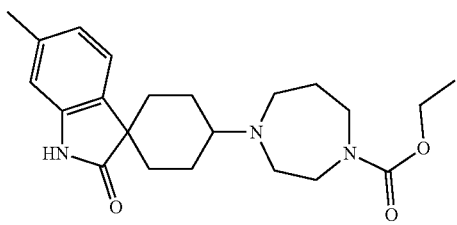 [SMILES: CCOC(=O)N1CCCN(C2CCC3(CC2)C(=O)Nc2cc(C)ccc23)CC1]
Example 4-6
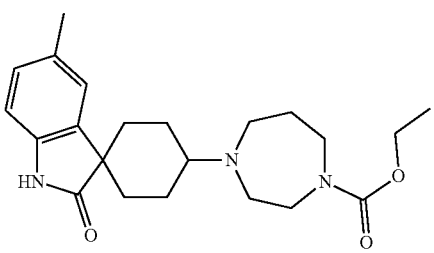 [SMILES: CCOC(=O)N1CCCN(C2CCC3(CC2)C(=O)Nc2ccc(C)cc23)CC1]
Example 4-7
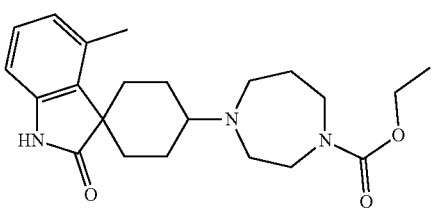 [SMILES: CCOC(=O)N1CCCN(C2CCC3(CC2)C(=O)Nc2cccc(C)c23)CC1]
Example 4-8
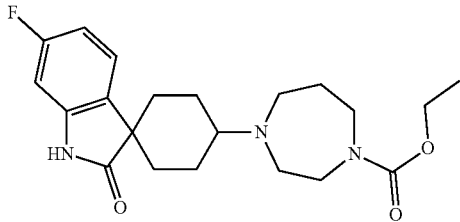 [SMILES: CCOC(=O)N1CCCN(C2CCC3(CC2)C(=O)Nc2cc(F)ccc23)CC1]
Example 4-9
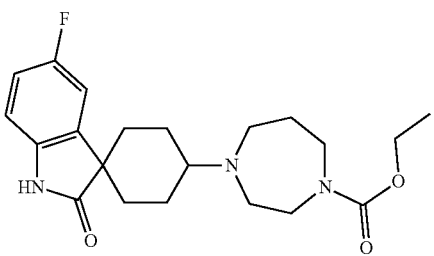 [SMILES: CCOC(=O)N1CCCN(C2CCC3(CC2)C(=O)Nc2ccc(F)cc23)CC1]
Example 4-10

TABLE 1-continued
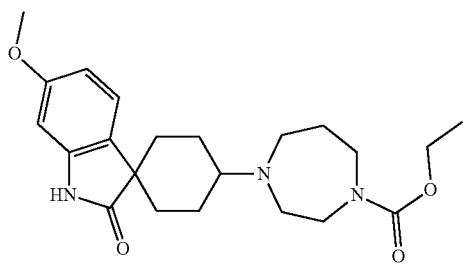 [SMILES: CCOC(=O)N1CCCN(C2CCC3(CC2)C(=O)Nc2cc(OC)ccc23)CC1]
Example 4-11
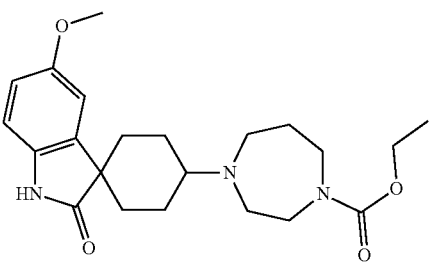 [SMILES: CCOC(=O)N1CCCN(C2CCC3(CC2)C(=O)Nc2ccc(OC)cc23)CC1]
Example 4-12
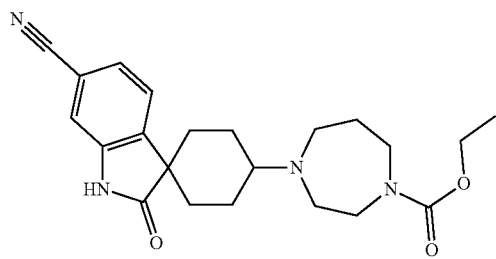 [SMILES: CCOC(=O)N1CCCN(C2CCC3(CC2)C(=O)Nc2cc(C#N)ccc23)CC1]
Example 4-13
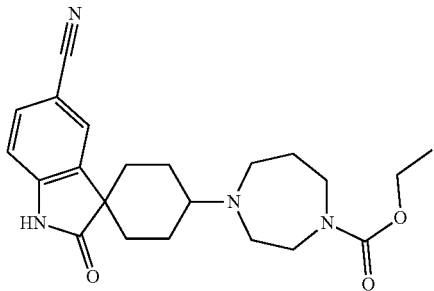 [SMILES: CCOC(=O)N1CCCN(C2CCC3(CC2)C(=O)Nc2ccc(C#N)cc23)CC1]
Example 4-14
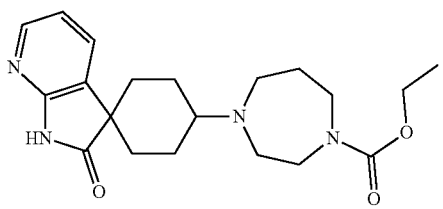 [SMILES: CCOC(=O)N1CCCN(C2CCC3(CC2)C(=O)Nc2ncccc23)CC1]
Example 4-15
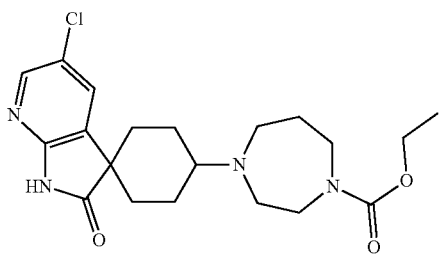 [SMILES: CCOC(=O)N1CCCN(C2CCC3(CC2)C(=O)Nc2ncc(Cl)cc23)CC1]
Example 4-16

TABLE 1-continued
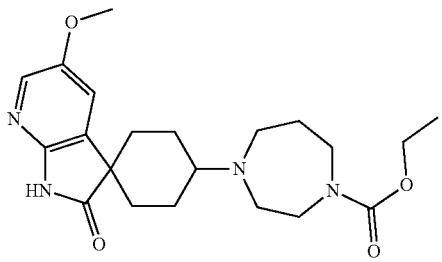 [SMILES: CCOC(=O)N1CCCN(C2CCC3(CC2)C(=O)Nc2ncc(OC)cc23)CC1]
Example 4-17
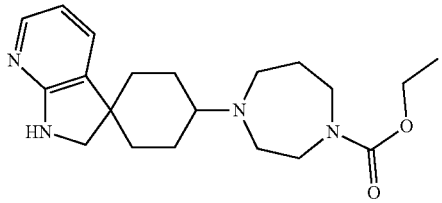 [SMILES: CCOC(=O)N1CCCN(C2CCC3(CC2)CNc2ncccc23)CC1]
Example 4-18
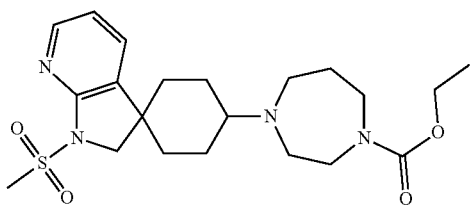 [SMILES: CCOC(=O)N1CCCN(C2CCC3(CC2)CN(S(C)(=O)=O)c2ncccc23)CC1]
Example 4-19
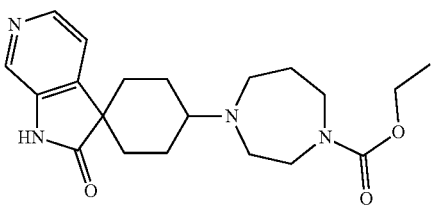 [SMILES: CCOC(=O)N1CCCN(C2CCC3(CC2)C(=O)Nc2cnccc23)CC1]
Example 4-20
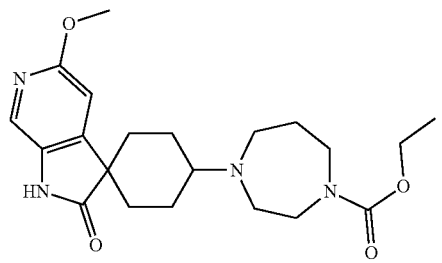 [SMILES: CCOC(=O)N1CCCN(C2CCC3(CC2)C(=O)Nc2cnc(OC)cc23)CC1]
Example 4-21
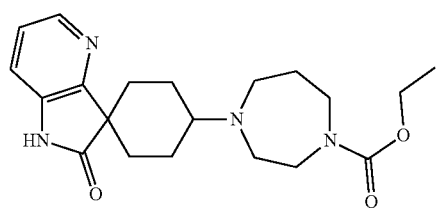 [SMILES: CCOC(=O)N1CCCN(C2CCC3(CC2)C(=O)Nc2cccnc23)CC1]
Example 4-22
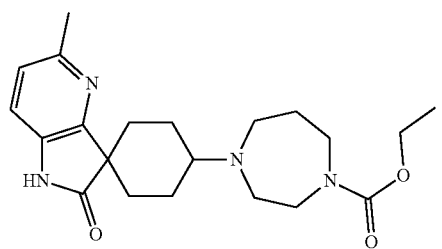 [SMILES: CCOC(=O)N1CCCN(C2CCC3(CC2)C(=O)Nc2ccc(C)nc23)CC1]
Example 4-23

TABLE 1-continued
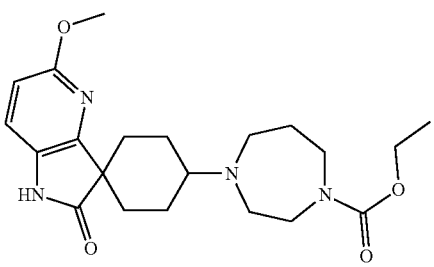 [SMILES: CCOC(=O)N1CCCN(C2CCC3(CC2)C(=O)Nc2ccc(OC)nc23)CC1]
Example 4-24
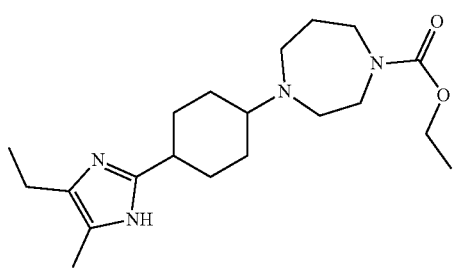 [SMILES: CCOC(=O)N1CCCN(C2CCC(c3nc(CC)c(C)[nH]3)CC2)CC1]
Example 5-1
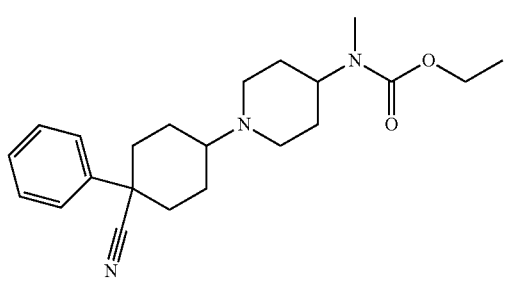 [SMILES: CCOC(=O)N(C)C1CCN(C2CCC(C#N)(c3ccccc3)CC2)CC1]
Example 6-1
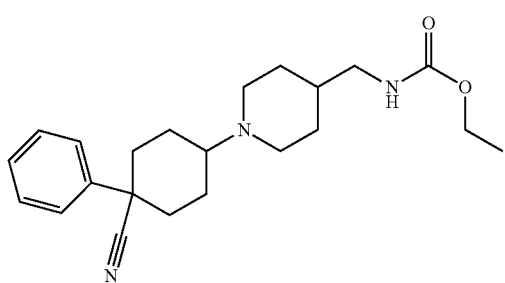 [SMILES: CCOC(=O)NCC1CCN(C2CCC(C#N)(c3ccccc3)CC2)CC1]
Example 6-2
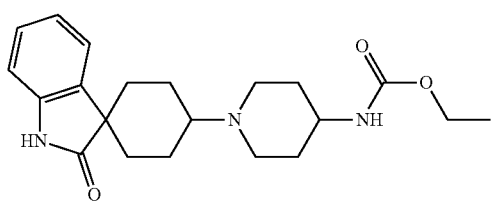 [SMILES: CCOC(=O)NC1CCN(C2CCC3(CC2)C(=O)Nc2ccccc23)CC1]
Example 7-1
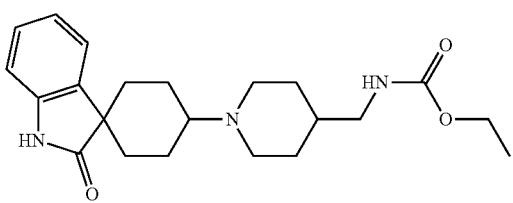 [SMILES: CCOC(=O)NCC1CCN(C2CCC3(CC2)C(=O)Nc2ccccc23)CC1]
Example 7-2

TABLE 1-continued
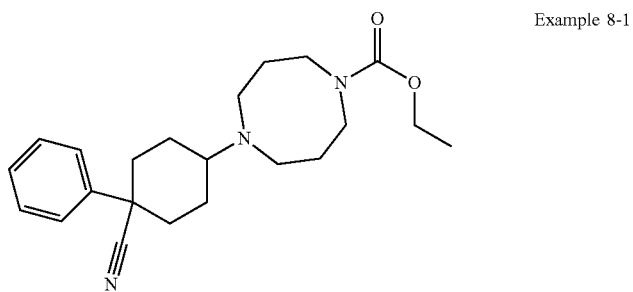
Example 8-1
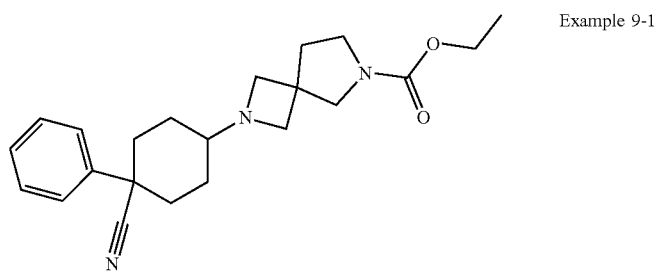
Example 9-1
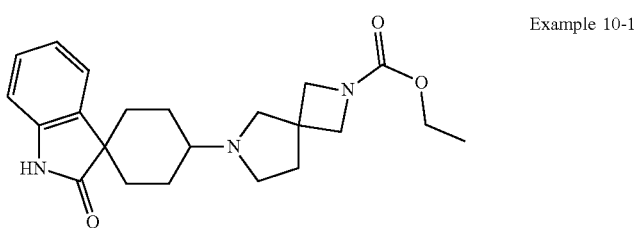
Example 10-1
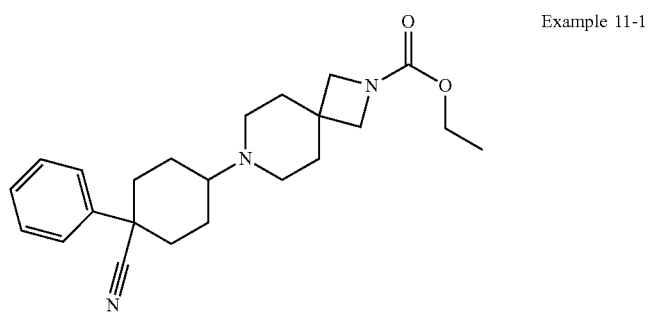
Example 11-1
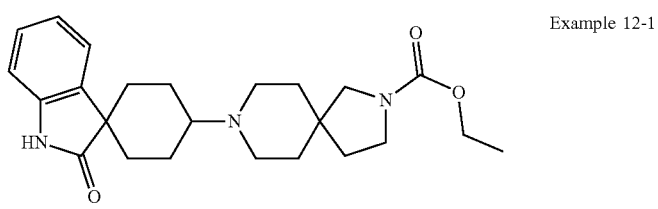
Example 12-1
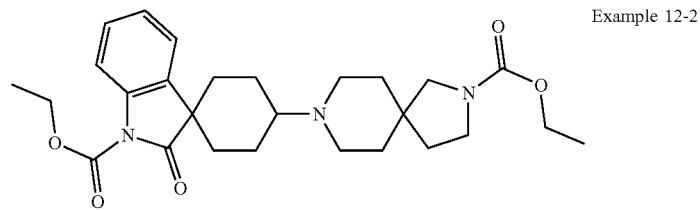
Example 12-2

TABLE 1-continued
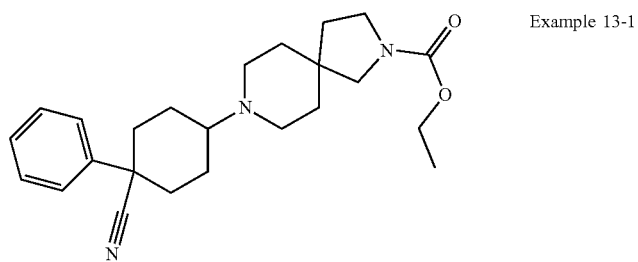 Example 13-1
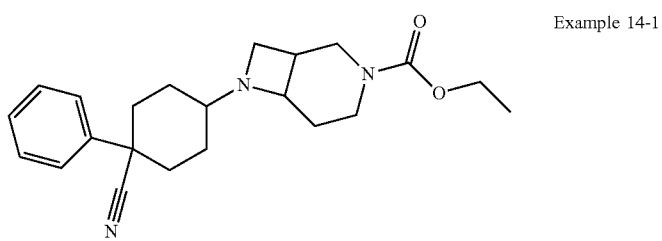 Example 14-1
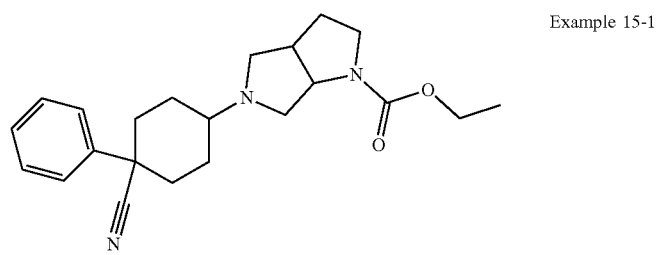 Example 15-1
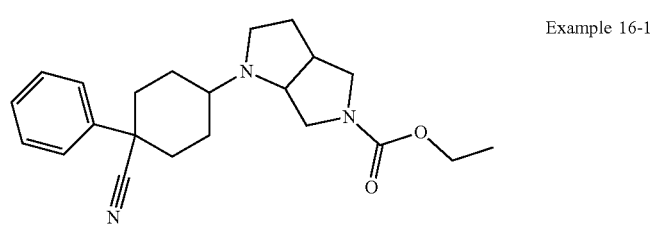 Example 16-1
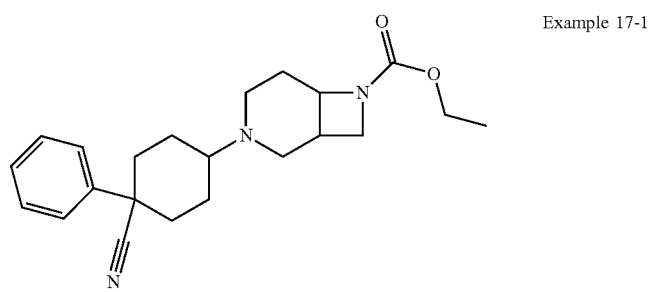 Example 17-1
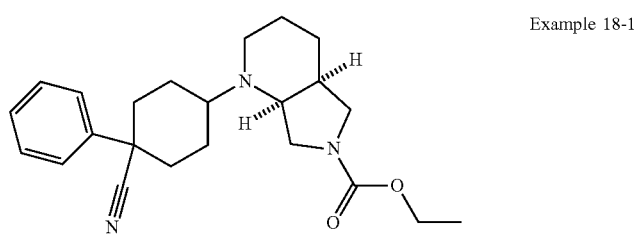 Example 18-1

TABLE 1-continued
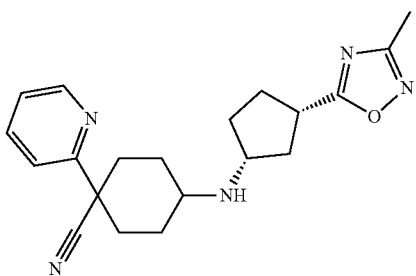 [SMILES: Cc1noc([C@H]2CC[C@@H](NC3CCC(C#N)(c4ccccn4)CC3)C2)n1]
Example 19-1
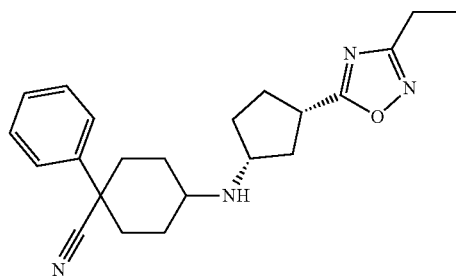 [SMILES: CCc1noc([C@H]2CC[C@@H](NC3CCC(C#N)(c4ccccc4)CC3)C2)n1]
Example 19-2
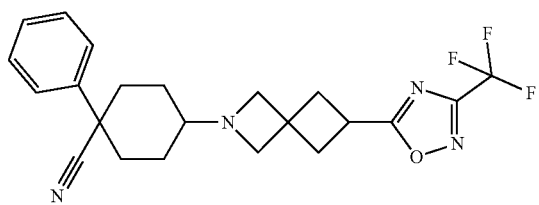 [SMILES: N#CC1(c2ccccc2)CCC(N2CC3(CC(c4nc(C(F)(F)F)no4)C3)C2)CC1]
Example 20-1
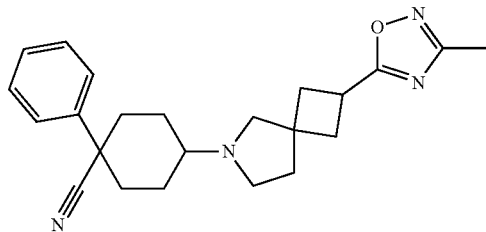 [SMILES: Cc1noc(C2CC3(CCN(C4CCC(C#N)(c5ccccc5)CC4)C3)C2)n1]
Example 21-1
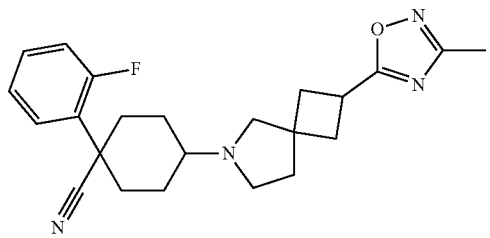 [SMILES: Cc1noc(C2CC3(CCN(C4CCC(C#N)(c5ccccc5F)CC4)C3)C2)n1]
Example 21-2
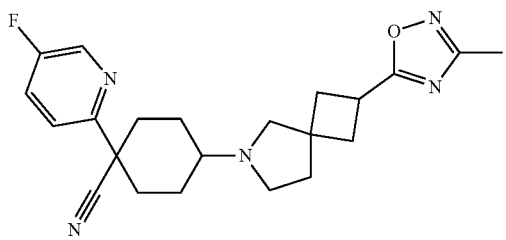 [SMILES: Cc1noc(C2CC3(CCN(C4CCC(C#N)(c5ccc(F)cn5)CC4)C3)C2)n1]
Example 21-3

TABLE 1-continued
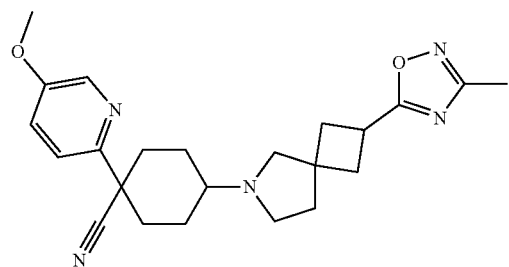 [SMILES: COc1ccc(C2(C#N)CCC(N3CCC4(CC(c5nc(C)no5)C4)C3)CC2)nc1]
Example 21-4
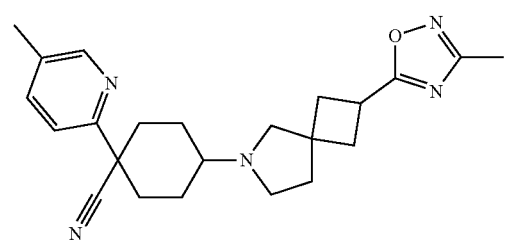
Example 21-5
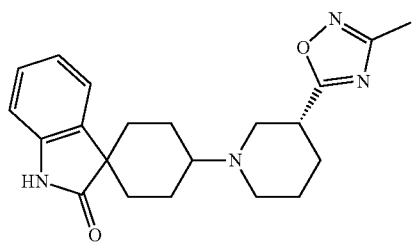 [SMILES: Cc1noc([C@@H]2CCCN(C3CCC4(CC3)C(=O)Nc3ccccc34)C2)n1]
Example 22-1
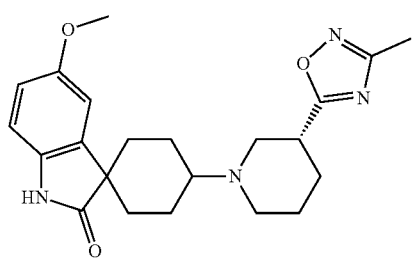 [SMILES: COc1ccc2c(c1)C1(CCC(N3CCC[C@@H](c4nc(C)no4)C3)CC1)C(=O)N2]
Example 22-2
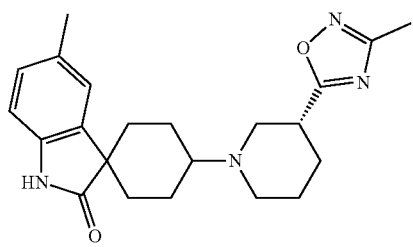 [SMILES: Cc1ccc2c(c1)C1(CCC(N3CCC[C@@H](c4nc(C)no4)C3)CC1)C(=O)N2]
Example 22-3
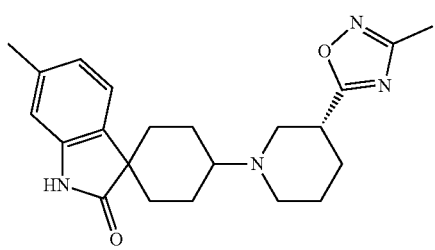
Example 22-4

TABLE 1-continued
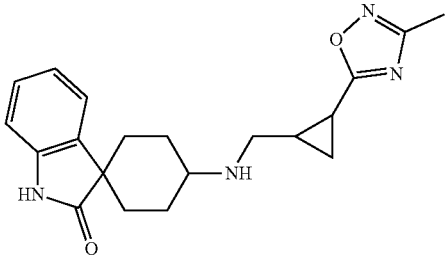 [SMILES: Cc1noc(C2CC2CNC2CCC3(CC2)C(=O)Nc2ccccc23)n1] Example 23-1
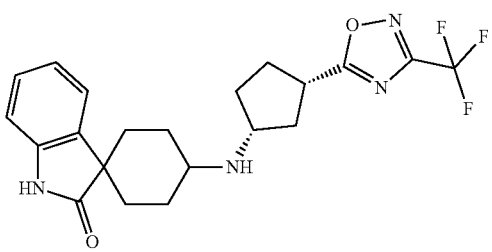 [SMILES: O=C1Nc2ccccc2C12CCC(N[C@@H]1CC[C@H](c3nc(C(F)(F)F)no3)C1)CC2] Example 24-1
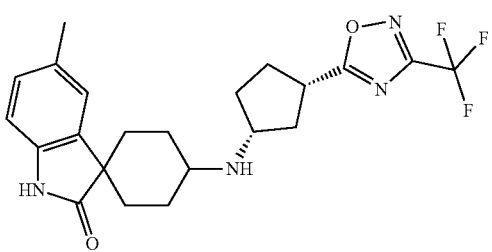 [SMILES: Cc1ccc2c(c1)C1(CCC(N[C@@H]3CC[C@H](c4nc(C(F)(F)F)no4)C3)CC1)C(=O)N2] Example 24-2
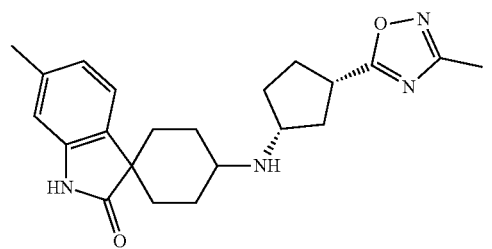 Example 24-3
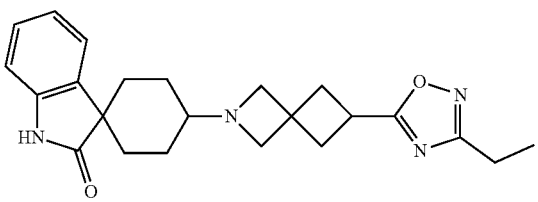 [SMILES: CCc1noc(C2CC3(C2)CN(C2CCC4(CC2)C(=O)Nc2ccccc24)C3)n1] Example 25-1
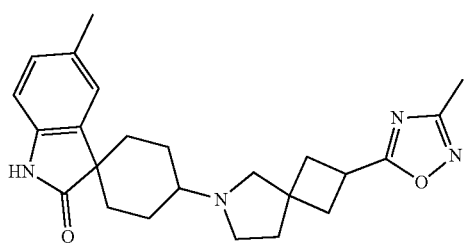 [SMILES: Cc1ccc2c(c1)C1(CCC(N3CCC4(CC(c5nc(C)no5)C4)C3)CC1)C(=O)N2] Example 26-1

TABLE 1-continued

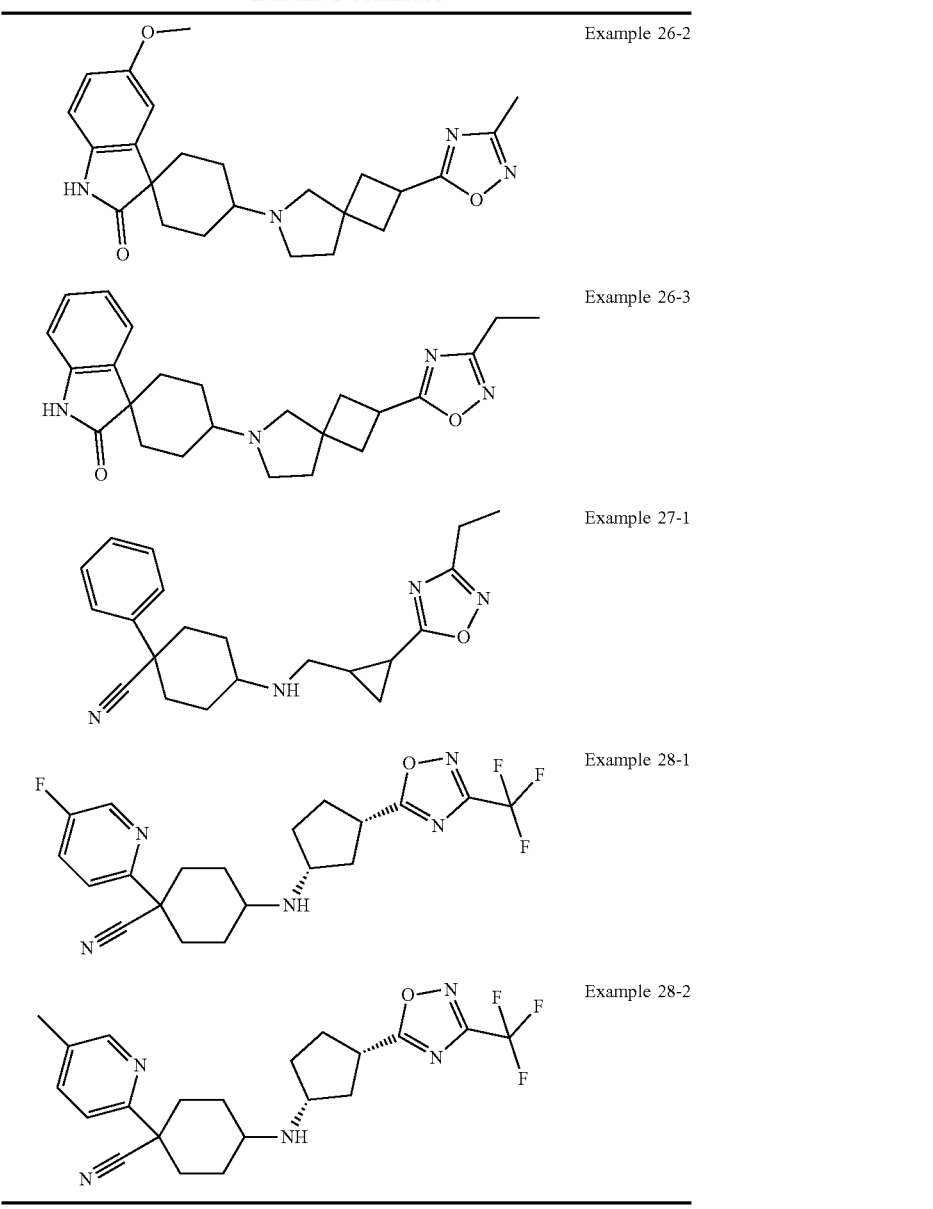

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. (⊐)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as Jvalues, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and the Silica gel F254 as a stationary phase from Merck. Microwave-mediated reactions were performed in Biotage Initiator or CEM Discover microwave reactors.

Mass spectroscopy was carried out on Shimadzu LC-2010 EV, Waters ZQ-2000, UPLC-Mass SQD-3100 or Applied Biosystem API-2000 spectrometers using electrospray conditions as specified for each compound in the detailed experimental section.

Preparative HPLC was typically carried out under the following conditions, (Waters HPLC): Column: XSelect CSH Prep C-18, 19×50 mm, 5 µm; Mobile phase: Gradients of water and MeCN (each containing 0.1% Formic Acid); gradient 5% MeCN in 0.1 HCOOH in water (30 sec), 5% to 40% (over 7 min) then 95% MeCN in 0.1 HCOOH in water (1 min) then 5% MeCN in 0.1 HCOOH in water (1.5 min) at 28 mL/min. Additionally, preparative HPLC was also carried out using Method A below:

Preparative HPLC Method A

Instruments: Gilson Semi Preparative HPLC system including a 321 Pump, GX-271 Liquid Handler with Gilson Trilution software and Gilson 171 DAD with collection at 205 nm unless otherwise stated; Column: Phenomenex Gemini-NX C-18, 5 micron, 30×100 mm; Flow rate: 30 mL/min; Solvents: solvent C=2.5 L of water and 5 mL of 28% ammonia in water solution, solvent D=2.5 L of acetonitrile; Gradient: all narrow gradients follow the same profile exemplified for 5-95% below, written in the format, [Time (min)/% C:% D], 12.5 min 5-95% gradient: [0.00/95:5], [0.3/95:5], [9.0/5:95], [9.5/5:95], [9.7/0:100], [10.7/0:100], [10.9/95:5], [11.5/95:5]

LCMS experiments were typically carried out using electrospray conditions as specified for each compound under the following conditions:

Method A

Instruments: Waters Alliance 2795, Waters 2996 PDA detector, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method A: 0.00/2, 0.10/2, 2.50/95, 3.50/95, 3.55/2, 4.00/2; Solvents: solvent C=2.5 L $H_2O$+2.5 mL ammonia solution; solvent D=2.5 L MeCN+135 mL $H_2O$+2.5 mL ammonia solution); Injection volume 3 uL; UV detection 230 to 400 nM; column temperature 45° C.; Flow rate 1.5 mL/min.

Method B

Instruments: Waters Alliance 2795, Waters 2996 PDA detector, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: 0.00/2, 0.10/2, 8.40/95, 9.40/95, 9.50/2, 10.00/2; Solvents: solvent C=2.5 L $H_2O$+2.5 mL ammonia solution; solvent D=2.5 L MeCN+135 mL $H_2O$+2.5 mL ammonia solution); Injection volume 3 µL; UV detection 230 to 400 nM; column temperature 45° C.; Flow rate 1.5 mL/min.

Method C

Instruments: Agilent 1260 Infinity LC with Diode Array Detector, Agilent 6120B Single Quadrupole MS with API-ES Source; Column: Phenomenex Gemini-NX C-18, 3 micron, 2.0×30 mm; Gradient [time (min)/solvent B in A (%)]: Method: 0.00/5, 2.00/95, 2.50/95, 2.60/5, 3.00/5; Solvents: solvent A=2.5 L $H_2O$+2.5 mL of (28% $NH_3$ in $H_2O$); solvent B=2.5 L MeCN+129 mL $H_2O$+2.7 mL of (28% $NH_3$ in $H_2O$); Injection volume 0.5 µL; UV detection 190 to 400 nM; column temperature 40° C.; Flow rate 1.5 mL/min.

Method D

Instrument: Waters Acquity H-class UPLC with SQ detector using BEH C18 (50*2.1 mm id 1.7 µm) and using water (0.1% Ammonium Hydroxide) and MeCN (0.1% Ammonium Hydroxide) as the mobile phase. The eluent gradient program was MeCN (0.1% Ammonium Hydroxide) from 10% to 100% for 2.5 min, 100% MeCN (0.1% Ammonium Hydroxide) for 2 min and MeCN (0.1% Ammonium Hydroxide) from 100% to 10% for 0.5 min. The flow rate was 0.3 mL/min.

Method E

Instruments: HP 1100 with G1315A DAD, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: 0.00/2, 0.10/2, 8.40/95, 10.00/95; Solvents: solvent C=2.5 L $H_2O$+2.5 mL 28% ammonia in $H_2O$ solution; solvent D=2.5 L MeCN+135 mL $H_2O$+2.5 mL 28% ammonia in $H_2O$ solution); Injection volume 1 µL; UV detection 230 to 400 nM; Mass detection 130 to 800 AMU (+ve and -ve electrospray); column temperature 45° C.; Flow rate 1.5 mL/min.

Method F

Instruments: Waters Acquity H Class, Photo Diode Array, SQ Detector; Column: BEH C18, 1.7 micron, 2.1×50 mm; Gradient [time (min)/solvent B in A (%)]: 0.00/5, 0.40/5, 0.8/35, 1.20/55, 2.50/100, 3.30/100 4.00/5; Solvents: solvent A=5 mM Ammonium acetate and 0.1% formic acid in $H_2O$; solvent B=0.1% formic acid in MeCN; Injection volume 2 µL; UV detection 200 to 400 nM; Mass detection 100 to 1200 AMU (+ve electrospray); column at ambient temperature; Flow rate 0.5 mL/min.

Method G

Instruments: Waters 2695, Photo Diode Array, ZQ-2000 Detector; Column: X-Bridge C18, 5 micron, 150×4.6 mm; Gradient [time (min)/solvent B in A (%)]: 0.00/10, 5.00/90, 7.00/100, 11.00/100, 11.01/10 12.00/10; Solvents: solvent A=0.1% ammonia in $H_2O$; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

Method H

Instruments: Waters 2695, Photo Diode Array, ZQ-2000 Detector; Column: X-Bridge C18, 5 micron, 150×4.6 mm; Gradient [time (min)/solvent B in A (%)]: 0.00/100, 7.00/50, 9.00/0, 11.00/0, 11.01/100, 12.00/100; Solvents: solvent A=0.1% ammonia in $H_2O$; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

Method I

Instruments: Waters 2695, Photo Diode Array, ZQ-2000 Detector; Column: X-Bridge C18, 3.5 micron, 150×4.6 mm; Gradient [time (min)/solvent B in A (%)]: 0.00/5, 5.00/90, 5.80/95, 10/95; Solvents: solvent A=0.1% ammonia in $H_2O$; solvent B=0.1% ammonia in MeCN; Injection volume 10 ⊐L; UV detection 200 to 400 nM; Mass detection 60 to 1000 AMU (+ve electrospray); column at ambient temperature; Flow rate 1.0 mL/min.

Method K

Instruments: Waters 2695, Photo Diode Array, ZQ-2000 Detector; Column: X-Bridge C18, 3.5 micron, 50×4.6 mm; Gradient [time (min)/solvent B in A (%)]: 0.01/0, 0.20/0, 5.00/90, 5.80/95, 7.20/95, 7.21/100, 10.00/100; Solvents: solvent A=0.1% ammonia in $H_2O$; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

Method L

Instruments: Waters Acquity UPLC, Waters 3100 PDA Detector, SQD; Column: Acquity BEH C-18, 1.7 micron, 2.1×100 mm; Gradient [time (min)/solvent B in A (%)]: 0.00/2, 2.00/2, 7.00/50, 8.50/80, 9.50/2, 10.0/2; Solvents: solvent A=5 mM ammonium acetate in water; solvent B=acetonitrile; Injection volume 1 µL; Detection wavelength 214 nm; Column temperature 30° C.; Flow rate 0.3 mL per min.

Method O

Instruments: Waters Acquity UPLC, Waters 3100 PDA Detector, SQD; Column: Acquity HSS-T3, 1.8 micron, 2.1×100 mm; Gradient [time (min)/solvent B in A (%)]: 0.00/10, 1.00/10, 2.00/15, 4.50/55, 6.00/90, 8.00/90, 9.00/10, 10.00/10; Solvents: solvent A=0.1% trifluoroacetic acid in water; solvent B=acetonitrile; Injection volume 1 µL; Detection wavelength 214 nm; Column temperature 30° C.; Flow rate 0.3 mL per min.

Method P

Instruments: Waters Acquity H Class, Waters 3100 PDA Detector, SQD; Column: BEH C18 2.1×50 mm, 1.7 micron; Gradient [time (min)/solvent B in A (%)]: 0.00/5, 0.40/5, 2.50/95, 3.50/95, 3.51/5, 4.00/5; Solvents: solvent A=5 mM ammonium acetate and 0.1% formic acid in water; solvent B=0.1% formic acid in acetonitrile.

Method Q

Instruments: Waters Acquity H Class, Waters 3100 PDA Detector, SQD; Column: BEH C18 2.1×50 mm, 1.7 micron; Gradient [time (min)/solvent B in A (%)]: 0.00/5, 0.40/5, 0.80/35, 1.20/55, 2.70/95, 3.30/95, 3.31/5, 4.00/5; Solvents: solvent A=5 mM ammonium acetate and 0.1% formic acid in water; solvent B=0.1% formic acid in acetonitrile.

Method R

Instruments: Shimadzu Nexera, Photo Diode Array, LCMS-2020 Detector, Column: X-Bridge C18, 3.5 micron, 50×4.6 mm; Gradient [time (min)/solvent B in A (%)]: 0.01/5, 5.00/90, 5.80/95, 7.20/95, 7.21/100, 10.00/100; Solvents: solvent A=0.1% ammonia in $H_2O$; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

Method S

Instruments: Agilent 1290 RRLC with Agilent 6120 Mass detector, Photo Diode Array, Agilent 6120 Detector, Column: X-Bridge C18, 3.5 micron, 50×4.6 mm; Gradient [time (min)/solvent B in A (%)]: 0.01/5, 5.00/90, 5.80/95, 7.20/95, 7.21/100, 10.00/100; Solvents: solvent A=0.1% ammonia in $H_2O$; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

LCMS data in the experimental section are given in the format: Mass ion, retention time, UV activity.

Abbreviations

AcOH=acetic acid
aq.=aqueous
d=day(s)
DCM=dichloromethane
DIPEA=diisopropylethylamine
DMF=dimethylformamide
DMSO=dimethylsulfoxide
ES=electro spray ionisation
EtOAc=ethyl acetate
h=hour(s)
HATU=1-[bis(dimethylamino)methylene]-1H-1,2,3-triazolo[4,5-b]pyridinium 3-oxid hexafluorophosphate
HCl=hydrogen chloride, hydrochloric acid
HPLC=high performance liquid chromatography
LC=liquid chromatography
MeCN=acetonitrile
MeOH=Methanol
min, mins=minute(s)
MS=mass spectrometry
NMR=nuclear magnetic resonance
rt, RT=room temperature
sat.=saturated
sol.=solution
STAB=sodium triacetoxyborohydride
TFA=trifluoroacetic acid
THF=tetrahydrofuran
TLC=thin layer chromatography Prefixes n-, s-, i-, t- and tert- have their usual meanings: normal, secondary, iso, and tertiary.

Synthesis of Intermediates:

Route 1

Typical Procedure for the Preparation of Amines, as Exemplified by the Preparation of Intermediate 6, Trifluoroacid Salt of ethyl 2,8-diazaspiro[4.5]decane-2-carboxylate

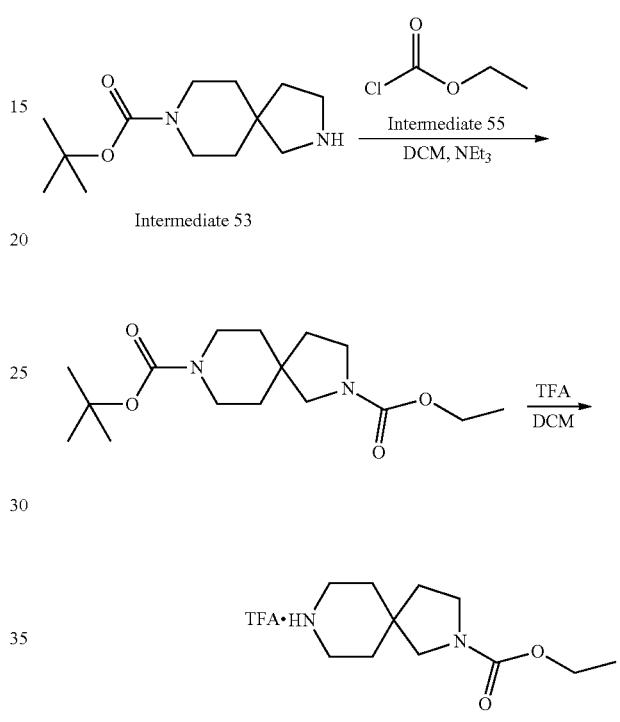

tert-Butyl 2,8-diazaspiro[4.5]decane-8-carboxylate (481 mg, 2.0 mmol) was dissolved in DCM (20.0 mL) and triethylamine (0.61 g, 0.84 mL, 6.0 mmol) was added. The reaction mixture was cooled to 0° C., ethyl chloroformate (0.33 g, 0.29 mL, 3.0 mmol) was added and the reaction mixture was stirred at rt overnight. The reaction mixture was partitioned between water (20 mL) and DCM (20 mL), the aqueous layer was further extracted with DCM (3×20 mL), the organic layers were combined and dried ($Na_2SO_4$). The solvent was removed in vacuo to give crude 8-tert-butyl 2-ethyl 2,8-diazaspiro[4.5]decane-2,8-dicarboxylate as a colourless gum which was used directly without further purification.

LCMS (Method C): m/z 313 (M+H)$^+$ (ES$^+$), at 1.45 min, UV inactive.

8-tert-Butyl 2-ethyl 2,8-diazaspiro[4.5]decane-2,8-dicarboxylate (assumed 2.0 mmol) was dissolved in DCM (5 mL), cooled to 0° C., trifluoroacetic acid (5 mL) was added and the reaction mixture was stirred at rt overnight. The solvents were removed in vacuo, the residue was dissolved in toluene (20 mL), and then concentrated in vacuo (three times), to give ethyl 2,8-diazaspiro[4.5]decane-2-carboxylate trifluoroacetate salt (0.65 g, 99%) as a colourless gum which was used directly without further purification.

The data for Intermediate 6 are in Table 2
Route 2

Typical Procedure for the Preparation of Amines, as Exemplified by the Preparation of Intermediate 13, ethyl (3S)-pyrrolidin-3-ylcarbamate hydrochloride

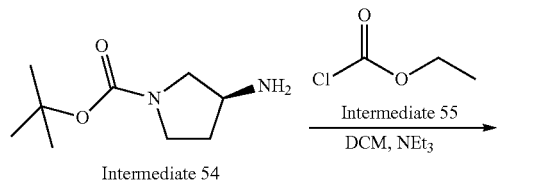

Intermediate 54

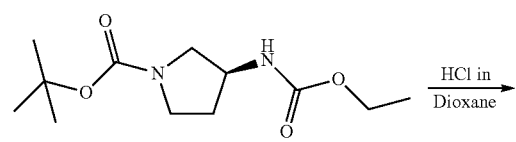

Intermediate 13 tert-Butyl (3S)-3-aminopyrrolidine-1-carboxylate (1.00 g, 5.37 mmol) was dissolved in DCM (25.0 mL) and NEt₃ (1.63 g, 16.12 mmol) was added. The resulting reaction mixture was cooled to 0° C. and ethyl chloroformate (0.70 g, 6.45 mmol) was added. The reaction mixture was stirred for 30 min at rt, then partitioned between water (25 mL) and EtOAc (30 mL), the aqueous layer was further extracted with EtOAc (2×30 mL), and the organic layers were combined and dried (Na₂SO₄). The solvent was removed in vacuo to give tert-butyl (3S)-3-[(ethoxycarbonyl)amino]pyrrolidine-1-carboxylate (1.3 g, 94.2%) as a colourless gum.

Mass: (ESI +ve): 259 (M+H)⁺.

tert-Butyl (3S)-3-[(ethoxycarbonyl)amino]pyrrolidine-1-carboxylate (1.3 g, 5.03 mmol) was dissolved in 1,4-Dioxane (10 mL) and HCl in 1,4-Dioxane (20.0 mL, 1.0M) was added. The reaction mixture was stirred at rt for 16 h. The solvent was removed in vacuo, and the residue was purified by trituration with acetone (2×10 mL) to give ethyl (3S)-pyrrolidin-3-ylcarbamate hydrochloride (0.5 g, 62.8%) as a white solid.

The data for Intermediate 13 are in Table 2
Route 3

Typical Procedure for the Preparation of Cyclohexanones Containing Substituted Aryl Groups, as Exemplified by the Preparation of Intermediate 20, 1-(3-fluorophenyl)-4-oxocyclohexanecarbonitrile

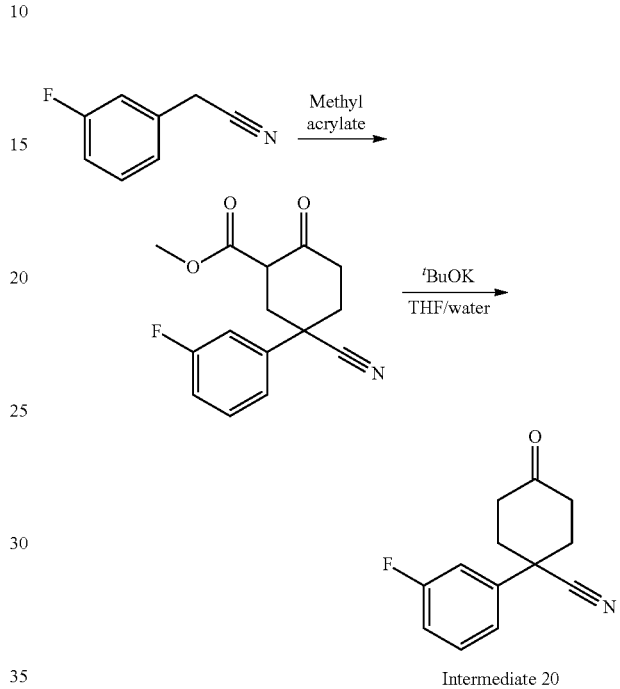

Intermediate 20

2-(3-Fluorophenyl) acetonitrile (2.0 g, 14.8 mmol) and methyl acrylate (2.67 g, 31.07 mmol) were dissolved in THF (70 mL). The reaction mixture was cooled to 0° C. and t-BuOK (1.0 M in THF, 17.73 mL, 17.75 mmol) was added. The reaction mixture was stirred at rt for 1 h and then quenched with ice cold water, and the pH adjusted to pH=4 with aqueous 8% citric acid (54 mL). The reaction mixture was extracted with EtOAc (4×75 mL), the organic layers were combined and dried (Na₂SO₄). The solvent was removed in vacuo, and the residue was purified by column chromatography (normal phase, silica, 60-120 mesh, gradient 0% to 5% EtOAc in hexane) to give methyl 5-cyano-5-(3-fluorophenyl)-2-oxocyclohexanecarboxylate (3.2 g, 78.8%) as an off white solid.

Mass: (ESI +ve): 276 (M+H)⁺.

Methyl 5-cyano-5-(3-fluorophenyl)-2-oxocyclohexanecarboxylate (1.05 g, 3.81 mmol) was dissolved in THF/Water (2:1) (36 mL) and t-BuOK (514 mg, 4.58 mmol) was added at rt. The reaction mixture was heated at 105° C. for 5 h, then cooled to rt and partitioned between EtOAc (100 mL) and water (50 mL). The aqueous layer was extracted with EtOAc (2×100 mL) and the organic layers were combined and dried (Na₂SO₄). The solvent was removed in vacuo and the residue was purified by column chromatography (normal phase silica, 0 to 11% EtOAc in hexane) to give 1-(3-fluorophenyl)-4-oxocyclohexanecarbonitrile (0.51 g, 64.6%) as an off white solid.

The data for Intermediate 20 are in Table 2
Route 4

Typical Procedure for the Preparation of Cyclohexanones Containing Substituted Pyridyl Groups, as Exemplified by the Preparation of Intermediate 27, 1-(5-fluoropyridin-2-yl)-4-oxocyclohexanecarbonitrile

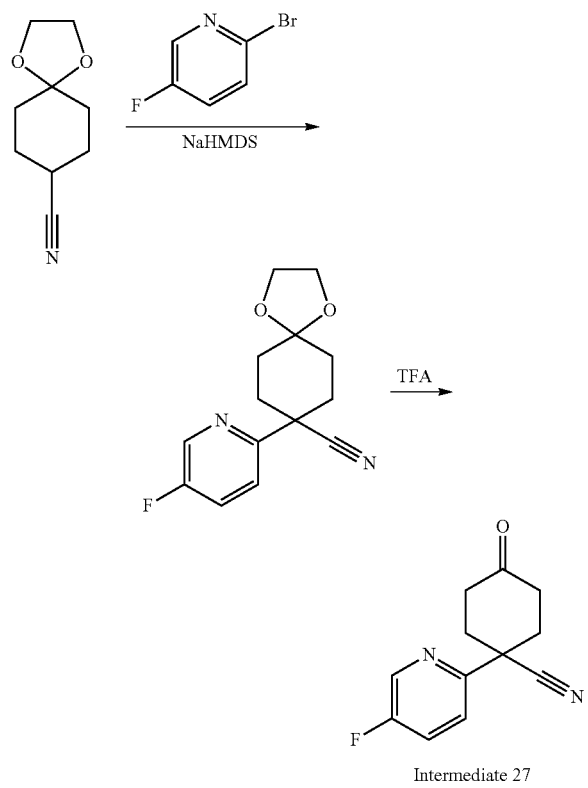

1,4-Dioxaspiro-(4,5)-decane-8-carbonitrile (2.0 g, 11.9 mmol) was dissolved in PhMe (20.0 mL) and 2-bromo-5-fluoropyridine (2.0 g, 11.9 mmol) was added. The reaction mixture was cooled to −78° C. and NaHMDS (5.47 g, 29.9 mL 1.0M in THF, 29.9 mmol) was added. The reaction mixture was stirred for 30 minutes at −78 OC and warmed to rt overnight, then quenched with water (100 mL). The reaction mixture was partitioned between PhMe (100 mL) and water (50 mL), the aqueous layer was extracted with PhMe (2×100 mL) and the organic layers were combined and dried (Na$_2$SO$_4$). The solvents were removed in vacuo, and the residue was purified by column chromatography (normal phase, silica, 60-120 mesh, gradient 0% to 12% EtOAc in Hexane) to give 8-(5-fluoropyridin-2-yl)-1,4-dioxaspiro[4.5]decane-8-carbonitrile (1.2 g, 40%).

8-(5-Fluoropyridin-2-yl)-1,4-dioxaspiro[4.5]decane-8-carbonitrile (1.0 g, 3.81 mmol) was dissolved in DCM (5.0 mL) and TFA (3.0 mL) was added. The reaction mixture was stirred at rt for 5 h. The reaction mixture was partitioned between DCM (100 mL) and water (50 mL), the aqueous layer was extracted with DCM (2×100 mL) and the organic layers were combined washed with brine (25 mL) and dried (Na$_2$SO$_4$). The solvents were removed in vacuo, and the residue was purified by column chromatography (normal phase, silica, 60-120 mesh, gradient 0% to 10% EtOAc in hexane) to give 1-(5-fluoropyridin-2-yl)-4-oxocyclohexanecarbonitrile (0.8 g, 96%).

The data for Intermediate 27 are in Table 2
For less reactive substrates, heating conditions may be required for step 1.
Route 5

Typical Procedure for the Preparation of Cyclohexanone Carboxylates Containing Substituted Pyridyl Groups, as Exemplified by the Preparation of Intermediate 50, methyl 1-(3-chloropyridin-2-yl)-4-oxocyclohexanecarboxylate

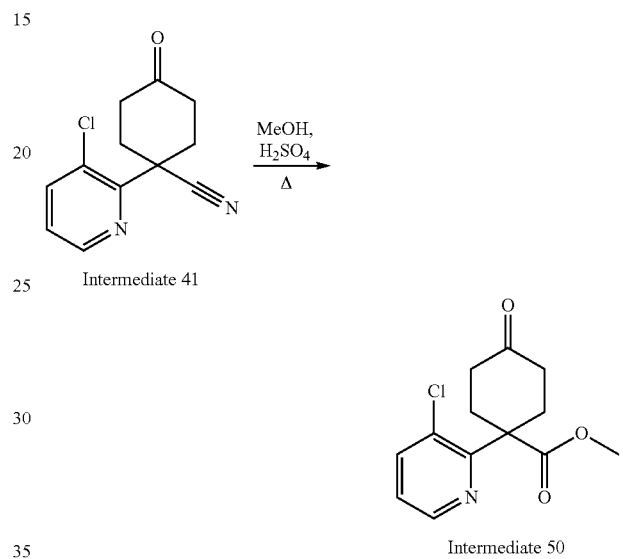

1-(3-Chloropyridin-2-yl)-4-oxocyclohexanecarbonitrile (4.0 g, 17.1 mmol) was dissolved in MeOH (40 mL) and H$_2$SO$_4$ (20 mL) was added. The reaction mixture was heated at 100° C. for 16 h, cooled to rt and DCM (100 mL) and water (50 mL) were added. The pH was adjusted to pH 8 with the addition of solid NaHCO$_3$. The aqueous layer was extracted with DCM (2×50 mL) and the organic layers were combined washed with brine (25 mL) and dried (Na$_2$SO$_4$). The solvents were removed in vacuo, and the residue was purified by column chromatography (normal phase, silica, 60-120 mesh, gradient 0% to 20% EtOAc in hexane) to give methyl 1-(3-chloropyridin-2-yl)-4-oxocyclohexanecarboxylate (0.4 g, 8.8%).

The data for Intermediate 50 are in Table 2
Route 6

Typical Procedure for the Preparation of Spiroketones from the Corresponding Oxindole, Exemplified by the Preparation of Intermediate 67, 7'-methyl-4H-spiro[cyclohexane-1,3'-indole]-2',4(1'H)-dione

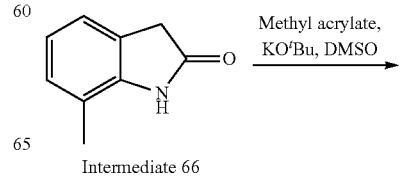

-continued

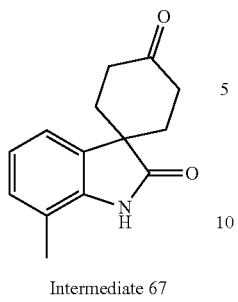

Intermediate 67

7-methyl-1,3-dihydro-2H-indol-2-one (2.00 g, 13.5 mmol) and anhydrous potassium tert-butoxide (0.08 g, 0.7 mmol) were dissolved in DMSO (10 mL) under $N_2$. Methyl acrylate (3.50 g, 40.7 mmol) was added dropwise over 30 min and the reaction mixture stirred at 45° C. for 15 min. Anhydrous potassium tert-butoxide (3.05 g, 27.2 mmol) was added portionwise over 40 min and the reaction mixture allowed to stir at 60° C. for 2 h. Water (20 mL) was added to the reaction mixture with further stirring at 80° C. for 8 h. The mixture was diluted with water (250 mL), extracted with EtOAc (3×100 mL), combined organics dried ($Na_2SO_4$) and the solvent removed in vacuo. The crude product was purified by column chromatography (normal phase, neutral silica gel, 60-120 mesh, 0 to 30% EtOAc in hexane) to give 7'-methylspiro[cyclohexane-1,3'-indoline]-2',4-dione (230 mg, 7%) as a brown solid.

The data for Intermediate 67 are in Table 2

Route 7

Procedure for the Preparation of Pyrrolidines, Exemplified by the Preparation of Intermediate 84, ethyl methyl[(3R)-pyrrolidin-3-yl]carbamate trifluoroacetic acid salt

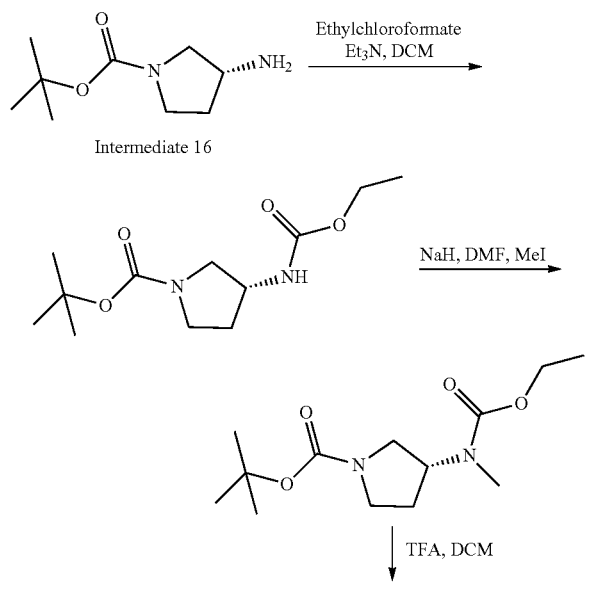

-continued

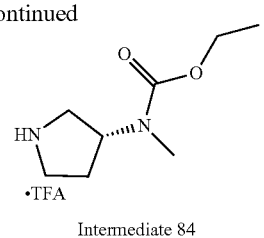

Intermediate 84

To a solution of (R)-tert-butyl 3-aminopyrrolidine-1-carboxylate (1.5 g, 8.0 mmol), $Et_3N$ (3.4 mL, 24.1 mmol) in DCM (20 mL) was added ethyl chloroformate (1.1 mL, 12.0 mmol) at 0° C. The reaction mixture was stirred at rt for 1 h, partitioned between cold $H_2O$ (25 mL) and DCM (50 mL) and the aqueous layer further extracted with DCM (2×50 mL). Combined organics were dried ($Na_2SO_4$) and the solvent removed in vacuo. The crude product was purified by column chromatography (normal-phase silica, 0 to 6% MeOH in DCM) to give (R)-tert-butyl 3-(ethoxycarbonylamino) pyrrolidine-1-carboxylate (1.0 g, 49%) as a reddish gum.

LCMS (Method F): m/z 259 $(M+H)^+$ $(ES^+)$, at 2.05 min, UV active.

To a solution of (R)-tert-butyl 3-(ethoxycarbonylamino) pyrrolidine-1-carboxylate (500 mg, 1.9 mmol) and NaH (60% w/w in mineral oil, 92 mg, 2.3 mmol) in DMF (10 mL) was added methyl iodide (230 µL, 3.7 mmol) at rt and the reaction stirred for 1 h. The mixture was partitioned between cold $H_2O$ (100 mL) and EtOAc (100 mL) and the aqueous layer further extracted with EtOAc (2×100 mL). Combined organics were dried ($Na_2SO_4$) and the solvent removed in vacuo to give tert-butyl (R)-3-((ethoxycarbonyl)(methyl) amino)pyrrolidine-1-carboxylate (500 mg, 97%) as a reddish gum.

LCMS (Method F): m/z 217 $[M+H-56]^+$ $(ES^+)$, at 2.23 min, UV active.

To a solution of (R)-tert-butyl 3-(ethoxycarbonyl(methyl) amino)pyrrolidine-1-carboxylate (650 mg, 2.3 mmol) in DCM (20 mL) was added TFA (540 µL, 7.1 mmol) at 0° C. and the reaction mixture stirred at rt for 16 h. The mixture was concentrated in vacuo to give (R)-ethyl methyl (pyrrolidin-3-yl) carbamate (400 mg, 61%) as a reddish gum.

The data for Intermediate 84 are in Table 2

Route 8

Typical Procedure for the Preparation of N-Alkylated Oxindoles, Exemplified by the Preparation of Intermediate 86, 1'-methyl-4H-spiro[cyclohexane-1, 3'-indole]-2',4(1'H)-dione

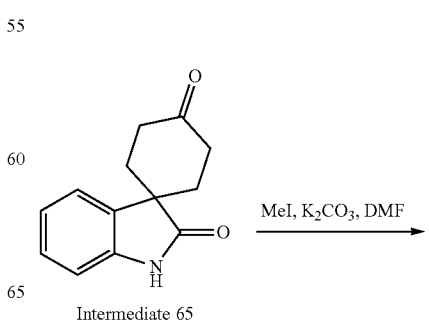

Intermediate 65

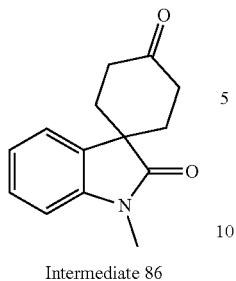

Intermediate 86

To 4H-spiro[cyclohexane-1,3'-indole]-2',4(1'H)-dione (395 mg, 1.8 mmol) and K$_2$CO$_3$ (507 mg, 3.7 mmol) in DMF (5 mL) at rt was added methyl iodide (286 mg, 2.0 mmol) dropwise and the reaction mixture heated to 100° C. for 16 h. The mixture was poured into ice cold water (100 mL), extracted with EtOAc (50 mL) and the aqueous layer further extracted with EtOAc (2×50 mL). Combined organics were dried (Na$_2$SO$_4$) and the solvent removed in vacuo. The crude product was purified using column chromatography (normal phase silica, 0 to 10% EtOAc in hexane) to yield 1'-Methyl-4H-spiro[cyclohexane-1,3'-indole]-2',4(1'H)-dione (250 mg, 57%) as an off-white solid.

The data for Intermediate 86 are in Table 2

Route 9

Typical Procedure for the Preparation of Oxindole Carbamates, Exemplified by the Preparation of Intermediate 87, ethyl 2',4-dioxospiro[cyclohexane-1,3'-indole]-1'(2'H)-carboxylate

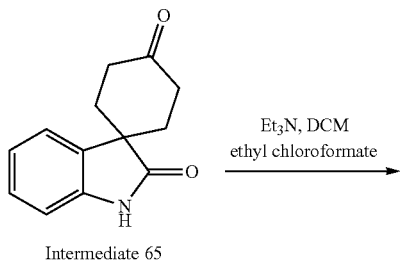

Intermediate 65

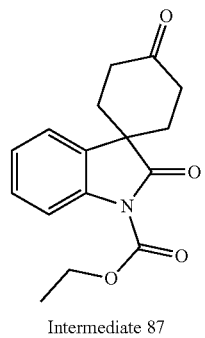

Intermediate 87

To a solution of spiro [cyclohexane-1,3'-indoline]-2',4-dione (100 mg, 0.5 mmol) and Et$_3$N (200 μL, 1.4 mmol) in DCM (5 mL) was added ethyl chloroformate (60 lL, 0.6 mmol) at 0° C. and the reaction mixture stirred at rt for 1 h. The mixture was then partitioned between cold H$_2$O (25 mL) and DCM (50 mL) and the aqueous layer further extracted with DCM (2×50 mL). Combined organics were dried (Na$_2$SO$_4$) and the solvent removed in vacuo. The crude product was purified by column chromatography (normal-phase silica, 0 to 6% MeOH in DCM) to give ethyl 2',4-dioxospiro[cyclohexane-1,3'-indoline]-1'-carboxylate (117 mg, 87%) as a reddish gum.

The data for Intermediate 87 are in Table 2

Route 10

Typical Procedure for the Preparation of Oxindoles from Fluoropyridines, Exemplified by the Preparation of Intermediate 90, 4H-spiro[cyclohexane-1,3'-pyrrolo[2,3-b]pyridine]-2',4(1'H)-dione

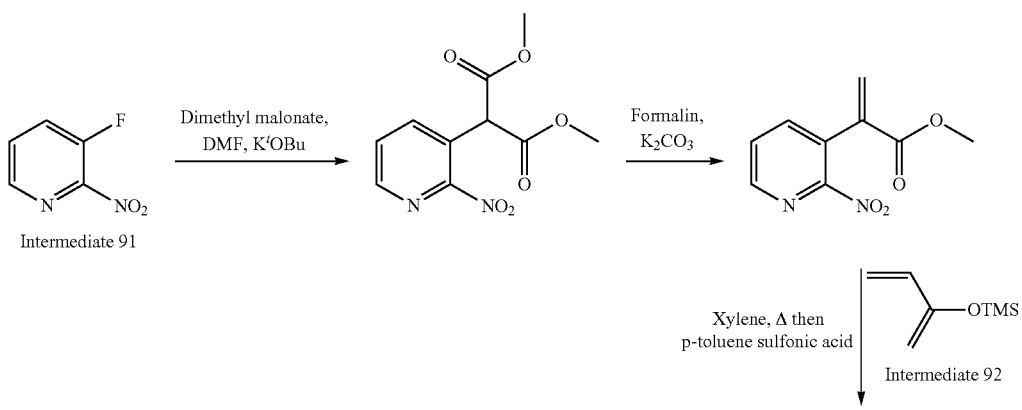

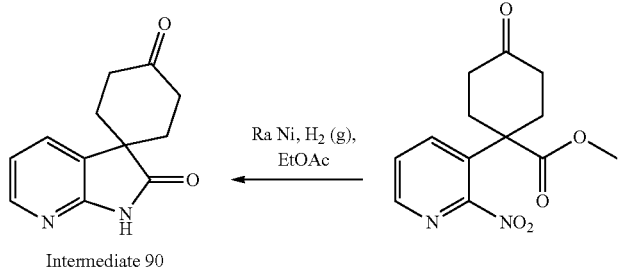

Intermediate 90

To dimethyl malonate (8.0 mL, 70.0 mmol) in DMF (10 mL) in a sealed tube at 0° C. was added potassium t-butoxide (4.1 g, 36.9 mmol) and the reaction mixture stirred for 10 min at 90° C. The mixture was then cooled to rt before addition of 3-fluoro-2-nitropyridine (2.5 g, 17.1 mmol) and heating at 90° C. for 2 h. The reaction mixture was poured into cold 5% aq. HCl (100 mL) and the organic layer extracted with EtOAc (50 mL). The aqueous layer was further extracted with EtOAc (2×100 mL), combined organics dried ($Na_2SO_4$) and the solvent removed in vacuo. The crude product was purified using column chromatography (normal phase silica, 0 to 18% EtOAc in hexane) to give dimethyl 2-(2-nitropyridin-3-yl)malonate (3.0 g, 67%) as yellow liquid.

LCMS (Method F): m/z 255 (M+H)$^+$ (ES$^+$), at 1.87 min, UV active.

To dimethyl 2-(2-nitropyridin-3-yl) malonate (5.8 g, 22.8 mmol) and 37-41% formalin (43.5 mL) in a sealed tube at rt was added a solution of $K_2CO_3$ (4.7 g, 34.0 mmol) in water (17.4 mL). The reaction mixture was stirred for 2 h at 60° C., diluted with ice cold water (250 mL), extracted with EtOAc (250 mL) and the aqueous layer further extracted with EtOAc (2×150 mL). Combined organics were dried ($Na_2SO_4$) and the solvent removed in vacuo. The crude product was purified by column chromatography (normal phase silica, 0 to 14% EtOAc in hexane) to give methyl 2-(2-nitropyridin-3-yl)acrylate (1.5 g, 31%) as a yellow liquid.

LCMS (Method F): m/z 209 (M+H)$^+$ (ES$^+$), at 1.87 min, UV active.

Methyl 2-(2-nitropyridin-3-yl) acrylate (1.48 g, 7.11 mmol) and 2-trimethylsilyloxy 1,3-butadiene (1.86 g, 13.09 mmol) in xylene (10 mL) were stirred for 20 h at 160° C. in a sealed tube. The resulting reaction mixture was cooled to rt before addition of p-toluene sulfonic acid monohydrate (1.08 g, 5.68 mmol) and further heating at 70° C. for 4 h. The reaction mixture was diluted with ice cold water (200 mL), extracted with EtOAc (200 mL) and the aqueous layer further extracted with EtOAc (2×100 mL). Combined organics were dried ($Na_2SO_4$), the solvent was removed in vacuo and the crude product purified by column chromatography (normal phase silica, 0 to 10% EtOAc in hexane) to give methyl 1-(2-nitropyridin-3-yl)-4-oxocyclohexane-1-carboxylate (0.40 g, 20%) as a yellow liquid.

LCMS (Method F): m/z 279 (M+H)$^+$ (ES$^+$).

To methyl 1-(2-nitropyridin-3-yl)-4-oxocyclohexane-1-carboxylate (146 mg, 0.52 mmol) in EtOAc (7 mL) was added Raney-Ni (146 mg, w/w) under $N_2$ and the reaction mixture stirred for 24 h. The mixture was filtered through celite, the filtrate concentrated in vacuo and the residue triturated in diethyl ether to give spiro [cyclohexane-1,3'-pyrrolo[2,3-b]pyridine]-2',4(1'H)-dione (60 mg, 53%) as an off-white solid.

The data for Intermediate 90 are in Table 2

Route 11

Typical Procedure for the Preparation of Spiro Oxindoles from the Corresponding Oxindole, Exemplified by the Preparation of Intermediate 93, 5'-chloro-4H-spiro[cyclohexane-1,3'-pyrrolo[2,3-b]pyridine]-2',4(1'H)-dione

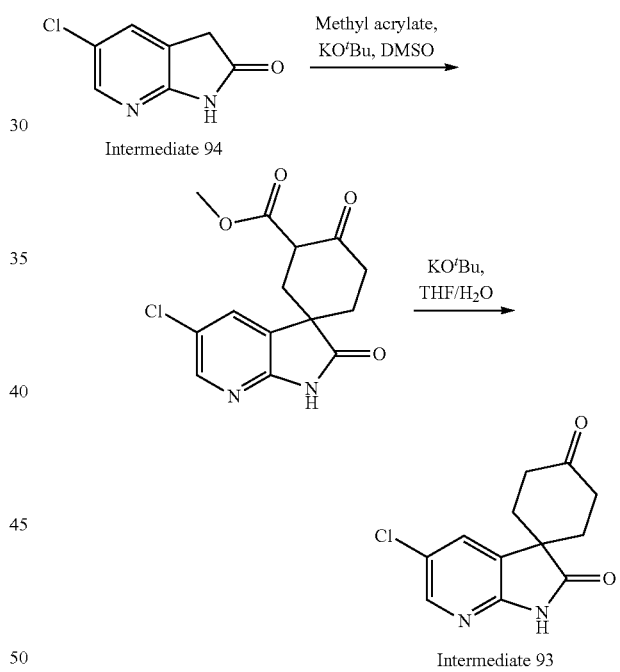

Intermediate 93

5-Chloro-1,3-dihydro-2H-pyrrolo[2,3-b]pyridin-2-one (1.00 g, 5.9 mmol), potassium t-butoxide (0.67 g, 5.9 mmol) and DMSO (5 mL) were heated at 45° C. before addition of methyl acrylate (1.66 mL, 18.3 mmol) dropwise over 20 min. The reaction mixture was stirred for 30 min at 45° C. before addition of potassium t-butoxide (1.33 g, 11.9 mmol) whilst the reaction temperature was maintained below 55° C. The reaction mixture was then heated at 100° C. for 2 h before addition of water and further stirring at 85° C. for 4 h. The mixture was cooled to rt and allowed to stir for 16 h, diluted with ice cold water (100 mL) and extracted with EtOAc (50 mL). The aqueous layer was further extracted with EtOAc (2×50 mL), combined organics dried ($Na_2SO_4$), the solvent removed in vacuo and the crude product purified using column chromatography (normal phase silica, 0 to 30% EtOAc in hexane) to give methyl 5'-chloro-2',4-dioxo-1',2'-dihydrospiro[cyclohexane-1,3'-pyrrolo[2,3-b]pyridine]-3-carboxylate (0.45 g, 25%) as a white solid.

LCMS (Method F): m/z 309 (M+H)+ (ES+), at 2.02 min, UV active.

To a solution of methyl 5'-chloro-2',4-dioxo-1',2'-dihydrospiro[cyclohexane-1,3'-pyrrolo[2,3-b]pyridine]-3-carboxylate (450 mg, 1.5 mmol) in THF/H$_2$O 2:1 (12 mL) at rt was added potassium t-butoxide (205 mg, 1.8 mmol) and the reaction heated to 105° C. for 5 h. The reaction was cooled to rt before addition of water and extraction with EtOAc (2×200 mL). Combined organics were dried (Na$_2$SO$_4$) and the solvent removed in vacuo to yield 5'-chlorospiro[cyclohexane-1,3'-pyrrolo[2,3-b]pyridine]-2',4(1'H)-dione (210 mg, 57%) as white solid. The crude product was taken on directly to the next step.

The data for Intermediate 93 are in Table 2

Route 12

Typical Procedure for the Preparation of Spiro Oxindoles, Exemplified by the Preparation of Intermediate 95, 5'-methoxy-4H-spiro[cyclohexane-1,3'-pyrrolo[2,3-c]pyridine]-2',4(1'H)-dione added sodium methoxide (48.3 mL, 2 M in MeOH, 96.6 mmol) dropwise at 0° C. The reaction mixture was stirred at rt for 16 h. After completion, the volatiles were removed in vacuo, water (100 mL) was added and the aqueous layer extracted with EtOAc (3×200 mL). The organic layers were combined and washed with brine, dried (Na$_2$SO$_4$) and concentrated in vacuo. The residue was purified by flash column chromatography [normal phase, silica gel (100-200 mesh), gradient 2% to 5% EtOAc in hexane] to give methyl 2-(2-methoxy-5-nitropyridin-4-yl)acetate (2.0 g, 46%) as a yellow solid.

MS (ESI +ve): 227

To a solution of methyl 2-(2-methoxy-5-nitropyridin-4-yl)acetate (6.1 g, 26.9 mmol) in toluene (100 mL), paraformaldehyde (2.3 g, 75.0 mmol), K$_2$CO$_3$ (11.1 g, 80.3 mmol) and catalytic tetrabutyl ammonium iodide (0.3 g) were added and refluxed for 30 min. The reaction mixture was cooled to rt, filtered through a pad of celite and washed with EtOAc (100 mL). Water (50 mL) was added to the filtrate and the organic layer was separated. The aqueous layer was extracted with EtOAc (2×50 mL). The organic layers were combined and washed with brine, dried (Na$_2$SO$_4$) and concentrated in vacuo. The residue was

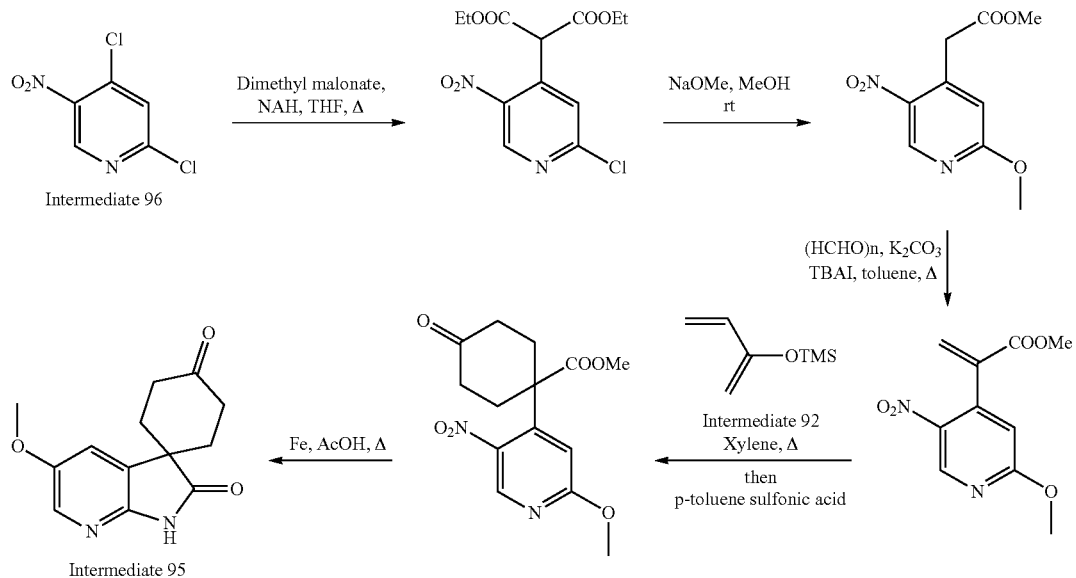

To a stirred solution of diethyl malonate (8.7 mL, 57.3 mmol) in dry THF (300 mL), sodium hydride (2.3 g, 60% w/w in mineral oil, 57.3 mmol) was added portionwise at 0° C. and stirred for 1 h. The reaction mixture was brought to rt and 2,4-dichloro-5-nitropyridine (10.0 g, 52.0 mmol) was added and refluxed for 14 h. After cooling to 0° C., the reaction mixture was carefully quenched with ice cold water and extracted with EtOAc (3×200 mL). The organic layers were combined, washed with brine, dried (Na$_2$SO$_4$) and concentrated in vacuo. The residue was purified by flash column chromatography [normal phase, silica gel (100-200 mesh), gradient 10% to 15% EtOAc in hexane] to give diethyl 2-(2-chloro-5-nitropyridin-4-yl)malonate (11.1 g, 68%) as a yellow liquid.

MS (ESI −ve): 315

To a stirred solution of diethyl 2-(2-chloro-5-nitropyridin-4-yl)malonate (6.1 g, 19.3 mmol) in MeOH (50 mL) was triturated with Et$_2$O to give methyl 2-(2-methoxy-5-nitropyridin-4-yl)acrylate (4.0 g, 62%) as a dark brown solid. This was used for the next step without further purification.

MS (ESI +ve): 239.

To a suspension of methyl 2-(2-methoxy-5-nitropyridin-4-yl)acrylate (1.0 g, 4.2 mmol) in xylene (65 mL), 2-(trimethylsilyloxy)-1,3-butadiene (3.3 mL, 18.9 mmol) was added at rt and the reaction mixture was refluxed for 24 h. After cooling to rt, catalytic pTSA (0.1 g) was added and the mixture stirred at rt for 1 h. The reaction mixture was diluted with EtOAc (50 mL), water (30 mL) was added and the organic layer was separated. The aqueous layer was extracted with EtOAc (2×200 mL). The organic layers were combined and washed with brine, dried (Na$_2$SO$_4$) and concentrated in vacuo to give crude methyl 1-(2-methoxy-5-nitropyridin-4-yl)-4-oxocyclohexane-1-carboxylate (1.2 g, 93%) as a light brown semi solid. The crude product was used for the next step without further purification.

MS (ESI +ve): 309.

To a solution of methyl 1-(2-methoxy-5-nitropyridin-4-yl)-4-oxocyclohexane-1-carboxylate (800 mg, 2.6 mmol) in acetic acid (15 mL), iron powder (695 mg, 12.4 mmol) was added at rt and refluxed for 3 h. The reaction mixture was cooled to rt, filtered through a pad of celite and washed with ethanol (50 mL). After removing the volatiles from the filtrate, water (50 mL) was added and organics extracted with EtOAc (3×25 mL). The organic layers were combined and washed with brine, dried (Na$_2$SO$_4$) and concentrated in vacuo. The residue was purified by flash column chromatography [normal phase, silica gel (100-200 mesh), gradient 2% to 3% EtOAc in hexane] to give 5'-methoxyspiro-[cyclohexane-1,3'-pyrrolo[2,3-c]pyridine]-2',4(1'H)-dione, (500 mg, 73% over 2 steps) as a yellow solid.

The data for Intermediate 95 are in Table 2

Route 13

Typical Procedure for the Preparation of Spiro Oxindoles, Exemplified by the Preparation of Intermediate 97, 5'-methoxy-4H-spiro[cyclohexane-1,3'-pyrrolo[3,2-b]pyridine]-2',4(1'H)-dione mixture was partitioned between cold H$_2$O (150 mL) and EtOAc (75 mL), the aqueous layer further extracted with EtOAc (2×75 mL), combined organics dried (Na$_2$SO$_4$) and the solvent removed in vacuo. The crude product was purified by column chromatography (normal phase silica, 0 to 12% EtOAc in hexane) to give ethyl 2-(6-methoxy-3-nitropyridin-2-yl)acetate (1.7 g, 17%) as a yellow gum.

LCMS (Method F): m/z 241 (M+H)$^+$ (ES$^+$), at 2.33 min, UV active.

To copper acetate monohydrate (0.12 g, 0.6 mmol), potassium acetate (0.92 g, 9.4 mmol) paraformaldehyde (1.87 g, 62.3 mmol) and ethyl 2-(6-methoxy-3-nitropyridin-2-yl)acetate (1.50 g, 6.2 mmol) under N$_2$ was added acetic acid (5 mL) and the solution degassed for 15 min, before stirring at 100° C. for 2 h. The reaction mixture was diluted with ice cold water (20 mL) and basified with aq. NaOH. The reaction mixture was partitioned between cold H$_2$O (25 mL) and EtOAc (20 mL), the aqueous layer further extracted with EtOAc (2×20 mL), combined organics dried (Na$_2$SO$_4$) and the solvent removed in vacuo. The crude product was purified by column chromatography (normal-phase silica, 0 to 10% EtOAc in hexane) to give ethyl 2-(6-methoxy-3-nitropyridin-2-yl)acrylate (1.50 g, 96%) as a yellow gum.

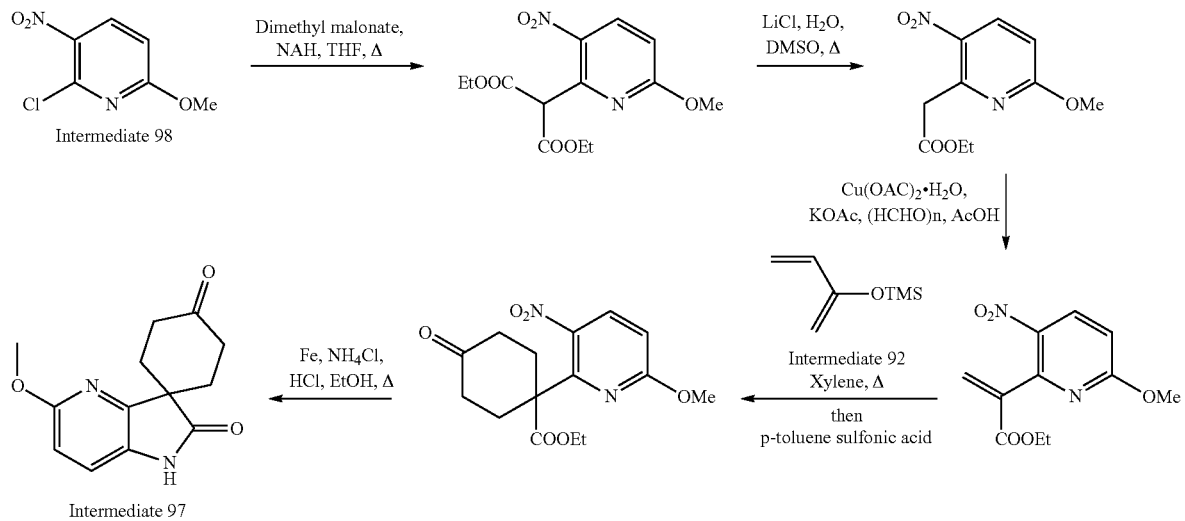

To NaH (4.24 g, 60% w/w in mineral oil, 106.0 mmol) in THF (80 mL) was added diethyl malonate (16.16 mL, 106.0 mmol) dropwise at 0° C. and the reaction mixture stirred for 1 h. 2-chloro-6-methoxy-3-nitropyridine (10.00 g, 53.0 mmol) in THF (20 mL) was added dropwise and the resulting mixture stirred at 80° C. for 16 h. The reaction mixture was partitioned between cold H$_2$O (250 mL) and EtOAc (100 mL), the aqueous layer further extracted with EtOAc (2×100 mL), combined organics dried (Na$_2$SO$_4$) and the solvent removed in vacuo. The crude product was purified by column chromatography (normal phase silica, 0 to 20% EtOAc in hexane) to give diethyl 2-(6-methoxy-3-nitropyridin-2-yl)malonate (13.21 g, 80%) as a light green solid.

LCMS (Method F): m/z 313 (M+H)$^+$ (ES$^+$), at 2.43 min, UV active.

Diethyl 2-(6-methoxy-3-nitropyridin-2-yl) malonate (13.0 g, 41.6 mmol), LiCl (4.4 g, 104.0 mmol), and H$_2$O (0.67 mL, 37.2 mmol) were dissolved in DMSO (130 mL) and the mixture stirred at 100° C. for 16 h. The reaction LCMS (Method F): m/z 253 (M+H)$^+$ (ES$^+$), at 2.41 min, UV active.

To a degassed solution of ethyl 2-(6-methoxy-3-nitropyridin-2-yl) acrylate (1.50 g, 5.9 mmol) in xylene (5 mL) was added 2-trimethylsilyloxyl-1,3-butadiene (3.1 mL, 17.8 mmol) and the mixture stirred at 150-160° C. for 21 h. To the mixture was then added pTSA (0.52 g, 3.0 mmol) with further heating at 100° C. for 4 h. The reaction mixture was partitioned between cold H$_2$O (25 mL) and EtOAc (15 mL), the aqueous layer further extracted with EtOAc (2×15 mL), combined organics dried (Na$_2$SO$_4$) and the solvent removed in vacuo. The crude product was purified by column chromatography (normal phase silica, 0 to 20% EtOAc in hexane) to give ethyl 1-(6-methoxy-3-nitropyridin-2-yl)-4-oxocyclohexane-1-carboxylate (0.83 g, 43%) as a yellow gum.

LCMS (Method F): m/z 323 (M+H)$^+$ (ES$^+$), at 2.31 min, UV active.

A mixture of ethyl 1-(6-methoxy-3-nitropyridin-2-yl)-4-oxocyclohexane-1-carboxylate (0.55 g, 1.7 mmol), Fe Powder (0.48 g, 8.5 mmol), NH$_4$Cl (0.27 g, 5.1 mmol), H$_2$O (2 mL) and conc. HCl (0.50 mL) in ethanol (8 mL) was stirred at 90° C. for 16 h in a sealed tube. The reaction mixture was partitioned between cold H$_2$O (25 mL) and EtOAc (15 mL), the aqueous layer further extracted with EtOAc (2×15 mL), combined organics dried (Na$_2$SO$_4$) and the solvent removed in vacuo to give 5'-methoxyspiro[cyclohexane-1,3'-pyrrolo[3,2-b]pyridine]-2',4(1'H)-dione (320 mg, 76%) as a yellow solid.

The data for Intermediate 97 are in Table 2

Route 14

Typical Procedure for the Preparation of Piperidines, Exemplified by the Preparation of Intermediate 103, 4-[4-(aminomethyl)piperidin-1-yl]spiro[cyclohexane-1,3'-indol]-2'(1'H)-one di-trifluoroacetic acid salt, mixture of two isomers

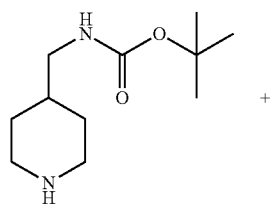

Intermediate 2

+

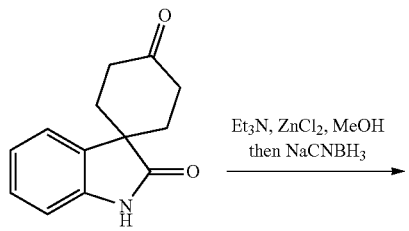

Intermediate 65

Et$_3$N, ZnCl$_2$, MeOH then NaCNBH$_3$
→

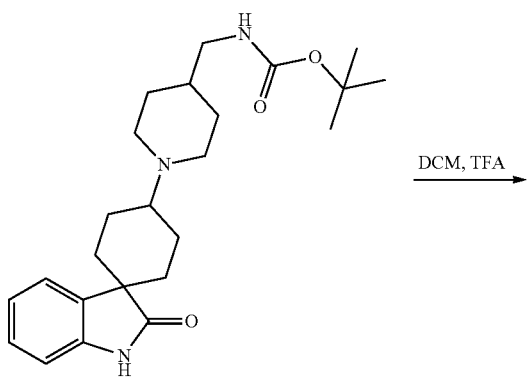

DCM, TFA
→

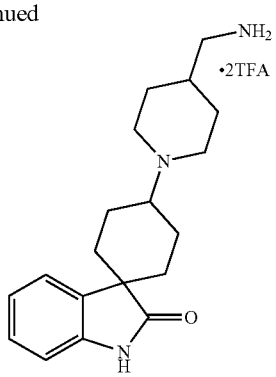

Intermediate 103

A solution of spiro[cyclohexane-1,3'-indoline]-2',4-dione (200 mg, 0.9 mmol), tert-butyl piperidin-4-ylmethylcarbamate (218 mg, 1.0 mmol), ZnCl$_2$ (37 mg, 0.3 mmol) and Et$_3$N (470 mg, 4.6 mmol) in MeOH (10 mL) was stirred at 50° C. for 1 h. The mixture was cooled to 0° C. before portionwise addition of NaBH$_3$CN (243 mg, 3.9 mmol) and further stirring at 50° C. for 7 h. The reaction mixture was concentrated in vacuo, the residue partitioned between H$_2$O (80 mL) and EtOAc (50 mL), the aqueous layer extracted with EtOAc (2×50 mL), combined organics dried (Na$_2$SO$_4$) and the solvent removed in vacuo. The residue was purified by column chromatography (normal silica, mesh size: 60-120, 0% to 2% MeOH in DCM) to give tert-butyl (1-(2'-oxospiro[cyclohexane-1,3'-indoline]-4-yl)piperidin-4-yl)methylcarbamate (300 mg, 78%) as a yellow gum as a mixture of isomers.

LCMS (Method F): m/z 414 (M+H)$^+$ (ES$^+$), at 1.78 min (isomer 1) and 1.82 min (isomer 2), UV active.

To a solution of tert-butyl (1-(2'-oxospiro[cyclohexane-1,3'-indoline]-4-yl)piperidin-4-yl)methylcarbamate (300 mg, 0.7 mmol) in DCM (20 mL) under N$_2$ at 0° C. was added TFA (248 mg, 2.2 mmol) and the reaction mixture warmed to rt over 2 h. The solvent was removed in vacuo to give 4-(4-(aminomethyl)piperidin-1-yl)spiro[cyclohexane-1,3'-indolin]-2'-one di-TFA salt (200 mg, 53%) as a colorless liquid as a mixture of isomers. The data for Intermediate 103 are in Table 2

Route 15

Typical Procedure for the Preparation of 1,4-diazepanes, Exemplified by the Preparation of Intermediate 107, 1-(1,4-diazepan-1-yl)but-2-en-1-one trifluoroacetic acid salt

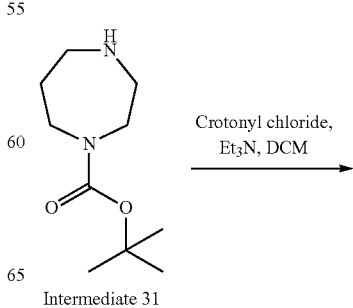

Crotonyl chloride, Et$_3$N, DCM
→

Intermediate 31

-continued

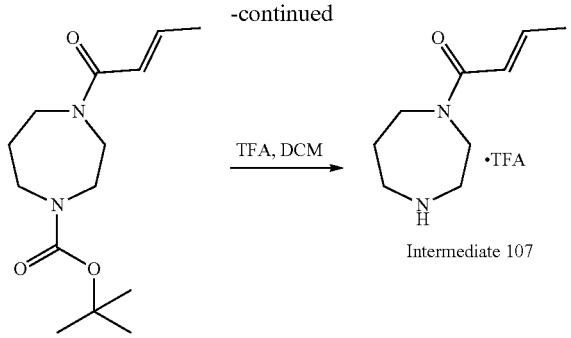

Intermediate 107

To a solution of tert-butyl 1,4-diazepane-1-carboxylate (1.50 g, 7.5 mmol) and Et₃N (2.28 g, 22.5 mmol) in DCM (5 mL) at 0° C. was added crotonyl chloride (1.18 g, 11.3 mmol) and the reaction mixture stirred at rt for 1 h. The mixture was partitioned between cold H₂O (25 mL) and EtOAc (15 mL), the aqueous layer further extracted with EtOAc (2×15 mL), combined organics dried (Na₂SO₄) and the solvent removed in vacuo to yield tert-butyl 4-but-2-enoyl-1,4-diazepane-1-carboxylate (1.80 g, 90%) as a brown liquid.

LCMS (Method F): m/z 269 (M+H)⁺ (ES⁺), at 1.95 min UV active.

To a solution of tert-butyl 4-but-2-enoyl-1,4-diazepane-1-carboxylate (1.8 g, 6.7 mmol) in DCM (20 mL) was added TFA (10 mL) at 0° C. and the reaction mixture stirred for 3 h at rt. The reaction mixture was concentrated in vacuo and triturated with acetone (3×10 mL) to give 1-(1,4-diazepan-1-yl)but-2-en-1-one trifluoroacetic acid salt (1.0 g, 53%) as a brown liquid.

The data for Intermediate 107 are in Table 2

Route 16

Typical Procedure for the Preparation of Spiro Oxindoles, Exemplified by the Preparation of Intermediate 99, 4H-spiro[cyclohexane-1,3'-pyrrolo[3,2-b]pyridine]-2',4(1'H)-dione To NaH (60% in mineral oil, 51 g, 1.3 mol) in THF (300 mL) at 0° C. was added diethyl malonate (202 g, 1.3 mol) dropwise whilst the temperature was maintained between 0-10° C. and the resulting mixture stirred at 0-10° C. for 1 h until hydrogen emission ceased. A solution of 2-chloro-3-nitropyridine (100 g, 0.6 mol) in dry THF (300 mL) was added dropwise and the resulting solution refluxed overnight. The solvent was removed in vacuo, the residue dissolved in EtOAc (10 L), filtered, the organic phase washed with water (5×1 L), dried over Na₂SO₄ and concentrated in vacuo to afford crude diethyl (3-nitropyridin-2-yl)-malonate (50 g, 28%) which was used in the next step without purification To a solution of diethyl (3-nitropyridin-2-yl)-malonate (12.5 g, 44 mmol) in DMSO (150 mL) at rt under N₂ was added water (0.8 mL, 44 mmol) and lithium chloride (4.7 g, 110 mmol) and the reaction mixture heated at 100° C. for 12 h. A second batch of lithium chloride (1.0 g, 24 mmol) was then added and the mixture heated for 5 h, cooled to rt and diluted with brine (150 mL). The aqueous layer was then extracted with EtOAc (3×275 mL), combined organics dried over Na₂SO₄, the solution concentrated in vacuo and the resulting solid triturated with diethyl ether to afford ethyl 2-(3-nitropyridin-2-yl)acetate (8.6 g, 93%).

To a solution of ethyl 2-(3-nitropyridin-2-yl)acetate (50 g, 0.24 mol) in benzene (1 L) was added acetic acid (5 mL), piperidine (5 mL) and 1,3,5-trioxane (62 g, 0.69 mol). The reaction flask was fitted with a Dean-Stark trap and the yellow solution heated under reflux for 24 h. To the hot solution was added further 1,3,5-trioxane (60 g) and the resulting mixture heated for an additional 24 h. The solvents were removed in vacuo and the reside purified by column chromatography (silica, hexane/EtOAc=9:1) to afford ethyl 2-(3-nitropyridin-2-yl)acrylate (34 g, 64%).

A mixture of ethyl 2-(3-nitropyridin-2-yl)acrylate (5.0 g, 22.5 mmol), 2-trimethylsilyloxy-1,3-butadiene (4.8 g, 33.7 mmol) and xylene (50 mL) was heated in a sealed tube at 130° C. for 20 h. The mixture was then cooled to rt before addition of p-toluenesulfonic acid monohydrate (0.5 g, 2.6 mmol) and further stirring for 2 h. The mixture was then diluted with EtOAc (100 mL), washed with water (1×50

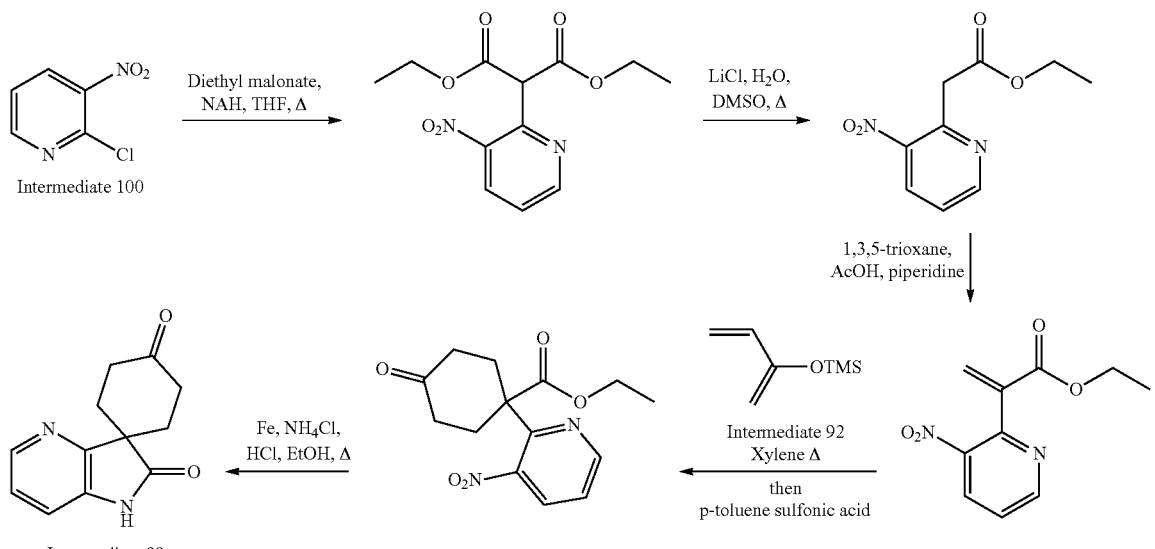

mL) and brine (1×50 mL), dried over Na$_2$SO$_4$ and concentrated in vacuo. The residue was purified by column chromatography (silica, EtOAc/hexane, 1:9 to EtOAc/hexane, 2:3) to afford ethyl 1-(3-nitropyridin-2-yl)-4-oxocyclohexanecarboxylate (5.0 g, 76%).

To ethyl 1-(3-nitropyridin-2-yl)-4-oxocyclohexanecarboxylate (2.5 g, 8.6 mmol) in EtOH (80 mL) was added NH$_4$Cl (0.1 g, 1.9 mmol), H$_2$O (0.5 mL), conc. HCl (0.5 mL) and iron powder (2.5 g, 44.6 mmol). The reaction mixture was heated at reflux for 2 h, neutralized with aq. sodium hydroxide (2N) to pH 8 and filtered. The filtrate was concentrated under reduced pressure and the resulting residue was triturated with H$_2$O to yield the desired product (1.0 g, 54%).

The data for Intermediate 99 are in Table 2

Route 17

Typical Procedure for the Preparation of Spiro Oxindoles, Exemplified by the Preparation of Intermediate 113, 5'-methoxy-4H-spiro[cyclohexane-1,3'-pyrrolo[2,3-b]pyridine]-2',4(1'H)-dione EtOAc (100 mL), washed with 10% aq Rochelle salt (20 mL), brine, dried (Na$_2$SO$_4$) and concentrated in vacuo. The residue was triturated with diethyl ether (2×20 mL) to give 5-methoxy-1,3-dihydro-2H-pyrrolo[2,3-b]pyridin-2-one (0.9 g, 59%) as a brown solid. This crude product was used for the next step without further purification.

MS (ESI +ve): 165

To a solution of 5-methoxy-1,3-dihydro-2H-pyrrolo[2,3-b]pyridin-2-one (2.00 g, 12.2 mmol) in DMSO (20 mL), $^t$BuOK (0.54 g, 4.8 mmol) was added at rt and stirred for 10 min. Methyl acrylate (3.0 mL, 33.1 mmol) was slowly added and the reaction mixture was stirred at 45° C. for 1 h. The reaction mixture was quenched with AcOH (3 mL) and poured into ice-water (100 mL) and extracted with EtOAc (3×20 mL). The organic layers were combined and washed with brine, dried (Na$_2$SO$_4$) and concentrated in vacuo. The residue was purified by flash column chromatography [normal phase, silica gel (100-200 mesh), gradient 1% to 5% EtOAc in hexane] to give trimethyl 3,3',3''-(5-methoxy-2-oxo-2,3-dihydro-1H-pyrrolo[2,3-b]pyridine-1,3,3-triyl)tripropionate (1.8 g, 35%) as a liquid.

MS (ESI +ve): 423

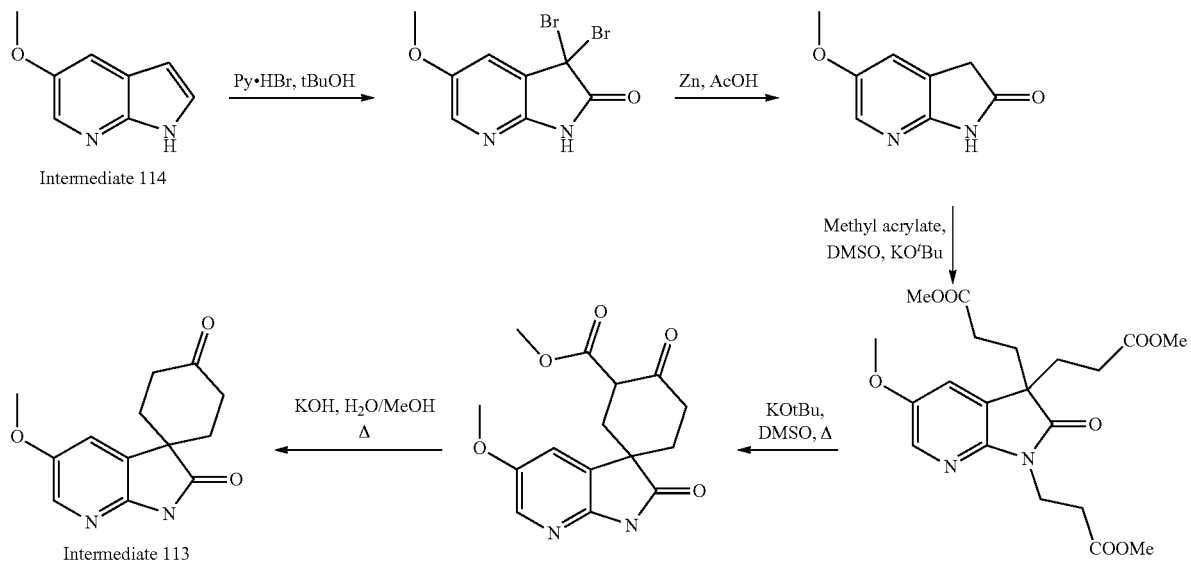

To a solution of 5-methoxy-1H-pyrrolo[2,3-b]pyridine (1.00 g, 6.8 mmol) in t-BuOH (60 mL), pyridinium tribromide (6.48 g, 20.3 mmol) was added and the reaction mixture was stirred at rt for 16 h. The reaction mixture was concentrated in vacuo and the residue was dissolved in EtOAc (50 mL). Water (50 mL) was added and the organic layer was separated. The aqueous layer was extracted with EtOAc (2×50 mL). The organic layers were combined and washed with sat. aq. NaHCO$_3$ solution (20 mL), brine (20 mL), dried (Na$_2$SO$_4$) and concentrated in vacuo. The residue was triturated with diethyl ether (1×10 mL) to give 3,3-dibromo-5-methoxy-1,3-dihydro-2H-pyrrolo[2,3-b]pyridin-2-one (1.5 g, 69%) as a brown solid. This product was used for the next step without further purification.

To a solution of 3,3-dibromo-5-methoxy-1,3-dihydro-2H-pyrrolo[2,3-b]pyridin-2-one (3.0 g, 9.3 mmol) in AcOH (60 mL), zinc dust (6.1 g, 93.2 mmol) was added and stirred at rt for 2 h. The reaction mixture was filtered through a pad of celite and washed with EtOAc (2×100 mL). The filtrate was concentrated in vacuo and the residue was dissolved in To a solution of trimethyl 3,3',3''-(5-methoxy-2-oxo-2,3-dihydro-1H-pyrrolo[2,3-b]pyridine-1,3,3-triyl)tripropionate (500 mg, 1.18 mmol) in DMSO (10 mL), $^t$BuOK (500 mg, 4.45 mmol) was added at rt and the reaction mixture was heated to 75° C. for 1 h. After cooling to rt, the reaction mixture was quenched with AcOH (5 mL), poured into ice-water (50 mL) and extracted with EtOAc (3×15 mL). The organic layers were combined and washed with brine, dried (Na$_2$SO$_4$) and concentrated in vacuo to give methyl 5'-methoxy-2',4-dioxo-1',2'-dihydrospiro[cyclohexane-1,3'-pyrrolo[2,3-b]pyridine]-3-carboxylate (300 mg, 83%) as a pale yellow solid. This crude product was used for the next step without further purification.

MS (ESI +ve): 305

To a solution of methyl 5'-methoxy-2',4-dioxo-1',2'-dihydrospiro[cyclohexane-1,3'-pyrrolo[2,3-b]pyridine]-3-carboxylate (800 mg, 2.63 mmol) in MeOH (20 mL), aq. KOH (1 M, 10 mL) was added at rt and the reaction mixture was refluxed for 7 h. After removal of volatiles, water (20 mL)

was added to the residue and extracted with EtOAc (3×20 mL). The organic layers were combined and washed with brine, dried (Na$_2$SO$_4$) and concentrated in vacuo to give methyl 5'-methoxy-2',4-dioxo-1',2'-dihydrospiro[cyclohexane-1,3'-pyrrolo[2,3-b]pyridine]-3-carboxylate (503 mg, 78%) as a pale yellow solid. This crude product was used for the next step without further purification.

The data for Intermediate 113 are in Table 2

Route 18

Typical Procedure for the Preparation of Spiro Oxindoles, Exemplified by the Preparation of Intermediate 116, 1',2'-dihydro-4H-spiro[cyclohexane-1, 3'-pyrrolo[2,3-b]pyridin]-4-one size: 60-120, 1.0% to 1.5% MeOH in DCM) to give 1-(2-chloropyridin-3-yl)-4-oxocyclohexane-1-carbonitrile (800 mg, 83%) as a yellow solid.

LCMS (Method H): m/z 235 (M+H)$^+$ (ES$^+$), at 7.19 min UV active.

To a solution of 1-(2-chloropyridin-3-yl)-4-oxocyclohexane-1-carbonitrile (800 mg, 3.4 mmol) in toluene (10 mL) was added p-toluene sulfonic acid (152 mg, 0.9 mmol) and ethylene glycol (500 µL, 9.0 mmol) and the resulting mixture stirred at 100° C. for 4 h. The solvents were removed in vacuo and the residue partitioned between H$_2$O (100 mL) and EtOAc (70 mL). The aqueous layer was extracted with EtOAc (2×70 mL), combined organics dried (Na$_2$SO$_4$) and the residue purified by column chromatography (normal silica, mesh size: 60-120, 1.0% to 1.5% MeOH

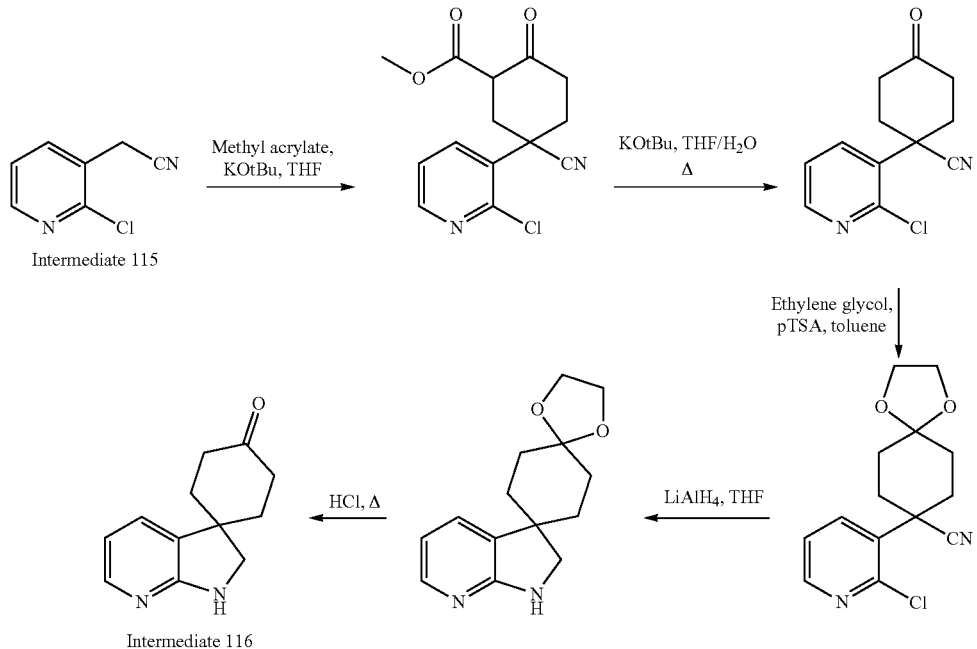

Intermediate 116

To a solution of 2-(2-methylpyridin-3-yl)acetonitrile (1.0 g, 6.6 mmol) and methyl acrylate (1.8 mL, 19.9 mmol) in THF (10 mL) at 0° C. was added potassium tert-butoxide (8.6 mL, 8.6 mmol, 1 M in THF) and the resulting reaction mixture stirred at 25° C. for 3 h. The mixture was partitioned between H$_2$O (100 mL) and EtOAc (80 mL), the aqueous layer further extracted with EtOAc (2×80 mL), combined organics dried (Na$_2$SO$_4$) and the solvent removed in vacuo. The residue was purified by column chromatography (normal silica, mesh size: 60-120, 0% to 0.5% MeOH in DCM) to give methyl 5-(2-chloropyridin-3-yl)-5-cyano-2-oxocyclohexane-1-carboxylate (1.2 g, 63%) as a yellow liquid.

LCMS (Method F): m/z 293 (M+H)$^+$ (ES$^+$), at 1.97 min UV active.

To a solution of methyl 5-(2-chloropyridin-3-yl)-5-cyano-2-oxocyclohexane-1-carboxylate (1.20 g, 4.1 mmol) in THF (5 mL) was added potassium tert-butoxide (1.03 g, 9.2 mmol) in water (10 mL), and the resulting mixture stirred at 80° C. for 17 h. The solvents were removed in vacuo and the residue partitioned between H$_2$O (120 mL) and EtOAc (80 mL). The aqueous layer was extracted with EtOAc (2×80 mL), combined organics dried (Na$_2$SO$_4$) and the residue purified by column chromatography (normal silica, mesh in DCM) to give 8-(2-chloropyridin-3-yl)-1,4-dioxaspiro [4.5]decane-8-carbonitrile (900 mg, 95%) as a yellow solid.

LCMS (Method F): m/z 279 (M+H)$^+$ (ES$^+$), at 1.99 min UV active.

To 8-(2-chloropyridin-3-yl)-1,4-dioxaspiro[4.5]decane-8-carbonitrile (1.0 g, 3.6 mmol) in THF (10 mL) at 0° C. was added LiAlH$_4$ (9.9 mL, 9.9 mmol, 1 M in THF) dropwise and the resulting mixture stirred at 25° C. for 3 h. The reaction mixture was partitioned between H$_2$O (100 mL) and EtOAc (70 mL), the aqueous layer extracted with EtOAc (2×70 mL), combined organics dried (Na$_2$SO$_4$) and the solvent removed in vacuo. The residue was purified by column chromatography (normal silica, mesh size: 60-120, 2.0% to 3.5% MeOH in DCM) to give 1,2-dihydrodispiro [pyrrolo[2,3-b]pyridine-3,1'-cyclohexane-4',2"-[1,3]dioxolane] (700 mg, 79%) as a light yellow solid.

LCMS (Method F): m/z 247 (M+H)$^+$ (ES$^+$), at 1.53 min UV active.

A solution of (1,2-dihydrodispiro[pyrrolo[2,3-b]pyridine-3,1'-cyclohexane-4',2"-[1,3]dioxolane] (700 mg, 2.8 mmol) in 6 N HCl (10 mL) was stirred at 50° C. for 16 h. The solvent was then removed in vacuo, and the residue partitioned between H$_2$O (80 mL) and EtOAc (50 mL). The aqueous layer was extracted with EtOAc (2×50 mL) combined organics dried (Na₂SO₄) and the solvent removed in vacuo. The crude product was purified by column chromatography (normal silica, mesh size: 60-120, 3.0% to 3.5% MeOH in DCM) to give 1',2'-dihydrospiro[cyclohexane-1,3'-pyrrolo[2,3-b]pyridin]-4-one (500 mg, 87%) as a yellow solid.

The data for Intermediate 116 are in Table 2

Route 19

Typical Procedure for the Preparation of Sulfonamides, Exemplified by the Preparation of Intermediate 117, 1'-(methylsulfonyl)-1',2'-dihydro-4H-spiro[cyclohexane-1,3'-pyrrolo[2,3-b]pyridin]-4-one

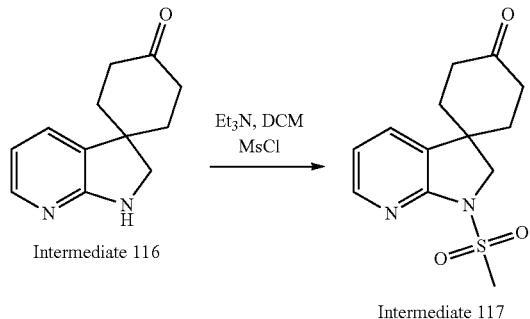 [SMILES: O=C1CCC2(CC1)CNc1ncccc12 ; CS(=O)(=O)N1CC2(CCC(=O)CC2)c2cccnc21]

To a solution of 1',2'-dihydrospiro[cyclohexane-1,3'-pyrrolo[2,3-b]pyridin]-4-one (400 mg, 2.0 mmol) and Et₃N (600 µL, 4.3 mmol) in DCM (5 mL) at 0° C. was added methanesulfonyl chloride (200 µL, 2.6 mmol) dropwise and the resulting mixture stirred at 25° C. for 1 h. The reaction mixture was partitioned between H₂O (70 mL) and EtOAc (50 mL), the aqueous layer further extracted with EtOAc (2×50 mL), combined organics dried (Na₂SO₄) and the solvent removed in vacuo. The crude residue was purified by column chromatography (normal silica, mesh size: 60-120, 0.5% to 1.0% MeOH in DCM) to give 1'-(methylsulfonyl)-1',2'-dihydrospiro[cyclohexane-1,3'-pyrrolo[2,3-b]pyridin]-4-one (400 mg, 72%) as a yellow gum.

The data for Intermediate 117 are in Table 2

Route 20

Typical Procedure for the Preparation of Ethyl Carbamates, Exemplified by the Preparation of Intermediate 6, ethyl 2,8-diazaspiro[4.5]decane-2-carboxylate

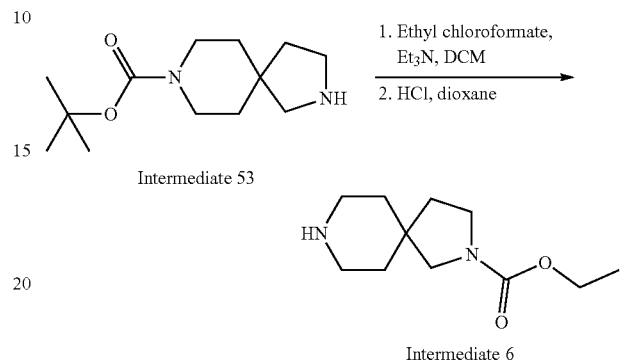

To a solution of tert-butyl 2,8-diazaspiro[4.5]decane-8-carboxylate (0.96 g, 4 mmol) in DCM (25 mL) at rt was added Et₃N (2.78 mL, 20 mmol) and ethyl chloroformate (0.71 mL, 7 mmol) and the mixture stirred at rt for 16 h. Sat. aq. NaHCO₃ (10 mL) was then added and the layers separated. The aqueous layer was extracted with DCM (4×25 mL), combined organics dried through a Biotage Phase Separator cartridge and the solvent removed in vacuo. To the residue was added ether (50 mL) and 4 M HCl in dioxane (5 mL) and the mixture stirred at rt for 16 h. The solvent was then removed in vacuo, the residue dissolved in MeOH (8 mL) and to the solution was added K₂CO₃ (607 mg) as a solution in water (2 mL) and the mixture stirred at rt for 1 h. The solvent was then removed in vacuo and the residue suspended in DCM, filtered and the solvent removed in vacuo to yield Ethyl 2,8-diazaspiro[4.5]decane-2-carboxylate (0.23 g, 27%).

The data for Intermediate 6 are in Table 2

Route 21

Typical Procedure for the Preparation of 1,2,4-oxadiazoles as Exemplified by the Preparation of Intermediate 126, (1R,3S)-3-(3-methyl-1,2,4-oxadiazol-5-yl)cyclopentanamine hydrochloride salt

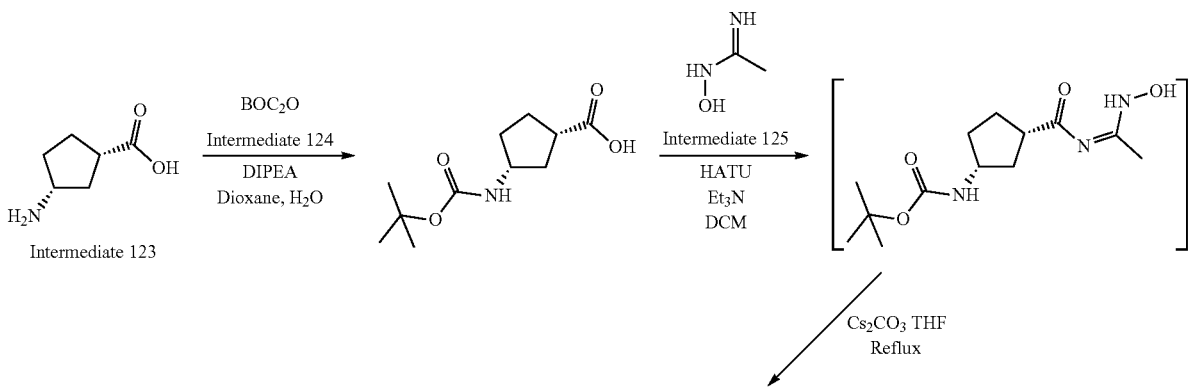

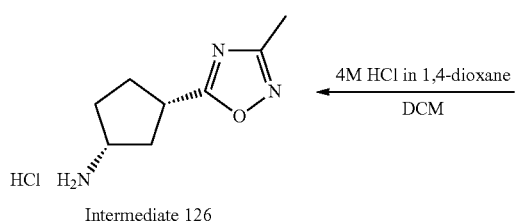

Intermediate 126

4M HCl in 1,4-dioxane
DCM

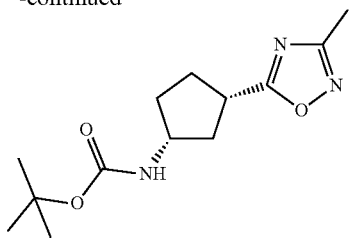

di-tert-Butyl dicarbonate (1.25 g, 5.75 mmol) and DIPEA (2.61 mL, 15.0 mmol) were added to a solution of (1S,3R)-3-aminocyclopentanecarboxylic acid (0.646 g, 5.0 mmol) in 1,4-dioxane (5 mL) and water (5 mL) and the resulting mixture was stirred at RT for 3 h. The reaction mixture was acidified to pH 2 using 1 M aqueous HCl and extracted with DCM (×4). The combined organic extracts were passed through a phase separator cartridge and concentrated in-vacuo to give (1S,3R)-3-[(tert-butoxycarbonyl)amino]cyclopentanecarboxylic acid (1.13 g, 99%).

$^1$H NMR (400 MHz, CDCl3) δ: 1.44 (s, 9H), 1.56-2.06 (m, 5H), 2.16-2.33 (m, 1H), 2.79-2.93 (m, 1H), 3.87-4.18 (m, 1H), 4.86 (br. s., 1H). One exchangeable proton not observed.

Triethylamine (2.1 mL, 15.0 mmol) and HATU (2.09 g, 5.5 mmol) were added to a solution of (1S,3R)-3-[(tert-butoxycarbonyl)amino]cyclopentanecarboxylic acid (1.13 g, 5.0 mmol) and N-hydroxyethanimidamide (0.37 g, 5.0 mmol) in DCM (25 mL) and the resulting mixture was stirred at RT overnight. The reaction mixture was diluted with sat. aq. NaHCO$_3$ and extracted with DCM (×3). The combined organic phases were passed through a phase separator cartridge and concentrated in-vacuo to give the crude uncyclised product, which was immediately dissolved in THF (50 mL), treated with Cs$_2$CO$_3$ (3.26 g, 10 mmol) and heated at reflux at 70° C. overnight. The reaction mixture was concentrated to remove the THF and the residue was partitioned between sat. aq. NaHCO$_3$ and EtOAc. The phases were separated and the aqueous phase was extracted further with EtOAc (×2). The combined organic phases were passed through a phase separator cartridge and concentrated. The crude residue was purified by flash chromatography (normal silica, mesh size: 60-120, 0% to 10% MeOH in DCM) to give tert-butyl [(1R,3S)-3-(3-methyl-1,2,4-oxadiazol-5-yl)cyclopentyl]carbamate (1.15 g, 87%).

LCMS (Method C): m/z 168 [M-BOC+H]$^+$ (ES$^+$), at 1.23 min, UV active.

tert-Butyl [(1R,3S)-3-(3-methyl-1,2,4-oxadiazol-5-yl)cyclopentyl]carbamate (1.15 g, 4.32 mmol) was dissolved in DCM (22 mL) and treated with 4.0 M HCl in 1,4-dioxane (5.4 mL, 21.6 mmol). The resulting solution was stirred at RT overnight, then diluted with diethyl ether to precipitate a solid that was collected by filtration to give (1R,3S)-3-(3-methyl-1,2,4-oxadiazol-5-yl)cyclopentanamine hydrochloride salt (0.655 g, 91%) as a white solid.

The data for Intermediate 126 are in Table 2.

Route 22

Typical Procedure for the Preparation of 1,2,4-oxadiazoles as Exemplified by the Preparation of Intermediate 131, 6-[3-(trifluoromethyl)-1,2,4-oxadiazol-5-yl]-2-azaspiro[3.3]heptane trifluoroacetic acid salt

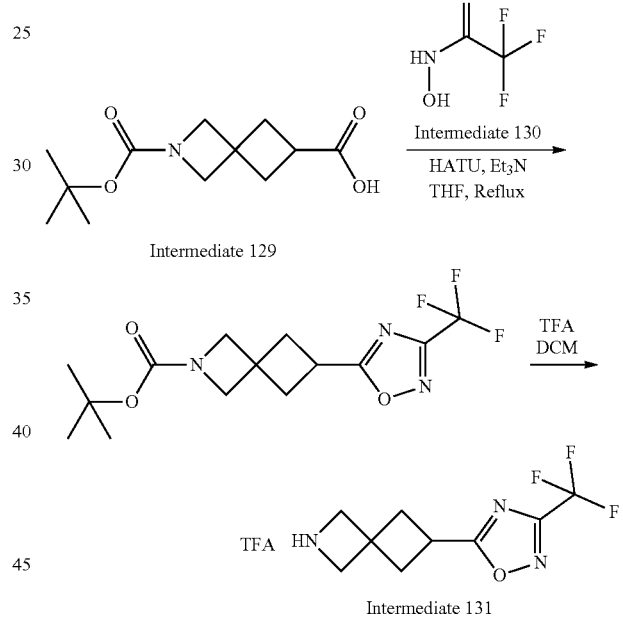

Triethylamine (1.67 mL, 12.0 mmol) and HATU (1.67 g, 4.4 mmol) were added to a solution of 2-(tert-butoxycarbonyl)-2-azaspiro[3.3]heptane-6-carboxylic acid (0.965 g, 4.0 mmol) and 2,2,2-trifluoro-N-hydroxyethanimidamide (0.512 g, 4.0 mmol) in THF (20 mL) and the resulting mixture was stirred at RT for 4 h then heated at reflux at 80° C. overnight. The reaction mixture was concentrated to remove the THF and the residue was partitioned between sat. aq. NaHCO$_3$ (containing some Na$_2$CO$_3$) and DCM. The phases were separated and the aqueous phase was extracted further with DCM (×2). The combined organic phases were passed through a phase separator cartridge and concentrated. The crude residue was purified by flash chromatography (normal silica, mesh size: 60-120, 0% to 10% MeOH in DCM) to give impure tert-butyl 6-[3-(trifluoromethyl)-1,2,4-oxadiazol-5-yl]-2-azaspiro[3.3]heptane-2-carboxylate (2.05 g, >100%).

LCMS (Method C): m/z 278 [M-$^t$Bu+H]$^+$ (ES$^+$), at 1.59 min, UV active.

tert-Butyl 6-[3-(trifluoromethyl)-1,2,4-oxadiazol-5-yl]-2-azaspiro[3.3]heptane-2-carboxylate (2.05 g crude, assumed 4.0 mmol) was dissolved in DCM (20 mL) and treated with TFA (5 mL). The resulting solution was stirred at RT overnight, then concentrated in-vacuo. The residue was re-dissolved in DCM and concentrated to give 6-[3-(trifluoromethyl)-1,2,4-oxadiazol-5-yl]-2-azaspiro[3.3]heptane trifluoroacetic acid salt (>100%).

The data for Intermediate 131 are in Table 2.

Route 23

Typical Procedure for the Preparation of 1,2,4-oxadiazoles as Exemplified by the Preparation of Intermediate 133, 2-(3-methyl-1,2,4-oxadiazol-5-yl)-6-azaspiro[3.4]octane hydrochloride salt

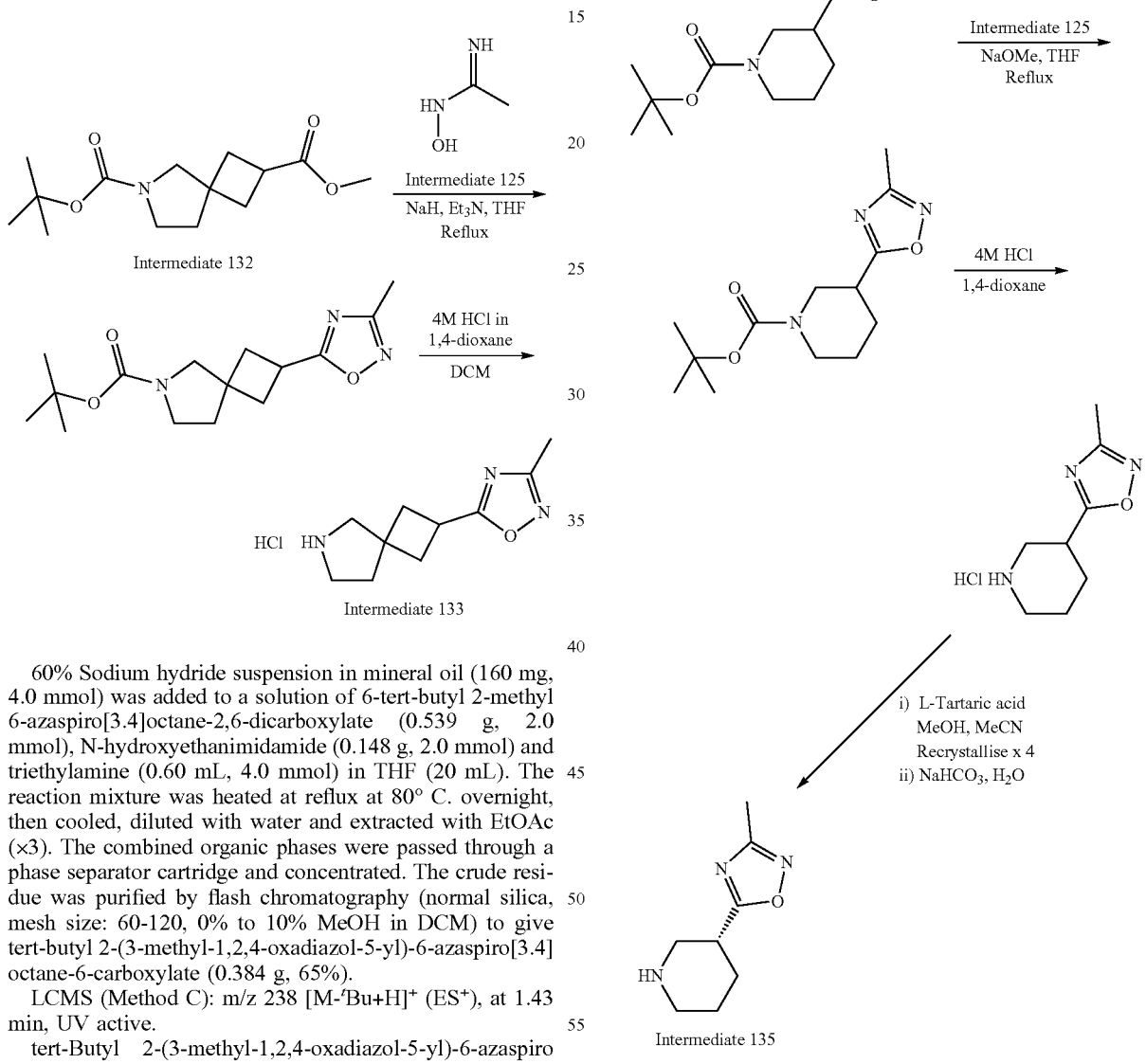

60% Sodium hydride suspension in mineral oil (160 mg, 4.0 mmol) was added to a solution of 6-tert-butyl 2-methyl 6-azaspiro[3.4]octane-2,6-dicarboxylate (0.539 g, 2.0 mmol), N-hydroxyethanimidamide (0.148 g, 2.0 mmol) and triethylamine (0.60 mL, 4.0 mmol) in THF (20 mL). The reaction mixture was heated at reflux at 80° C. overnight, then cooled, diluted with water and extracted with EtOAc (×3). The combined organic phases were passed through a phase separator cartridge and concentrated. The crude residue was purified by flash chromatography (normal silica, mesh size: 60-120, 0% to 10% MeOH in DCM) to give tert-butyl 2-(3-methyl-1,2,4-oxadiazol-5-yl)-6-azaspiro[3.4]octane-6-carboxylate (0.384 g, 65%).

LCMS (Method C): m/z 238 [M-$^t$Bu+H]$^+$ (ES$^+$), at 1.43 min, UV active.

tert-Butyl 2-(3-methyl-1,2,4-oxadiazol-5-yl)-6-azaspiro[3.4]octane-6-carboxylate (0.384 g, 1.3 mmol) was dissolved in DCM (13 mL) and treated with 4.0 M HCl in 1,4-dioxane (1.7 mL, 6.5 mmol). The resulting solution was stirred at RT overnight, then concentrated in-vacuo to give 2-(3-methyl-1,2,4-oxadiazol-5-yl)-6-azaspiro[3.4]octane hydrochloride salt (0.282 g, 94%).

The data for Intermediate 133 are in Table 2.

Route 24

Typical procedure for the preparation of 1,2,4-oxadiazoles as exemplified by the preparation of Intermediate 135, (3R)-3-(3-methyl-1,2,4-oxadiazol-5-yl)piperidine Triethylamine (36 mL, 254 mmol) and di-tert-butyl dicarbonate (41.6 mL, 191 mmol) were added to a solution of ethyl piperidine-3-carboxylate (20.0 g, 127 mmol) in DCM (150 mL), pre-cooled to 0° C. The resulting reaction mixture was stirred at 0° C. for 2 h. The solvents were then removed in-vacuo, the residue was partitioned between H$_2$O (400 mL) and EtOAc (250 mL) and the layers were separated. The aqueous layer was further extracted with EtOAc (2×250 mL), and the combined organic layers were dried (Na$_2$SO$_4$)

and the solvent was removed in-vacuo to give 1-tert-butyl 3-ethyl piperidine-1,3-dicarboxylate (32.0 g, 98%) as a liquid.

LCMS (Method I): m/z 258 (M+H)$^+$ (ES$^+$), at 4.93 min, UV active.

1-tert-Butyl 3-ethyl piperidine-1,3-dicarboxylate (30.0 g, 117.0 mmol) was dissolved in THF (200 mL) and treated with N-hydroxyethanimidamide (10.36 g, 140 mmol). The reaction mixture was stirred at 25° C. for 10 mins then sodium methoxide (12.6 g, 233 mmol) was added slowly. The resulting reaction mixture was stirred at 65° C. for 6 h, the solvents were removed in-vacuo, and the residue was partitioned between H$_2$O (400 mL) and EtOAc (300 mL). The layers were separated and the aqueous layer was further extracted with EtOAc (2×300 mL). The combined organic layers were dried (Na$_2$SO$_4$), the solvent was removed in-vacuo and residue was purified by column chromatography (Normal neutral activated alumina, 10% to 15% EtOAc in hexane) to give tert-butyl 3-(3-methyl-1,2,4-oxadiazol-5-yl) piperidine-1-carboxylate (15.80 g, 51%) as a liquid.

LCMS (Method F): m/z 268 (M+H)$^+$ (ES$^+$), at 2.12 min, UV active.

tert-Butyl 3-(3-methyl-1,2,4-oxadiazol-5-yl)piperidine-1-carboxylate (15.5 g, 58.0 mmol) was dissolved in 1,4-dioxane (40 mL) and cooled to 0° C. 4.0 M HCl in 1,4-dioxane (50 mL) was added dropwise and the resulting reaction mixture was stirred at 25° C. for 8 h. The solvents were removed in-vacuo, and residue was purified by triturating with diethyl ether (3×20 mL) to give 3-(3-methyl-1,2,4-oxadiazol-5-yl)piperidine hydrochloride salt (9.10 g, 77%) as a solid.

LCMS (Method I): m/z 168 (M+H)$^+$ (ES$^+$), at 2.61 min, UV active.

3-(3-Methyl-1,2,4-oxadiazol-5-yl)piperidine hydrochloride salt (5.0 g, 29.9 mmol) was dissolved in a mixture of acetonitrile (250 mL) and MeOH (100 mL). L-Tartaric acid (4.49 g, 29.9 mmol) was added and the mixture was heated at reflux for 15 mins, then cooled to RT. Acetonitrile (250 mL) was added and the mixture was stirred at 25° C. for 16 h. The precipitated amine salt was removed by filtration, washed with a solution of MeOH (50 mL) in acetonitrile (125 mL), and dried. The solid was recrystallized 4 times from a solution of MeOH (50 mL) in acetonitrile 125 mL, isolated by filtration, and dried to give (3R)-3-(3-methyl-1,2,4-oxadiazol-5-yl)piperidine L-tartaric acid salt. The salt was dissolved in sat. aq. NaHCO$_3$ and extracted with a 10% solution of MeOH in DCM (×3). The combined organic layers were dried (Na$_2$SO$_4$) and the solvent was removed in-vacuo to give (3R)-3-(3-methyl-1,2,4-oxadiazol-5-yl)piperidine (980 mg, 20%) as a liquid.

The data for Intermediate 135 are in Table 2.

Route 25

Typical Procedure for the Preparation of 1,2,4-oxadiazoles as Exemplified by the Preparation of Intermediate 137, 1-[2-(3-methyl-1,2,4-oxadiazol-5-yl)cyclopropyl]methanamine hydrochloride salt

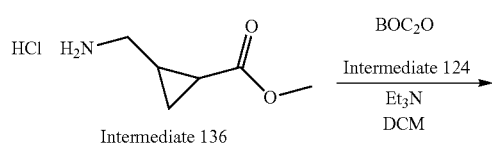

Intermediate 136

BOC$_2$O
Intermediate 124
Et$_3$N
DCM

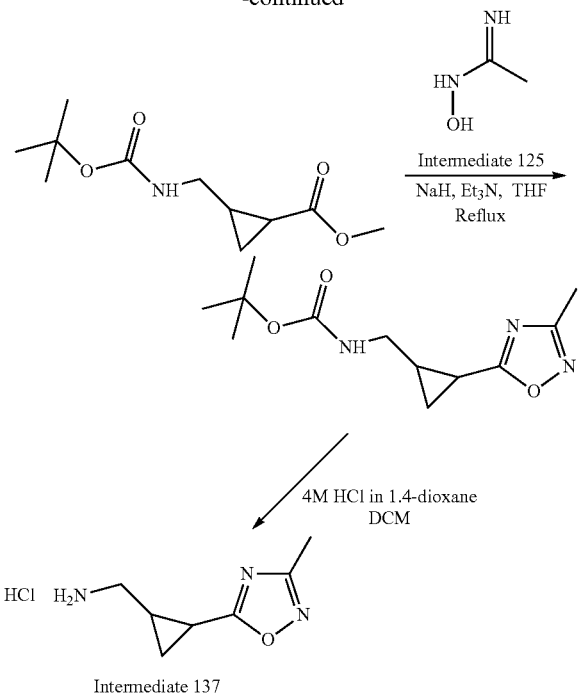

Intermediate 137

Triethylamine (1.7 mL, 12.0 mmol) and di-tert-butyl dicarbonate (0.917 g, 4.2 mmol) were added to a solution of methyl 2-(aminomethyl)cyclopropanecarboxylate hydrochloride salt (0.497 g, 3.0 mmol) in DCM (30 mL). The mixture was stirred at RT overnight, then diluted with sat. aq. NaHCO$_3$ and extracted with EtOAc (×3). The combined organic phases were passed through a phase separator cartridge and concentrated to give methyl 2-{[(tert-butoxycarbonyl)amino]methyl}cyclopropanecarboxylate (0.795 g, >100%).

$^1$H NMR (400 MHz, CDCl3) δ: 0.80-0.89 (m, 1H), 1.16-1.24 (m, 1H), 1.45 (s, 9H), 1.51-1.65 (m, 2H), 2.96-3.09 (m, 1H), 3.11-3.23 (m, 1H), 3.68 (s, 3H), 4.64 (br. s., 1H).

2-{[(tert-Butoxycarbonyl)amino] methyl}cyclopropanecarboxylate (0.688 g, 3.0 mmol), N-hydroxyethanimidamide (0.222 g, 3.0 mmol) and triethylamine (0.90 mL, 6.0 mmol) were dissolved in THF (30 mL) and treated with 60% sodium hydride suspension in mineral oil (0.24 g, 6.0 mmol). The resulting mixture was heated at reflux overnight, then cooled, diluted with water and extracted with EtOAc (×3). The combined organic phases were passed through a phase separator cartridge and concentrated. The crude residue was purified by flash chromatography (normal silica, mesh size: 60-120, 0% to 10% MeOH in DCM) to give tert-butyl {[2-(3-methyl-1,2,4-oxadiazol-5-yl)cyclopropyl]methyl}carbamate (0.378 g, 50%).

LCMS (Method C): m/z 198 [M-$^t$Bu+H]$^+$ (ES$^+$), at 1.19 min, UV active.

tert-Butyl {[2-(3-methyl-1,2,4-oxadiazol-5-yl)cyclopropyl]methyl}carbamate (0.378 g, 1.5 mmol) was dissolved in DCM (15 mL) and treated with 4.0 M HCl in 1,4-dioxane (1.9 mL, 7.5 mmol). The resulting solution was stirred at RT overnight, then more 4.0 M HCl in 1,4-dioxane (0.95 mL, 3.8 mmol) was added and the mixture was stirred over an additional night. The mixture was then concentrated in-vacuo and the residue triturated with diethyl ether to afford a solid that was removed by filtration to give 1-[2-(3-methyl-1,2,4-oxadiazol-5-yl)cyclopropyl]methanamine hydrochloride salt (0.134 g, 47%).

The data for Intermediate 137 are in Table 2.

General Synthetic Procedures:

Route a

Typical procedure for the preparation of cyclohexanes via Intermediate 32 and Intermediate 44 as exemplified by the preparation of Example 3-19, ethyl 4-[4-(5-methoxypyridin-2-yl)-4-cyanocyclohexyl]-1,4-diazepane-1-carboxylate

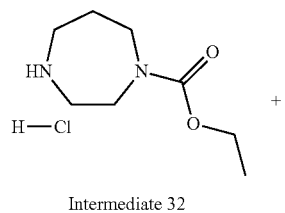

Intermediate 32

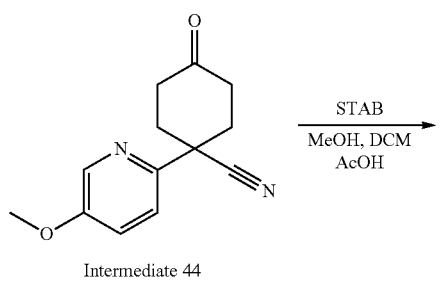

Intermediate 44

1-(5-Methoxypyridin-2-yl)-4-oxocyclohexanecarbonitrile (0.20 g, 0.87 mmol) and ethyl 1,4-diazepane-1-carboxylate hydrochloride (0.18 g, 1.01 mmol) were dissolved in DCM (20 mL) and MeOH (2 mL) and acetic acid (5 drops) were added. The reaction mixture was stirred at rt for 4 h and then cooled to 0° C. STAB (0.73 g, 3.47 mmol) was added portionwise and the reaction mixture stirred at rt overnight. NaHCO₃ (saturated aq., 40 mL) was added, and the reaction mixture was stirred at rt for 1 h, then extracted with DCM (4×40 mL). The organic layers were combined and dried (MgSO₄). The solvents were removed in vacuo to and the residue was purified by column chromatography (normal phase, [Biotage SNAP cartridge KP-sil 25 g, 40-63 ⊐m, 60 Å, 25 mL per min, gradient 0% to 10% MeOH in DCM]). The residue further purified by Prep HPLC [reverse phase HPLC (X-Bridge, 250×19 mm, 5 um, 19 mL per min, gradient 35% (over 25 min) 0.1% NH₃ in MeCN/water] to give ethyl 4-[4-(5-methoxypyridin-2-yl)-4-cyanocyclohexyl]-1,4-diazepane-1-carboxylate, Example 3-19 isomer 1 (0.05 g, 14.9%) as a pale yellow gum and ethyl 4-[4-(5-methoxypyridin-2-yl)-4-cyanocyclohexyl]-1,4-diazepane-1-carboxylate, Example 3-19 isomer 2 (0.03 g, 8.9%) as a pale yellow gum.

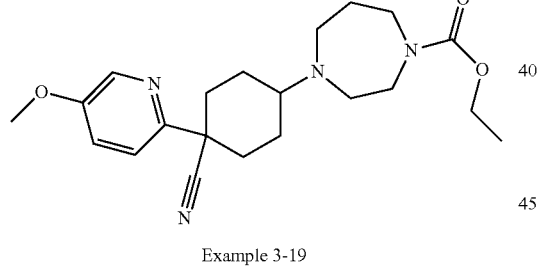

Example 3-19

The data for Example 3-19 Isomer 2 are in Table 3.

Route b

Typical Procedure for the Preparation of Substituted Cyclohexyl Derivatives Via Intermediate 15 and Intermediate 28 as Exemplified by the Preparation of Example 1-15, ethyl {(3S)-1-[trans-4-(5-chloropyridin-2-yl)-4-cyanocyclohexyl]pyrrolidin-3-yl}carbamate

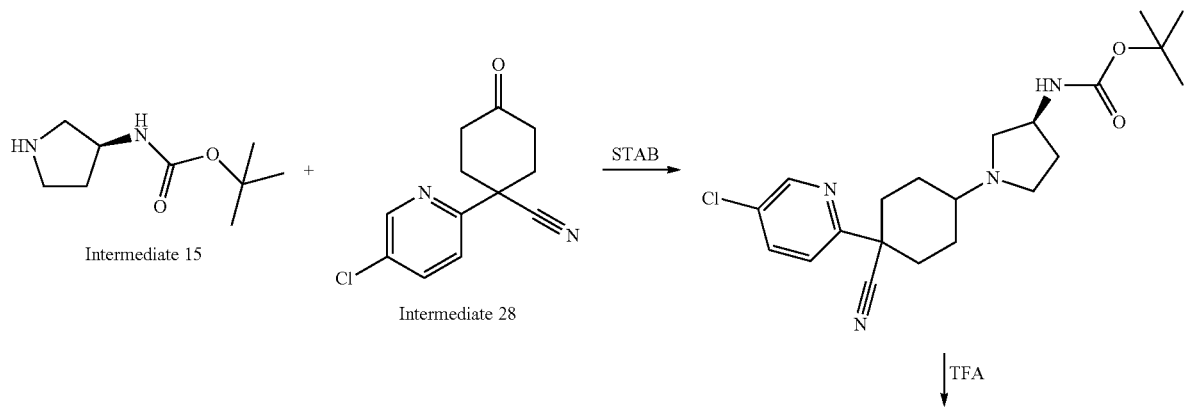

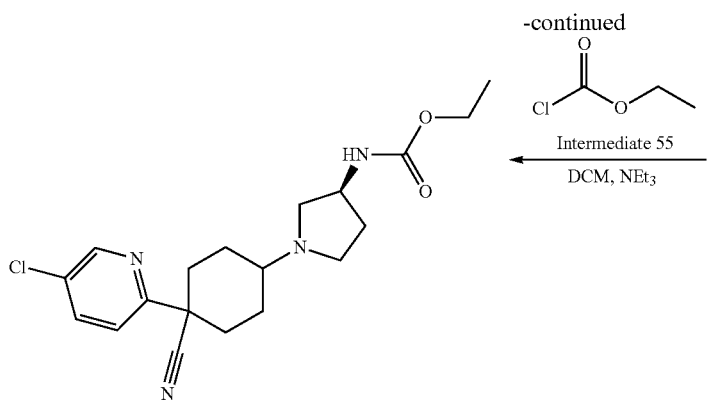

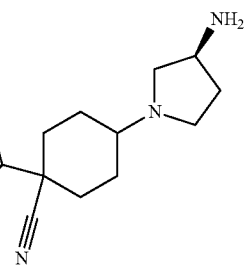

Example 1-15 tert-Butyl (3S)-pyrrolidin-3-ylcarbamate (0.75 mL, 2.0 mmol) and 1-(5-chloropyridin-2-yl)-4-oxocyclohexanecarbonitrile (0.83 mL, 2.2 mmol) were dissolved in DCM (7.5 mL), and acetic acid (5-10 drops) was added. The reaction mixture was stirred at rt for 4 h and then cooled to 0° C. STAB (0.64 g, 3.0 mmol) was added portionwise and the reaction mixture stirred at rt overnight. NaHCO$_3$ (saturated aq., 30 mL) was added, and the reaction mixture was stirred at rt for 1 h, then extracted with DCM (4×30 mL) and the organic layers were combined and dried (MgSO$_4$). The solvents were removed in vacuo to give a crude mixture of tert-butyl {(3S)-1-[4-(5-chloropyridin-2-yl)-4-cyanocyclohexyl]pyrrolidin-3-yl}carbamate which was used directly without further purification. The residue was dissolved in DCM (10 mL) and cooled to 0° C., trifluoroacetic acid (4 mL) was added and the reaction mixture was stirred at rt overnight. The solvents were removed in vacuo, the residue was dissolved in toluene (20 mL), and then concentrated in vacuo (three times), to give the trifluoroacetic acid salt of a mixture of 4-[(3S)-3-aminopyrrolidin-1-yl]-1-(5-chloropyridin-2-yl)cyclohexanecarbonitrile diastereomers which were used directly without further purification. A portion of the residue (assumed 0.75 mmol) was dissolved in DCM (8 mL) and NEt$_3$ (0.52 mL, 3.75 mmol) was added, the reaction mixture was cooled to 0° C. and ethyl chloroformate (0.11 mL, 1.13 mmol) was added. The reaction mixture was stirred at rt overnight and then partitioned between DCM (30 mL) and sat. NaHCO$_3$ sol. (20 mL), the aqueous layer was extracted with DCM (3×30 mL) and the organic layers were combined washed with brine (25 mL) and dried (MgSO$_4$). The residue was purified by column chromatography (normal phase, [Biotage SNAP cartridge KP-sil 50 g, 40-63 ⊐m, 60 Å, 40 mL per min, gradient 0% to 10% MeOH in DCM]) to give ethyl {(3S)-1-[trans-4-(5-chloropyridin-2-yl)-4-cyanocyclohexyl]pyrrolidin-3-yl}carbamate, which was further purified by preparative HPLC [(reverse phase X-Bridge-C18, 250×19×5 μm, Flow rate: 19 mL per min, gradient 50% to 100% (over 16 min) then 50% (2 min) 0.1% NH$_3$ in MeCN/water, Wavelength-202 nm] to give ethyl {(3S)-1-[cis-4-(5-chloropyridin-2-yl)-4-cyanocyclohexyl]pyrrolidin-3-yl}carbamate, Example 1-15 isomer 1 (104 mg, 36.7%) as a colourless solid and ethyl {(3S)-1-[trans-4-(5-chloropyridin-2-yl)-4-cyanocyclohexyl]pyrrolidin-3-yl}carbamate, Example 1-15 isomer 2 (37 mg, 13.0%) as a colourless gum.

The data for Example 1-15 isomer 1 and isomer 2 are in Table 3 below.

The absolute stereochemistry of isomer 1 was determined by small molecule x-ray crystallography. Isomers can also be separated by preparative TLC.

Route c

Typical Procedure for the Preparation of Substituted Cyclohexyl Derivatives Via Intermediate 13 and Intermediate 20 as Exemplified by the Preparation of Example 1-3, ethyl {(3S)-1-[4-cyano-4-(3-fluorophenyl)cyclohexyl]pyrrolidin-3-yl}carbamate

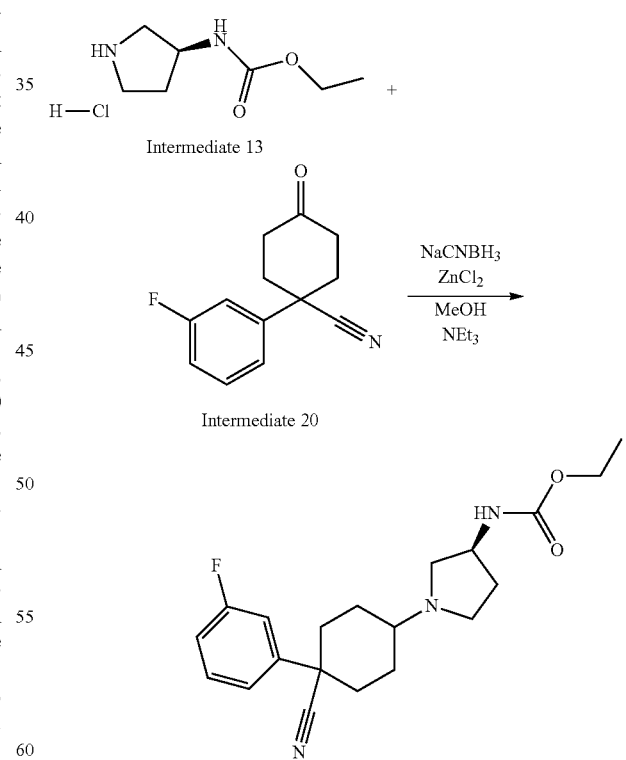

Example 1-3

1-(3-Fluorophenyl)-4-oxocyclohexanecarbonitrile (200 mg, 0.92 mmol) and ethyl (3S)-pyrrolidin-3-ylcarbamate hydrochloride (160 mg, 1.01 mmol) were dissolved in MeOH (6.5 mL) and triethylamine (0.64 mL, 4.60 mmol)

were added at rt under $N_2$. ZnCl2 (6.2 mg, 0.046 mmol) was added and the reaction mixture was heated at 55° C. for 1 h. The reaction mixture was cooled to 0° C. and sodium cyanoborohydride (289 mg, 4.60 mmol) was added in three portions. The reaction mixture was then warmed to rt and stirred for at rt for 14 h. The reaction mixture was partitioned between $H_2O$ (100 mL) and EtOAc (100 mL), the aqueous layer was further extracted with EtOAc (2×100 mL) and the organic layers were combined and dried ($Na_2SO_4$). Solvent was removed in vacuo and the residue was purified by preparative TLC to give (ethyl {(3S)-1-[4-cyano-4-(3-fluorophenyl)cyclohexyl]pyrrolidin-3-yl}carbamate, Example 1-3 isomer 1 (95 mg, 28.8%) as a colourless gum and ethyl {(3S)-1-[4-cyano-4-(3-fluorophenyl)cyclo hexyl]pyrrolidin-3-yl}carbamate, Example 1-3 isomer 2 (55 mg, 16.6%) as a colourless gum.

The data for Example 1-3 isomer 2 are in Table 3.

Route d

Typical Procedure for the Preparation of Cyclohexanes Via Intermediate 31 and Intermediate 12 as Exemplified by the Preparation of Example 3-28, methyl 4-(4-cyano-4-phenylcyclohexyl)-1,4-diazepane-1-carboxylate 4-Oxo-1-phenyl cyclohexanecarbonitrile (10.0 g, 50.2 mmol), tert-butyl 1,4-diazepane-1-carboxylate (12.0 g, 60.3 mmol), and AcOH (3.44 mL, 60.2 mmol) were dissolved in DCE (100 mL) and heated at 80° C. for 2 h. STAB (16.0 g, 75.4 mmol) was added portionwise and the reaction mixture heated at reflux for 16 h. The reaction mixture was cooled to rt and partitioned between $H_2O$ (100 mL) and DCM (100 mL). The aqueous layer was further extracted with DCM (2×50 mL) and the organic extracts were combined and dried ($Na_2SO_4$). The solvent was removed in vacuo to give tert-butyl 4-(4-cyano-4-phenylcyclohexyl)-1,4-diazepane-1-carboxylate (5.50 g, 28.6%) as a yellow gum.

Mass: (ESI +ve): 384 $(M+H)^+$ tert-Butyl 4-(4-cyano-4-phenylcyclohexyl)-1,4-diazepane-1-carboxylate (5.50 g, 14.3 mmol) was dissolved in 1,4-dioxane (50 mL) and HCl in 1,4-dioxane (50 mL, 1.0M) was added. The reaction mixture was stirred at rt for 2 h. The solvent was removed in vacuo, and the residue was purified by triturating with diethyl ether (2×10 mL) to give 4-(1,4-diazepan-1-yl)-1-phenylcyclohexanecarbonitrile hydrochloride (1.18 g, 25.7%) as a white solid.

Mass: (ESI +ve): 284 $(M+H)^+$ 4-(1,4-Diazepan-1-yl)-1-phenylcyclohexanecarbonitrile hydrochloride (0.50 g, 1.56 mmol) and $NEt_3$ (0.3 mL, 2.12

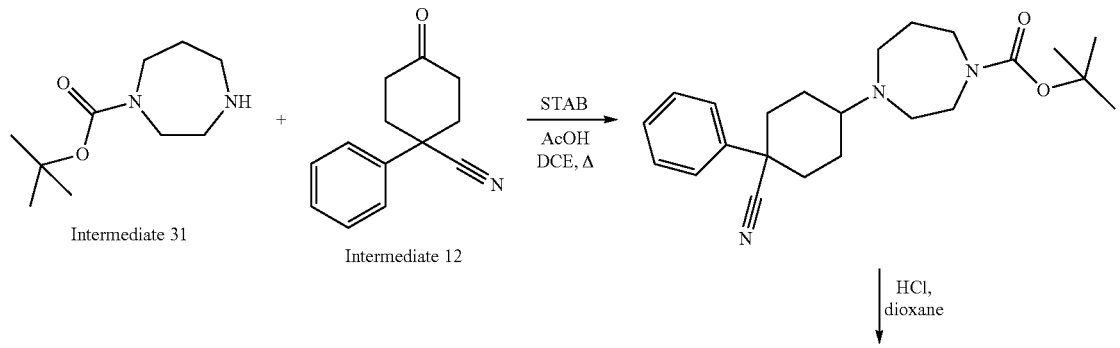

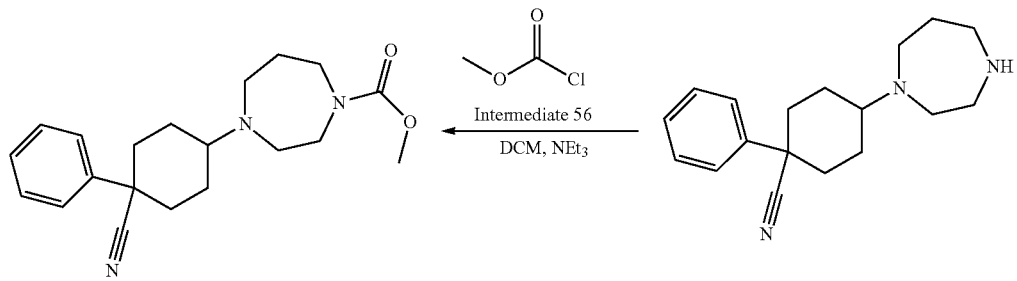

Example 3-28 mmol) were dissolved in DCM (5.0 mL) and cooled to 0° C. A solution of methylchloroformate (0.17 g, 2.12 mmol) in DCM (5.0 mL) was added and the reaction was stirred at rt for 1 h. The solvent was removed in vacuo, and the residue was purified by by column chromatography (normal phase, silica, 60-120 mesh, gradient 0% to 5% MeOH in DCM) to give methyl 4-(4-cyano-4-phenylcyclohexyl)-1,4-diazepane-1-carboxylate, Example 3-28 (0.035 g, 6.6%) as a pale yellow gum.

The data for Example 3-28 are in Table 3 below.
Route e

Typical Procedure for the Preparation of Cyclohexanes Via Intermediate 31 and Intermediate 44 as Exemplified by the Preparation of Example 3-31, prop-2-yn-1-yl 4-[4-cyano-4-(5-methoxypyridin-2-yl)cyclohexyl]-1,4-diazepane-1-carboxylate LCMS (Method C): m/z 415 (M+H)+ (ES+), at 2.59 min.

tert-Butyl 4-[4-cyano-4-(5-methoxypyridin-2-yl)cyclohexyl]-1,4-diazepane-1-carboxylate (800 mg, 1.93 mmol) was dissolved in 1,4-dioxane (5.0 mL) and HCl in 1,4-dioxane (15 mL, 1.0M) was added. The reaction mixture was stirred at rt for 16 h. The solvent was removed in vacuo, and the residue was purified by triturating with diethyl ether (3×10 mL) to give 4-(1,4-diazepan-1-yl)-1-(5-methoxypyridin-2-yl)cyclohexanecarbonitrile (660 mg, 97.6%) as a white solid.

LCMS (Method C): m/z 315 (M+H)+ (ES+), at 1.98 min.

4-(1,4-Diazepan-1-yl)-1-(5-methoxypyridin-2-yl)cyclohexanecarbonitrile (300 mg, 0.86 mmol), prop-2-yn-1-ol (0.1 mL, 1.55 mmol) and NEt3 (0.5 mL, 3.43 mmol) were dissolved in toluene (5 mL) and stirred at 0° C. for 1 h. Triphosgene (306 mg, 1.03 mmol) was added portionwise and the reaction mixture was stirred at 25° C. for 1 h. The solvent was removed in vacuo, and the residue was parti-

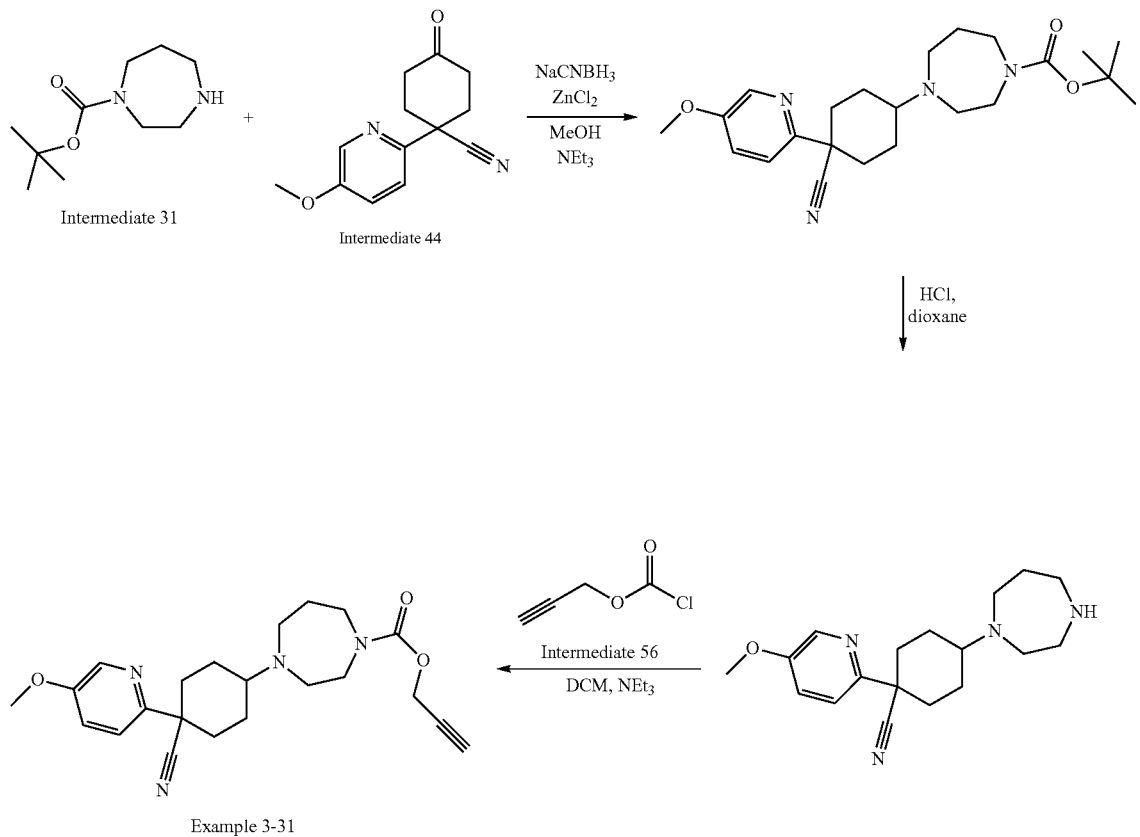

Example 3-31

1-(5-Methoxypyridin-2-yl)-4-oxocyclohexanecarbonitrile (632 mg, 2.75 mmol), tert-butyl *1,4-diazepane-1-carboxylate (500 mg, 2.50 mmol), ZnCl2 (102 mg, 0.750 mmol) and NEt3 (1.8 mL, 12.5 mmol) were dissolved in MeOH (15 mL) and stirred at 50° C. for 1 h. NaBH3CN (630 mg., 4.50 mmol) was added portionwise at 0° C. and the reaction mixture was stirred at 50° C. for 7 h. The reaction mixture was partitioned between H2O (80 mL) and EtOAc (50 mL), aqueous layer was further extracted with EtOAc (2×50 mL) and the organic layers were combined and dried (Na2SO4). The solvent was removed in vacuo to give tert-butyl 4-[4-cyano-4-(5-methoxypyridin-2-yl)cyclohexyl]-1,4-diazepane-1-carboxylate (800 mg, 77.3%) as a pale yellow solid.

tioned between H2O (50 mL) and EtOAc (30 mL). The aqueous layer was extracted with EtOAc (2×30 mL) and the organic layers were combined and dried (Na2SO4). The solvent was removed in vacuo and crude reaction mixture was purified by Prep HPLC [reverse phase HPLC (X-Bridge, 250×19 mm, 5 um, 19 mL per min, gradient 35% (over 25 min) 0.1% NH3 in MeCN/water] to give prop-2-yn-1-yl 4-[4-cyano-4-(5-methoxypyridin-2-yl)cyclohexyl]-1,4-diazepane-1-carboxylate, Example 3-31 isomer 1 (9 mg, 2.6%) as a yellow gum and prop-2-yn-1-yl 4-[4-cyano-4-(5-methoxypyridin-2-yl)cyclohexyl]-1,4-diazepane-1-carboxylate, Example 3-31 isomer 2 (10 mg, 3.0%) as a yellow gum.

The data for Example 3-31 isomer 1 are in Table 3 below.

Route f

Typical Procedure for the Preparation of Imidazoles Via Intermediate 32 as Exemplified by the Preparation of Example 5-1, ethyl 4-[4-(4-ethyl-5-methyl-1H-imidazol-2-yl)cyclohexyl]-1,4-diazepane-1-carboxylate solvents were removed in vacuo, and the residue was purified by tituration with diethyl ether (3×10 mL) to give 4-[4-(ethoxycarbonyl)-1,4-diazepan-1-yl]cyclohexanecarboxylic acid lithium salt (750 mg, 82.0%) as a white solid.

LCMS (Method C): m/z 299 (M+H)⁺ (ES⁺), at 1.90 min.

4-[4-(Ethoxycarbonyl)-1,4-diazepan-1-yl]cyclohexanecarboxylic acid lithium salt (400 mg, 1.34 mmol), HATU (611 mg, 1.61 mmol), DIPEA (0.7 mL, 4.02 mmol) and

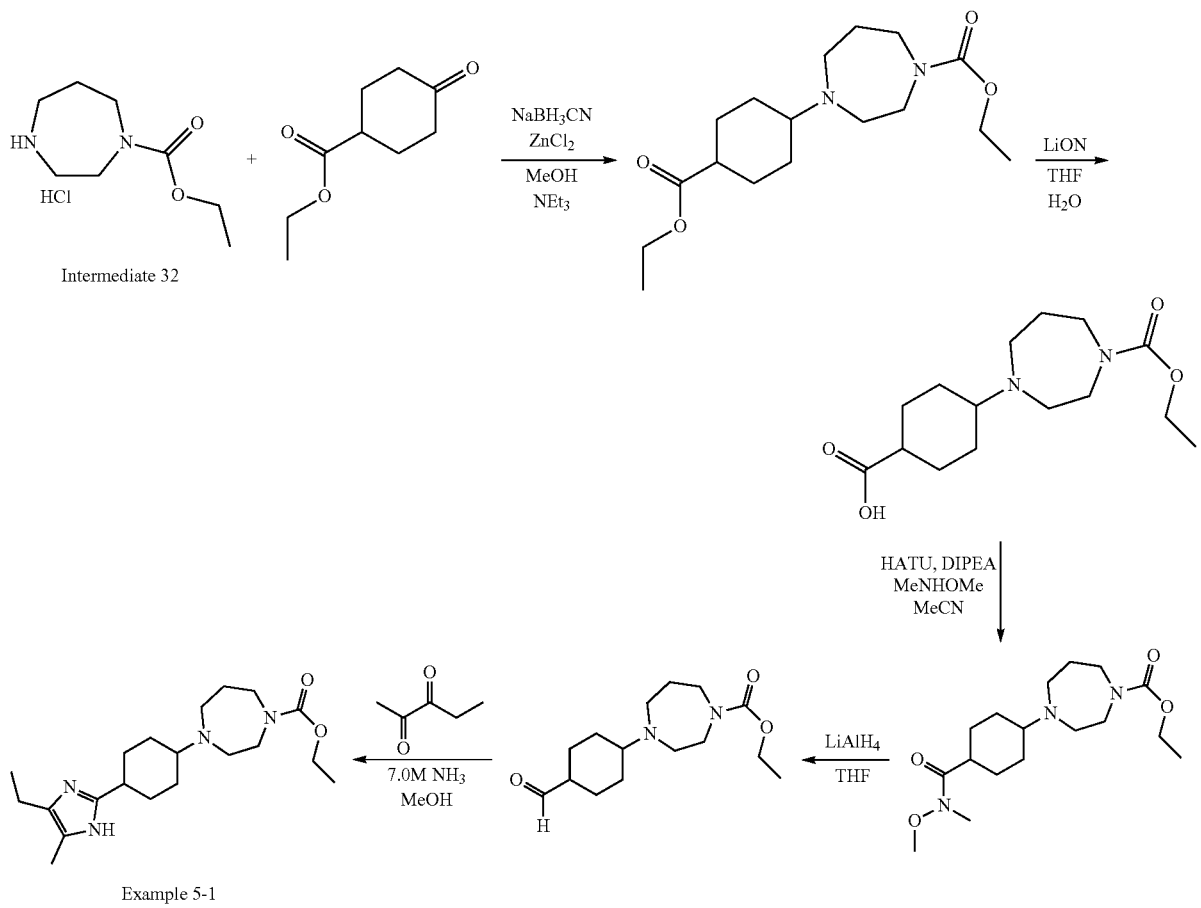

Ethyl 1,4-diazepane-1-carboxylate hydrochloride (2.0 g, 9.66 mmol), ethyl 4-oxocyclohexanecarboxylate (1.80 g, 10.6 mmol), ZnCl₂ (394 mg, 2.90 mmol) and NEt₃ (6.9 mL, 48.3 mmol) were dissolved in MeOH (20 mL) and stirred at 50° C. for 1 h. The reaction mixture was cooled to 0° C. and NaBH₃CN (2.43 g., 38.6 mmol) was added portionwise. The reaction mixture was stirred at 50° C. for 7 h and then the solvents were removed in vacuo, and the residue was partitioned between H₂O (100 mL) and EtOAc (50 mL). The aqueous layer was extracted with EtOAc (2×50 mL) and the organic layers were combined and dried (Na₂SO₄). The solvents were removed in vacuo and the residue was purified by column chromatography (normal silica, mesh size: 60-120, 0% to 1.5% MeOH in DCM) to give ethyl 4-[4-(ethoxycarbonyl)-cyclohexyl]-1,4-diazepane-1-carboxylate (1.80 g, 58.0%) as a pale yellow gum.

LCMS (Method C): m/z 327 (M+H)⁺ (ES⁺), at 2.66 min.

Ethyl 4-[4-(ethoxycarbonyl)cyclohexyl]-1,4-diazepane-1-carboxylate (1.0 g, 3.07 mmol), LiOH (211 mg, 9.20 mmol) and H₂O (10 mL) were dissolved in THF (10 mL) The reaction mixture was stirred at 80° C. for 16 h. The N,O-dimethylhydroxylaminehydrochloride (156 mg, 1.61 mmol) were dissolved in acetonitrile (10.0 mL). The reaction mixture was stirred at 25° C. for 4 hrs and solvent was removed in vacuo, the residue was partitioned between H₂O (50 mL) and EtOAc (30 mL), aqueous layer extracted with EtOAc (2×30 mL), organic layers were combined and dried (Na₂SO₄). The solvents were removed in vacuo and the residue was purified by column chromatography (normal silica, mesh size: 60-120, 0% to 1.5% Methanol in DCM) to give ethyl 4-{4-[methoxy(methyl)carbamoyl]cyclohexyl}-1,4-diazepane-1-carboxylate (300 mg, 66.0%) as a yellow gum.

LCMS (Method C): m/z 342 (M+H)⁺ (ES⁺), at 2.31 min.

Ethyl 4-{4-[methoxy(methyl)carbamoyl]cyclohexyl}-1,4-diazepane-1-carboxylate (200 mg, 0.590 mmol) was dissolved in THF (5 mL) and cooled to 0° C. for 15 min, LiAlH₄ (1.2 mL, 1.2 mmol, 1.0M sol. in THF) was added slowly and the reaction mixture was stirred at 10° C. for 1 h. The reaction was then quenched with a saturated solution of Na₂SO₄ (15 mL) diluted with H₂O (30 mL), extracted with EtOAc (2×20 mL), and the organic layers were combined and dried (Na$_2$SO$_4$). The solvents were removed in vacuo, to ethyl 4-(4-formylcyclohexyl)-1,4-diazepane-1-carboxylate (110 mg, 66.0%) as a pale yellow gum.

LCMS (Method C): m/z 283 (M+H)$^+$ (ES$^+$), at 2.24 min.

Ethyl 4-(4-formylcyclohexyl)-1,4-diazepane-1-carboxylate (100 mg, 0.354 mmol) and pentane-2,3-dione (42 mg, 0.425 mmol) were dissolved in MeOH (2 mL) and 7 M methanolic ammonia (10 mL) was added. The reaction mixture was degassed with nitrogen and heated at 50° C. for 1 h. The solvents were removed in vacuo and the residue was purified by Prep HPLC [reverse phase HPLC (UPLC BEH-C18, 50×2.1 mm, 1.7 um, 0.4 mL per min, gradient 10% to 90% (over 3 min), 100% (1 min) then 10% (over 1 min), 0.1% NH$_3$ in MeCN/water] to give ethyl 4-[4-(4-ethyl-5-methyl-1H-imidazol-2-yl)cyclohexyl]-1,4-diazepane-1-carboxylate, Example 5-1 isomer 1 (8 mg, 6.2%) as a colourless gum and ethyl 4-[4-(4-ethyl-5-methyl-1H-imidazol-2-yl)cyclohexyl]-1,4-diazepane-1-carboxylate, Example 5-1 isomer 2 (10 mg, 8.0%) as a colourless gum.

The data for Example 5-1 isomer 2 are in Table 3 below

Route g

Typical Procedure for the Preparation of Pyrrolidines Via Sodium Cyanoborohydride Mediated Reductive Amination, Exemplified by Example 2-19, ethyl [(3S)-1-(5'-methoxy-2'-oxo-1',2'-dihydrospiro[cyclohexane-1,3'-pyrrolo[2,3-c]pyridin]-4-yl)pyrrolidin-3-yl]carbamate Isomer 2

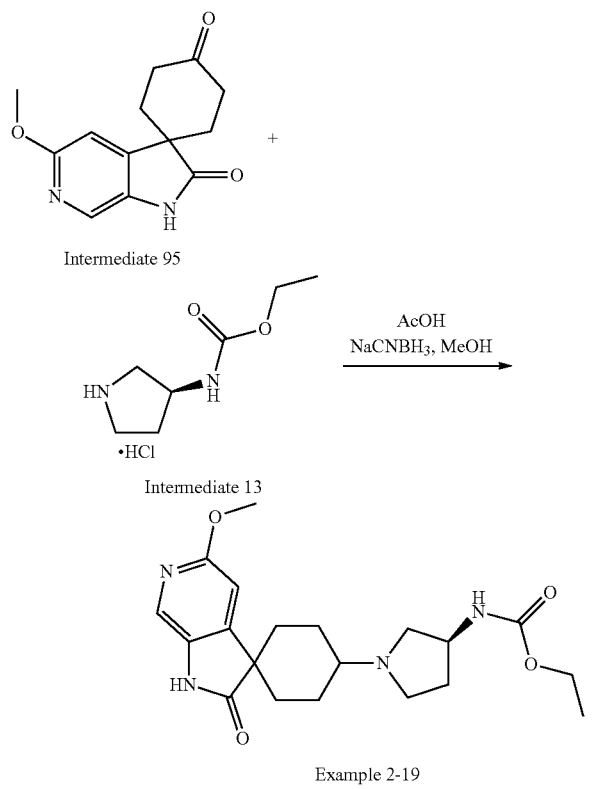

To a solution of 5'-methoxyspiro[cyclohexane-1,3'-pyrrolo[2,3-c]pyridine]-2',4(1'H)-dione (343 mg, 1.4 mmol) and ethyl (S)-pyrrolidin-3-yl-carbamate hydrochloride (270 mg, 1.4 mmol) in MeOH (5 mL), catalytic acetic acid was added and the mixture stirred at rt for 1 h. After cooling to 0° C., NaCNBH$_3$ (262 mg, 4.2 mmol) was added portionwise and stirred at rt for 4 h. The solvent was removed in vacuo before addition of water (20 mL) and DCM (3×30 mL) and the layers separated. Combined organics were washed with brine, dried (Na$_2$SO$_4$) and concentrated in vacuo. The residue was purified by prep-HPLC (reverse phase, X BRIDGE SHIELD, 19×250 mm, 5p, gradient 10% to 95% MeCN in water containing 0.1% NH$_4$OH, 210 nm to yield ethyl [(3S)-1-(5'-methoxy-2'-oxo-1',2'-dihydrospiro[cyclohexane-1,3'-pyrrolo[2,3-c]pyridin]-4-yl)pyrrolidin-3-yl]carbamate, Example 2-19 isomer 1 (77 mg, 14%) as a white solid and ethyl [(3S)-1-(5'-methoxy-2'-oxo-1',2'-dihydrospiro[cyclohexane-1,3'-pyrrolo[2,3-c]pyridin]-4-yl)pyrrolidin-3-yl]carbamate, Example 2-19 isomer 2 (38 mg, 7%) as a white solid.

The data for Example 2-19 isomer 1 are in Table 3 below.

Route h

Typical Procedure for the Preparation of Ethyl Carbamates, Exemplified by the Preparation of Example 7-2, ethyl {[1-(2'-oxo-1',2'-dihydrospiro[cyclohexane-1,3'-indol]-4-yl)piperidin-4-yl]methyl}carbamate

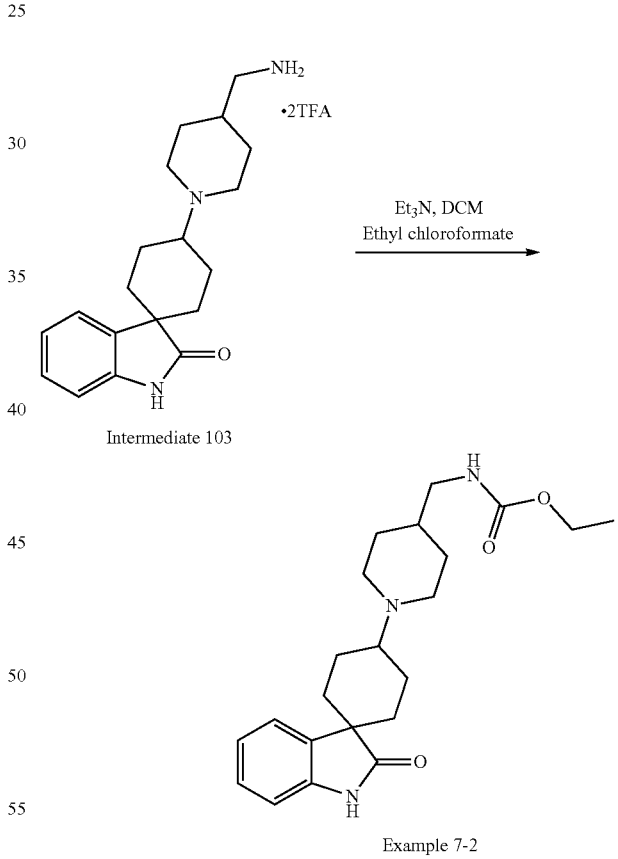

To a solution of 4-(4-(aminomethyl)piperidin-1-yl)spiro[cyclohexane-1,3'-indolin]-2'-one di-TFA salt (200 mg, 0.37 mmol), Et$_3$N (207 mg, 2.05 mmol) in DCM (10 mL) at 0° C. was added ethyl chloroformate (103 mg, 0.95 mmol) and the reaction mixture stirred at rt for 1 h. The mixture was partitioned between cold H$_2$O (25 mL) and EtOAc (3×15 mL), combined organics dried (Na$_2$SO$_4$) and the solvent removed in vacuo. The crude compound was purified by Prep HPLC (X-bridge-C18, 150×30 mm, 19 mL per min, gradient 38% to 62% (over 13 min) then 100% (2 min) 0.1% NH₃ in MeCN/water] to give ethyl ((1-(2'-oxospiro[cyclohexane-1,3'-indolin]-4-yl)piperidin-4-yl)methyl)carbamate Example 7-2 isomer 1 (21 mg, 15%) as a colourless gum and ethyl ((1-(2'-oxospiro[cyclohexane-1,3'-indolin]-4-yl)piperidin-4-yl)methyl)carbamate Example 7-2 isomer 2 (4 mg, 3%) as a colourless gum.

The data for Example 7-2 isomer 1 and isomer 2 are in Table 3 below.

Route i

Typical Procedure for the Preparation of 1,4-diazepanes, Exemplified by the Preparation of Example 4-17, ethyl 4-(5'-methoxy-2'-oxo-1',2'-dihydrospiro-[cyclohexane-1,3'-pyrrolo[2,3-b]pyridin]-4-yl)-1,4-diazepane-1-carboxylate

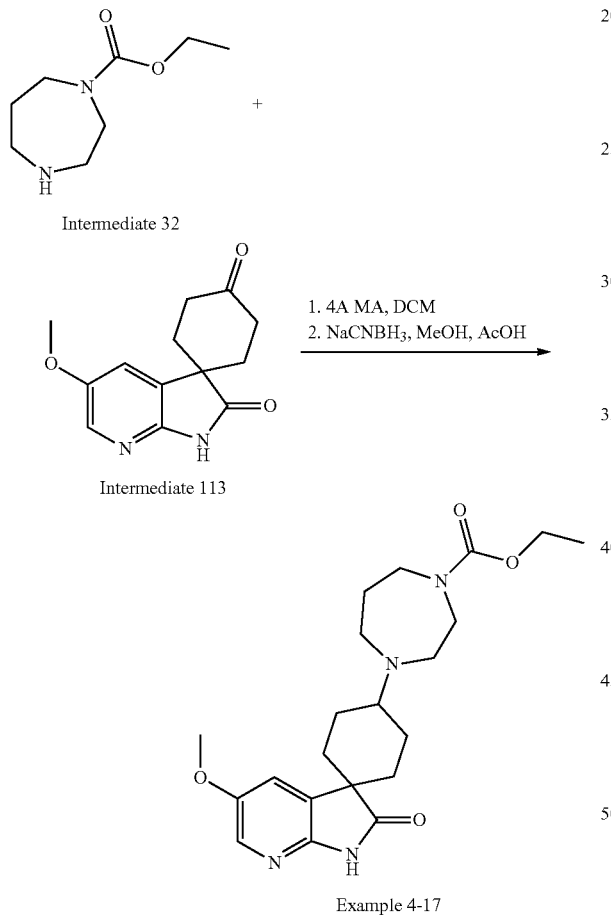

To a solution of 5'-methoxyspiro[cyclohexane-1,3'-pyrrolo[2,3-b]pyridine]-2',4(1'H)-dione (230 mg, 0.93 mmol) in DCM (10 mL), ethyl 1,4-diazepane-1-carboxylate (160 mg, 0.93 mmol) and activated 4 A molecular sieves were added and stirred at rt for 16 h. After concentration in vacuo the residue was dissolved in methanol (10 mL) and cooled to 0° C. To the reaction mixture NaCNBH₃ (175 mg, 2.78 mmol) and acetic acid (cat.) were added and stirred at rt for 16 h. After removing the volatiles, water (20 mL) was added to the reaction mixture and extracted with DCM (3×30 mL). The organic layers were combined and washed with brine, dried (Na₂SO₄) and concentrated in vacuo. The residue was purified by prep-HPLC (reverse phase, X BRIDGE C-18, 19×250 mm, 5µ, gradient 20% to 95% MeCN in H₂O containing 0.1% NH₄OH, 210 nm) to yield ethyl 4-(5'-methoxy-2'-oxo-1',2'-dihydrospiro-[cyclohexane-1,3'-pyrrolo[2,3-b]pyridin]-4-yl)-1,4-diazepane-1-carboxylate, Example 4-17 isomer 1 (19 mg, 5%) and ethyl 4-(5'-methoxy-2'-oxo-1',2'-dihydrospiro-[cyclohexane-1,3'-pyrrolo[2,3-b]pyridin]-4-yl)-1,4-diazepane-1-carboxylate, Example 4-17 isomer 2 (38 mg, 10%) both as white solids.

The data for Example 4-17 isomer 1 and isomer 2 are in Table 3 below.

Route j

Preparation of Oxindoles Via Sodium Triacetoxyborohydride and Titanium Isopropoxide Reductive Amination, Exemplified by the Preparation of Example 10-1, ethyl 6-(2'-oxo-1',2'-dihydrospiro [cyclohexane-1,3'-indol]-4-yl)-2,6-diazaspiro[3.4] octane-2-carboxylate

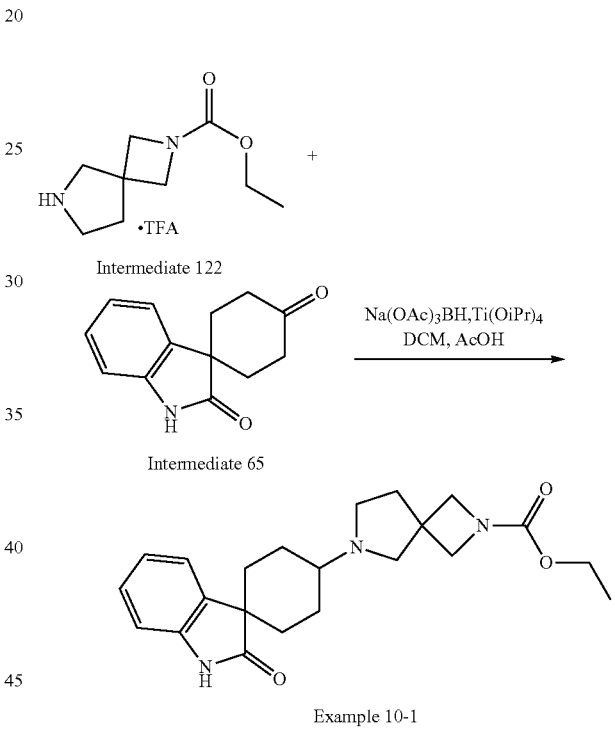

To ethyl 2,6-diazaspiro[3.4]octane-2-carboxylate trifluoroacetic acid salt (assumed 0.52 mmol) in MeOH was added K₂CO₃ (0.52 mmol) as a solution in H₂O (0.5 mL). The solvent was removed in vacuo and azeotroped with toluene (3×5 mL). The residue was diluted with DCM (10 mL) and the mixture treated with 4H-spiro[cyclohexane-1,3'-indole]-2',4(1'H)-dione (112 mg, 0.52 mmol) and Ti(OⁱPr)₄ (148 mg, 0.52 mmol). The mixture was stirred at rt for 2 h before addition of STAB (220 mg, 1.04 mmol) and glacial acetic acid (7 drops) and further stirring at rt for 16 h. To the mixture was added sat. aq. NaHCO₃ (10 mL) and the layers separated. The aqueous layer was further washed with DCM and combined organics washed with brine and dried through a Biotage Phase Separator cartridge. The solvent was removed in vacuo and the crude residue purified using a 10 g SNAP cartridge and eluting with 0-7% MeOH in DCM to yield ethyl 6-(2'-oxo-1',2'-dihydrospiro[cyclohexane-1,3'-indol]-4-yl)-2,6-diazaspiro[3.4]octane-2-carboxylate, Example 10-1 (10 mg, 5%).

The data for Example 10-1 mixture of isomers are in Table 3 below.

Route k

Procedure for Preparation of Oxindoles Via Reductive Amination with Sodium Triacetoxyborohydride, Exemplified by the Preparation of Example 12-1, ethyl 8-(2'-oxo-1',2'-dihydrospiro[cyclohexane-1,3'-indol]-4-yl)-2,8-diazaspiro[4.5]decane-2-carboxylate

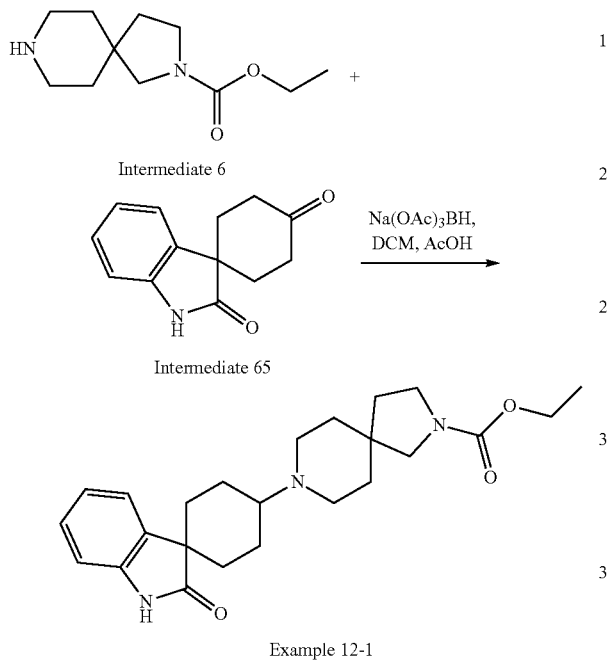

Example 12-1

To a solution of ethyl 2,8-diazaspiro[4.5]decane-2-carboxylate (203 mg, 0.94 mmol) and 4H-spiro[cyclohexane-1,3'-indole]-2',4(1'H)-dione (200 mg, 0.94 mmol) in DCM (5 mL) at rt was added AcOH (5 drops) and the mixture stirred for 4 h. STAB (797 mg, 3.76 mmol) was then added and the mixture stirred at rt for 16 h. To the mixture was added NaOH (20 mL) and the aqueous layer extracted with DCM (4×25 mL). Combined organics were dried and the solvent removed in vacuo. The residue was loaded onto a 25 g SNAP chromatography cartridge and eluted with 0-10% MeOH in DCM to yield ethyl 8-(2'-oxo-1',2'-dihydrospiro[cyclohexane-1,3'-indol]-4-yl)-2,8-diazaspiro[4.5]decane-2-carboxylate, Example 12-1 isomer 1 (3 mg, 1%) and ethyl 8-(2'-oxo-1',2'-dihydrospiro[cyclohexane-1,3'-indol]-4-yl)-2,8-diazaspiro[4.5]decane-2-carboxylate, Example 12-1 isomer 2 (18 mg, 5%).

The data for Example 12-1 isomer 1 and isomer 2 are in Table 3 below.

Route l

Procedure for Preparation of Amines Via Reductive Amination with Sodium Triacetoxyborohydride in DMF, Exemplified by the Preparation of Example 19-1, 4-{[(1R,3S)-3-(3-methyl-1,2,4-oxadiazol-5-yl)cyclopentyl]amino}-1-(pyridin-2-yl)cyclohexanecarbonitrile

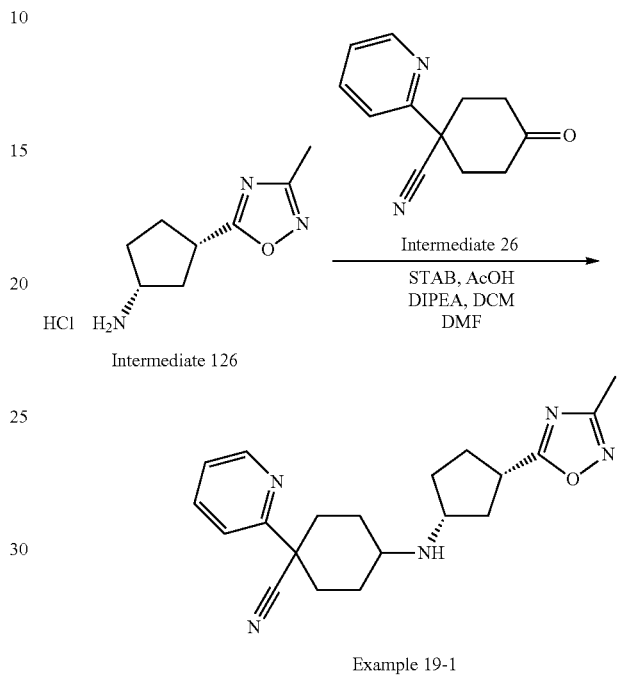

Example 19-1

(1R,3S)-3-(3-Methyl-1,2,4-oxadiazol-5-yl)cyclopentanamine hydrochloride salt (41 mg, 0.20 mmol) and 4-oxo-1-(pyridin-2-yl)cyclohexanecarbonitrile (40 mg, 0.20 mmol) were dissolved in DMF (0.66 mL) and treated with DIPEA (0.04 mL, 0.24 mmol), AcOH (0.08 mL, 1.4 mmol) and STAB (85 mg, 0.40 mmol) in that order. The resulting mixture was stirred under an atmosphere of nitrogen overnight. Water (10 mL) was added and the mixture was concentrated. The residue was partitioned between sat. aq. NaHCO$_3$ (containing some Na$_2$CO$_3$) and DCM. The phases were separated and the aqueous phase was extracted further with DCM (×2). The combined organic phases were passed through a phase separator cartridge and concentrated to give 4-{[(1R,3S)-3-(3-methyl-1,2,4-oxadiazol-5-yl)cyclopentyl]amino}-1-(pyridin-2-yl)cyclohexanecarbonitrile as a mixture of diastereomers (73 mg, >100%). The isomers were separated using preparative HPLC (Method A, 30-60% gradient) to afford 4-{[(1R,3S)-3-(3-methyl-1,2,4-oxadiazol-5-yl)cyclopentyl]amino}-1-(pyridin-2-yl)cyclohexanecarbonitrile, Example 19-1 Isomer 1 (39 mg, 55%) and 4-{[(1R,3S)-3-(3-methyl-1,2,4-oxadiazol-5-yl)cyclopentyl]amino}-1-(pyridin-2-yl)cyclohexanecarbonitrile, Example 19-1 Isomer 2 (18 mg, 25%).

The data for Example 19-1 Isomer 2 are in Table 3 below.

TABLE 2

| | Intermediates | | | |
|---|---|---|---|---|
| Intermediate number | Name | Synthetic method | Intermediates used | Data |
| 1 | tert-Butyl methyl(piperidin-4-yl)carbamate | — | — | Commercially available, CAS: 108612-54-0 |

TABLE 2-continued

Intermediates

| Intermediate number | Name | Synthetic method | Intermediates used | Data |
|---|---|---|---|---|
| 2 | tert-Butyl (piperidin-4-ylmethyl)carbamate | — | — | Commercially available, CAS: 135632-53-0 |
| 3 | Ethyl 1,5-diazocane-1-carboxylate trifluoroacetate salt | 1 | 55 and 59 | LCMS (Method A): m/z 187 (M + H)$^+$ (ES+), at 1.02 min, UV inactive |
| 4 | tert-Butyl 2,6-diazaspiro[3.4]octane-6-carboxylate | — | — | Commercially available, CAS: 885270-86-0 |
| 5 | tert-Butyl 2,7-diazaspiro[3.5]nonane-2-carboxylate | — | — | Commercially available, CAS: 236406-55-6 |
| 6 | Ethyl 2,8-diazaspiro[4.5]decane-2-carboxylate | 20 | 53 and 55 | LCMS (Method C): m/z 213 (M + H)$^+$ (ES+), at 1.06 min, UV inactive |
| 7 | Ethyl 3,7 diazabicyclo[4.2.0]octane-3-carboxylate trifluoroacetate salt | 1 | 55 and 60 | LCMS (Method A): m/z 185 (M + H)$^+$ (ES+), at 0.95 min, UV inactive |
| 8 | Ethyl hexahydropyrrolo[3,4-b]pyrrole-1(2H)-carboxylate trifluoroacetate salt | 1 | 55 and 61 | LCMS (Method A): m/z 185 (M + H)$^+$ (ES+), at 0.96 min, UV inactive |
| 9 | tert-Butyl hexahydropyrrolo[3,4-b]pyrrole-5(1H)-carboxylate | — | — | Commercially available, CAS: 180975-51-3 |
| 10 | tert-Butyl 3,7-diazabicyclo[4.2.0]octane-7-carboxylate | — | — | Commercially available, CAS: 885271-73-8 |
| 11 | Ethyl (4aS,7aS)-octahydro-6H-pyrrolo[3,4-b]pyridine-6-carboxylate trifluoroacetate salt | 1 | 55 and 62 | LCMS (Method A): m/z 199 (M + H)$^+$ (ES+), at 1.10 min, UV inactive |
| 12 | 4-Oxo-1-phenylcyclohexanecarbonitrile | — | — | Commercially available, CAS: 25115-74-6 |
| 13 | Ethyl (3S)-pyrrolidin-3-ylcarbamate hydrochloride | 2 | 54 and 55 | (LCMS Method G) m/z 159 (M + H)$^+$ (ES$^+$) at 5.32 min, UV active |
| 14 | Ethyl (3R)-pyrrolidin-3-ylcarbamate hydrochloride | 2 | 55 and 63 | (LCMS Method Q) m/z 159 (M + H)$^+$ (ES$^+$) at 2.01 min, UV active |
| 15 | tert-Butyl (3S)-pyrrolidin-3-ylcarbamate | — | — | Commercially available, CAS: 147081-44-5 |
| 16 | tert-Butyl (3R)-pyrrolidin-3-ylcarbamate | — | — | Commercially available, CAS: 147081-49-0 |
| 17 | tert-Butyl methyl[(3S)-pyrrolidin-3-yl]carbamate | — | — | Commercially available, CAS: 169750-01-0 |
| 18 | tert-Butyl methyl[(3R)-pyrrolidin-3-yl]carbamate | — | — | Commercially available, CAS: 392338-15-7 |
| 19 | 1-(2-Fluorophenyl)-4-oxocyclohexanecarbonitrile | 3 | — | Mass: (ESI +ve): 218 (M + H)$^+$ $^1$H NMR (400 MHz, DMSO-d$_6$) δ: 2.35-2.45 (m, 4H), 2.53-2.58 (m, 2H), 2.69-2.78 (m, 2H), 7.29-7.39 (m, 2H), 7.47-7.54 (m, 2H). |
| 20 | 1-(3-Fluorophenyl)-4-oxocyclohexanecarbonitrile | 3 | — | Mass: (ESI +ve): 218 (M + H)$^+$ $^1$H NMR (400 MHz, DMSO-d$_6$) δ: 2.38-2.47 (m, 6H), 2.66-2.74 (m, 2H), 7.22-7.27 (m, 1H), 7.45-7.55 (m, 3H). |
| 21 | 1-(4-Fluorophenyl)-4-oxocyclohexanecarbonitrile | — | — | Commercially available, CAS: 56326-98-8 |
| 22 | 1-(2-Methylphenyl)-4-oxocyclohexanecarbonitrile | 3 | — | Mass: (ESI +ve): 214 (M + H)$^+$ $^1$H NMR (400 MHz, DMSO-d$_6$) δ: 2.29-2.45 (m, 4H), 2.54-2.58 (m, 2H), 2.62 (s, 3H) 2.70-2.79 (m, 2H), |

TABLE 2-continued

Intermediates

| Intermediate number | Name | Synthetic method | Intermediates used | Data |
|---|---|---|---|---|
| 23 | 1-(3-Methylphenyl)-4-oxocyclohexanecarbonitrile | 3 | — | 7.25-7.32 (m, 3H), 7.37-7.39 (d, J = 7.2 Hz, 1H).<br>Mass: (ESI +ve): 214 (M + H)$^+$<br>$^1$H NMR (400 MHz, DMSO-d$_6$) δ:<br>2.35-2.48 (m, 9H), 2.65-2.74 (m, 2H), 7.20 (d, J = 7.2 Hz, 1H), 7.32-7.43 (m, 3H). |
| 24 | 1-(3-Chlorophenyl)-4-oxocyclohexanecarbonitrile | 3 | — | Mass: (ESI +ve): 234 (M + H)$^+$<br>$^1$H NMR (400 MHz, DMSO-d$_6$) δ:<br>2.37-2.48 (m, 6H), 2.64-2.74 (m, 2H), 7.46-7.53 (m, 2H), 7.59-7.62 (m, 1H), 7.67-7.68 (m, 1H). |
| 25 | 1-(3-Methoxyphenyl)-4-oxocyclohexanecarbonitrile | 3 | — | Mass: (ESI +ve): 230 (M + H)$^+$<br>$^1$H NMR (400 MHz, DMSO-d$_6$) δ:<br>2.34-2.47 (m, 6H), 2.65-2.74 (m, 2H), 3.79 (s, 3H), 6.95-6.98 (m, 1H), 7.13 (t, J = 2.4 Hz, 1H), 7.17-7.20 (m, 1H), 7.38 (t, J = 8.0 Hz, 1H). |
| 26 | 4-Oxo-1-(pyridin-2-yl)cyclohexanecarbonitrile | 4 | — | Mass: (ESI +ve): 201 (M + H)$^+$<br>$^1$H NMR (400 MHz, DMSO-d$_6$) δ:<br>2.35-2.48 (m, 6H), 2.60-2.74 (m, 2H), 7.39-7.46 (m, 1H), 7.65-7.73 (m, 1H), 7.91-7.99 (m, 1H), 8.60-8.65 (m, 1H). |
| 27 | 1-(5-Fluoropyridin-2-yl)-4-oxocyclohexanecarbonitrile | 4 | — | Mass: (ESI +ve): 219 (M + H)$^+$<br>$^1$H NMR (400 MHz, DMSO-d$_6$) δ:<br>2.35-2.50 (m, 6H), 2.64-2.69 (m, 2H), 7.79 (m, 1H), 7.89 (m, 1H), 8.65 (d, J = 2.8 Hz, 1H). |
| 28 | 1-(5-Chloropyridin-2-yl)-4-oxocyclohexanecarbonitrile | 4 | — | Mass: (ESI +ve): 235 (M + H)$^+$<br>$^1$H NMR (400 MHz, DMSO-d$_6$) δ:<br>1.90-2.29 (m, 6H), 2.53-2.58 (m, 2H), 7.70 (d, J = 8.4 Hz, 1H), 8.02-8.06 (m, 1H), 8.68 (d, J = 2.4 Hz, 1H). |
| 29 | 1-(4-Methylpyridin-2-yl)-4-oxocyclohexanecarbonitrile | 4 | — | Mass: (ESI +ve): 215 (M + H)$^+$<br>$^1$H NMR (400 MHz, DMSO-d$_6$) δ:<br>2.11-2.31 (m, 6H), 2.33 (s, 3H), 2.50-2.57 (m, 2H), 7.24 (m, 1H), 7.53 (s, 1H), 8.44 (m, 1H). |
| 30 | 1-(6-Methylpyridin-2-yl)-4-oxocyclohexanecarbonitrile | 4 | — | LCMS (Method A): m/z 215 (M + H)$^+$ (ES$^+$), at 1.26 min, 95%.<br>$^1$H NMR (400 MHz, DMSO-d$_6$) δ:<br>2.38-2.46 (m, 6H), 2.49 (s, 3H), 2.62-2.70 (m, 2H), 7.96 (d, J = 8, 1H), 8.04 (d, J = 8, 1H), 7.79 (t, J = 8, 1H). |
| 31 | tert-Butyl 1,4-diazepane-1-carboxylate | — | — | Commercially available, CAS: 112275-50-0 |
| 32 | Ethyl 1,4-diazepane-1-carboxylate hydrochloride | 2 | 31 and 55 | LCMS (Method C): m/z 173 (M + H)$^+$ (ES$^+$), at 1.53 min.<br>$^1$H NMR (400 MHz, |

TABLE 2-continued

| Intermediate number | Name | Synthetic method | Intermediates used | Data |
|---|---|---|---|---|
| | | | | DMSO-$d_6$) δ: 1.20 (t, J = 7.0 Hz, 3H), 1.93-1.98 (m, 2H), 3.10-3.17 (m, 4H), 3.39-3.50 (m, 4H), 4.06 (q, J = 7.0 Hz, 2H), 9.30 (br. s, 2H). |
| 33 | Ethyl 6-hydroxy-1,4-diazepane-1-carboxylate hydrochloride | 2 | 51 and 55 | LCMS (Method C): m/z 189 (M + H)$^+$ (ES$^+$), at 3.33 min. $^1$H NMR (400 MHz, DMSO-$d_6$) δ: 1.20 (t, J = 7.2 Hz, 3H), 3.09-3.24 (m, 4H), 3.36-3.67 (m, 5H), 4.06 (q, J = 7.2 Hz, 2H), 5.80 (br. s, 1H), 8.48 (br. s, 1H), 9.05 (br. s, 1H). |
| 34 | Ethyl 6-fluoro-1,4-diazepane-1-carboxylate hydrochloride | 2 | 52 and 55 | LCMS (Method A): m/z 191 (M + H)$^+$ (ES$^+$), at 0.91 min. $^1$H NMR (400 MHz, DMSO-$d_6$) δ: 1.21-1.27 (m, 3H), 3.38-3.80 (m, 8H), 4.05-4.10 (m, 2H), 5.14 (d, J = 43.2, 1H), 8.85 (br. s, 1H), 9.48 (br. s, 1H). |
| 35 | 1-(2-Chlorophenyl)-4-oxocyclohexanecarbonitrile | — | — | Commercially available, CAS: 65618-88-4 |
| 36 | 1-(4-Chlorophenyl)-4-oxocyclohexanecarbonitrile | — | — | Commercially available, CAS: 25115-75-7 |
| 37 | 1-(4-Methoxyphenyl)-4-oxocyclohexanecarbonitrile | — | — | Commercially available, CAS: 5309-14-8 |
| 38 | 4-Oxo-1-[2-(trifluoromethyl)phenyl]cyclohexanecarbonitrile | — | — | Commercially available, CAS: 943326-34-9 |
| 40 | 4-Oxo-1-(pyridin-4-yl)cyclohexanecarbonitrile | 4 | — | Mass: (ESI +ve): 201 (M + H)$^+$ $^1$H NMR (400 MHz, DMSO-$d_6$) δ: 2.17-2.26 (m, 4H), 2.35-2.39 (m, 4H), 7.91-7.93 (m, 2H), 8.52-8.53 (m, 2H). |
| 41 | 1-(3-Chloropyridin-2-yl)-4-oxocyclohexanecarbonitrile | 4 | — | Mass: (ESI +ve): 235 (M + H)$^+$ $^1$H NMR (400 MHz, DMSO-$d_6$) δ: 2.41-2.44 (m, 2H), 2.54-2.55 (m, 2H), 2.64-2.71 (m, 4H), 7.53-7.53 (m, 1H), 8.08-8.11 (m, 1H), 8.60-8.62 (m, 1H). |
| 42 | 1-(5-Bromopyridin-2-yl)-4-oxocyclohexanecarbonitrile | 4 | — | LCMS (Method A): m/z 280/282 (M + H)$^+$ (ES$^+$), at 1.49 min. $^1$H NMR (400 MHz, CDCl$_3$) δ: 2.39-2.61 (m, 6H), 2.81-2.93 (m, 2H), 7.60-7.64 (m, 1H), 7.91-7.95 (m, 1H), 8.60-8.62 (m, 1H). |
| 43 | 1-(5-Methylpyridin-2-yl)-4-oxocyclohexanecarbonitrile | 4 | — | Mass: (ESI +ve): 215 (M + H)$^+$ $^1$H NMR (400 MHz, CDCl$_3$) δ: 2.29-2.34 (m, 4H), 2.58-2.60 (m, 4H), 2.61 (s, 3H), 7.78-7.84 (m, 1H), 7.91-7.99 (m, 1H), 8.84-8.89 (m, 1H). |
| 44 | 1-(5-Methoxypyridin-2-yl)-4-oxocyclohexanecarbonitrile | 4 | — | LCMS (Method A): m/z 231 (M + H)$^+$ (ES$^+$), at 1.15 min. $^1$H NMR (400 MHz, DMSO-$d_6$) δ: 2.36-2.44 (m, 4H), 2.51-2.69 (m, |

TABLE 2-continued

Intermediates

| Intermediate number | Name | Synthetic method | Intermediates used | Data |
|---|---|---|---|---|
| | | | | 4H), 3.85 (s, 3H), 7.49-7.52 (m, 1H), 7.62-7.65 (m, 1H), 8.32-8.36 (m, 1H). |
| 45 | 1-(5-Ethoxypyridin-2-yl)-4-oxocyclohexanecarbonitrile | 4 | — | LCMS (Method C): m/z 244 (M + H)$^+$ (ES$^+$), at 3.03 min.<br>$^1$H NMR (400 MHz, DMSO-d$_6$) δ: 1.35 (t, J = 6.8 Hz, 3H), 2.37-2.46 (m, 2H), 2.62-2.67 (m, 2H), 3.47-3.51 (m, 2H), 3.65-3.76 (m, 2H), 4.13 (q, J = 6.8 Hz, 2H), 7.47-7.50 (m, 1H), 7.59-7.61 (m, 1H), 8.32 (s, 1H). |
| 46 | 4-Oxo-1-[5-(trifluoromethyl)pyridin-2-yl]cyclohexanecarbonitrile | 4 | — | Mass: (ESI +ve): 269 (M + H)$^+$<br>$^1$H NMR (400 MHz, DMSO-d$_6$) δ: 2.43-2.63 (m, 6H), 2.84-2.90 (m, 2H), 7.86-7.91 (m, 2H), 8.05-8.06 (m, 1H). |
| 47 | 4-Oxo-1-[6-(trifluoromethyl)pyridin-2-yl]cyclohexanecarbonitrile | 4 | — | LCMS (Method A): m/z 269 (M + H)$^+$ (ES$^+$), at 1.60 min.<br>$^1$H NMR (400 MHz, DMSO-d$_6$) δ: 2.41-2.45 (m, 2H), 2.50-2.53 (m, 4H), 2.65-2.73 (m, 2H), 7.96-7.98 (m, 1H), 8.03-8.06 (m, 1H), 8.23-8.27 (m, 1H). |
| 48 | 4-Oxo-1-(thiophen-2-yl)cyclohexanecarbonitrile | — | — | Commercially available, CAS: 65619-58-1 |
| 49 | Methyl 4-oxo-1-phenylcyclohexanecarboxylate | — | — | Commercially available, CAS: 75945-90-3 |
| 50 | Methyl 1-(3-chloropyridin-2-yl)-4-oxocyclohexanecarboxylate | 5 | — | Mass: (ESI +ve): 268 (M + H)$^+$<br>$^1$H NMR (400 MHz, DMSO-d$_6$) δ: 2.39-2.49 (m, 6H), 2.52-2.56 (m, 2H), 3.64 (s, 3H), 7.39-7.43 (m, 1H), 7.93-7.95 (m, 1H), 8.53-8.56 (m, 1H). |
| 51 | tert-Butyl 6-hydroxy-1,4-diazepane-1-carboxylate | — | — | Commercially available, CAS: 956317-40-1 |
| 52 | tert-Butyl-6-fluoro-1,4 diazepane-1 carboxylate | — | — | Commercially available, CAS: 1261297-63-5 |
| 53 | tert-Butyl 2,8-diazaspiro[4.5]decane-8-carboxylate | — | — | Commercially available, CAS: 236406-39-6 |
| 55 | Ethyl chloroformate | — | — | Commercially available, CAS: 541-41-3 |
| 56 | Methyl chloroformate | — | — | Commercially available, CAS: 79-22-1 |
| 57 | Propargyl chloroformate | — | — | Commercially available, CAS: 35718-08-2 |
| 58 | 2-Butynyl chloroformate | — | — | Commercially available, CAS: 202591-85-3 |
| 59 | tert-Butyl 1,5-diazocane-1-carboxylate | — | — | Commercially available, CAS: 223797-64-6 |
| 61 | tert-Butyl 2,7-diazabicyclo[3.3.0]octane-7-carboxylate | — | — | Commercially available, CAS: 132414-81-4 |
| 62 | (4AS,7aS)-Octahydro-1H-pyrrolo[3,4-b]pyridine-1-carboxylic acid tert-butyl ester | — | — | Commercially available, CAS: 159991-07-8 |
| 64 | 2-Fluoroethyl chloroformate | — | — | Commercially available, CAS: 462-27-1 |
| 65 | 4H-Spiro[cyclohexane-1,3'-indole]-2',4(1'H)-dione | — | — | Commercially available, CAS: 52140-59-7 |
| 66 | 7-Methyl-1,3-dihydro-2H-indol-2-one | — | — | Commercially available, CAS: 3680-28-2 |

TABLE 2-continued

Intermediates

| Intermediate number | Name | Synthetic method | Intermediates used | Data |
|---|---|---|---|---|
| 67 | 7'-Methyl-4H-spiro[cyclohexane-1,3'-indole]-2',4(1'H)-dione | 6 | 66 | LCMS (Method F): m/z 230 (M + H)$^+$ (ES$^+$), at 1.91 min, UV active. |
| 68 | 6'-Methyl-4H-spiro[cyclohexane-1,3'-indole]-2',4(1'H)-dione | 6 | 69 | LCMS (Method F): m/z 230 (M + H)$^+$ (ES$^+$), at 1.90 min, UV active. |
| 69 | 6-Methyl-1,3-dihydro-2H-indol-2-one | — | — | Commercially available, CAS: 56341-38-9 |
| 70 | 5'-Methyl-4H-spiro[cyclohexane-1,3'-indole]-2',4(1'H)-dione | 6 | 71 | LCMS (Method F): m/z 230 (M + H)$^+$ (ES$^+$), at 1.87 min, UV active. |
| 71 | 5-Methyl-1,3-dihydro-2H-indol-2-one | — | — | Commercially available, CAS: 3484-35-3 |
| 72 | 4'-Methyl-4H-spiro[cyclohexane-1,3'-indole]-2',4(1'H)-dione | 6 | 73 | LCMS (Method F): m/z 230 (M + H)$^+$ (ES$^+$), at 1.86 min, UV active. |
| 73 | 4-Methyl-1,3-dihydro-2H-indol-2-one | — | — | Commercially available, CAS: 13220-46-7 |
| 74 | 6'-Fluoro-4H-spiro[cyclohexane-1,3'-indole]-2',4(1'H)-dione | 6 | 75 | LCMS (Method F): m/z 234 (M + H)$^+$ (ES$^+$), at 1.83 min, UV active. |
| 75 | 6-Fluoro-1,3-dihydro-2H-indol-2-one | — | — | Commercially available, CAS: 56341-39-0 |
| 76 | 5'-Fluoro-4H-spiro[cyclohexane-1,3'-indole]-2',4(1'H)-dione | 6 | 77 | LCMS (Method F): m/z 234 (M + H)$^+$ (ES$^+$), at 1.81 min, UV active. |
| 77 | 5-Fluoro-1,3-dihydro-2H-indol-2-one | — | — | Commercially available, CAS: 56341-41-4 |
| 78 | 6'-Methoxy-4H-spiro[cyclohexane-1,3'-indole]-2',4(1'H)-dione | 6 | 79 | LCMS (Method F): m/z 244 [M − H]$^-$ (ES$^-$), at 1.83 min, UV active. |
| 79 | 6-Methoxy-1,3-dihydro-2H-indol-2-one | — | — | Commercially available, CAS: 7699-19-6 |
| 80 | 5'-Methoxy-4H-spiro[cyclohexane-1,3'-indole]-2',4(1'H)-dione | 6 | 81 | LCMS (Method F): m/z 246 (M + H)$^+$ (ES$^-$), at 1.81 min, UV active. |
| 81 | 5-Methoxy-1,3-dihydro-2H-indol-2-one | — | — | Commercially available, CAS: 7699-18-5 |
| 82 | Ethyl methyl[(3S)-pyrrolidin-3-yl]carbamate trifluoroacetic acid salt | 1 | 55 and 83 | LCMS (Method F): m/z 173 (M + H)$^+$ (ES$^+$), at 0.95 min, UV active. |
| 83 | tert-Butyl (3S)-3-(methylamino)pyrrolidine-1-carboxylate | — | — | Commercially available, CAS: 147081-59-2 |
| 84 | Ethyl methyl[(3R)-pyrrolidin-3-yl]carbamate trifluoroacetic acid salt | 7 | 16, 55 and 85 | LCMS (Method F): m/z 173 (M + H)$^+$ (ES$^+$), at 0.95 min, UV active. |
| 85 | Methyl iodide | — | — | Commercially available, CAS: 74-88-4 |
| 86 | 1'-Methyl-4H-spiro[cyclohexane-1,3'-indole]-2',4(1'H)-dione | 8 | 65 and 85 | LCMS (Method F): m/z 230 (M + H)$^+$ (ES$^+$), at 1.91 min, UV active. |
| 87 | Ethyl 2',4-dioxospiro[cyclohexane-1,3'-indole]-1'(2'H)-carboxylate | 9 | 55 and 65 | LCMS (Method F): m/z 288 (M + H)$^+$ (ES$^+$), at 2.18 min, UV active. |
| 88 | 2-(2',4-Dioxospiro[cyclohexane-1,3'-indol]-1'(2'H)-yl)acetamide | 8 | 65 and 89 | LCMS (Method F): m/z 273 (M + H)$^+$ (ES$^+$), at 1.69 min, UV active. |
| 89 | 2-Chloroacetamide | — | — | Commercially available, CAS: 79-07-2 |
| 90 | 4H-Spiro[cyclohexane-1,3'-pyrrolo[2,3-b]pyridine]-2',4(1'H)-dione | 10 | 91 and 92 | LCMS (Method F): m/z 217 (M + H)$^+$ (ES$^+$), at 1.51 min, UV active. |
| 91 | 3-Fluoro-2-nitropyridine | — | — | Commercially available, CAS: 54231-35-5 |
| 92 | (Buta-1,3-dien-2-yloxy)(trimethyl)silane | — | — | Commercially available, CAS: 38053-91-7 |
| 93 | 5'-Chloro-4H-spiro[cyclohexane-1,3'-pyrrolo[2,3-b]pyridine]-2',4(1'H)-dione | 11 | 94 | LCMS (Method F): m/z 251 (M + H)$^+$ (ES$^+$), at 1.73 min, UV active. |
| 94 | 5-Chloro-1,3-dihydro-2H-pyrrolo[2,3-b]pyridin-2-one | — | — | Commercially available, CAS: 1190314-60-3 |

TABLE 2-continued

Intermediates

| Intermediate number | Name | Synthetic method | Intermediates used | Data |
|---|---|---|---|---|
| 95 | 5'-Methoxy-4H-spiro[cyclohexane-1,3'-pyrrolo[2,3-c]pyridine]-2',4(1'H)-dione | 12 | 92 and 96 | LCMS (Method L): m/z 247 (M + H)$^+$(ES$^+$), at 3.64 min, UV active. |
| 96 | 2,4-Dichloro-5-nitropyridine | — | — | Commercially available, CAS: 4487-56-3 |
| 97 | 5'-Methoxy-4H-spiro[cyclohexane-1,3'-pyrrolo[3,2-b]pyridine]-2',4(1'H)-dione | 13 | 92 and 98 | LCMS (Method F): m/z 247 (M + H)$^+$(ES$^+$), at 1.93 min, UV active |
| 98 | 2-Chloro-6-methoxy-3-nitropyridine | — | — | Commercially available, CAS: 38533-61-8 |
| 99 | 4H-Spiro[cyclohexane-1,3'-pyrrolo[3,2-b]pyridine]-2',4(1'H)-dione | 16 | 92 and 100 | LCMS (Method E): m/z 217 (M + H)$^+$(ES$^+$), at 1.62 min, UV active |
| 100 | 2-Chloro-3-nitropyridine | — | — | Commercially available, CAS: 5470-18-8 |
| 101 | Ethyl piperidin-4-ylcarbamate trifluoroacetic acid salt | 1 | 55 and 102 | LCMS (Method F): m/z 173 (M + H)$^+$(ES$^+$), at 3.97 min, UV active |
| 102 | tert-Butyl 4-aminopiperidine-1-carboxylate | — | — | Commercially available, CAS: 87120-72-7 |
| 103 | 4-[4-(Aminomethyl)piperidin-1-yl]spiro[cyclohexane-1,3'-indol]-2'(1'H)-one di-trifluoroacetic acid salt, mixture of two isomers | 14 | 2 and 65 | LCMS (Method F): m/z 314 (M + H)$^+$(ES$^+$), at 0.76 min (isomer 1) and 1.47 (isomer 2), UV active |
| 104 | Methyl 1,4-diazepane-1-carboxylate hydrochloride | 2 | 31 and 56 | LCMS (Method H): m/z 159 (M + H)$^+$(ES$^+$), at 5.25 min, UV active |
| 105 | 1-(1,4-Diazepan-1-yl)butan-1-one hydrochloride | 2 | 31 and 106 | LCMS (Method Q): m/z 171 (M + H)$^+$(ES$^+$), at 2.92 min, UV active |
| 106 | Butyryl chloride | — | — | Commercially available, CAS: 141-75-3 |
| 107 | 1-(1,4-Diazepan-1-yl)but-2-en-1-one trifluoroacetic acid salt | 15 | 31 and 108 | LCMS (Method H): m/z 169 (M + H)$^+$(ES$^+$), at 5.28 min, UV active |
| 108 | Crotonyl chloride | — | — | Commercially available, CAS: 625-35-4 |
| 109 | 2-Oxo-2,3-dihydro-1H-indole-6-carbonitrile | — | — | Commercially available, CAS: 199327-63-4 |
| 110 | 2',4-Dioxo-1',2'-dihydrospiro[cyclohexane-1,3'-indole]-6'-carbonitrile | 6 | 109 | LCMS (Method F): m/z 239 (M − H)$^-$(ES$^-$), at 1.72 min, UV active |
| 111 | 2-Oxo-2,3-dihydro-1H-indole-5-carbonitrile | — | — | Commercially available, CAS: 61394-50-1 |
| 112 | 2',4-Dioxo-1',2'-dihydrospiro[cyclohexane-1,3'-indole]-5'-carbonitrile | 6 | 111 | Mass: (ESI −ve):: 239 (M − H)$^-$ |
| 113 | 5'-Methoxy-4H-spiro[cyclohexane-1,3'-pyrrolo[2,3-b]pyridine]-2',4(1'H)-dione | 17 | 114 | Mass: (ESI +ve): 247 (M + H)$^+$ |
| 114 | 5-Methoxy-1H-pyrrolo[2,3-b]pyridine | — | — | Commercially available, CAS: 183208-36-8 |
| 115 | (2-Chloropyridin-3-yl)acetonitrile | — | — | Commercially available, CAS: 101012-32-2 |
| 116 | 1',2'-Dihydro-4H-spiro[cyclohexane-1,3'-pyrrolo[2,3-b]pyridin]-4-one | 18 | 115 | LCMS (Method G): m/z 203 (M + H)$^+$ (ES$^+$), at 4.12 min, UV active |
| 117 | 1'-(Methylsulfonyl)-1',2'-dihydro-4H-spiro[cyclohexane-1,3'-pyrrolo[2,3-b]pyridin]-4-one | 19 | 116 | LCMS (Method F): m/z 281 (M + H)$^+$ (ES$^+$), at 1.73 min, UV active |
| 118 | 4H-Spiro[cyclohexane-1,3'-pyrrolo[2,3-c]pyridine]-2',4(1'H)-dione | 13 | 119 | LCMS (Method G): m/z 217 (M + H)$^+$ (ES$^+$), at 3.39 min, UV active |
| 119 | 4-Chloro-3-nitropyridine | — | — | Commercially available, CAS: 13091-23-1 |

TABLE 2-continued

Intermediates

| Intermediate number | Name | Synthetic method | Intermediates used | Data |
|---|---|---|---|---|
| 120 | 5'-Methyl-4H-spiro[cyclohexane-1,3'-pyrrolo[3,2-b]pyridine]-2',4(1'H)-dione | 13 | 121 | LCMS (Method F): m/z 231 (M + H)$^+$ (ES$^+$), at 1.67 min, UV active |
| 121 | 2-Chloro-6-methyl-3-nitropyridine | — | — | Commercially available, CAS: 56057-19-3 |
| 122 | Ethyl 2,6-diazaspiro[3.4]octane-2-carboxylate trifluoroacetic acid salt | 1 | 4 and 55 | LCMS (Method K): m/z 185 (M + H)$^+$ (ES$^+$), at 3.50 min, UV active |
| 123 | (1S,3R)-3-Aminocyclopentanecarboxylic acid | — | — | Commercially available, CAS: 71830-07-4 |
| 124 | Di-tert-butyl dicarbonate | — | — | Commercially available, CAS: 24424-99-5 |
| 125 | N-Hydroxyethanimidamide | — | — | Commercially available, CAS: 22059-22-9 |
| 126 | (1R,3S)-3-(3-Methyl-1,2,4-oxadiazol-5-yl)cyclopentanamine hydrochloride salt | 21 | 123, 124 and 125 | LCMS (Method E): m/z 168 (M + H)$^+$ (ES$^+$), at 1.20 min, UV active |
| 127 | N-Hydroxypropanimidamide | — | — | Commercially available, CAS: 29335-36-2 |
| 128 | (1R,3S)-3-(3-Ethyl-1,2,4-oxadiazol-5-yl)cyclopentanamine hydrochloride salt | 21 | 123, 124 and 127 | LCMS (Method E): m/z 182 (M + H)$^+$ (ES$^+$), at 1.82 min, UV active |
| 129 | 2-(tert-Butoxycarbonyl)-2-azaspiro[3.3]heptane-6-carboxylic acid | — | — | Commercially available, CAS: 1211526-53-2 |
| 130 | 2,2,2-Trifluoro-N-hydroxyethanimidamide | — | — | Commercially available, CAS: 4314-35-6 |
| 131 | 6-[3-(Trifluoromethyl)-1,2,4-oxadiazol-5-yl]-2-azaspiro[3.3]heptane trifluoroacetic acid salt | 22 | 129 and 130 | LCMS (Method E): m/z 234 (M + H)$^+$ (ES$^+$), at 2.96 min, UV active |
| 132 | 6-tert-Butyl 2-methyl 6-azaspiro[3.4]octane-2,6-dicarboxylate | — | — | Commercially available, CAS: 203662-61-7 |
| 133 | 2-(3-Methyl-1,2,4-oxadiazol-5-yl)-6-azaspiro[3.4]octane hydrochloride salt | 23 | 132 and 125 | LCMS (Method E): m/z 194 (M + H)$^+$ (ES$^+$), at 1.57 min, UV active |
| 134 | Ethyl piperidine-3-carboxylate | — | — | Commercially available, CAS: 5006-62-2 |
| 135 | (3R)-3-(3-Methyl-1,2,4-oxadiazol-5-yl)piperidine | 24 | 134, 124 and 125 | LCMS (Method I): m/z 168 (M + H)$^+$ (ES$^+$), at 2.57 min, UV active |
| 136 | Methyl 2-(aminomethyl)cyclopropanecarboxylate hydrochloride salt | — | — | Commercially available, CAS: 1630906-92-1 |
| 137 | 1-[2-(3-Methyl-1,2,4-oxadiazol-5-yl)cyclopropyl]methanamine hydrochloride salt | 25 | 136, 124 and 125 | LCMS (Method E): m/z 154 (M + H)$^+$ (ES$^+$), at 0.71 min, UV active |
| 138 | (1R,3S)-3-[3-(Trifluoromethyl)-1,2,4-oxadiazol-5-yl]cyclopentanamine hydrochloride salt | 21 | 123, 124 and 130 | LCMS (Method E): m/z 222 (M + H)$^+$ (ES$^+$), at 2.71 min, UV active. |
| 139 | 2-(tert-Butoxycarbonyl)-2-azaspiro[3.3]heptane-6-carboxylic acid | — | — | Commercially available, CAS: 1211526-53-2 |
| 140 | 6-(3-Ethyl-1,2,4-oxadiazol-5-yl)-2-azaspiro[3.3]heptane trifluoroacetic acid salt | 22 | 129 and 127 | LCMS (Method E): m/z 194 (M + H)$^+$ (ES$^+$), at 2.21 min, UV active. |
| 141 | 2-(3-Ethyl-1,2,4-oxadiazol-5-yl)-6-azaspiro[3.4]octane hydrochloride salt | 22 | 132 and 127 | LCMS (Method B): m/z 208 (M + H)$^+$ (ES$^+$), at 1.83 min, UV active |
| 142 | Cyclopropanecarboxylic acid, 2-[[[(1,1-dimethylethoxy)carbonyl]amino]methyl]- | — | — | Commercially available, CAS: 1000535-88-5 |

TABLE 2-continued

Intermediates

| Intermediate number | Name | Synthetic method | Intermediates used | Data |
|---|---|---|---|---|
| 143 | 1-[2-(3-Ethyl-1,2,4-oxadiazol-5-yl)cyclopropyl]methanamine hydrochloride salt | 22 | 142 and 127 | LCMS (Method B): m/z 168 (M + H)$^+$ (ES$^+$), at 1.33 min, UV active |

TABLE 3

| Ex. No. | Name | Intermediate | Synthetic method | $^1$H NMR | LCMS Method | LCMS data |
|---|---|---|---|---|---|---|
| 1-1 | Isomer 2: ethyl [(3S)-1-(4-cyano-4-phenylcyclohexyl)pyrrolidin-3-yl]carbamate | 12 and 13 | c | (400 MHz, CDCl$_3$) δ: 1.26 (t, J = 5.6 Hz, 3H), 1.47-1.52 (m, 1H) 1.63-1.65 (m, 1H), 1.90-1.98 (m, 5H), 2.28-2.39 (m, 5H) 2.56-2.82 (m, 3H), 4.12-4.14 (m, 2H), 4.22-4.28 (m, 1H), 4.83-4.89 (m, 1H), 7.33 (t, J = 4, 1H), 7.43 (t, J = 7.2 Hz, 2H), 7.39 (d, J = 7.6 Hz, 2H). | D | m/z 342 (M + H)$^+$ (ES$^+$), at 5.87 min, UV active |
| 1-2 | Isomer 2: ethyl [(3R)-1-(4-cyano-4-H), phenylcyclohexyl)pyrrolidin-3-yl]carbamate | 12 and 14 | c | (400 MHz, CDCl$_3$) δ: 1.24 (t, J = 6.6 Hz, 3H), 1.60-1.65 (m, 1H), 1.87-1.97 (m, 6H), 2.22-2.27 (m, 3H), 2.34-2.40 (m, 2H) 2.52-2.56 (m, 1H), 2.65-2.66 (m, 1H), 2.79-2.80 (m, 1H), 4.08-4.12 (m, 2H), 4.20-4.18 (m, 1H), 4.83-4.88 (m, 1H), 7.34 (t, J = 7.2 Hz, 1H), 7.39 (t, J = 7.6 Hz, 2H), 7.48 (d, J = 7.6 Hz, 2H). | D | m/z 342 (M + H)$^+$ (ES$^+$), at 5.85 min, UV active |
| 1-3 | Isomer 2: ethyl {(3S)-1-[4-cyano-4-(3-fluorophenyl)cyclohexyl]pyrrolidin-3-yl}carbamate | 13 and 20 | c | (400 MHz, DMSO-d$_6$) δ: 1.14 (t, J = 7.2 Hz, 3H), 1.49-1.65 (m, 1H), 1.66-1.82 (m, 2H), 1.82-2.14 (m, 6H), 2.15-2.31 (m, 3H), 2.31-2.42 (m, 1H), 2.58-2.70 (m, 1H), 2.70-2.85 (m, 1H) 3.96 (q, J = 7.2 Hz, 3H), 7.17-7.26 (m, 1H), 7.29-7.42 (m, 2H), 7.45-7.55 (m, 1H). N-H not observed. | C | m/z 360 (M + H)$^+$ (ES$^+$), at 2.97 min, UV active |
| 1-4 | Isomer 2: ethyl {(3S)-1-[4-cyano-4-(4-fluorophenyl)cyclohexyl]pyrrolidin-3-yl}carbamate | 13 and 21 | c | (400 MHz, DMSO-d$_6$) δ: 1.14 (t, J = 7.0 Hz, 3H), 1.57-1.60 (m, 1H), 1.69-1.81 (m, 2H), 1.85-1.99 (m, 4H), 2.01-2.12 (m, 2H), 2.17-2.25 (m, 2H), 2.30-2.42 (m, 2H), 2.60-2.67 (m, 1H), 2.68-2.75 (m, 2H), 3.96 (q, J = 7.0 Hz, 3H), 7.26-7.33 (m, 2H), 7.55-7.58 (m, 2H). | C | m/z 360 (M + H)$^+$ (ES$^+$), at 2.97 min, UV active |
| 1-5 | Isomer 2: ethyl {(3R)-1-[4-cyano-4-(2-fluorophenyl)cyclohexyl]pyrrolidin-3-yl}carbamate | 14 and 19 | c | (400 MHz, DMSO-d$_6$) δ: 1.13 (t, J = 7.2 Hz, 3H), 1.54-1.59 (m, 1H), 1.78-1.92 (m, 2H), 1.96-2.05 (m, 5H), 2.19-2.34 (m, 4H), 2.42-2.45 (m, 1H), 2.53-2.58 (m, 1H), 2.71-2.75 (m, 1H), 3.95 (q, J = 7.2 Hz, 3H), 7.26-7.34 (m, 3H), 7.43-7.53 (m, 2H). | C | m/z 360 (M + H)$^+$ (ES$^+$), at 2.89 min, UV active |
| 1-6 | Isomer 2: ethyl {(3R)-1-[4-cyano-4-(3-fluorophenyl)cyclohexyl]pyrrolidin-3-yl}carbamate | 14 and 20 | c | (400 MHz, DMSO) δ: 1.14 (t, J = 7.2 Hz, 3H), 1.56-1.61 (m, 1H), 1.74-1.78 (m, 2H), 1.87-1.90 (m, 3H), 2.01-2.08 (m, 1H), 2.15-2.51 (m, 6H), 2.63-2.66 (m, 2H), 3.93-3.98 (m, 3H), 7.20-7.25 (m, 1H), 7.35-7.39 (m, 3H), 7.48-7.54 (m, 1H). | C | m/z 360 (M + H)$^+$ (ES$^+$), at 2.97 min, UV active |
| 1-7 | Isomer 2: ethyl {(3R)-1-[4-cyano-4-(4-fluorophenyl)cyclohexyl]pyrrolidin-3-yl}carbamate | 14 and 21 | c | (400 MHz, DMSO-d$_6$) δ: 1.15 (t, J = 6.8 Hz, 3H), 1.59-1.65 (m, 1H), 1.74-1.80 (m, 2H), 1.81-1.96 (m, 4H), 2.01-2.10 (m, 2H), 2.15-2.55 (m, 4H), 2.60-2.73 (m, 2H), 3.93-4.00 (m, 3H), 7.22-7.28 (m, 3H), 7.50-7.61 (m, 2H). | C | m/z 360 (M + H)$^+$ (ES$^+$), at 2.93 min, UV active |
| 1-8 | Isomer 2: ethyl {(3R)-1-[4-cyano-4-(2-methylphenyl)cyclohexyl]pyrrolidin-3-yl}carbamate | 14 and 22 | c | (400 MHz, DMSO-d$_6$) δ: 1.14 (t, J = 7.2 Hz, 3H), 1.55-1.60 (m, 1H), 1.77-1.83 (m, 2H), 1.92-2.05 (m, 5H), 2.18-2.20 (m, 2H), 2.31-2.34 (m, 2H), 2.41-2.45 (m, 2H), 2.57 (s, 3H), 2.65-2.74 (m, 2H), 3.95 (q, J = 7.2 Hz, 3H), 7.25-7.30 (m, 3H), 7.40-7.42 (t, J = 6.4 Hz, 1H). | C | m/z 360 (M + H)$^+$ (ES$^+$), at 3.02 min, UV active |
| 1-9 | Isomer 2: ethyl {(3S)-1-[4-cyano-4-(3 methylphenyl)cyclohexyl]pyrrolidin-3-yl}carbamate | 13 and 23 | c | (400 MHz, DMSO-d$_6$) δ: 1.15 (t, J = 6.8 Hz, 3H), 1.48-1.59 (m, 1H), 1.70-2.10 (m, 7H), 2.18-2.39 (m, 2H), 2.40-2.50 (m, 5H), 2.64-2.87 (m, 2H), 3.94-4.00 (q, J = 7.2 Hz, 3H), 7.15-7.17 (m, 1H), 7.27-7.34 (m, 3H). | C | m/z 356 (M + H)$^+$ (ES$^+$), at 2.71 min, UV active |

TABLE 3-continued

| Ex. No. | Name | Intermediate | Synthetic method | ¹H NMR | LCMS Method | LCMS data |
|---|---|---|---|---|---|---|
| 1-10 | Isomer 2: ethyl {(3S)-1-[4-(3-chlorophenyl)-4-cyanocyclohexyl]pyrrolidin-3-yl}carbamate | 13 and 24 | c | (400 MHz, DMSO-$d_6$) δ: 1.14 (t, J = 6.8 Hz, 3H), 1.57-1.60 (m, 1H), 1.71-1.77 (m, 3H), 1.87-1.89 (m, 4H), 2.03-2.07 (m, 1H), 2.17-2.32 (m, 3H), 2.25-2.40 (m, 2H), 2.59-2.68 (m, 2H), 3.96 (q, J = 6.8 Hz, 3H), 7.32 (d, J = 7.6 Hz, 1H), 7.44-7.54 (m, 3H). | C | m/z 376 (M + H)$^+$ (ES$^+$), at 3.10 min, UV active |
| 1-11 | Isomer 2: ethyl {(3S)-1-[4-cyano-4-(3-methoxyphenyl)cyclohexyl]pyrrolidin-3-yl}carbamate | 13 and 25 | c | (400 MHz, DMSO-$d_6$) δ: 1.14 (t, J = 6.4 Hz, 3H), 1.85-1.99 (m, 1H), 1.74-2.09 (m, 7H), 2.20-2.41 (m, 5H), 2.61-2.67 (m, 2H), 3.79 (s, 3H), 3.95 (q, J = 6.4 Hz, 3H), 6.95 (d, J = 8.0 Hz, 1H), 7.01 (s, 1H), 7.09 (d, J = 7.6 Hz, 1H), 7.30-7.39 (m, 2H). | C | m/z 372 (M + H)$^+$ (ES$^+$), at 2.67 min, UV active |
| 1-12 | Isomer 2: ethyl {(3S)-1-[4-cyano-4-(pyridin-2-yl)cyclohexyl]pyrrolidin-3-yl}carbamate | 13 and 26 | c | (400 MHz, H), CD$_3$OD) δ: 1.23 (t, J = 7.2 Hz, 3H), 1.70-1.74 (m, 1H), 1.80-2.05 (m, 7H), 2.17-2.30 (m, 1H), 2.47-2.55 (m, 1H), 2.57-2.67 (m, 4H), 2.87-2.93 (m, 2H), 4.06 (q, J = 7.2 Hz, 2H), 4.10-4.21 (m, 1H), 7.39 (dd, J = 7.2 Hz, 5.2, 1H), 7.69 (d, J = 7.6 Hz, 1H), 7.91 (t, J = 8.0 Hz, 1H), 8.61 (d, J = 4.4 Hz, 1H). | C | m/z 343 (M + H)$^+$ (ES$^+$), at 2.50 min, UV active |
| 1-13 | Isomer 2: ethyl {(3R)-1-[4-cyano-4-(pyridin-2-yl)cyclohexyl]pyrrolidin-3-yl}carbamate | 14 and 26 | c | (400 MHz, CD$_3$OD) δ: 1.20 (t, J = 7.2 Hz, 3H), 1.71-1.76 (m, 1H), 1.83-2.05 (m, 7H), 2.17-2.30 (m, 1H), 2.50-2.70 (m, 5H) 2.87-2.95 (m, 2H), 4.07 (q, J = 7.2 Hz, 2H), 4.11-4.20 (m, 1H), 7.28 (d, J = 7.2 Hz, 1H), 7.70 (d, J = 7.2 Hz, 1H), 7.91 (t, J = 6.8 Hz, 1H), 8.62 (d, J = 4.8 Hz, 1H). | C | m/z 343 (M + H)$^+$ (ES$^+$), at 2.52 min, UV active |
| 1-14 | Isomer 2: ethyl {(3S)-1-[4-cyano-4-(5-fluoropyridin-2-yl)cyclohexyl]pyrrolidin-3-yl}carbamate | 13 and 27 | c | (400 MHz, DMSO-$d_6$) δ: 1.15 (t, J = 6.8 Hz, 3H), 1.56-1.62 (m, 1H), 1.66-2.15 (m, 8H), 2.21-2.45 (m, 4H), 2.46-2.52 (m, 1H), 2.70-2.80 (m, 1H), 3.92-4.01 (m, 3H), 7.28 (d, J = 7.2 Hz, 1H), 7.68-7.72 (m,1H), 7.82-7.86 (m, 1H), 8.64-8.66 (m, 1H). | C | m/z 361 (M + H)$^+$ (ES$^+$), at 2.62 min, UV active |
| 1-15 | Isomer 2: ethyl {(3S)-1-[trans-4-(5-chloropyridin-2-yl)-4-cyanocyclohexyl]pyrrolidin-3-yl}carbamate | 15, 28 and 55 | b | (400 MHz, DMSO-$d_6$) δ: 1.14 (t, J = 7.0 Hz, 3H), 1.38-1.66 (m, 1H), 1.66-2.19 (m, 8H), 2.13-2.37 (m, 4H), 2.40-2.43 (m, 1H), 2.74 (t, J = 8.0 Hz, 1H), 3.87-3.95 (m, 1H), 3.96 (q, J = 7.0 Hz, 2H), 7.27 (d, J = 7.0 Hz, 1H), 7.66 (dd, J = 8.5 Hz, 0.8, 1H), 8.04 (dd, J = 8.5 Hz, 2.5 Hz, 1H) and 8.70 (dd, J = 2.5 Hz, 0.8, 1H). | B | m/z 377 (M + H)$^+$ (ES$^+$), at 3.95 min, UV active |
| 1-16 | Isomer 2: ethyl {(3R)-1-[4-(5-chloropyridin-2-yl)-4-cyanocyclohexyl]pyrrolidin-3-yl}carbamate | 16, 28 and 55 | b | (400 MHz, DMSO-d6) δ: 1.14 (t, J = 7.0 Hz, 3H), 1.48-1.66 (m, 1H), 1.66-2.19 (m, 8H), 2.24-2.37 (m, 3H), 2.41-2.49 (m, 1H), 2.53-2.60 (m, 1H), 2.75 (t, J = 8.0 Hz, 1H), 3.87-3.95 (m, 1H), 3.96 (q, J = 7.0 Hz, 2H), 7.27 (d, J = 7.0 Hz, 1H), 7.66 (dd, J = 8.5, 0.8 Hz, 1H), 8.04 (dd, J = 8.5, 2.5 Hz, 1H), 8.70 (dd, J = 2.5, 0.8 Hz, 1H). | B | m/z 377 (M + H)$^+$ (ES$^+$), at 3.97 min, UV active |
| 1-17 | Isomer 2: ethyl {(3S)-1-[4-cyano-4-(4-methylpyridin-2-yl)cyclohexyl]pyrrolidin-3-yl}carbamate | 13 and 29 | c | (400 MHz, DMSO-d6) δ: 1.14 (t, J = 7.0 Hz, 3H), 1.56-1.60 (m, 1H), 1.70-1.93 (m, 6H), 2.00-2.08 (m, 2H), 2.25-2.37 (m, 4H), 2.38 (s, 3H), 2.47-2.50 (m, 1H), 2.74-2.78 (m, 1H), 3.99-3.99 (m, 3H), 7.22-7.23 (m, 1H), 7.27-7.29 (m,1H), 7.43 (s, 1H), 8.46-8.48 (m, 1H). | C | m/z 357 (M + H)$^+$ (ES$^+$), at 2.66 min, UV active |
| 1-18 | Isomer 2: ethyl {(3S)-1-[4-cyano-4-(6-methylpyridin-2-yl)cyclohexyl]pyrrolidin-3-yl}carbamate | 13 and 30 | c | (400 MHz, CDCl$_3$) δ: 1. 28 (t, J .2 Hz, 3H), 1.80-2.00 (m, 6H), 2.19-2.40 (m, 8H), 2.55 (s, 3H), 2.64-2.95 (m, 2H), 3.05-3.35 (m, 2H), 4.12 (q, J = 7.2 Hz, 2H), 4.30-4.45 (m, 1H), 7.10 (d, J = 8 Hz, 1H), 7.43 (d, J = 8 Hz, 1H), 7.62 (t, J = 8, 1H). N-H not observed. | C | m/z 358 (M + H)$^+$ (ES$^+$), at 2.65 min, UV active |
| 1-19 | Isomer 2: ethyl {(3R)-1-[4-cyano-4-(4-methylpyridin-2-yl)cyclohexyl]pyrrolidin-3-yl}carbamate | 14 and 29 | c | (400 MHz, DMSO-$d_6$) δ: 1.14 (t, J = 7.2 Hz, 3H), 1.56-1.61 (m, 1H), 1.70-2.10 (m, 8H), 2.25-2.37 (m, 4H), 2.38 (s, 3H), 2.45-2.50 (m, 1H), 2.72-2.77 (m, 1H), 3.93-4.05 (m, 3H), 7.23 (d, J = 4.8 Hz, 1H), 7.27 (d, J = 8.0 Hz, 1H), 7.43 (s, 1H), 8.47 (d, J = 5.2 Hz, 1H). | C | m/z 357 (M + H)$^+$ (ES$^+$), at 7.15 min, UV active |
| 1-20 | Isomer 2: ethyl [(3S)-1-(4-cyano-4-phenylcyclohexyl)pyrrolidin-3-yl]methylcarbamate | 12, 17 and 55 | b | (400 MHz, DMSO-$d_6$) δ: 1.10 (t, J = 7.1 Hz, 3H), 1.56-1.84 (m, 5H), 1.84-2.22 (m, 7H), 2.34 (dd, J = 9.5, 8.3 Hz, 1H), 2.64 (dd, J = 9.9, 3.4, 1H), 2.74 (s, 3H), 2.82 (td, J = 8.4 and 2.8 Hz, 1H), | B | m/z 356 (M + H)$^+$ (ES$^+$), at 5.00 min, |

TABLE 3-continued

| Ex. No. | Name | Intermediate | Synthetic method | ¹H NMR | LCMS Method | LCMS data |
|---|---|---|---|---|---|---|
| | | | | 3.94 (q, J = 7.1 Hz, 2H), 4.63 (br. s., 1H), 7.26-7.32 (m, 1H), 7.34-7.45 (m, 4H). | | UV active |
| 1-21 | Isomer 2: ethyl [(3R)-1-(4-cyano-4-phenylcyclohexyl) pyrrolidin-3-yl] methylcarbamate | 12, 18 and 55 | b | (400 MHz, DMSO-d$_6$) δ: 1.17 (t, J = 7.2 Hz, 3H), 1.65-2.01 (m, 6H), 2.01-2.30 (m, 6H), 2.35-2.45 (m, 1H), 2.65-2.75 (m, 1H), 2.82 (s, 3H), 2.85-2.95 (m, 1H), 4.01 (q, J = 7.2 Hz, 2H), 4.70 (br. s., 1H), 7.33-7.39 (m, 1H), 7.42-7.52 (m, 4H). | B | m/z 356 (M + H)⁺ (ES⁺), at 4.94 min, UV active |
| 1-22 | Isomer 2: ethyl {(3R)-1-[4-(5-chloropyridin-2-yl)-4-cyanocyclohexyl] pyrrolidin-3-yl} methylcarbamate | 17, 28 and 55 | b | (500 MHz, CDCl$_3$) δ: 1.25 (t, J = 7.0 Hz, 3H), 1.49-1.65 (m, 2H), 1.70-1.81 (m, 1H), 1.82-2.02 (m, 4H), 2.03-2.33 (m, 4H), 2.34-2.55 (m, 3H), 2.68 (dd, J = 10.0, 3.0 Hz, 1H), 2.88 (s, 3H), 4.11 (q, J = 7.0 Hz, 2H), 4.77-5.01 (m, 1H), 7.50 (d, J = 8.5 Hz, 1H), 7.69 (dd, J = 8.5, 2.5 Hz, 1H), 8.54 (d, J = 2.5 Hz, 1H). | | m/z 391 (M + H)⁺ (ES⁺), at 4.72 min, UV active |
| 2-1 | Isomer 1: ethyl [(3S)-1-(2'-oxo-1',2'-dihydrospiro[cyclohexane-1,3'-indol]-4-yl)pyrrolidin-3-yl]carbamate | 13 and 65 | c | (400 MHz, DMSO-d6) ⊐: 1.16 (t, J = 7.0 Hz, 3H), 1.52-1.72 (m, 6H), 1.93-2.43 (m, 5H), 2.53-2.69 (m, 3H), 2.79-2.91 (m, 1H), 3.95-4.00 (m, 3H), 6.87 (d, J = 7.5 Hz, 1H), 6.96 (td, J = 7.5, 1.0 Hz, 1H), 7.20 (td, J = 7.5, 1.0 Hz, 1H), 7.26-7.32 (m, 1H), 7.44 (d, J = 7.5 Hz, 1H), 10.40 (s, 1H). | B | m/z 358 (M + H)⁺ (ES⁺), at 2.67 min, UV active |
| 2-2 | Isomer 1: ethyl [(3R)-1-(2'-oxo-1',2'-dihydrospiro[cyclohexane-1,3'-indol]-4-yl)pyrrolidin-3-yl]carbamate | 14 and 65 | c | (400 MHz, DMSO-d$_6$) ⊐: 1.16 (t, J = 7.0 Hz, 3H), 1.48-1.73 (m, 7H), 1.95-2.11 (m, 3H), 2.27-2.31 (m, 1H), 2.61-2.81 (m, 3H), 2.91-2.95 (m, 1H), 3.95-4.01 (m, 3H), 6.87 (d, J = 7.5 Hz, 1H), 6.97 (t, J = 7.5 Hz, 1H), 7.20 (t, J = 7.5 Hz, 1H), 7.31-7.33 (m, 1H), 7.46 (d, J = 7.5 Hz, 1H), 10.41 (s, 1H) | F | m/z 358 (M + H)⁺ (ES⁺), at 1.62 min, UV active |
| 2-2 | Isomer 2: ethyl [(3R)-1-(2'-oxo-1',2'-dihydrospiro[cyclohexane-1,3'-indol]-4-yl)pyrrolidin-3-yl]carbamate | 14 and 65 | c | (400 MHz, DMSO-d$_6$) ⊐: 1.16 (t, J = 7.0 Hz, 3H), 1.65-1.83 (m, 7H), 2.02-2.13 (m, 3H), 2.36-2.42 (m, 1H), 2.57-2.63 (m, 2H), 2.73-2.91 (m, 1H), 3.00-3.11 (m, 1H), 3.95-4.06 (m, 3H), 6.81 (d, J = 7.5 Hz, 1H), 6.95 (t, J = 7.5 Hz, 1H), 7.16 (t, J = 7.5 Hz, 1H), 7.27 (d, J = 7.5 Hz, 1H), 7.35-7.36 (m, 1H), 10.27 (s, 1H). | F | m/z 358 (M + H)⁺ (ES⁺), at 1.69 min, UV active |
| 2-3 | Isomer 1: ethyl [(3S)-1-(7'-methyl-2'-oxo-1',2'-dihydrospiro[cyclohexane-1,3'-indol]-4-yl)pyrrolidin-3-yl]carbamate | 13 and 67 | c | (400 MHz, DMSO-d$_6$) ⊐: 1.16 (t, J = 7.0 Hz, 3H), 1.52-1.71 (m, 7H), 1.96-2.09 (m, 3H), 2.16-2.21 (m, 4H), 2.37-2.41 (m, 1H), 2.66-2.56 (m, 2H), 2.82-2.86 (m, 1H), 3.95-4.00 (m, 3H), 6.88 (t, J = 7.5 Hz, 1H), 7.02 (d, J = 7.5 Hz, 1H), 7.24-7.29 (m, 2H), 10.42 (s, 1H) | F | m/z 372 (M + H)⁺ (ES⁺), at 1.63 min, UV active |
| 2-4 | Isomer 1: ethyl [(3S)-1-(6'-methyl-2'-oxo-1',2'-dihydrospiro[cyclohexane-1,3'-indol]-4-yl)pyrrolidin-3-yl]carbamate | 13 and 68 | c | (400 MHz, DMSO-d$_6$) ⊐: 1.16 (t, J = 7.0 Hz, 3H), 1.43-1.75 (m, 6H), 1.92-2.10 (m, 3H), 2.13-2.22 (m, 1H), 2.27 (s, 3H), 2.36-2.40 (m, 1H), 2.57-2.68 (m, 3H), 2.82-2.86 (m, 1H), 3.95-4.00 (m, 3H), 6.69 (s, 1H),6.77 (d, J = 7.5 Hz, 1H), 7.29 (m, 2H), 10.34 (s, 1H) | F | m/z 372 (M + H)⁺ (ES⁺), at 1.67 min, UV active |
| 2-5 | Isomer 1: ethyl [(3S)-1-(5'-methyl-2'-oxo-1',2'-dihydrospiro[cyclohexane-1,3'-indol]-4-yl)pyrrolidin-3-yl]carbamate | 13 and 70 | c | (400 MHz, DMSO-d$_6$) ⊐: 1.16 (t, J = 7.0 Hz, 3H), 1.51-1.71 (m, 7H), 1.93-2.21 (m, 4H), 2.29 (s, 3H), 2.32-2.43 (m, 1H), 2.55-2.70 (m, 2H), 2.85-2.90 (m, 1H), 3.95-4.01 (m, 3H), 6.76 (d, J = 7.5 Hz, 1H), 7.00 (d, J = 7.5 Hz, 1H), 7.23 (s, 1H), 7.28 (d, J = 7.0 Hz, 1H), 10.29 (s, 1H) | F | m/z 372 (M + H)⁺ (ES⁺), at 1.67 min, UV active |
| 2-6 | Isomer 1: ethyl [(3S)-1-(4'-methyl-2'-oxo-1',2'-dihydrospiro[cyclohexane-1,3'-indol]-4-yl)pyrrolidin-3-yl]carbamate | 13 and 72 | c | (400 MHz, DMSO-d6) ⊐: 1.14-1.20 (m, 4H), 1.61-1.71 (m, 3H), 1.95-2.44 (m, 10H), 2.56-2.63 (m, 3H), 2.81-2.85 (m, 1H), 3.95-4.01 (m, 3H), 6.60 (d, J = 7.5 Hz, 1H), 6.70 (d, J = 7.5 Hz, 1H), 7.02 (t, J = 7.5 Hz, 1H), 7.19 (d, J = 6.5 Hz, 1H), 10.11 (s, 1H) | F | m/z 372 (M + H)⁺ (ES⁺), at 1.73 min, UV active |
| 2-7 | Isomer 1: ethyl [(3S)-1-(6'-fluoro-2'-oxo-1',2'-dihydrospiro[cyclohexane-1,3'-indol]-4-yl)pyrrolidin-3-yl]carbamate | 13 and 74 | c | (400 MHz, DMSO-d$_6$) ⊐: 1.16 (t, J = 7.0 Hz, 3H), 1.52-1.70 (m, 7H), 1.97-2.09 (m, 3H), 2.15-2.24 (m, 1H), 2.36-2.40 (m, 1H), 2.57-2.67 (m, 2H), 2.82-2.86 (m, 1H), 3.95-4.00 (m, 3H), 6.68 (dd, J = 9.0, 2.5 Hz, 1H), 6.74-6.79 (m, 1H), 7.28 (d, J = 7.0 Hz, 1H), 7.43 (dd, J = 8.0, 5.5 Hz, 1H), 10.56 (bs, 1H) | F | m/z 376 (M + H)⁺ (ES⁺), at 1.72 min, UV active |
| 2-7 | Isomer 2: ethyl [(3S)-1-(6'-fluoro-2'-oxo-1',2'-dihydrospiro[cyclohexane- | 13 and 74 | c | (400 MHz, DMSO-d$_6$) ⊐: 1.16 (t, J = 7.0 Hz, 3H), 1.54-1.76 (m ,7H), 1.92-2.09 (m, 3H), 2.19-2.24 (m, 1H), 2.33-2.37 (m, 1H), | F | m/z 376 (M + H)⁺ (ES⁺), |

TABLE 3-continued

| Ex. No. | Name | Intermediate | Synthetic method | ¹H NMR | LCMS Method | LCMS data |
|---|---|---|---|---|---|---|
| | 1,3'-indol]-4-yl)pyrrolidin-3-yl]carbamate | | | 2.54-2.65 (m, 2H), 2.80-2.84 (m, 1H), 3.90-4.00 (m, 3H), 6.61 (dd, J = 9.0, 2.0 Hz, 1H), 6.70-6.76 (m, 1H), 7.27 (d, J = 7.0 Hz, 1H), 7.33 (dd, J = 8.0, 6.0 Hz, 1H), 10.38 (s, 1H) | | at 1.96 min, UV active |
| 2-8 | Isomer 1: ethyl [(3S)-1-(5'-fluoro-2'-oxo-1',2'-dihydrospiro[cyclohexane-1,3'-indol]-4-yl)pyrrolidin-3-yl]carbamate | 13 and 76 | c | (400 MHz, DMSO-d₆) ᴅ: 1.16 (t, J = 7.0 Hz, 3H), 1.50-1.70 (m, 7H), 1.95-2.11 (m, 3H), 2.15-2.26 (m, 1H), 2.39-2.43 (m, 1H), 2.66-2.71 (m, 2H), 2.79-2.83 (m, 1H), 3.95-4.00 (m, 3H), 6.86 (dd, J = 8.5, 4.5 Hz, 1H), 7.02-7.07 (m, 1H), 7.21-7.24 (m, 1H), 7.30 (d, J = 7.0 Hz, 1H), 10.42 (s, 1H) | F | m/z 376 (M + H)⁺ (ES⁺), at 1.64 min, UV active |
| 2-8 | Isomer 2: ethyl [(3S)-1-(5'-fluoro-2'-oxo-1',2'-dihydrospiro[cyclohexane-1,3'-indol]-4-yl)pyrrolidin-3-yl]carbamate | 13 and 76 | c | (400 MHz, DMSO-d6) ᴅ: 1.16 (t, J = 7.0 Hz, 3H), 1.53-1.81 (m, 7H), 1.89-2.09 (m, 3H), 2.17-2.27 (m, 1H), 2.32-2.40 (m, 1H), 2.55-2.66 (m, 2H), 2.80-2.84 (m, 1H), 3.90-4.03 (m, 3H), 6.78 (dd, J = 8.5, 4.5 Hz, 1H), 6.95-7.00 (m, 1H), 7.24-7.32 (m, 2H), 10.25 (s, 1H) | F | m/z 376 (M + H)⁺ (ES⁺), at 1.72 min, UV active |
| 2-9 | Isomer 1: ethyl [(3S)-1-(6'-methoxy-2'-oxo-1',2'-dihydrospiro[cyclohexane-1,3'-indol]-4-yl)pyrrolidin-3-yl]carbamate | 13 and 78 | c | (400 MHz, DMSO-d₆) ᴅ: 1.14-1.20 (m, 3H), 1.46-1.70 (m, 6H), 1.95-2.09 (m, 3H), 2.13-2.23 (m, 1H), 2.36-2.40 (m, 1H), 2.56-2.68 (m, 2H), 2.83-2.87 (m, 1H), 3.19-3.25 (m, 1H), 3.73 (s, 3H), 3.95-4.00 (m, 3H), 6.43 (d, J = 2.0 Hz, 1H), 6.51 (dd, J = 8.0, 2.0 Hz, 1H), 7.27 (d, J = 7.0 Hz, 1H), 7.32 (d, J = 8.0 Hz, 1H), 10.36 (s, 1H) | F | m/z 388 (M + H)⁺ (ES⁺), at 1.68 min, UV active |
| 2-10 | Isomer 1: ethyl [(3S)-1-(5'-methoxy-2'-oxo-1',2'-dihydrospiro[cyclohexane-1,3'-indol]-4-yl)pyrrolidin-3-yl]carbamate | 13 and 80 | c | (400 MHz, DMSO-d6) ᴅ: 1.10-1.22 (m, 4H), 1.53-1.70 (m, 6H), 1.91-2.11 (m, 2H), 2.15-2.25 (m, 1H), 2.38-2.42 (m, 1H), 2.55-2.72 (m, 2H), 2.79-2.85 (m, 1H), 2.94-3.17 (m, 1H), 3.72 (s, 3H), 3.95-4.00 (m, 3H), 6.79 (s, 2H), 6.98 (s, 1H), 7.28 (d, J = 7.0 Hz, 1H), 10.24 (s, 1H) | F | m/z 388 (M + H)⁺ (ES⁺), at 1.66 min, UV active |
| 2-11 | Isomer 1: ethyl methyl[(3S)-1-(2'-oxo-1',2'-dihydrospiro[cyclohexane-1,3'-indol]-4-yl)pyrrolidin-3-yl]carbamate | 65 and 82 | c | (400 MHz, DMSO-d6) ᴅ: 1.19 (t, J = 7.0 Hz, 3H), 1.55-1.77 (m, 7H), 1.99-2.10 (m, 3H), 2.15-2.23 (m, 1H), 2.30-2.37 (m, 1H), 2.56-2.61 (m, 1H), 2.66-2.74 (m, 2H), 2.86-2.93 (m, 4H), 4.03 (q, J = 7.0 Hz, 2H), 6.86 (d, J = 7.5 Hz, 1 H), 6.97 (t, J = 7.5 Hz, 1H), 7.20 (t, J = 7.5 Hz, 1H), 7.36 (d, J = 7.5 Hz, 1H), 10.37 (s, 1H) | F | m/z 372 (M + H)⁺ (ES⁺), at 1.72 min, UV active |
| 2-12 | Isomer 1: ethyl methyl[(3R)-1-(2'-oxo-1',2'-dihydrospiro[cyclohexane-1,3'-indol]-4-yl)pyrrolidin-3-yl]carbamate | 65 and 84 | c | (400 MHz, MeOD-d₄) ᴅ: 1.29 (m, 3H), 1.59-1.70 (m, 2H), 1.79-1.98 (m, 5H), 2.06-2.23 (m, 3H), 2.35-2.48 (m, 1H), 2.68-2.83 (m, 2H), 2.94-3.02 (m, 5H), 4.15 (q, J = 7.0 Hz, 2H), 4.81-4.89 (m, 1H), 6.96 (d, J = 7.5 Hz, 1H), 7.04 (t, J = 7.5 Hz, 1H), 7.25 (t, J = 7.5 Hz, 1H), 7.66 (d, J = 7.5 Hz, 1H) | F | m/z 372 (M + H)⁺ (ES⁺), at 1.68 min, UV active |
| 2-12 | Isomer 2: ethyl methyl[(3R)-1-(2'-oxo-1',2'-dihydrospiro[cyclohexane-1,3'-indol]-4-yl)pyrrolidin-3-yl]carbamate | 65 and 84 | c | (400 MHz, DMSO-d₆, D₂O wash) ᴅ: 1.16 (t, J = 7.0 Hz, 3H), 1.57-2.09 (m, 10H), 2.56-2.86 (m, 7H), 2.88-2.99 (m, 1H), 4.00-4.03 (m, 2H), 4.57-4.75 (m, 1H), 6.84 (d, J = 7.5 Hz, 1H), 6.96 (t, J = 7.5 Hz, 1H), 7.15 (t, J = 7.5 Hz, 1H), 7.28 (d, J = 7.5 Hz, 1H) | G | m/z 372 (M + H)⁺ (ES⁺), at 1.65 min, UV active |
| 2-13 | Isomer 1: ethyl [(3S)-1-(1'-methyl-2'-oxo-1',2'-dihydrospiro[cyclohexane-1,3'-indol]-4-yl)pyrrolidin-3-yl]carbamate | 13 and 86 | c | (400 MHz, DMSO-d₆) ᴅ: 1.16 (t, J = 7.0 Hz, 3H), 1.53-1.76 (m, 6H), 1.95-2.12 (m, 3H), 2.17-2.29 (m, 1H), 2.38-2.41 (m, 1H), 2.56-2.70 (m, 3H), 2.83-2.87 (m, 1H), 3.14 (s, 3H), 3.95-4.01 (m, 3H), 7.03-7.07 (m, 2H), 7.27-7.33 (m, 2H), 7.48 (d, J = 7.5 Hz, 1H) | F | m/z 372 (M + H)⁺ (ES⁺), at 1.70 min, UV active |
| 2-14 | Isomer 2: ethyl 4-{(3S)-3-[(ethoxycarbonyl)amino]pyrrolidin-1-yl}-2'-oxospiro[cyclohexane-1,3'-indole]-1'(2'H)-carboxylate | 13 and 87 | c | (400 MHz, DMSO-d₆) ᴅ: 1.16 (t, J = 7.0 Hz, 3H), 1.34 (t, J = 7.0 Hz, 3H), 1.59-1.83 (m, 4H), 1.95-2.11 (m, 2H), 2.21-2.43 (m, 6H), 2.60-2.73 (m, 2H), 2.79-2.84 (m, 1H), 3.96-4.00 (m, 3H), 4.37 (q, J = 7.0 Hz, 2H), 7.21-7.38 (m, 3H), 7.52 (d, J = 7.5 Hz, 1H), 7.85 (d, J = 7.5 Hz, 1H) | F | m/z 430 (M + H)⁺ (ES⁺), at 1.82 min, UV active |
| 2-15 | Isomer 1: ethyl {(3S)-1-[1'-(2-amino-2-oxoethyl)-2'-oxo-1',2'-dihydrospiro[cyclohexane-1,3'-indol]-4-yl]pyrrolidin-3-yl}carbamate | 13 and 88 | c | (400 MHz, DMSO-d₆) ᴅ: 1.16(t, J = 7.0 Hz, 3H), 1.61-1.70 (m, 7H), 1.95-2.13 (m, 3H), 2.21-2.31 (m, 1H), 2.37-2.44 (m, 1H), 2.58-2.66 (m, 2H), 2.84-2.88 (m, 1H), 3.96-4.01 (m, 3H), 4.26 (s, 2H), 6.89 (d, J = 8.0 Hz, 1H), 7.04 (t, J = 7.5 Hz, 1H), 7.23-7.32 (m, 3H), 7.48 (d, J = 7.5 Hz, 1H), 7.62 (s, 1H) | G | m/z 415 (M + H)⁺ (ES⁺), at 4.40 min, UV active |

TABLE 3-continued

| Ex. No. | Name | Inter mediate | Synthetic method | ¹H NMR | LCMS Method | LCMS data |
|---|---|---|---|---|---|---|
| 2-15 | Isomer 2: ethyl {(3S)-1-[1'-(2-amino-2-oxoethyl)-2'-oxo-1',2'-dihydrospiro[cyclohexane-1,3'-indol]-4-yl}pyrrolidin-3-yl}carbamate | 13 and 88 | c | (400 MHz, DMSO-d₆) ⊐: 1.16 (t, J = 7.0 Hz, 3H), 1.54-1.84 (m, 7H), 1.91-2.12 (m, 3H), 2.19-2.28 (m, 1H), 2.35-2.43 (m, 1H), 2.56-2.66 (m, 2H), 2.77-2.90 (m, 1H), 3.95-4.00 (m, 3H), 4.23 (s, 2H), 6.83 (d, J = 7.5 Hz, 1H), 7.01 (t, J = 7.5 Hz, 1H), 7.19-7.35 (m, 4H), 7.61 (s, 1H) | G | m/z 415 (M + H)⁺ (ES⁺), at 4.88 min, UV active |
| 2-16 | Isomer 1: ethyl [(3S)-1-(2'-oxo-1',2'-dihydrospiro[cyclohexane-1,3'-pyrrolo[2,3-b]pyridin]-4-yl)pyrrolidin-3-yl]carbamate | 13 and 90 | c | (400 MHz, (MSO-d₆, D2O wash) ⊐: 1.15(t, J = 7.0 Hz, 3H), 1.53-1.79 (m, 7H), 2.21-2.36 (m, 2H), 2.59-2.73 (m, 5H), 2.89-2.97 (m, 1H), 3.92-4.03 (m, 3H), 6.97 (dd, J = 7.5, 5.5 Hz, 1H), 7.24-7.29 (m, 1H), 7.82 (d, J = 7.5 Hz, 1H), 8.08 (d, J = 5.5 Hz, 1H). | F | m/z 360 (M + H)⁺ (ES⁺), at 1.48 min, UV active |
| 2-17 | Isomer 1: ethyl [(3S)-1-(5'-chloro-2'-oxo-1',2'-dihydrospiro[cyclohexane-1,3'-pyrrolo[2,3-b]pyridin]-4-yl)pyrrolidin-3-yl]carbamate | 13 and 93 | c | (400 MHz, DMSO-d₆) ⊐: 1.16 (t, J = 7.0 Hz, 3H), 1.47-1.77 (m, 6H), 1.94-2.12 (m, 3H), 2.14-2.26 (m, 1H), 2.36-2.45 (m, 1H), 2.55-2.63 (m, 2H), 2.64-2.73 (m, 1H), 2.78-2.90 (m, 1H), 3.91-4.09 (m, 3H), 2.28 (d, J = 6.5 Hz, 1H), 7.77 (s, 1H), 8.16 (d, J = 2.0 Hz, 1H), 11.24 (s, 1H) | F | m/z 393 (M + H)⁺ (ES⁺), at 1.61 min, UV active |
| 2-18 | Isomer 1: ethyl methyl[(3R)-1-(2'-oxo-1',2'-dihydrospiro[cyclohexane-1,3'-pyrrolo[2,3-b]pyridin]-4-yl)pyrrolidin-3-yl]carbamate | 84 and 90 | c | (400 MHz, DMSO-d₆) ⊐: 1.19 (t, J = 7.0 Hz, 3H), 1.55-1.77 (m, 7H), 1.98-2.09 (m, 3H), 2.34-2.38 (m, 1H), 2.44-2.48 (m, 1H), 2.56-2.63 (m, 2H), 2.68-2.72 (m, 1H), 2.84-2.92 (m, 4H), 4.03 (q, J = 7.0 Hz, 2H), 6.98 (dd, J = 7.5, 5.5 Hz, 1H), 7.71-7.73 (m, 1H), 8.08 (dd, J = 5.5, 1.5 Hz, 1H), 11.01 (s, 1H) | G | m/z 373 (M + H)⁺ (ES⁺), at 4.68 min, UV active |
| 2-18 | Isomer 2: ethyl methyl[(3R)-1-(2'-oxo-1',2'-dihydrospiro[cyclohexane-1,3'-pyrrolo[2,3-b]pyridin]-4-yl)pyrrolidin-3-yl]carbamate | 84 and 90 | c | (400 MHz, DMSO-d₆, D₂O wash) ⊐: 1.17 (t, J = 7.0 Hz, 3H), 1.43-1.59 (m, 7H), 1.64-2.09 (m, 7H), 2.18-2.36 (m, 2H), 2.40-2.47 (m, 1H), 2.54-2.61 (m, 2H), 2.64-2.71 (m, 1H), 2.78-2.92 (m, 4H), 4.01 (q, J = 7.0 Hz, 2H), 6.95 (dd, J = 7.0, 5.5 Hz, 1H), 7.74-7.76 (m, 1H), 8.03-8.04 (m, 1H) | G | m/z 373 (M + H)⁺ (ES⁺), at 5.11 min, UV active |
| 2-19 | Isomer 1: ethyl [(3S)-1-(5'-methoxy-2'-oxo-1',2'-dihydrospiro[cyclohexane-1,3'-pyrrolo[2,3-c]pyridin]-4-yl)pyrrolidin-3-yl]carbamate | 13 and 95 | g | (400 MHz, CDCl₃) ⊐: 1.27-1.31 (m, 4H), 1.67-1.85 (m, 5H), 1.96-2.20 (m, 6H), 2.77-2.87 (m, 1H), 3.32-3.77 (m, 4H), 3.93 (s, 3H), 4.16 (q, J = 7.0 Hz, 2H), 7.03 (s, 1H), 7.35 (s, 1H) 7.77 (s, 1H) | L | m/z 389 (M + H)⁺ (ES⁺), at 4.00 min, UV active |
| 2-20 | Isomer 1: ethyl [(3S)-1-(5'-methoxy-2'-oxo-1',2'-dihydrospiro[cyclohexane-1,3'-pyrrolo[3,2-b]pyridin]-4-yl)pyrrolidin-3-yl]carbamate | 13 and 97 | c | (400 MHz, DMSO-d₆) ⊐: 1.15 (t, J = 7.0 Hz, 3H), 1.55-1.82 (m, 7H), 1.98-2.16 (m, 3H), 2.26-2.31 (m, 1H), 2.35-2.39 (m, 1H), 2.62-2.65 (m, 2H), 2.92 (t, J = 8.0 Hz, 1H), 3.82 (s, 3H), 3.88-4.05 (m, 3H), 6.65 (d, J = 8.5 Hz, 1H), 7.21-7.24 (m, 2H), 10.30 (s, 1H) | F | m/z 389 (M + H)⁺ (ES⁺), at 1.64 min, UV active |
| 2-21 | Isomer 2: ethyl methyl[(3R)-1-(2'-oxo-1',2'-dihydrospiro[cyclohexane-1,3'-pyrrolo[3,2-b]pyridin]-4-yl)pyrrolidin-3-yl]carbamate | 84 and 99 | c | (400 MHz, DMSO-d₆) ⊐: 1.19 (t, J = 7.0 Hz, 3H), 1.60-1.79 (m, 7H), 1.85-2.22 (m, 6H), 2.30-2.41 (m, 1H), 2.56-2.70 (m, 3H), 2.82-2.91 (m, 4H), 4.03 (q, J = 7.0 Hz, 2H), 7.19 (m, 2H), 8.10-8.12 (m, 1H), 10.57 (s, 1H) | F | m/z 373 (M + H)⁺ (ES⁺), at 1.64 min, UV active |
| 3-1 | Mixture of isomers: ethyl 4-(4-cyano-4-phenylcyclohexyl)-1,4-diazepane-1-carboxylate | 12 and 32 | a | (400 MHz, CDCl₃) δ: 1.27 (t, J = 7.0 Hz, 3H), 1.75-1.98 (m, 8H), 2.22-2.24 (m, 2H), 2.58-2.64 (m, 1H), 2.70-2.82 (m, 4H), 3.46-3.56 (m, 4H), 4.15 (q, J = 7.0, 2H), 7.28-7.33 (m, 1H), 7.35-7.42 (m, 2H), 7.47-7.51 (m, 2H). | B | m/z 356 (M + H)⁺ (ES⁺), at 4.25 and 4.50 min, UV active |
| 3-2 | Mixture of isomers: ethyl 4-[4-cyano-4-(3-fluorophenyl)cyclohexyl]-1,4-diazepane-1-carboxylate | 20 and 32 | a | (400 MHz, DMSO-d₆) δ: 1.18 (t, J = 7.0,3 H), 1.61-1.72 (m, 4H), 1.86-1.96 (m, 4H), 2.04-2.09 (m, 2H), 2.61-2.72 (m, 5H), 3.38-3.42 (m, 4H), 4.04 (q, J = 7.02, 2H), 7.19-7.24 (m, 1H), 7.36-7.40 (m, 2H), 7.46-7.54 (m, 1H). | B | m/z 374 (M + H)⁺ (ES⁺), at 2.54 and 2.68 min, UV active |
| 3-3 | Mixture of isomers: ethyl 4-[4-cyano-4-(4-fluorophenyl)cyclohexyl]-1,4-diazepane-1-carboxylate | 21 and 32 | a | (400 MHz, CDCl₃) δ: 1.26 (t, J = 7.0, 3H), 1.76-1.98 (m, 8H), 2.20-2.23 (m, 2H), 2.55-2.65 (m, 1H), 2.68-2.81 (m, 4 H), 3.46-3.53 (m, 4H), 4.14 (q, J = 7.0, 2H), 7.05-7.11 (m, 2H), 7.43-7.47 (m, 2H). | B | m/z 374 (M + H)⁺ (ES⁺), at 2.49 and 2.67 min, UV active |

TABLE 3-continued

| Ex. No. | Name | Intermediate | Synthetic method | $^1$H NMR | LCMS Method | LCMS data |
|---|---|---|---|---|---|---|
| 3-4 | Mixture of isomers: ethyl 4-[4-cyano-4-(2-chlorophenyl)cyclohexyl]-1,4-diazepane-1-carboxylate | 32 and 35 | a | (400 MHz, CDCl$_3$) δ: 1.27 (t, J = 7.0 Hz, 3H), 1.75-1.98 (m, 8H), 2.57-2.61 (m, 3H), 2.72-2.83 (m, 4H), 3.47-3.55 (m, 4H), 4.15 (q, J = 7.0, 2H), 7.29-7.33 (m, 2H), 7.43-7.46 (m, 2H). | A | m/z 390 (M + H)$^+$ (ES$^+$), at 1.79 and 1.89 min, UV active |
| 3-5 | Mixture of isomers: ethyl 4-[4-cyano-4-(3-chlorophenyl)cyclohexyl]-1,4-diazepane-1-carboxylate | 24 and 32 | a | (400 MHz, DMSO-d$_6$) δ: 1.18 (t, J = 7.0, 3H), 1.60-1.70 (m, 4H), 1.86-1.97 (m, 4H), 2.03-2.05 (m, 2H), 2.62-2.73 (m, 5H), 3.38-3.43 (m, 4H), 4.04 (q, J = 7.0, 2H), 7.43-7.49 (m, 4H). | B | m/z 390 (M + H)$^+$ (ES$^+$), at 2.48 and 2.72 min, UV active |
| 3-6 | Mixture of isomers: ethyl 4-[4-cyano-4-(4-chlorophenyl)cyclohexyl]-1,4-diazepane-1-carboxylate | 32 and 36 | a | (400 MHz, DMSO-d$_6$) δ: 1.18 (t, J = 7.0, 3H), 1.60-1.70 (m, 4H), 1.87-1.94 (m, 4H), 2.09-2.10 (m, 2H), 2.62-2.73 (m, 5H), 3.38-3.41 (m, 4H), 4.03 (q, J = 7.02, 2H), 7.46-7.56 (m, 4H). | B | m/z 390 (M + H)$^+$ (ES$^+$), at 2.68 and 2.86 min, UV active |
| 3-7 | Mixture of isomers: ethyl 4-[4-cyano-4-(2-methylphenyl)cyclohexyl]-1,4-diazepane-1-carboxylate | 22 and 32 | a | (400 MHz, CDCl$_3$) δ: 1.27 (t, J = 7.0 Hz, 3H), 1.77-1.97 (m, 8H), 2.43-2.46 (m, 2H), 2.57-2.63 (m, 1H), 2.64 (s, 3H), 2.67-2.84 (m, 4H) 3.47-3.55 (m, 4H), 4.15 (q, J = 7.0 Hz, 2H), 7.20-7.29 (m, 4H). | B | m/z 370 (M + H)$^+$ (ES$^+$), at 2.57 min, UV active |
| 3-8 | Mixture of isomers: ethyl 4-[4-cyano-4-(3-methylphenyl)cyclohexyl]-1,4-diazepane-1-carboxylate | 23 and 32 | a | (400 MHz, CDCl$_3$) δ: 1.27 (t, J = 7.0 Hz, 3H), 1.77-1.97 (m, 8H), 2.20-2.23 (m, 2H), 2.37 (s, 3H), 2.58-2.62 (m, 1H), 2.72-2.82 (m, 4H), 3.47-3.54 (m, 4H), 4.14 (q, J = 7.0 Hz, 2H), 7.12-7.17 (m, 1H), 7.25-7.29 (m, 3H). | B | m/z 370 (M + H)$^+$ (ES$^+$), at 2.35 and 2.48 min, UV active |
| 3-9 | Mixture of isomers: ethyl 4-[4-cyano-4-(4-methoxyphenyl)cyclohexyl]-1,4-diazepane-1-carboxylate | 32 and 37 | a | (400 MHz, DMSO-d$_6$) δ: 1.18 (t, J = 7.0 Hz, 3H), 1.60-1.72 (m, 4H), 1.83-1.91 (m, 4H), 2.09-2.12 (m, 3H), 2.62-2.71 (m, 5H), 3.38-3.41 (m, 4H), 3.76 (s, 3H), 4.04 (q, J = 7.02, 2H), 6.96-7.02 (m, 2H), 7.42-7.44 (m, 2H). | B | m/z 386 (M + H)$^+$ (ES$^+$), at 2.47 and 2.60 min, UV active |
| 3-10 | Mixture of isomers: ethyl 4-[4-cyano-4-[2-(trifluoromethyl)phenyl]cyclohexyl}-1,4-diazepane-1-carboxylate | 32 and 38 | a | (400 MHz, CDCl$_3$) δ: 1.27 (t, J = 6.8 Hz, 3H), 1.78-1.97 (m, 8H), 2.42-2.78 (m, 7H), 3.46-3.64 (m, 4H), 4.14-4.16 (m, 2H), 7.49-7.52 (m, 1H), 7.57-7.59 (m, 1H), 7.66-7.69 (m, 1H), 7.80-7.82 (m, 1H). | E | m/z 424 (M + H)$^+$ (ES$^+$), at 5.11 min, UV active |
| 3-11 | Mixture of isomers: ethyl 4-[4-cyano-4-(pyridin-2-yl)cyclohexyl]-1,4-diazepane-1-carboxylate | 26 and 32 | a | (400 MHz, CDCl$_3$) δ: 1.21-1.28 (m, 3H), 1.75-1.88 (m, 4H), 1.95-1.99 (m, 2H), 2.07-2.21 (m, 3H), 2.53-2.68 (m, 2H), 2.69-2.82 (m, 4H), 3.46-3.55 (m, 4H), 4.14 (m, 2H), 7.23-7.26 (m, 1H), 7.53-7.62 (m, 1H), 7.71-7.74 (m, 1H), 8.58-8.64 (m, 1H). | B | m/z 357 (M + H)$^+$ (ES$^+$), at 3.33 and 3.49 min, UV active |
| 3-12 | Mixture of isomers: ethyl 4-[4-cyano-4-(pyridin-4-yl)cyclohexyl]-1,4-diazepane-1-carboxylate | 32 and 40 | a | (400 MHz, CDCl$_3$) δ: 1.27 (t, J = 6.8 Hz, 3H), 1.647-1.99 (m, 8H), 2.19-2.26 (m, 2H), 2.65-2.93 (m, 5H), 3.49-3.56 (m, 4H), 4.13-4.16 (m, 2H), 7.37-7.39 (m, 2H), 8.64-8.66 (m, 2H). | E | m/z 357 (M + H)$^+$ (ES$^+$), at 4.10 min, UV active |
| 3-13 | Isomer 1: ethyl 4-[4-(3-chloropyridin-2-yl)-4-cyanocyclohexyl]-1,4-diazepane-1-carboxylate | 32 and 41 | a | (400 MHz, CDCl$_3$) δ: 1.25-1.27 (m, 3H), 1.78-2.16 (m, 10H), 2.55-2.79 (m, 5H), 3.48-3.61 (m, 4H), 4.13-4.17 (m, 2H), 7.26-7.27 (m, 1H), 7.74-7.76 (m, 1H), 8.46-8.49 (m, 1H). | B | m/z 391 (M + H)$^+$ (ES$^+$), at 3.88 min, UV active |
| 3-14 | Mixture of isomers: ethyl 4-[4-(4-methylpyridin-2-yl)-4-cyanocyclohexyl]-1,4-diazepane-1-carboxylate | 29 and 32 | a | (400 MHz, DMSO-d$_6$) δ: 1.16-1.24 (m, 3H), 1.61-1.68 (m, 5H), 1.85-2.01 (m, 3H), 2.13-2.18 (m, 1H), 2.36 (s, 1.5H), 2.38 (s, 1.5H), 2.58-2.77 (m, 6H), 3.38-3.44 (m, 4H), 3.95-4.03 (m, 2H), 7.20-7.23 (m, 1H), 7.41-7.46 (m, 1H), 8.43-8.48 (m, 1H). | C | m/z 371 (M + H)$^+$ (ES$^+$), at 1.81 min, UV active |

TABLE 3-continued

| Ex. No. | Name | Intermediate | Synthetic method | $^1$H NMR | LCMS Method | LCMS data |
|---|---|---|---|---|---|---|
| 3-15 | Mixture of isomers: ethyl 4-[4-(5-fluoropyridin-2-yl)-4-cyanocyclohexyl]-1,4-diazepane-1-carboxylate | 27 and 31 | e | (400 MHz, DMSO-d$_6$) δ: 1.27 (t, J = 7.0 Hz, 3H), 1.57-1.77 (m, 4H), 1.85-2.03 (m, 4H), 2.12-2.21 (m, 2H), 2.59-2.74 (m, 5H), 3.38-3.42 (m, 4H), 4.03 (q, J = 7.0 Hz, 2H), 7.66-7.70 (m, 1H), 7.80-7.86 (m, 1H), 8.61-8.63 (m, 1H). | B | m/z 375 (M + H)$^+$ (ES$^+$), at 3.64 min, UV active |
| 3-16 | Mixture of isomers: ethyl 4-[4-(5-chloropyridin-2-yl)-4-cyanocyclohexyl]-1,4-diazepane-1-carboxylate | 28 and 32 | a | (400 MHz, DMSO-d$_6$) δ: 1.15-1.23 (m, 3H), 1.58-1.69 (m, 4H), 1.85-1.99 (m, 4H), 2.14-2.19 (m, 2H), 2.59-2.73 (m, 5H), 3.38-3.45 (m, 4H), 4.00-4.05 (m, 2H), 7.63-7.65 (m, 1H), 8.01-8.04 (m, 1H), 8.65-8.67 (m, 1H). | B | m/z 391 (M + H)$^+$ (ES$^+$), at 4.06 min, UV active |
| 3-17 | Isomer 1: ethyl 4-[4-(5-bromopyridin-2-yl)-4-cyanocyclohexyl]-1,4-diazepane-1-carboxylate | 32 and 42 | a | (400 MHz, DMSO-d$_6$) δ: 1.18 (t, J = 7.0 Hz, 3H), 1.55-1.75 (m, 4H), 1.83-2.02 (m, 4H), 2.09-2.24 (m, 2H), 2.57-2.66 (m, 2H), 2.67-2.80 (m, 2H), 3.35-3.44 (m, 5H), 4.03 (q, J = 7.0 Hz, 2H), 7.59 (dd, J = 8.5, 0.8 Hz, 1H), 8.15 (dd, J = 8.5, 2.5 Hz, 1H), 8.75 (dd, J = 2.5, 0.8 Hz, 1H). | B | m/z 435 and 437 (M + H)$^+$ (ES$^+$), at 4.15, UV active |
| 3-18 | Mixture of isomers: ethyl 4-[4-(5-methylpyridin-2-yl)-4-cyanocyclohexyl]-1,4-diazepane-1-carboxylate | 32 and 43 | a | (400 MHz, DMSO-d$_6$) δ: 1.18 (t, J = 7.2 Hz, 3H), 1.56-1.68 (m, 4H), 1.85-2.01 (m, 4H), 2.11-2.16 (m, 2H), 2.29 (s, 3H), 2.57-2.75 (m, 5H), 3.38-3.44 (m, 4H), 4.02 (q, J = 7.2 Hz, 2H), 7.44-7.48 (m, 1H), 7.67-7.69 (m, 1H), 8.40-8.43 (m, 1H). | B | m/z 371 (M + H)$^+$ (ES$^+$), at 4.31 and 4.50 min, UV active |
| 3-19 | Isomer 2: ethyl 4-[4-(5-methoxypyridin-2-yl)-4-cyanocyclohexyl]-1,4-diazepane-1-carboxylate | 32 and 44 | a | (400 MHz, DMSO-d$_6$) δ: 1.12-1.16 (m, 3H), 1.56-1.68 (m, 6H), 1.88-1.95 (m, 2H), 2.12-2.18 (m, 2H), 2.56-2.70 (m, 5H), 3.38-3.42 (m, 4H), 3.86 (s, 3H), 3.96-4.02 (m, 2H), 7.45-7.49 (m, 1H), 7.55-7.59 (m, 1H), 8.34-8.35 (m, 1H). | B | m/z 387 (M + H)$^+$ (ES$^+$), at 3.66 min, UV active |
| 3-20 | Isomer 2: ethyl 4-[4-cyano-4-(5-ethoxypyridin-2-yl)cyclohexyl]-1,4-diazepane-1-carboxylate | 32 and 45 | a | (400 MHz, DMSO-d$_6$) δ: 1.16 (t, J = 7.0 Hz, 3H), 1.34 (t, J = 7.0 Hz, 3H), 1.58-1.67 (m, 4H), 1.85-1.94 (m, 4H), 2.14-2.18 (m, 2H), 2.62-2.73 (m, 5H), 3.30-3.41 (m, 4H), 4.03 (q, J = 7.0 Hz, 2H), 4.11 (q, J = 7.0 Hz, 2H), 7.42-7.45 (m, 1H), 7.48-7.51 (m, 1H), 8.28-8.29 (m, 1H). | B | m/z 401 (M + H)$^+$ (ES$^+$), at 4.07 min, UV active |
| 3-21 | Mixture of isomers: ethyl 4-{4-cyano-4[5-(trifluoromethyl)pyridin-2-yl]cyclohexyl}-1,4-diazepane-1-carboxylate | 32 and 46 | a | (400 MHz, DMSO-d$_6$) δ: 1.16 (t, J = 7.2 Hz, 3H), 1.32-1.34 (m, 2H), 1.58-1.80 (m, 6H), 1.98-2.03 (m, 2H), 2.62-2.73 (m, 5H), 3.30-3.41 (m, 4H), 4.03 (q, J = 7.2 Hz, 2H), 7.88-7.90 (m, 1H), 8.32-8.35 (m, 1H), 9.07 (s, 1H). | B | m/z 425 (M + H)$^+$ (ES$^+$), at 4.31 and 4.50 min, UV active |
| 3-22 | Mixture of isomers: ethyl 4-[4-(6-methylpyridin-2-yl)-4-cyanocyclohexyl]-1,4-diazepane-1-carboxylate | 30 and 32 | a | (400 MHz, CDCl$_3$) δ: 1.22-1.27 (m, 3H), 1.62-2.04 (m, 6H), 2.10-2.49 (m, 4H), 2.53 (s, 2.4H), 2.55 (s, 0.6H), 2.62-2.85 (m, 5H), 3.42-3.56 (m, 4H), 4.13-4.17 (m, 2H), 7.05-7.09 (m, 1H), 7.35-7.40 (m, 1H), 7.56-7.60 (m, 1H). | E | m/z 371 (M + H)$^+$ (ES$^+$), at 4.55 and 4.63 min, UV active |
| 3-23 | Mixture of isomers: ethyl 4-{4-cyano-4[6-(trifluoromethyl)pyridin-2-yl]cyclohexyl}-1,4-diazepane-1-carboxylate | 32 and 47 | a | (400 MHz, CDCl$_3$) δ: 1.24-1.28 (m, 3H), 1.68-2.40 (m, 10H), 2.56-3.01 (m, 5H), 3.38-3.54 (m, 4H), 4.12-4.21 (m, 2H), 7.65-7.69 (m, 1H), 7.83-7.87 (m, 1H), 7.95-7.99 (m, 1H). | D | m/z 425 (M + H)$^+$ (ES$^+$), at 6.11 and 6.22 min, UV active |
| 3-24 | Isomer 1: ethyl 4-[4-cyano-4-(thiophen-2-yl)cyclohexyl]-1,4-diazepane-1-carboxylate | 32 and 48 | a | (400 MHz, CDCl$_3$) δ: 1.27 ((t, J = 7.2 Hz, 3H), 1.70-2.01 (m, 8H), 2.38-2.48 (m, 2H), 2.53-2.85 (m, 5H), 3.44 (m, 4H), 4.15 (q, J = 7.2 Hz, 2H), 6.97-6.99 (m, 1H), 7.11-7.14 (m, 1H), 7.27-7.28 (m, 1H). | B | m/z 362 (M + H)$^+$ (ES$^+$), at 4.03 min, UV active |
| 3-25 | Mixture of isomers: ethyl 4-(4-cyano-4-phenylcyclohexyl)-6-fluoro-1,4-diazepane-1-carboxylate | 12 and 34 | a | (400 MHz, CDCl$_3$) δ: 1.09-1.26 (m, 3H), 1.47-1.70 (m, 2H), 1.73-1.99 (4H, m), 2.08 (d, J = 11.9, 2H), 2.58-2.72 (m, 2H), 2.72-3.02 (m, 3H), 3.24-3.36 (m, 1H), 3.36-3.60 (m, 2H), 3.71 (qd, J = 14.8, 5.0, 1H), 4.01 (d, J = 11.9, 2H), 4.56-4.86 (m, 1H), 7.21-7.35 (m, 1H), 7.35-7.44 (m, 2H), 7.44-7.56 (m, 2H). | B | m/z 374 (M + H)$^+$ (ES$^+$), at 4.56 min, UV active |
| 3-26 | Mixture of isomers: ethyl 4-(4-cyano-4-phenylcyclohexyl)-6- | 12 and 33 | a | (400 MHz, CDCl$_3$) δ: 1.21-1.33 (m, 5H), 1.81-2.08 (m, 6H), 2.19-2.31 (m, 2H), 2.60-2.89 (m, 4H), 2.91-3.02 (m,1H), | B | m/z 372 (M + H)$^+$ (ES$^+$), |

TABLE 3-continued

| Ex. No. | Name | Intermediate | Synthetic method | ¹H NMR | LCMS Method | LCMS data |
|---|---|---|---|---|---|---|
| | hydroxy-1,4-diazepane-1-carboxylate | | | 3.42-3.72 (m, 3H), 3.89-4.00 (m, 1H), 4.15 (qd, J = 6.9, 2.8 Hz, 2H), 7.30-7.36 (m, 1H), 7.39 (t, J = 7.5 Hz, 2H) 7.46-7.51 (m, 2H) | | at 3.66 min, UV active |
| 3-27 | Mixture of isomers: ethyl 4-[4-(5-chloropyridin-2-yl)-4-cyanocyclohexyl]-6-fluoro-1,4-diazepane-1-carboxylate | 28 and 34 | a | (400 MHz, DMSO-d₆) δ: 1.04-1.28 (m, 3H), 1.46-1.76 (m, 3H), 1.83-2.07 (m, 3H), 2.18-2.20 (m, 1H), 2.51-2.87 (m, 7H), 3.36-3.63 (m, 2H), 3.65-3.78 (m, 1H), 3.90-4.13 (m, 2H), 4.52-4.83 (m, 1H), 7.56-7.76 (m, 1H), 8.05 (ddd, J = 8.6, 6.2, 2.8 Hz, 1H), 8.69 (dd, J = 17.3, 2.3 Hz, 1H). | B | m/z 409 (M + H)⁺ (ES⁺), at 4.36 min, UV active |
| 3-28 | Mixture of isomers: methyl 4-(4-cyano-4-phenylcyclohexyl)-1,4-diazepane-1-carboxylate | 12, 31 and 56 | d | (400 MHz, CDCl₃) δ: 1.61-2.01 (m, 7H), 2.10-2.50 (m, 3H), 2.62-3.02 (m, 4H), 3.24-3.61 (m, 4H), 3.71 (s, 3H), 7.32-7.53 (m, 5H). | B | m/z 342 (M + H)⁺ (ES⁺), at 3.78 min, UV active |
| 3-29 | Mixture of isomers: 2-fluoroethyl 4-(4-cyano-4-phenylcyclohexyl)-1,4-diazepane-1-carboxylate | 12, 31 and 64 | d | (400 MHz, CDCl₃) δ: 1.53-2.41 (m, 11H), 2.60-3.11 (m, 4H), 3.47-3.73 (m, 4H), 4.40 (d, J = 29.2, 2H), 4.64 (d, J = 47.6, 2H), 7.32-7.53 (m, 5H). | B | m/z 374 (M + H)⁺ (ES⁺), at 3.98 min, UV active |
| 3-30 | Isomer 1: but-2-yn-1-yl 4-[4-cyano-4-(pyridin-4-yl)cyclohexyl]-1,4-diazepane-1-carboxylate | 31, 40 and 58 | e | (400 MHz, DMSO-d₆) δ: 1.50-1.71 (m, 4H), 1.80 (s, 3H), 1.85-1.95 (m, 4H), 2.11-2.16 (m, 2H), 2.62-2.74 (m, 5H), 3.39-3.43 (m, 4H), 4.63-4.65 (m, 2H), 7.54-7.56 (m, 2H), 8.62-8.64 (m, 2H). | B | m/z 381 (M + H)⁺ (ES⁺), at 3.28 min, UV active |
| 3-31 | Isomer 1: prop-2-yn-1-yl 4-[4-cyano-4-(5-methoxypyridin-2-yl)cyclohexyl]-1,4-diazepane-1-carboxylate | 31, 44 and 57 | e | (400 MHz, DMSO-d₆) δ: 1.55-1.71 (m, 4H), 1.84-1.95 (m, 4H), 2.14-2.19 (m, 2H), 2.58-2.76 (m, 5H), 3.39-3.52 (m, 4H), 3.84 (s, 3H), 4.58-4.61 (m, 1H), 4.67-4.68 (m, 2H), 7.43-7.47 (m, 1H), 7.50-7.53 (m, 1H), 8.30-8.31 (m, 1H). | C | m/z 397 (M + H)⁺ (ES⁺), at 5.82 min, UV active |
| 3-32 | Isomer 1: but-2-yn-1-yl 4-[4-cyano-4-(5-methoxypyridin-2-yl)cyclohexyl]-1,4-diazepane-1-carboxylate | 31, 49 and 58 | e | (400 MHz, DMSO-d₆) δ: 1.59-1.70 (m, 4H), 1.82-1.83 (m, 3H), 1.83-1.95 (m, 4H), 2.14-2.19 (m, 2H), 2.58-2.74 (m, 5H), 3.39-3.44 (m, 4H), 3.84 (s, 3H), 4.62-4.64 (m, 2H), 7.43-7.47 (m, 1H), 7.50-7.53 (m, 1H), 8.30-8.31 (m, 1H). | B | m/z 411 (M + H)⁺ (ES⁺), at 3.80 min, UV active |
| 3-33 | Isomer 2: ethyl 4-[4-(methoxycarbonyl)-4-phenylcyclohexyl]-1,4-diazepane-1-carboxylate | 32 and 49 | a | (400 MHz, CDCl₃) δ: 1.26 (t, J = 7.2 Hz, 3H), 1.60-2.00 (m, 10H), 2.50-2.85 (m, 5H), 3.42-3.58 (m, 4H), 3.66 (s, 3H), 4.14 (q, J = 7.0 Hz, 2H), 7.22-7.24 (m, 1H), 7.28-7.36 (m, 4H). | B | m/z 389 (M + H)⁺ (ES⁺), at 4.36 min, UV active |
| 3-34 | Mixture of isomers: ethyl 4-[4-(3-chloropyridin-2-yl)-4-(methoxycarbonyl)cyclohexyl]-1,4-diazepane-1-carboxylate | 32 and 50 | a | (400 MHz, CDCl₃) δ: 1.23-1.28 (m, 3H), 1.62-2.08 (m, 10H), 2.48-2.79 (m, 5H), 3.42-3.56 (m, 4H), 3.64 (s, 1.4H), 3.68 (s, 1.6H), 4.12-4.16 (m, 2H), 7.15-7.19 (m, 1H), 7.61-7.64 (m, 5.49 and 1H), 8.44-8.51 (m, 1H). | D | m/z 424 (M + H)⁺ (ES⁺), at 5.54 min, UV active |
| 4-1 | Isomer 2: methyl 4-(2'-oxo-1',2'-dihydrospiro[cyclohexane-1,3'-indol]-4-yl)-1,4-diazepane-1-carboxylate | 65 and 104 | c | (400 MHz, DMSO-d₆) ⊐: 1.51-1.82 (m, 8H), 2.06-2.19 (m, 2H), 2.61-2.78 (m, 5H), 3.39-3.43 (m, 4H), 3.59 (s, 3H), 6.78 (d, J = 7.5 Hz, 1H), 6.94 (t, J = 7.5 Hz, 1H), 7.13 (t, J = 7.5 Hz, 1H), 7.21 (d, J = 7.5 Hz, 1H), 10.26 (s, 1H) | P | m/z 358 (M + H)⁺ (ES⁺), at 1.86 min, UV active |
| 4-2 | Isomer 1: ethyl 4-(2'-oxo-1',2'-dihydrospiro[cyclohexane-1,3'-indol]-4-yl)-1,4-diazepane-1-carboxylate | 32 and 65 | c | (400 MHz, DMSO-d₆) ⊐: 1.18 (t, J = 7.0 Hz, 3H), 1.42-1.53 (m, 2H), 1.67-1.82 (m, 8H), 2.62-2.86 (m, 5H), 3.39-3.48 (m, 4H), 4.04 (q, J = 7.0 Hz, 2H), 6.88 (d, J = 7.5 Hz, 1H), 6.98 (t, J = 7.5 Hz, 1H), 7.22 (t, J = 7.5 Hz, 1H), 7.50 (d, J = 7.5 Hz, 1H), 10.42 (s, 1H) | P | m/z 372 (M + H)⁺ (ES⁺), at 1.90 min, UV active |
| 4-2 | Isomer 2: ethyl 4-(2'-oxo-1',2'-dihydrospiro[cyclohexane-1,3'-indol]-4-yl)-1,4-diazepane-1-carboxylate | 32 and 65 | c | (400 MHz, DMSO-d₆) ⊐: 1.18 (t, J = 7.0 Hz, 3H), 1.51-1.60 (m, 2H), 1.62-1.83 (m, 6H), 2.06-2.19 (m, 2H), 2.61-2.78 (m, 5H), 3.38-3.42 (m, 4H), 4.04 (q, J = 7.0 Hz, 2H), 6.79 (d, J = 7.5 Hz, 1H), 6.94 (t, J = 7.5 Hz, 1H), 7.13 (t, J = 7.5 Hz, 1H), 7.20 (d, J = 7.5 Hz, 1H), 10.26 (s, 1H) | P | m/z 372 (M + H)⁺ (ES⁺), at 1.94 min, UV active |
| 4-3 | Isomer 2: 4-(4-butanoyl-1,4-diazepan-1-yl)spiro[cyclohexane-1,3'-indol]-2'(1'H)-one | 65 and 105 | c | (400 MHz, DMSO-d₆) ⊐: 0.89 (t, J = 7.5 Hz, 3H), 1.37-1.80 (m, 11H), 2.05-2.34 (m, 4H), 2.59-2.84 (m, 4H), 3.42-3.55 (m, 4H), 6.79 (d, J = 7.5 Hz, 1H), 6.94 (t, J = 7.5 Hz, 1H), 7.14 (t, J = 7.5 Hz, 1H), 7.21 (d, J = 7.5 Hz, 1H), 10.26 (s, 1H) | P | m/z 370 (M + H)⁺ (ES⁺), at 1.92 min, UV active |

TABLE 3-continued

| Ex. No. | Name | Intermediate | Synthetic method | $^1$H NMR | LCMS Method | LCMS data |
|---|---|---|---|---|---|---|
| 4-4 | Isomer 2: 4-{4-[(2E)-but-2-enoyl]-1,4-diazepan-1-yl}spiro[cyclohexane-1,3'-indol]-2'(1'H)-one | 65 and 107 | c | (400 MHz, MeOD-d$_4$) ⊐: 1.72-1.96 (m, 11H), 2.24-2.34 (m, 2H), 2.76-2.83 (m, 3H), 2.92-2.96 (m, 2H), 3.60-3.71 (m, 4H), 6.44-6.49 (m, 1H), 6.81-6.91 (m, 2H), 7.01 (t, J = 7.5 Hz, 1H), 7.18 (t, J = 8.0 Hz, 2H) | F | m/z 368 (M + H)$^+$ (ES$^+$), at 1.62 min, UV active |
| 4-5 | Isomer 2: ethyl 4-(7'-methyl-2'-oxo-1',2'-dihydrospiro[cyclohexane-1,3'-indol]-4-yl)-1,4-diazepane-1-carboxylate | 32 and 67 | c | (400 MHz, DMSO-d$_6$) ⊐: 1.18 (t, J = 7.0 Hz, 3H), 1.54-1.78 (m, 8H), 2.08-2.21 (m, 5H), 2.74-2.66 (m, 5H), 3.37-3.42 (m, 4H), 4.03 (q, J = 7.0 Hz, 2H), 6.85 (t, J = 7.5 Hz, 1H), 6.95 (d, J = 7.5 Hz, 1H), 7.01 (d, J = 7.5 Hz, 1H). NH not observed. | F | m/z 387 (M + H)$^+$ (ES$^+$), at 1.72 min, UV active |
| 4-6 | Isomer 1: ethyl 4-(6'-methyl-2'-oxo-1',2'-dihydrospiro[cyclohexane-1,3'-indol]-4-yl)-1,4-diazepane-1-carboxylate | 32 and 68 | c | (400 MHz, DMSO-d$_6$) ⊐: 1.18 (t, J = 7.0 Hz, 3H), 1.43-1.47 (m, 2H), 1.71-1.76 (m, 8H), 2.28 (s, 3H), 2.59-2.79 (m, 5H), 3.40-3.43 (m, 4 H), 4.04 (q, J = 7.0 Hz, 2H), 6.70 (s, 1H), 6.78 (d, J = 7.5 Hz, 1H), 7.37 (d, J = 7.5 Hz, 1H), 10.36 (s, 1H) | F | m/z 386 (M + H)$^+$ (ES$^+$), at 1.72 min, UV active |
| 4-6 | Isomer 2: ethyl 4-(6'-methyl-2'-oxo-1',2'-dihydrospiro[cyclohexane-1,3'-indol]-4-yl)-1,4-diazepane-1-carboxylate | 32 and 68 | c | (400 MHz, DMSO-d$_6$) ⊐: 1.18 (t, J = 7.0 Hz, 3H), 1.53 1.77 (m, 8H), 2.05-2.16 (m, 2H), 2.25 (s, 3H), 2.65-2.73 (m, 5H), 3.37-3.42 (m, 4H), 4.03 (q, J = 7.0 Hz, 2H), 6.60 (s, 1H), 6.74 (d, J = 7.5 Hz, 1H), 7.07 (d, J = 7.5 Hz, 1H), 10.20 (s, 1H) | F | m/z 386 (M + H)$^+$ (ES$^+$), at 1.76 min, UV active |
| 4-7 | Isomer 1: ethyl 4-(5'-methyl-2'-oxo-1',2'-dihydrospiro[cyclohexane-1,3'-indol]-4-yl)-1,4-diazepane-1-carboxylate | 32 and 70 | c | (400 MHz, DMSO-d$_6$) ⊐: 1.19 (t, J = 7.0 Hz, 3H), 1.41-1.52 (m, 2H), 1.65-1.83 (m, 8H), 2.30 (s, 3H), 2.60-2.86 (m, 5H), 3.39-3.47 (m, 4H), 4.05 (q, J = 7.0 Hz, 2H), 6.77 (d, J = 8.0 Hz, 1H), 7.02 (d, J = 8.0 Hz, 1H), 7.28 (s, 1H), 10.30 (s, 1H) | F | m/z 386 (M + H)$^+$ (ES$^+$), at 1.69 min, UV active |
| 4-7 | Isomer 2: ethyl 4-(5'-methyl-2'-oxo-1',2'-dihydrospiro[cyclohexane-1,3'-indol]-4-yl)-1,4-diazepane-1-carboxylate | 32 and 70 | c | (400 MHz, DMSO-d$_6$) ⊐: 1.18 (t, J = 7.0 Hz, 3H), 1.54-1.77 (m, 8H), 2.07-2.16 (m, 2H), 2.24 (s, 3H), 2.61-2.79 (m, 5H), 3.37-3.42 (m, 4H), 4.04 (q, J = 7.0 Hz, 2H), 6.67 (d, J = 7.5 Hz, 1H), 6.93 (d, J = 7.5 Hz, 1H), 7.02 (s, 1H), 10.15 (s, 1H) | F | m/z 386 (M + H)$^+$ (ES$^+$), at 1.73 min, UV active |
| 4-8 | Isomer 1: ethyl 4-(4'-methyl-2'-oxo-1',2'-dihydrospiro[cyclohexane-1,3'-indol]-4-yl)-1,4-diazepane-1-carboxylate | 32 and 72 | c | (400 MHz, MeOD-d$_4$) ⊐: 1.27-1.35 (m, 3H), 1.74-1.86 (m, 4H), 2.30-2.47 (m, 8H), 2.78-2.97 (m, 6H), 3.53-3.60 (m, 4H), 4.15 (q, J = 7.0 Hz, 2H), 6.70 (d, J = 7.5 Hz, 1H), 6.77 (d, J = 7.5 Hz, 1H), 7.07 (t, J = 7.5 Hz, 1H) | F | m/z 386 (M + H)$^+$ (ES$^+$), at 1.77 min, UV active |
| 4-8 | Isomer 2: ethyl 4-(4'-methyl-2'-oxo-1',2'-dihydrospiro[cyclohexane 1,3'-indol]-4-yl)-1,4-diazepane-1-carboxylate | 32 and 72 | c | (400 MHz, MeOD-d$_4$) ⊐: 1.27-1.36 (m, 3H), 1.84-1.93 (m, 4H), 2.38-2.54 (m, 8H), 2.78-2.97 (m, 6H), 3.54-3.61 (m, 4H), 4.14-4.19 (m, 2H), 6.68 (d, J = 8.0 Hz, 1H), 6.78 (d, J = 8.0 Hz, 1H), 7.05 (t, J = 8.0 Hz, 1H) | F | m/z 386 (M + H)$^+$ (ES$^+$), at 1.77 min, UV active |
| 4-9 | Isomer 1: ethyl 4-(6'-fluoro-2'-oxo-1',2'-dihydrospiro[cyclohexane-1,3'-indol]-4-yl)-1,4-diazepane-1-carboxylate | 32 and 74 | c | (400 MHz, DMSO-d$_6$) ⊐: 1.18 (t, J = 7.0 Hz, 3H), 1.47-1.50 (m, 2H), 1.71-1.78 (m, 8H), 2.61-2.85 (m, 5H), 3.40-3.43 (m, 4H), 4.04 (q, J = 7.0 Hz, 2H), 6.69 (dd, J = 2.5 Hz, 1H), 6.74-6.79 (m, 1H), 7.49-7.52 (m, 1H), 10.57 (s, 1H) | F | m/z 390 (M + H)$^+$ (ES$^+$), at 1.70 min, UV active |
| 4-9 | Isomer 2: ethyl 4-(6'-fluoro-2'-oxo-1',2'-dihydrospiro[cyclohexane-1,3'-indol]-4-yl)-1,4-diazepane-1-carboxylate | 32 and 74 | c | (400 MHz, DMSO-d$_6$) ⊐: 1.18 (t, J = 7.0 Hz, 3H), 1.54-1.80 (m, 8H), 2.05-2.14 (m, 2H), 2.60-2.77 (m, 5H), 3.37-3.41 (m, 4H), 4.03 (q, J = 7.0 Hz, 2H), 6.59 (dd, J = 9.0, 2.0 Hz, 1H), 6.71-6.76 (m, 1H), 7.23 (dd, J = 8.0, 5.5 Hz, 1H), 10.41 (br s, 1H) | F | m/z 390 (M + H)$^+$ (ES$^+$), at 1.72 min, UV active |
| 4-10 | Isomer 1: ethyl 4-(5'-fluoro-2'-oxo-1',2'-dihydrospiro[cyclohexane-1,3'-indol]-4-yl)-1,4-diazepane-1-carboxylate | 32 and 76 | c | (400 MHz, DMSO-d$_6$) ⊐: 1.18 (t, J = 7.0 Hz, 3H), 1.49-1.52 (m, 2H), 1.63-1.78 (m, 8H), 2.63-2.80 (m, 5H), 3.42-3.43 (m, 4H), 4.04 (q, J = 7.0 Hz, 2H), 6.87 (dd, J = 8.5, 4.5 Hz, 1H), 7.04-7.09 (m, 1H), 7.29-7.31 (m, 1H), 10.45 (s, 1H) | F | m/z 390 (M + H)$^+$ (ES$^+$), at 1.68 min, UV active |
| 4-10 | Isomer 2: ethyl 4-(5'-fluoro-2'-oxo-1',2'-dihydrospiro[cyclohexane-1,3'-indol]-4-yl)-1,4-diazepane-1-carboxylate | 32 and 76 | c | (400 MHz, DMSO-d$_6$) ⊐: 1.18 (t, J = 7.0 Hz, 3H), 1.49-1.85 (m, 8H), 2.04-2.17 (m, 2H), 2.61-2.78 (m, 5H), 3.37-3.42 (m, 4H), 4.04 (q, J = 7.0 Hz, 2H), 6.76 (dd, J = 8.5, 4.5 Hz, 1H), 6.93-6.99 (m, 1H), 7.18 (dd, J = 2.5, 8.5 Hz, 1H), 10.28 (s, 1H) | F | m/z 390 (M + H)$^+$ (ES$^+$), at 2.00 min, UV active |
| 4-11 | Isomer 1: ethyl 4-(6'-methoxy-2'-oxo-1',2'-dihydrospiro[cyclohexane-1,3'-indol]-4-yl)-1,4-diazepane- | 32 and 78 | c | (400 MHz, DMSO-d$_6$) ⊐: 1.18 (t, J = 7.0 Hz, 3H), 1.38-1.48 (m, 2H), 1.63-1.80 (m, 8H), 2.60-2.84 (m, 5H), 3.40-3.51 (m, 4H), 3.73 (s, 3H), 4.04 (q, J = 7.0 Hz, 2H), | F | m/z 402 (M + H)$^+$ (ES$^+$), at |

TABLE 3-continued

| Ex. No. | Name | Intermediate | Synthetic method | ¹H NMR | LCMS Method | LCMS data |
|---|---|---|---|---|---|---|
| | diazepane-1-carboxylate | | | 6.45 (s, 1H), 6.52 (d, J = 8.0 Hz, 1H), 7.39 (d, J = 8.0 Hz, 1H), 10.38 (s, 1H) | | 1.72 min, UV active |
| 4-11 | Isomer 2: ethyl 4-(6'-methoxy-2'-oxo-1',2'-dihydrospiro[cyclohexane-1,3'-indol]-4-yl)-1,4-diazepane-1-carboxylate | 32 and 78 | c | (400 MHz, DMSO-d₆) ⊐: 1.18 (t, J = 7.0 Hz, 3H), 1.53-1.76 (m, 8H), 2.05-2.15 (m, 2H), 2.58-2.78 (m, 5H), 3.38-3.41 (m, 4H), 3.71 (s, 3H), 4.03 (q, J = 7.0 Hz, 2H), 6.35 (d, J = 2.5 Hz, 1H), 6.48 (dd, J = 2.5, 8.0 Hz, 1H), 7.09 (d, J = 8.0 Hz, 1H), 10.21 (s, 1H) | F | m/z 402 (M + H)⁺ (ES⁺), at 1.74 min, UV active |
| 4-12 | Isomer 1: ethyl 4-(5'-methoxy-2'-oxo-1',2'-dihydrospiro[cyclohexane-1,3'-indol]-4-yl)-1,4-diazepane-1-carboxylate | 32 and 80 | c | (400 MHz, DMSO-d₆) ⊐:1.18 (t, J = 7.0 Hz, 3H), 1.44-1.53 (m, 2H), 1.65-1.83 (m, 8H), 2.62-2.86 (m, 5H), 3.40-3.52 (m, 4H), 3.73 (s, 3H), 4.04 (q, J = 7.0 Hz, 2H), 6.80 (m, 2H), 7.01 (s, 1H), 10.27 (s, 1H) | F | m/z 402 (M + H)⁺ (ES⁺), at 1.70 min, UV active |
| 4-12 | Isomer 2: ethyl 4-(5'-methoxy-2'-oxo-1',2'-dihydrospiro[cyclohexane-1,3'-indol]-4-yl)-1,4-diazepane-1-carboxylate | 32 and 80 | c | (400 MHz, DMSO-d₆) ⊐: 1.18 (t, J = 7.0 Hz, 3H), 1.53-1.80 (m, 8H), 2.08-2.16 (m, 2H), 2.64-2.73 (m, 5H), 3.38-3.41 (m, 4H), 3.69 (s, 3H), 4.03 (q, J = 7.0 Hz, 2H), 6.69 (m, 2H), 6.87 (s, 1H), 10.08 (s, 1H) | F | m/z 402 (M + H)⁺ (ES⁺), at 1.73 min, UV active |
| 4-13 | Isomer 2: ethyl 4-(6'-cyano-2'-oxo-1',2'-dihydrospiro[cyclohexane-1,3'-indol]-4-yl)-1,4-diazepane-1-carboxylate | 32 and 110 | c | (400 MHz, DMSO-d₆) ⊐: 1.18 (t, J = 7.0 Hz, 3H), 1.55-1.88 (m, 8H), 2.04-2.14 (m, 2H), 2.63-2.77 (m, 5H), 3.39-3.48 (m, 4H), 4.03 (q, J = 7.0 Hz, 2H), 7.13 (s, 1H), 7.42-7.47 (m, 2H). NH not observed. | F | m/z 397 (M + H)⁺ (ES⁺), at 1.70 min, UV active |
| 4-14 | Isomer 1: ethyl 4-(5'-cyano-2'-oxo-1',2'-dihydrospiro[cyclohexane-1,3'-indol]-4-yl)-1,4-diazepane-1-carboxylate | 32 and 112 | c | (400 MHz, DMSO-d₆) ⊐: 1.18 (t, J = 7.0 Hz, 3H), 1.53-1.60 (m, 2H), 1.65-1.84 (m, 8H), 2.59-2.88 (m, 5H), 3.40-3.46 (m, 4H), 4.04 (q, J = 7.0 Hz, 2H), 7.04 (d, J = 8.0 Hz, 1H), 7.72 (d, J = 8.0 Hz, 1H), 7.85 (s, 1H), 10.95 (s, 1H) | F | m/z 398 (M + H)⁺ (ES⁺), at 1.62 min, UV active |
| 4-14 | Isomer 2: ethyl 4-(5'-cyano-2'-oxo-1',2'-dihydrospiro[cyclohexane-1,3'-indol]-4-yl)-1,4-diazepane-1-carboxylate | 32 and 112 | c | (400 MHz, DMSO-d₆ with D₂O wash) ⊐: 1.17 (t, J = 7.0 Hz, 3H), 1.55-2.22 (m, 10H), 2.65-2.94 (m, 5H), 3.34-3.51 (m, 4H), 4.03 (q, J = 7.0 Hz, 2H), 6.97 (d, J = 8.0 Hz, 1H), 7.64 (d, J = 8.0 Hz, 1H), 7.72 (s, 1H) | F | m/z 398 (M + H)⁺ (ES⁺), at 1.64 min, UV active |
| 4-15 | Isomer 2: ethyl 4-(2'-oxo-1',2'-dihydrospiro[cyclohexane-1,3'-pyrrolo[2,3-b]pyridin]-4-yl)-1,4-diazepane-1-carboxylate | 32 and 90 | c | (400 MHz, DMSO-d₆ with D₂O wash) ⊐: 1.17 (t, J = 7.0 Hz, 3H), 1.59-1.84 (m, 8H), 2.01-2.14 (m, 2H), 2.68-2.81 (m, 5H), 3.36-3.46 (m, 4H), 4.02 (q, J = 7.0 Hz, 2H), 6.94-6.97 (m, 1H), 7.60 (d, J = 7.0 Hz, 1H), 8.01 (d, J = 4.5 Hz, 1H) | F | m/z 374 (M + H)⁺ (ES⁺), at 1.52 min, UV active |
| 4-16 | Isomer 1: ethyl 4-(5'-chloro-2'-oxo-1',2'-dihydrospiro[cyclohexane-1,3'-pyrrolo[2,3-b]pyridin]-4-yl)-1,4-diazepane-1-carboxylate | 32 and 93 | c | (400 MHz, DMSO-d₆) ⊐: 1.18 (t, J = 7.0 Hz, 3H), 1.52-1.86 (m, 8H), 2.00-2.14 (m, 2H), 2.59-2.77 (m, 5H), 3.37-3.42 (m, 4H), 4.03 (q, J = 7.0 Hz, 2H), 7.77 (s, 1H), 8.05 (d, J = 2.0 Hz, 1H). NH not observed. | F | m/z 407 (M + H)⁺ (ES⁺), at 1.64 min, UV active |
| 4-16 | Isomer 2: ethyl 4-(5'-chloro-2'-oxo-1',2'-dihydrospiro[cyclohexane-1,3'-pyrrolo[2,3-b]pyridin]-4-yl)-1,4-diazepane-1-carboxylate | 32 and 93 | c | (400 MHz, DMSO-d₆) ⊐: 1.18 (t, J = 7.0 Hz, 3H), 1.53-1.89 (m, 10H), 2.61-2.88 (m, 5H), 3.39-3.49 (m, 4H), 4.04 (q, J = 7.0 Hz, 2H), 7.83 (d, J = 2.0 Hz, 1H), 8.17 (d, J = 2.0 Hz, 1H), 11.26 (s, 1H) | F | m/z 407 (M + H)⁺ (ES⁺), at 1.66 min, UV active |
| 4-17 | Isomer 1: ethyl 4-(5'-methoxy-2'-oxo-1',2'-dihydrospiro[cyclohexane-1,3'-pyrrolo[2,3-b]pyridin]-4-yl)-1,4-diazepane-1-carboxylate | 32 and 113 | i | (400 MHz, CDCl₃)i: 1.27 (t, J = 7.0 Hz, 3H), 1.61-2.05 (m, 10H), 2.69-2.88 (m, 5H), 3.44-3.60 (m, 4H), 3.87 (s, 3H), 4.15 (q, J = 7.0 Hz, 2H), 7.39 (s, 1H), 7.80 (s, 1H), 9.16-9.19 (m, 1H) | O | m/z 403 (M + H)⁺ (ES⁺), at 3.99 min, UV active |
| 4-17 | Isomer 2: ethyl 4-(5'-methoxy-2'-oxo-1',2'-dihydrospiro[cyclohexane-1,3'-pyrrolo[2,3-b]pyridin]-4-yl)-1,4-diazepane-1-carboxylate | 32 and 113 | i | (400 MHz, CDCl₃) ⊐: 1.26 (t, J = 7.0 Hz, 3H), 1.61-1.95 (m, 8H), 2.19-2.29 (m, 2H), 2.62-2.84 (m, 5H), 3.44-3.57 (m, 4H), 3.83 (s, 3H), 4.14 (q, J = 7.0 Hz, 2H), 7.02-7.03 (m, 1H), 7.74-7.76 (m, 1H), 8.32-8.36 (m, 1H) | O | m/z 403 (M + H)⁺ (ES⁺), at 4.02 min, UV active |
| 4-18 | Isomer 2: ethyl 4-(1',2'-dihydrospiro[cyclohexane-1,3'-pyrrolo[2,3-b]pyridin]-4-yl)-1,4-diazepane-1-carboxylate | 32 and 116 | c | (400 MHz, DMSO-d₆) ⊐: 1.18 (t, J = 7.0 Hz, 3H), 1.31-1.40 (m, 2H), 1.52-1.72 (m, 8H), 2.54-2.73 (m, 5H), 3.30 (s, 2H), 3.35-3.40 (m, 4H), 4.03 (q, J = 7.0 Hz, 2H), 6.35 (s, 1H), 6.39-6.42 (m, 1H), 7.16-7.18 (m, 1H), 7.68 (dd, J = 5.0, 1.5 Hz, 1H) | G | m/z 359 (M + H)⁺ (ES⁺), at 5.25 min, UV active |
| 4-19 | Isomer 1: ethyl 4-[1'-(methylsulfonyl)-1',2'-dihydrospiro[cyclohexane- | 32 and 117 | c | (400 MHz, DMSO-d₆) ⊐: 1.18 (t, J = 7.0 Hz, 3H), 1.31-1.51 (m, 2H), 1.60-1.84 (m, 8H), 2.58-2.84 (m, 5H), 3.31 (s, 3H), 3.39-3.48 (m, 4H), | G | m/z 437 (M + H)⁺ (ES⁺), |

TABLE 3-continued

| Ex. No. | Name | Intermediate | Synthetic method | ¹H NMR | LCMS Method | LCMS data |
|---|---|---|---|---|---|---|
| | 1,3'-pyrrolo[2,3-b]pyridin]-4-yl]-1,4-diazepane-1-carboxylate | | | 3.84 (s, 2H), 4.03 (q, J = 7.0 Hz, 2H), 7.00-7.03 (m, 1H), 7.63-7.65 (m, 1H), 8.11-8.12 (m, 1H) | | at 5.39 min, UV active |
| 4-19 | Isomer 2: ethyl 4-[1'-(methylsulfonyl)-1',2'-dihydrospiro[cyclohexane-1,3,-pyrrolo[2,3-b]pyridin]-4-yl]-1,4-diazepane-1-carboxylate | 32 and 117 | c | (400 MHz, MeOD-d₄) ⊐: 1.29 (t, J = 7.0 Hz, 3H), 1.51-1.60 (m, 4H), 1.76-1.96 (m, 8H), 2.78-3.03 (m, 5H), 3.28 (s, 3H), 3.52-3.65 (m, 4H), 3.95 (s, 2H), 4.16 (q, J = 7.0 Hz, 2H), 7.01-7.04(m, 1H), 7.61-7.63(m, 1H), 8.10 (dd, J = 1.0, 5.0 Hz, 1H) | G | m/z 437 (M + H)⁺ (ES⁺), at 5.49 min, UV active |
| 4-20 | Isomer 2: ethyl 4-(2'-oxo-1',2'-dihydrospiro[cyclohexane-1,3'-pyrrolo[2,3-c]pyridin]-4-yl)-1,4-diazepane-1-carboxylate | 32 and 118 | c | (400 MHz, MeOD-d₄) ⊐: 1.29 (t, J = 7.0 Hz, 3H), 1.76-1.97 (m, 8H), 2.23-2.33 (m, 2H), 2.79-2.91 (m, 5H), 3.50-3.61 (m, 4H), 4.15 (q, J = 7.0 Hz, 2H), 7.36 (d, J = 5.0 Hz, 1H), 8.12 (s, 1H), 8.25 (d, J = 5.0 Hz, 1H) | G | m/z 373 (M + H)⁺ (ES⁺), at 4.55 min, UV active |
| 4-21 | Isomer 1: ethyl 4-(5'-methoxy-2'-oxo-1',2'-dihydrospiro[cyclohexane-1,3'-pyrrolo[2,3-c]pyridin]-4-yl)-1,4-diazepane-1-carboxylate | 32 and 95 | i | (400 MHz, CDCl₃) ⊐: 1.26 (t, J = 7.0 Hz, 3H), 1.54-1.98 (m, 8H), 2.15-2.29 (m, 2H), 2.63-2.87 (m, 5H), 3.45-3.57 (m, 4H), 3.89 (s, 3H), 4.14 (q, J = 7.0 Hz, 2H), 6.56 (s, 1H), 7.33 (s, 1H), 7.67 (s, 1H) | O | m/z 403 (M + H)⁺ (ES⁺), at 3.96 min, UV active |
| 4-22 | Isomer 2: ethyl 4-(2'-oxo-1',2'-dihydrospiro[cyclohexane-1,3'-pyrrolo]3,2-b]pyridin]-4-yl)-1,4-diazepane-1-carboxylate | 32 and 99 | c | (400 MHz, DMSO-d₆) ⊐: 1.18 (t, J = 7.0 Hz, 3H), 1.57-1.86 (m, 8H), 2.00-2.12 (m, 2H), 2.60-2.79 (m, 5H), 3.38-3.42 (m, 4H), 4.04 (q, J = 7.0 Hz, 2H), 7.13-7.14 (m, 2H), 8.07-8.08 (m, 1H), 10.48 (s, 1H) | F | m/z 373 (M + H)⁺ (ES⁺), at 1.53 min, UV active |
| 4-23 | Isomer 1: ethyl 4-(5'-methyl-2'-oxo-1',2'-dihydrospiro[cyclohexane-1,3'-pyrrolo]3,2-b]pyridin]-4-yl)-1,4-diazepane-1-carboxylate | 32 and 120 | c | (400 MHz, DMSO-d₆) ⊐: 1.18 (t, J = 7.0 Hz, 3H), 1.60-1.87 (m, 8H), 2.00-2.13 (m, 2H), 2.39 (s, 3H), 2.64-2.82 (m, 5H), 3.39-3.44 (m, 4H), 4.04 (q, J = 7.0 Hz, 2H), 6.99 (d, J = 8.0 Hz, 1H), 7.04 (d, J = 8.0 Hz, 1H), 10.35 (s, 1H) | F | m/z 388 (M + H)⁺ (ES⁺), at 1.57 min, UV active |
| 4-24 | Isomer 1: ethyl 4-(5'-methoxy-2'-oxo-1',2'-dihydrospiro[cyclohexane-1,3'-pyrrolo]3,2-b]pyridin]-4-yl)-1,4-diazepane-1-carboxylate | 32 and 97 | c | (400 MHz, DMSO-d₆) ⊐: 1.17 (t, J = 7.0 Hz, 3H), 1.53-1.76 (m, 8H), 2.21-2.36 (m, 2H), 2.68-2.80 (m, 5H), 3.39-3.51 (m, 4H), 3.83 (s, 3H), 4.03 (q, J = 7.0 Hz, 2H), 6.67 (d, J = 8.5 Hz, 1H), 7.23 (d, J = 8.5 Hz, 1H), 10.30 (s, 1H) | G | m/z 403 (M + H)⁺ (ES⁺), at 5.48 min, UV active |
| 4-24 | Isomer 2: ethyl 4-(5'-methoxy-2'-oxo-1',2'-dihydrospiro[cyclohexane-1,3'-pyrrolo]3,2-b]pyridin]-4-yl)-1,4-diazepane-1-carboxylate | 32 and 97 | c | (400 MHz, DMSO-d₆) ⊐: 1.18 (t, J = 7.0 Hz, 3H), 1.68-1.78 (m, 8H), 2.00-2.13 (m, 2H), 2.61-2.81 (m, 5H), 3.38-3.47 (m, 4H), 3.80 (s, 3H), 4.04 (q, J = 7.0 Hz, 2H), 6.60 (d, J = 8.5 Hz, 1H), 7.16 (d, J = 8.5 Hz, 1H), 10.20 (s, 1H) | G | m/z 403 (M + H)⁺ (ES⁺), at 5.61 min, UV active |
| 5-1 | Isomer 2: ethyl 4-[4-(4-ethyl-5-methyl-1 H-imidazol-2-yl)cyclohexyl]-1,4-diazepane-1-carboxylate | 31 | f | (400 MHz, DMSO-d₆) δ: 0.91-1.23 (m, 7H), 1.45-1.68 (m, 7H), 1.90-2.10 (m, 5H), 2.28-2.49 (m, 3H), 2.57-2.62 (m, 2H), 2.64-2.75 (m, 3H), 3.38-3.43 (m, 4H), 4.01 (q, J = 6.8 Hz, 2H), 10.97 (br. s, 1H) | B | m/z 363 (M + H)⁺ (ES⁺), at 3.22 min, UV active |
| 6-1 | Isomer 2: ethyl [1-(4-cyano-4-phenylcyclohexyl)piperidin-4-yl]methylcarbamate | 1, 12 and 55 | b | (400 MHz, DMSO-d₆) ⊐: 1.17 (t, J = 7.2 Hz, 3H), 1.45-1.80 (m, 7H), 1.81-1.99 (m, 5H), 2.24-2.40 (m, 3H), 2.70 (s, 3H), 2.95-3.10 (m, 2H), 3.68-3.85 (m, 1H), 4.02 (q, J = 7.2 Hz, 2H), 7.32-7.41 (m, 1H), 7.41-7.49 (m, 2H) and 7.50-7.57 (m, 2H). | B | m/z 370 (M + H)⁺ (ES⁺), at 4.57 min, UV active |
| 6-2 | Isomer 2: ethyl {[1-(4-cyano-4-phenylcyclohexyl)piperidin-4-yl]methyl}carbamate | 2, 12 and 55 | b | (400 MHz, DMSO-d₆) ⊐: 1.05-1.11 (m, 2H), 1.14 (t, J = 7.0 Hz, 3H), 1.24-1.32 (m, 1H), 1.59-1.92 (m, 10H), 2.23-2.30 (m, 3H), 2.82-2.85 (m, 2H), 2.91-2.96 (m, 2H), 3.96 (q, J = 7.0 Hz, 2H), 7.11 (br. s, 1H), 7.35-7.39 (m, 1H), 7.44-7.48 (m, 2H) and 7.51-7.54 (m, 2H). | B | m/z 370 (M + H)⁺ (ES⁺), at 4.17 min, UV active |
| 7-1 | Isomer 1: ethyl [1-(2'-oxo-1',2'-dihydrospiro[cyclohexane 1,3'-indol]-4-yl)piperidin-4-yl]carbamate | 65 and 101 | c | (400 MHz, MeOD-d₄) ⊐: 1.26 (t, J = 7.0 Hz, 3H), 1.72-2.25 (m, 12H), 3.13-3.26 (m, 2H), 3.35-3.42 (m, 1H), 3.59-3.78 (m, 3H), 4.08-4.13 (m, 2H), 7.00 (d, J = 7.5 Hz, 1H), 7.08 (t, J = 7.5 Hz, 1H), 7.29 (t, J = 7.5 Hz, 1H), 7.64 (d, J = 7.5 Hz, 1H), 8.54 (br s, 1H) | F | m/z 372 (M + H)⁺ (ES⁺), at 1.61 min, UV active |
| 7-1 | Isomer 2: ethyl [1-(2'-oxo-1',2'-dihydrospiro[cyclohexane 1,3'-indol]-4-yl)piperidin-4-yl]carbamate | 65 and 101 | c | (400 MHz, MeOD-d₄) ⊐: 1.26 (t, J = 7.0 Hz, 3H), 1.76-2.20 (m, 10H), 2.48-2.57 (m, 2H), 3.20-3.26 (m, 2H), 3.37-3.54 (m, 3H), 3.67-3.80 (m, 1 H), 4.08-4.13 (m, 2H), 6.90 (d, J = 7.5 Hz, 1H), 7.04 (t, J = 7.5 Hz, 1H), 7.20-7.23 (m, 2H), 8.56 (br s, 1H) | F | m/z 372 (M + H)⁺ (ES⁺), at 1.64 min, UV active |

TABLE 3-continued

| Ex. No. | Name | Inter mediate | Synthetic method | $^1$H NMR | LCMS Method | LCMS data |
|---|---|---|---|---|---|---|
| 7-2 | Isomer 1: ethyl {[1-(2'-oxo-1',2'-dihydrospiro[cyclohexane 1,3'-indol]-4-yl)piperidin-4-yl]methyl}carbamate | 55 and 103 | h | (400 MHz, MeOD-d$_4$) ⊐: 1.22-1.39 (m, 5H), 1.49-1.67 (m, 3H), 1.80-2.06 (m, 8H), 2.34-2.39 (m, 2H), 2.55-2.64 (m, 1H), 3.03 (d, J = 6.5 Hz, 2H), 3.15-3.18 (m, 2H), 4.06-4.17 (m, 2H), 6.97 (d, J = 7.5 Hz, 1H), 7.05 (t, J = 7.5 Hz, 1H), 7.26 (t, J = 7.5 Hz, 1H), 7.63 (d, J = 7.5 Hz, 1H) | F | m/z 386 (M + H)$^+$ (ES$^+$), at 1.63 min, UV active |
| 7-2 | Isomer 2: ethyl 1[1-(2'-oxo-1',2'-dihydrospiro[cyclohexane-1,3'-indol]-4-yl)piperidin-4-yl]methyl}carbamate | 55 and 103 | h | (400 MHz, DMSO-d$_6$) ⊐: 1.05-1.39 (m, 6H), 1.59-1.78 (m, 9H), 2.09-2.24 (m, 4H), 2.84-2.89 (m, 4H), 3.97 (q, J = 7.0 Hz, 2H), 6.79 (d, J = 7.5 Hz, 1H), 6.94 (t, J = 7.5 Hz, 1H), 7.10-7.15 (m, 2H), 7.22 (d, J = 7.0 Hz, 1H), 10.23 (s, 1H) | F | m/z 386 (M + H)$^+$ (ES$^+$), at 1.67 min, UV active |
| 8-1 | Mixture of isomers: ethyl 5-(4-cyano-4-phenylcyclohexyl)-1,5-diazocane-1-carboxylate | 3 and 12 | a | (400 MHz, DMSO-d$_6$) ⊐: 1.17 (t, J = 7.1 Hz, 3H), 1.54-1.73 (m, 6H), 1.82-2.01 (m, 5H), 2.03-2.30 (m, 3H), 2.54-2.66 (m, 4H), 2.95-3.10 (m, 2H), 3.68-3.85 (m, 1H), 4.03 (q, J = 7.1 Hz, 2H), 7.32-7.39 (m, 1H), 7.40-7.47 (m, 2H) and 7.50-7.57 (m, 2H). | B | m/z 370 (M + H)$^+$ (ES$^+$), at 5.07 min, UV active |
| 9-1 | Isomer 1: ethyl 2-(4-cyano-4-phenylcyclohexyl)-2,6-diazaspiro[3.4]octane-6-carboxylate | 4, 12 and 55 | b | (400 MHz, DMSO-d$_6$) ⊐: 1.14 (t, J = 6.9 Hz, 3H), 1.19-1.36 (m, 2H), 1.75-1.89 (m, 4H), 1.89-1.98 (m, 2H), 2.01-2.11 (m, 3H), 2.98-3.11 (m, 4H), 3.20-3.35 (m, 4H), 3.97 (q, J = 6.9 Hz, 2H), 7.29-7.35 (m, 1H), 7.36-7.43 (m, 2H) and 7.45-7.55 (m, 2H). | B | m/z 368 (M + H)$^+$ (ES$^+$), at 3.96 min, UV active |
| 9-1 | Isomer 2: ethyl 2-(4-cyano-4-phenylcyclohexyl)-2,6-diazaspiro[3.4]octane-6-carboxylate | 4, 12 and 55 | b | (400 MHz, DMSO-d$_6$) ⊐: 1.17 (t, J = 7.0 Hz, 3H), 1.63-1.73 (m, 4H), 1.76-1.85 (m, 2H), 1.85-2.09 (m, 2H), 2.11-2.26 (m, 2H), 2.38-2.49 (m, 1H), 2.99-3.10 (m, 4H), 3.22-3.43 (m, 4H), 4.01 (q, J = 7.0 Hz, 2H), 7.34-7.40 (m, 1H) and 7.41-7.55 (m, 4H). | B | m/z 368 (M + H)$^+$ (ES$^+$), at 4.59 min, UV active |
| 10-1 | Mixture of isomers: ethyl 6-(2'-oxo-1',2'-dihydrospiro[cyclohexane-1,3'-indol]-4-yl)-2,6-diazaspiro[3.4]octane-2-carboxylate | 65 and 122 | j | (400 MHz, DMSO-d$_6$) ⊐: 1.53 (t, J = 7.0 Hz, 3H), 1.55-2.32 (m, 10H), 2.55-2.88 (m, 5H), 3.74-3.90 (m, 4H), 3.99 (q, J = 7.0 Hz, 2H), 6.80 (d, J = 7.5 Hz, 1H), 6.91-6.95 (m, 1H), 7.14 (td, J = 7.5, 1.0 Hz, 1H), 7.29 (d, J = 7.5 Hz, 1H), 10.22 (s, 1H) | B | m/z 384 (M + H)$^+$ (ES$^+$), at 3.74 min, UV active |
| 11-1 | Isomer 2: ethyl 7-(4-cyano-4-phenylcyclohexyl)-2,7-diazaspiro[3.5]nonane-2-carboxylate | 5, 12 and 55 | b | (400 MHz, CDCl$_3$) ⊐: 1.24 (t, J = 7.2 Hz, 3H), 1.48-1.59 (m, 3H), 1.67-2.06 (m, 8H), 2.20-2.51 (m, 4H), 2.53-2.67 (m, 1H), 2.69-2.84 (m, 1H), 2.89-3.02 (m, 1H), 3.44-3.56 (m, 1H), 3.63-3.76 (m, 2H), 4.10 (q, J = 7.2 Hz, 2H) and 7.27-7.70 (m, 5H). | B | m/z 382 (M + H)$^+$ (ES$^+$), at 4.45 min, UV active |
| 12-1 | Isomer 1: ethyl 8-(2'-oxo-1',2'-dihydrospiro[cyclohexane-1,3'-indol]-4-yl)-2,8-diazaspiro[4.5]decane-2-carboxylate | 6 and 65 | k | (400 MHz, CDCl$_3$) ⊐: 1.15-1.23 (m, 3H), 1.39-2.10 (m, 11H), 2.28-2.80 (m, 6H), 3.06-3.46 (m, 6H), 4.03-4.11 (m, 2H), 6.76-7.17 (m, 3H), 7.39-7.72 (m, 2H) | B | m/z 412 (M + H)$^+$ (ES$^+$), at 3.58 min, UV active |
| 12-2 | Isomer 1: ethyl 4-[2-(ethoxycarbonyl)-2,8-diazaspiro[4.5]dec-8-yl]-2'-oxospiro[cyclohexane-1,3'-indole]-1'(2'H)-carboxylate | Ex 12-1 and 55 | h | (400 MHz, CDCl$_3$) ⊐: 1.17-1.22 (m, 3H), 1.39 (t, J = 9.5 Hz, 3H), 1.47-1.28 (m, 16H), 2.46-2.70 (m, 5H), 3.07-3.42 (m, 5H), 3.79-3.87 (m, 1H), 4.07 (q, J = 9.5 Hz, 2H), 4.41 (q, J = 9.5 Hz, 2H), 7.06-7.16 (m, 2H), 7.25-7.30 (m, 1H), 7.89 (d, J = 11.0 Hz, 1H) | B | m/z 484 (M + H)$^+$ (ES$^+$), at 4.54 min, UV active |
| 13-1 | Isomer 2: ethyl 8-(4-cyano-4-phenylcyclohexyl)-2,8-diazaspiro[4.5]decane-2-carboxylate | 6 and 12 | a | (400 MHz, CDCl$_3$) ⊐: 1.26 (t, J = 7.2 Hz, 3H), 1.50-1.62 (m, 5H), 1.63-1.77 (m, 2H), 1.81-2.06 (m, 6H), 2.24-2.38 (m, 4H), 2.45-2.60 (m, 2H), 3.13-3.25 (m, 2H), 3.34-3.48 (m, 2H), 4.13 (q, J = 7.2 Hz, 2H), 7.31 (t, J = 7.6 Hz, 1H), 7.40 (d, J = 7.6 Hz, 2H) and 7.51 (d, J = 7.6 Hz, 2H). | B | m/z 396 (M + H)$^+$ (ES$^+$), at 4.71 min, UV active |
| 14-1 | Isomer 1: ethyl 7-(4-cyano-4-phenylcyclohexyl)-3,7-diazabicyclo[4.2.0]octane-3-carboxylate | 7 and 12 | a | (400 MHz, DMSO-d$_6$) ⊐: 1.19 (t, J = 6.8 Hz, 3H), 1.26-1.42 (m, 1H), 1.52-1.69 (m, 2H), 1.80-2.00 (m, 6H), 2.04-2.12 (m, 2H), 2.18-2.27 (m, 1H), 2.38 (t, J = 7.0 Hz, 1H), 2.91 (t, J = 7.2 Hz, 1H), 3.00 (d, J = 6.0 Hz, 1H), 3.30-3.39 (m, 2H), 3.47-3.60 (m, 1H), 3.81-3.89 (m, 1H), 4.04 (q, J = 6.8 Hz, 2H), 7.33-7.38 (m, 1H), 7.40-7.47 (m, 2H) and 7.50-7.56 (m, 2H). | B | m/z 368 (M + H)$^+$ (ES$^+$), at 4.31 min, UV active |
| 14-2 | Isomer 2: ethyl 7-(4-cyano-4-phenylcyclohexyl)-3,7-diazabicyclo[4.2.0]octane-3-carboxylate | 7 and 12 | a | (400 MHz, DMSO-d$_6$) ⊐: 1.08-1.22 (m, 3H), 1.59-1.85 (m, 8H), 2.04-2.27 (m, 2H), 2.30-2.44 (m, 1H), 2.87 (t, J = 6.8 Hz, 1H), 3.01 (dd, J = 7.0 and 2.3, 1H), 3.37-3.41 (m, 1H), 3.42-3.77 (m, 5H), 4.03 (q, J = 7.0 Hz, 2H), 7.33-7.42 (m, 1H) and 7.40-7.58 (m, 4H). | B | m/z 368 (M + H)$^+$ (ES$^+$), at 5.01 min, UV active |

TABLE 3-continued

| Ex. No. | Name | Intermediate | Synthetic method | ¹H NMR | LCMS Method | LCMS data |
|---|---|---|---|---|---|---|
| 15-1 | Isomer 2: ethyl 5-(4-cyano-4-phenylcyclohexyl)hexahydropyrrolo[3,4-b]pyrrole-1(2H)-carboxylate | 8 and 12 | a | (400 MHz, DMSO-$d_6$) ⊐: 1.08-1.24 (m, 3H), 1.62-1.99 (m, 7H), 2.01-2.43 (m, 5H), 2.55-2.97 (m, 4H), 3.12-3.29 (m, 1H), 3.42-3.59 (m, 1H), 3.91-4.06 (m, 2H), 4.07-4.22 (m, 1H), 7.28-7.39 (m, 1H) and 7.40-7.56 (m, 4H). | B | m/z 368 (M + H)$^+$ (ES$^+$), at 4.92 min, UV active |
| 16-1 | Isomer 1: ethyl 1-(4-cyano-4-phenylcyclohexyl)hexahydropyrrolo[3,4-b]pyrrole-5(1H)-carboxylate | 9, 12 and 55 | b | (400 MHz, DMSO-$d_6$) ⊐: 1.18 (t, J = 7.2 Hz, 3H), 1.42-1.68 (m, 4H), 1.87-2.19 (m, 8H), 2.41-2.56 (m, 2H), 2.64-2.79 (m, 2H), 2.96-3.06 (m, 1H), 3.21-3.41 (m, 2H), 4.02 (q, J = 7.2 Hz, 2H), 7.33-7.39 (m, 1H), 7.41-7.49 (m, 2H) and 7.50-7.58 (m, 2H). | B | m/z 368 (M + H)$^+$ (ES$^+$), at 4.10 min, UV active |
| 16-1 | Isomer 2: ethyl 1-(4-cyano-4-phenylcyclohexyl)hexahydropyrrolo[3,4-b]-pyrrole-5(1H)-carboxylate | 9, 12 and 55 | b | (400 MHz, DMSO-$d_6$) ⊐: 0.96-1.13 (m, 3H), 1.32-1.48 (m, 2H), 1.63-1.96 (m, 8H), 2.07-2.23 (m, 2H), 2.37 (td, J = 9.1 and 6.15, 1H), 2.41-2.52 (m, 2H), 2.59-2.71 (m, 1H), 2.76-2.84 (m, 1H), 3.14-3.33 (m, 2H), 3.92 (q, J = 7.0 Hz, 2H), 7.27-7.33 (m, 1H), 7.35-7.42 (m, 2H) and 7.42-7.49 (m, 2H). | B | m/z 368 (M + H)$^+$ (ES$^+$), at 4.60 min, UV active |
| 17-1 | Isomer 2: ethyl 3-(4-cyano-4-phenylcyclohexyl)-3,7-diazabicyclo[4.2.0]octane-7-carboxylate | 10, 12 and 55 | b | (400 MHz, DMSO-$d_6$) ⊐: 1.00-1.12 (m, 3H), 1.15-1.25 (m, 2H), 1.48-1.77 (m, 3H), 1.77-1.94 (m, 4H), 2.03-2.12 (m, 1H), 2.13-2.28 (m, 2H), 2.31-2.56 (m, 3H), 2.70 (dd, J = 12 and 5.7, 1H), 3.40-3.49 (m, 1H), 3.69-3.82 (m, 1H), 3.84-4.02 (m, 2H), 4.14-4.25 (m, 1H), 7.25-7.33 (m, 1H), 7.34-7.41 (m, 2H) and 7.42-7.51 (m, 2H). | B | m/z 368 (M + H)$^+$ (ES$^+$), at 4.43 min, UV active |
| 18-1 | Isomer 1: ethyl (4aS,7aS)-1-(4-cyano-4-phenylcyclohexyl)octahydro-6H-pyrrolo[3,4-b]pyridine-6-carboxylate | 11 and 12 | a | (400 MHz, DMSO-$d_6$) ⊐: 1.12-1.21 (m, 3H), 1.22-1.68 (m, 7H), 1.71-1.84 (m, 2H), 1.86-2.26 (m, 6H), 2.58-2.74 (m, 1H), 3.07-3.31 (m, 3H), 3.36-3.59 (m, 2H), 3.95-4.09 (m, 2H), 7.32-7.40 (m, 1H), 7.40-7.48 (m, 2H) and 7.51-7.58 (m, 2H). | B | m/z 382 (M + H)$^+$ (ES$^+$), at 4.39 min, UV active |
| 19-1 | Isomer 2: 4-{[(1R,3S)-3-(3-methyl-1,2,4-oxadiazol-5-yl)cyclopentyl]amino}-1-(pyridin-2-yl)cyclohexane carbonitrile | 26 and 126 | l | (400 MHz, CDCl$_3$) ⊐: 1.55-1.66 (m, 2H), 1.69-1.81 (m, 2H), 1.88-2.16 (m, 8H), 2.37 (s, 3H), 2.38-2.55 (m, 3H), 2.97-3.06 (m, 1H), 3.25-3.40 (m, 2H), 7.21-7.27 (m, 1H), 7.53-7.61 (m, 1H), 7.73 (t, J = 7.4 Hz, 1H), 8.62 (d, J = 5.1 Hz, 1H). | E | m/z 352 (M + H)$^+$ (ES$^+$), at 3.58 min, UV active |
| 19-2 | Isomer 2: 4-{[(1R,3S)-3-(3-ethyl-1,2,4-oxadiazol-5-yl)cyclopentyl]amino}-1-phenylcyclohexane carbonitrile | 12 and 128 | l | (400 MHz, CDCl$_3$) ⊐: 1.32 (t, J = 7.4 Hz, 3H), 1.55-1.66 (m, 1H), 1.70-1.82 (m, 3H), 1.84-1.93 (m, 3H), 1.97-2.17 (m, 5H), 2.24-2.35 (m, 2H), 2.38-2.49 (m, 1H), 2.74 (q, J = 7.7 Hz, 2H), 3.02-3.08 (m, 1H), 3.24-3.42 (m, 2H), 7.29-7.35 (m, 1H), 7.40 (t, J = 7.8 Hz, 2H), 7.47-7.54 (m, 2H). | E | m/z 365 (M + H)$^+$ (ES$^+$), at 5.02 min, UV active |
| 20-1 | Isomer 2: 1-phenyl-4-{6-[3-(trifluoromethyl)-1,2,4-oxadiazol-5-yl]-2-azaspiro[3.3]hept-2-yl}cyclohexanecarbonitrile | 12 and 131 | l | (400 MHz, CDCl$_3$) ⊐: 1.68-1.76 (m, 2H), 1.78-1.93 (m, 4H), 2.20-2.31 (m, 2H), 2.33-2.40 (m, 1H), 2.57-2.74 (m, 4H), 3.16 (s, 2H), 3.25 (s, 2H), 3.67-3.80 (m, 1H), 7.28-7.34 (m, 1H), 7.40 (t, J = 7.8 Hz, 2H), 7.52 (d, J = 7.0 Hz, 2H). | E | m/z 417 (M + H)$^+$ (ES$^+$), at 5.90 min, UV active |
| 21-1 | Isomer 3: 4-[2-(3-methyl-1,2,4-oxadiazol-5-yl)-6-azaspiro[3.4]oct-6-yl]-1-phenylcyclohexane carbonitrile | 12 and 133 | l | (400 MHz, CDCl$_3$) ⊐: 1.82-1.90 (m, 2H), 1.91-1.97 (m, 4H), 2.00-2.06 (m, 2H), 2.24-2.37 (m, 3H), 2.38 (s, 3H), 2.40-2.52 (m, 4H), 2.59-2.67 (m, 4H), 3.62-3.73 (m, 1H), 7.28-7.34 (m, 1H), 7.39 (t, J = 7.6 Hz, 2H), 7.50 (d, J = 7.0 Hz, 2H). | E | m/z 377 (M + H)$^+$ (ES$^+$), at 5.31 min, UV active |
| 21-2 | Isomer 3: 1-(2-fluorophenyl)-4-[2-(3-methyl-1,2,4-oxadiazol-5-yl)-6-azaspiro[3.4]oct-6-yl]cyclohexanecarbonitrile | 19 and 133 | l | (400 MHz, CDCl$_3$) ⊐: 1.90-2.05 (m, 7H), 2.33-2.51 (m, 8H), 2.38 (d, J = 1.2 Hz, 3H), 2.58-2.68 (m, 4H), 3.60-3.71 (m, 1H), 7.06-7.19 (m, 2H), 7.28-7.35 (m, 1H), 7.46 (t, J = 7.8 Hz, 1H). | E | m/z 395 (M + H)$^+$ (ES$^+$), at 5.35 min, UV active |
| 21-3 | Isomer 3: 1-(5-fluoropyridin-2-yl)-4-[2-(3-methyl-1,2,4-oxadiazol-5-yl)-6-azaspiro[3.4]oct-6-yl]cyclohexanecarbonitrile | 27 and 133 | c | (400 MHz, MeOD-$d_4$) ⊐: 1.70-1.84 (m, 2H), 1.85-2.10 (m, 5H), 2.28-2.36 (m, 4H), 2.38-2.46 (m, 4H), 2.51-2.61 (m, 3H), 2.63-2.71 (m, 4H), 3.65-3.75 (m, 1H), 7.61-7.75 (m, 2H), 8.47-8.57 (m, 1H). | R | m/z 396 (M + H)$^+$ (ES$^+$), at 4.23 min, UV active |
| 21-3 | Isomer 4: 1-(5-fluoropyridin-2-yl)-4-[2-(3-methyl-1,2,4-oxadiazol-5-yl)-6-azaspiro[3.4]oct-6-yl]cyclohexanecarbonitrile | 27 and 133 | c | (400 MHz, MeOD-$d_4$) ⊐: 1.77-2.02 (m, 7H), 2.31-2.45 (m, 6H), 2.45-2.54 (m, 3H), 2.54-2.64 (m, 4H), 2.78 (s, 2H), 3.65-3.75 (m, 1H), 7.61-7.73 (m, 2H), 8.50 (d, J = 2.8 Hz, 1H). | R | m/z 396 (M + H)$^+$ (ES$^+$), at 4.43 min, UV active |

TABLE 3-continued

| Ex. No. | Name | Intermediate | Synthetic method | ¹H NMR | LCMS Method | LCMS data |
|---|---|---|---|---|---|---|
| 21-4 | Isomer 4: 1-(5-methoxypyridin-2-yl)-4-[2-(3-methyl-1,2,4-oxadiazol-5-yl)-6-azaspiro[3.4]oct-6-yl]cyclohexanecarbonitrile | 44 and 133 | c | (400 MHz, MeOD-d4) ⊐: 1.75-2.01 (m, 10H), 2.30-2.45 (m, 5H), 2.54-2.65 (m, 5H), 2.78 (s, 2H), 3.63-3.72 (m, 1H), 3.88 (s, 3H), 7.42 (dd, J = 8.8, 3.0 Hz, 1H), 7.55 (d, J = 8.8 Hz, 1H), 8.26 (d, J = 3.0 Hz, 1H). | R | m/z 408 (M + H)⁺ (ES⁺), at 4.25 min, UV active |
| 21-5 | Isomer 1: 4-[2-(3-methyl-1,2,4-oxadiazol-5-yl)-6-azaspiro[3.4]oct-6-yl]-1-(5-methylpyridin-2-yl)cyclohexanecarbonitrile | 43 and 133 | c | (400 MHz, MeOD-d₄) ⊐: 1.32 (s, 2H), 1.66-1.82 (m, 3H), 1.97 (dd, J = 13.3, 3.0 Hz, 2H), 2.05-2.26 (m, 10H), 2.34-2.50 (m, 5H), 2.68-2.78 (m, 1H), 3.12 (s, 2H), 3.63-3.77 (m, 1H), 7.40 (d, J = 8.1 Hz, 1H), 7.57 (dd, J = 8.0, 2.3 Hz, 1H), 8.29 (d, J = 2.2 Hz, 1H). | R | m/z 392 (M + H)⁺ (ES⁺), at 3.50 min, UV active |
| 21-5 | Isomer 2: 4-[2-(3-methyl-1,2,4-oxadiazol-5-yl)-6-azaspiro[3.4]oct-6-yl]-1-(5-methylpyridin-2-yl)cyclohexanecarbonitrile | 43 and 133 | c | (400 MHz, MeOD-d₄) ⊐: 1.81 (dt, J = 13.7, 10.2 Hz, 2H), 2.00 (t, J = 7.2 Hz, 2H), 2.09 (td, J = 13.9, 3.6 Hz, 2H), 2.19-2.29 (m, 5H), 2.34 (s, 3H), 2.36 (s, 3H), 2.40-2.50 (m, 2H), 2.54-2.64 (m, 2H), 2.85 (t, J = 7.2 Hz, 2H), 3.06 (s, 2H), 3.65-3.79 (m, 1H), 7.53 (d, J = 8.1 Hz, 1H), 7.69 (dd, J = 8.1, 2.3 Hz, 1H), 8.41 (d, J = 2.2 Hz, 1H). | R | m/z 392 (M + H)⁺ (ES⁺), at 3.60 min, UV active |
| 22-1 | Isomer 1: 4-[(3R)-3-(3-methyl-1,2,4-oxadiazol-5-yl)piperidin-1-yl]spiro(cyclohexane-1,3'-indol]-2'(1'H)-one | 65 and 135 | 1 | (400 MHz, CDCl₃) ⊐: 1.59-1.98 (m, 9H), 2.12-2.22 (m, 1H), 2.28-2.38 (m, 2H), 2.40 (s, 3H), 2.42-2.54 (m, 1H), 2.60-2.82 (m, 2H), 2.96-3.12 (m, 1H), 3.20-3.39 (m, 2H), 6.85 (d, J = 7.4 Hz, 1H), 7.03 (t, J = 8.2 Hz, 1H), 7.09-7.23 (m, 2H), 7.78 (s, 1H). | E | m/z 367 (M + H)⁺ (ES⁺), at 3.95 min, UV active |
| 22-2 | Isomer 1: 5'-methoxy-4-[(3R)-3-(3-methyl-1,2,4-oxadiazol-5-yl)piperidin-1-yl]spiro[cyclohexane-1,3'-indol]-2'(1'H)-one | 80 and 135 | c | (400 MHz, MeOD-d₄) ⊐: 1.59-1.80 (m, 4H), 1.87-2.06 (m, 7H), 2.11-2.20 (m, 1H), 2.36 (s, 3H), 2.44-2.52 (m, 1H), 2.59-2.75 (m, 2H), 3.02-3.10 (m, 1H), 3.19-3.27 (m, 1H), 3.33-3.39 (m, 1H), 3.79 (s, 3H), 6.78-6.91 (m, 2H), 7.14-7.21 (m, 1H). One exchangeable proton not observed. | I | m/z 397 (M + H)⁺ (ES⁺), at 4.87 min UV active |
| 22-3 | Isomer 1: 5'-methyl-4-[(3R)-3-(3-methyl-1,2,4-oxadiazol-5-yl)piperidin-1-yl]spiro[cyclohexane-1,3'-indol]-2'(1'H)-one | 70 and 135 | c | (400 MHz, MeOD-d₄) ⊐: 1.61 (d, J = 8.9 Hz, 2H), 1.70-1.80 (m, 2H), 1.87-1.94 (m, 6H), 2.00-2.10 (m, 2H), 2.16 (d, J = 7.5 Hz, 1H), 2.34 (s, 3H), 2.36 (s, 3H), 2.42-2.52 (m, 1H), 2.58-2.76 (m, 2H), 3.06-3.42 (m, 2H), 6.83 (d, J = 7.9 Hz, 1H), 7.06 (d, J = 8.2 Hz, 1H), 7.43 (s, 1H). NH not observed. | R | m/z 381 (M + H)⁺ (ES⁺), at 3.57 min, UV active |
| 22-4 | Isomer 1: 6'-methyl-4-[(3R)-3-(3-methyl-1,2,4-oxadiazol-5-yl)piperidin-1-yl]spiro[cyclohexane-1,3'-indol]-2'(1'H)-one | 68 and 135 | c | (400 MHz, MeOD-d₄) ⊐: 1.59 (d, J = 8.4 Hz, 2H), 1.65-1.79 (m, 2H), 1.80-2.03 (m, 7H), 2.10-2.20 (m, 1H), 2.33 (s, 3H), 2.36 (s, 3H), 2.49 (t, J = 10.5 Hz, 1H), 2.60-2.76 (m, 2H), 3.05 (d, J = 11.4 Hz, 1H), 3.18-3.38 (m, 2H), 6.78 (s, 1H), 6.86 (d, J = 7.8 Hz, 1H), 7.46 (d, J = 7.7 Hz, 1H). NH not observed. | R | m/z 381 (M + H)⁺ (ES⁺), at 3.61 min, UV active |
| 23-1 | Isomer 1: 4-({[2-(3-methyl-1,2,4-oxadiazol-5-yl)cyclopropyl]methyl}amino)spiro[cyclohexane-1,3'-indol]-2'(1'H)-one | 65 and 137 | 1 | (400 MHz, CDCl₃) ⊐: 1.14-1.21 (m, 1H), 1.43-1.49 (m, 1H), 1.64-1.74 (m, 3H), 1.81-1.90 (m, 1H), 1.91-1.98 (m, 2H), 1.98-2.11 (m, 4H), 2.34 (s, 3H), 2.72-2.87 (m, 4H), 6.93 (d, J = 7.8 Hz, 1H), 7.02 (t, J = 7.2 Hz, 1H), 7.24 (t, J = 7.8 Hz, 1H), 7.58 (d, J = 7.8 Hz, 1H), 7.98-8.23 (m, 1H). | E | m/z 353 (M + H)⁺ (ES⁺), at 3.12 min, UV active |
| 24-1 | Isomer 1: 4-({(1R,3S)-3-[3-(trifluoromethyl)-1,2,4-oxadiazol-5-yl]cyclopentyl}amino)spiro [cyclohexane-1,3'-indol]-2'(1'H)-one | 65 and 138 | 1 | (400 MHz, CDCl₃) ⊐: 1.54-1.77 (m, 5H), 1.85-2.15 (m, 7H), 2.17-2.34 (m, 2H), 2.34-2.57 (m, 1H), 2.75-2.88 (m, 1H), 3.45-3.57 (m, 1H), 3.58-3.78 (m, 1H), 6.93-6.98 (m, 1H), 6.98-7.04 (m, 1H), 7.24 (t, J = 7.8 Hz, 1H), 7.52-7.65 (m, 1H), 8.52 (br. s., 1H). | E | m/z 421 (M + H)⁺ (ES⁺), at 4.42 min, UV active |
| 24-2 | Isomer 1: 5'-methyl-4-({(1R,3S)-3-[3-(trifluoromethyl)-1,2,4-oxadiazol-5-yl]cyclopentyl}amino)spiro]cyclohexane-1,3'-indol]-2'(1'H)-one | 70 and 138 | 1 | (400 MHz, MeOD-d₄) ⊐: 1.47-1.62 (m, 3H), 1.63-1.85 (m, 3H), 1.85-1.98 (m, 4H), 1.98-2.09 (m, 2H), 2.09-2.33 (m, 1H), 2.35 (s, 3H), 2.35-2.68 (m, 1H), 2.79-2.91 (m, 1H), 3.54-3.84 (m, 3H), 6.83 (d, J = 7.8 Hz, 1H), 7.05 (d, J = 7.9 Hz, 1H), 7.57 (s, 1H). NH not observed. | R | m/z 435 (M + H)⁺ (ES⁺), at 4.19 min, UV active |
| 24-3 | Isomer 1: 6'-methyl-4-{[(1R,3S)-3-(3-methyl-1,2,4-oxadiazol-5-yl)cyclopentyl]amino}spiro]cyclohexane-1,3'-indol]-2'(1'H)-one | 68 and 126 | 1 | (400 MHz, MeOD-d₄) ⊐: 1.29 (s, 1H), 1.59-1.77 (m, 1H), 1.73-1.81 (m, 4H), 1.81-1.92 (m, 3H), 2.00-2.20 (m, 5H), 2.30 (s, 3H), 2.33 (s, 3H), 2.49 (dt, J = 13.6, 7.0 Hz, 1H), 2.71-2.81 (m, 1H), 3.32-3.53 (m, 2H), 6.70 (s, 1H), 6.82 (d, J = 7.7 Hz, 1H), 7.08 (d, J = 7.7 Hz, 1H). NH not observed. | R | m/z 381 (M + H)⁺ (ES⁺), at 3.41 min, UV active |
| 25-1 | Isomer 1: 4-[6-(3-ethyl-1,2,4-oxadiazol-5-yl)-2-azaspiro[3.3]hept-2-yl] | 65 and 140 | 1 | (400 MHz, CDCl₃) ⊐: 1.33 (t, J = 7.6 Hz, 3H), 1.49-1.61 (m, 2H), 1.62-1.79 (m, 2H), 1.82-1.95 (m, 4H), 2.14-2.25 (m, 1H), | E | m/z 393 (M + H)⁺ (ES⁺), |

TABLE 3-continued

| Ex. No. | Name | Intermediate | Synthetic method | $^1$H NMR | LCMS Method | LCMS data |
|---|---|---|---|---|---|---|
| | spiro[cyclohexane-1,3'-indol]-2'(1'H)-one | | | 2.56-2.70 (m, 4H), 2.76 (q, J = 7.8 Hz, 2H), 3.28 (s, 2H), 3.38 (s, 2H), 3.57-3.68 (m, 1H), 6.91 (d, J = 7.8 Hz, 1H), 6.98 (t, J = 7.6 Hz, 1H), 7.22 (t, J = 7.4 Hz, 1H), 7.60 (d, J = 7.4 Hz, 1H), 8.08 (br. s., 1H). | | at 3.77 min, UV active |
| 26-1 | Isomer 2: 5'-methyl-4-[2-(3-methyl-1,2,4-oxadiazol-5-yl)-6-azaspiro[3.4]oct-6-yl] spiro[cyclohexane-1,3'-indol]-2'(1'H)-one | 70 and 133 | c | (400 MHz, MeOD-d$_4$) ⊐: 1.55 (d, J = 10.7 Hz, 2H), 1.80-1.96 (m, 4H), 2.01 (t, J = 7.2 Hz, 2H), 2.06-2.17 (m, 3H), 2.34 (s, 2 × 3H), 2.42-2.53 (m, 2H), 2.61 (t, J = 10.5 Hz, 2H), 2.78 (t, J = 7.1 Hz, 2H), 2.98 (s, 2H), 3.65-3.77 (m, 1H), 6.82 (d, J = 7.9 Hz, 1H), 7.05 (d, J = 8.0 Hz, 1H), 7.61 (s, 1H). NH not observed. | R | m/z 407 (M + H)$^+$ (ES$^+$), at 3.11 min, UV active |
| 26-2 | Isomer 1: 5'-methoxy-4-[2-(3-methyl-1,2,4-oxadiazol-5-yl)-6-azaspiro[3.4]oct-6-yl] spiro[cyclohexane-1,3'-indol]-2'(1'H)-one | 80 and 133 | c | (400 MHz, MeOD-d$_4$) ⊐: 1.54-1.64 (m, 2H), 1.76-1.96 (m, 4H), 2.02 (t, J = 7.3 Hz, 1H), 2.05-2.15 (m, 2H), 2.15-2.21 (m, 1H), 2.28-2.38 (m, 3H), 2.47-2.65 (m, 4H), 2.75-2.95 (m, 4H), 2.99 (s, 1H), 3.63-3.83 (m, 4H), 6.78-6.90 (m, 2H), 7.36 (dd, J = 9.5, 2.3 Hz, 1H). NH not observed. | S | m/z 423 (M + H)$^+$ (ES$^+$), at 3.00 min, UV active |
| 26-2 | Isomer 3: 5'-methoxy-4-[2-(3-methyl-1,2,4-oxadiazol-5-yl)-6-azaspiro[3.4]oct-6-yl] spiro[cyclohexane-1,3'-indol]-2'(1'H)-one | 80 and 133 | c | (400 MHz, MeOD-d$_4$) ⊐: 1.76-1.92 (m, 4H), 2.06-2.27 (m, 4H), 2.34 (s, 3H), 2.36 (d, J = 12.1 Hz, 1H), 2.43-2.51 (m, 5H), 2.75-2.90 (m, 5H), 3.68-3.82 (m, 4H), 6.69-6.85 (m, 3H). NH not observed. | S | m/z 423 (M + H)$^+$ (ES$^+$), at 3.29 min, UV active |
| 26-3 | Isomer 1: 4-[2-(3-ethyl-1,2,4-oxadiazol-5-yl)-6-azaspiro[3.4]oct-6-yl] spiro[cyclohexane-1,3'-indol]-2'(1'H)-one | 65 and 141 | l | (400 MHz, CDCl$_3$) ⊐: 1.27-1.37 (m, 3H), 1.64-2.02 (m, 7H), 2.00-2.15 (m, 3H), 2.20-2.33 (m, 1H), 2.40-2.58 (m, 4H), 2.64-2.89 (m, 6H), 3.56-3.72 (m, 1H), 6.92 (d, J = 7.8 Hz, 1H), 6.99 (td, J = 7.6, 5.0 Hz, 1H), 7.17-7.27 (m, 1H), 7.59 (d, J = 7.6 Hz, 1H), 8.44 (s, 1H). | E | m/z 407 (M + H)$^+$ (ES$^+$), at 4.02 min, UV active |
| 27-1 | Isomer 2: 4-(1[2-(3-ethyl-1,2,4-oxadiazol-5-yl)cyclopropyl]methyl} amino)-1-phenylcyclohexane carbonitrile | 12 and 143 | l | (400 MHz, CDCl$_3$) ⊐: 1.12 (ddd, J = 8.6, 6.4, 4.7 Hz, 1H), 1.30 (t, J = 7.6 Hz, 3H), 1.42 (dt, J = 9.2, 4.8 Hz, 1H), 1.72-1.92 (m, 5H), 1.96-2.08 (m, 3H), 2.24-2.36 (m, 3H), 2.61 (dd, J = 12.4, 6.8 Hz, 1H), 2.64-2.75 (m, 3H), 2.95-3.05 (m, 1H), 7.25-7.35 (m, 1H), 7.39 (dd, J = 8.6, 6.8 Hz, 2H), 7.44-7.54 (m, 2H). | E | m/z 351 (M + H)$^+$ (ES$^+$), at 4.52 min, UV active |
| 28-1 | Isomer 2: 1-(5-fluoropyridin-2-yl)-4-({(1R,3S)-3-[3-(trifluoromethyl)-1,2,4-oxadiazol-5-yl] cyclopentyl}amino) cyclohexanecarbonitrile | 27 and 138 | c | (400 MHz, MeOD-d$_4$) ⊐: 1.48-1.85 (m, 4H), 1.86-2.10 (m, 3H), 2.17-2.40 (m, 2H), 2.45-2.60 (m, 3H), 2.91-2.97 (m, 1H), 3.29-3.33 (m, 1H), 3.34-3.44 (m, 1H), 3.52-3.77 (m, 1H), 7.61-7.76 (m, 2H), 8.50 (t, J = 2.6 Hz, 1H). | R | m/z 424 (M + H)$^+$ (ES$^+$), at 4.70 min, UV active |
| 28-2 | Isomer 2: 1-(5-methylpyridin-2-yl)-4-({(1R,3S)-3-[3-(trifluoromethyl)-1,2,4-oxadiazol-5-yl] cyclopentyl}amino) cyclohexanecarbonitrile | 43 and 138 | c | (400 MHz, MeOD-d$_4$) ⊐: 1.64-1.71 (m, 5H), 1.85-2.05 (m, 5H), 2.08-2.28 (m, 2H), 2.30-2.40 (m, 4H), 2.40-2.56 (m, 2H), 2.90-2.98 (m, 1H), 3.29-3.50 (m, 1H), 3.50-3.76 (m, 1H), 7.56 (d, J = 8.4 Hz, 1H), 7.71 (d, J = 8.4 Hz, 1H), 8.44 (s, 1H). | R | m/z 420 (M + H)$^+$ (ES$^+$), at 4.98 min, UV active |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen*, 2008). ERK1/2 phosphorylation is a downstream consequence of both Gq/11 and Gi/o protein coupled receptor activation, making it highly suitable for the assessment of M1, M3 (Gq/11 coupled) and M2, M4 receptors (Gi/o coupled), rather than using different assay formats for different receptor subtypes. CHO cells stably expressing the human muscarinic M1, M2, M3 or M4 receptor were plated (25K/well) onto 96-well tissue culture plates in MEM-alpha+10% dialysed FBS. Once adhered, cells were serum-starved overnight. Agonist stimulation was performed by the addition of 5 µL agonist to the cells for 5 min (37° C.). Media was removed and 50 µL of lysis buffer added. After 15 min, a 4 µL sample was transferred to 384-well plate and 7 µL of detection mixture added. Plates were incubated for 2 h with gentle agitation in the dark and then read on a PHERAstar plate reader.

pEC$_{50}$ and E$_{max}$ figures were calculated from the resulting data for each receptor subtype.

The results are a range of examples are set out in Table 4 below.

For each example at least two diastereomers exist which, when indicated, have been separated, and assigned based on their retention time on analytical LCMS. Analytical data for all active isomers is reported in Table 3.

TABLE 4

| Ex. No. | Muscarinic Activity | | | |
|---|---|---|---|---|
| | pEC$_{50}$ M1 (% Emax cf. ACh) | pEC$_{50}$ M2 (% Emax cf. ACh) | pEC$_{50}$ M3 (% Emax cf. ACh) | pEC$_{50}$ M4 (% Emax cf. ACh) |
| ACh | 8.33 (102) | 7.82 (105) | 8.12 (115) | 8.09 (110) |
| 1-1 Isomer 2 | 7.29 (117) | <4.7 (3) | <4.7 (18) | <4.7 (18) |
| 1-2 Isomer 2 | 6.68 (102) | <4.7 (23) | <4.7 (1) | 6.13 (52) |
| 1-3 Isomer 2 | 7.51 (119) | <4.7 (0) | <4.7 (1) | <4.7 (13) |
| 1-4 Isomer 2 | 7.45 (98) | <4.7 (3) | <4.7 (8) | <4.7 (7) |
| 1-5 Isomer 2 | 6.94 (125) | <4.7 (5) | <4.7 (33) | <4.7 (46) |
| 1-6 Isomer 2 | 6.64 (116) | NT | NT | 5.75 (49) |
| 1-8 Isomer 2 | 6.6 (120) | NT | NT | <4.7 (0) |
| 1-9 Isomer 2 | 7.56 (99) | <4.7 (6) | <4.7 (2) | <4.7 (12) |
| 1-10 Isomer 2 | 7.55 (106) | <4.7 (6) | <4.7 (9) | <4.7 (24) |
| 1-11 Isomer 2 | 6.83 (99) | <4.7 (0) | <4.7 (1) | <4.7 (9) |
| 1-14 Isomer 2 | 6.91 (89) | <4.7 (2) | <4.7 (0) | <4.7 (32) |
| 1-15 Isomer 2 | 6.57 (39) | NT | NT | <4.7 (7) |
| 1-20 Isomer 2 | 6.83 (78) | <4.7 (0) | <4.7 (0) | <4.7 (19) |
| 1-21 Isomer 2 | 6.96 (64) | <4.7 (1) | <4.7 (5) | <4.7 (15) |
| 2-1 isomer 1 | 7.13 (74) | <4.7 (2) | <4.7 (4) | <4.7 (10) |
| 2-2 isomer 1 | 6.80 (103) | NT | NT | 6.06 (84) |
| 2-3 isomer 1 | 7.11 (32) | NT | NT | <4.7 (1) |
| 2-4 isomer 1 | 7.18 (65) | <4.8 (3) | <4.8 (11) | <4.8 (11) |
| 2-5 isomer 1 | 8.11 (49) | <4.7 (13) | <4.7 (15) | <4.8 (5) |
| 2-6 isomer 1 | 6.73 (66) | <4.7 (11) | <4.7 (16) | 7.22 (54) |
| 2-7 isomer 2 | 7.28 (89) | <4.7 (5) | <4.7 (2) | <4.7 (16) |
| 2-7 isomer 1 | 5.75 (35) | NT | NT | <4.7 (1) |
| 2-8 isomer 1 | 7.03 (59) | NT | NT | <4.7 (10) |
| 2-9 isomer 1 | 6.55 (77) | NT | NT | <4.7 51) |
| 2-10 isomer 1 | 8.10 (64) | <4.7 (27) | <4.7 (4) | <4.7 (39) |
| 2-14 isomer 2 | 6.93 (77) | NT | NT | <4.7 56) |
| 2-17 isomer 1 | 7.25 (48) | <4.7 (7) | <4.7 (7) | <4.7 (18) |
| 2-18 isomer 1 | 6.83 (122) | <4.7 (21) | <4.7 (11) | 6.76 (141) |
| 2-19 isomer 1 | 5.68 (63) | NT | NT | <4.7 (19) |
| 2-20 isomer 1 | 6.43 (32) | NT | NT | <4.7 (16) |
| 2-21 isomer 2 | 6.33 (58) | NT | NT | 6.61 (86) |
| 3-2 mixture of isomers | 7.60 (96) | <4.7 (7) | <4.7 (46) | 7.13 (76) |
| 3-3 mixture of isomers | 8.01 (101) | <4.7 (38) | <4.7 (35) | 7.20 (85) |
| 3-4 mixture of isomers | 6.53 (86) | <4.7 (12) | <4.7 (40) | 6.08 (46) |
| 3-5 mixture of isomers | 7.08 (101) | <4.7 (5) | <4.7 (36) | 6.51 (47) |
| 3-6 mixture of isomers | 8.02 (105) | <4.7 (11) | <4.7 (38) | 7.00 (62) |
| 3-7 mixture of isomers | 6.41 (101) | <4.7 (35) | <4.7 (34) | 5.77 (48) |
| 3-8 mixture of isomers | 7.45 (106) | <4.7 (18) | <4.7 (7) | 6.98 (62) |
| 3-9 mixture of isomers | 6.94 (98) | <4.7 (33) | <4.7 (0) | <4.7 (2) |
| 3-11 mixture of isomers | 7.14 (97) | <4.7 (43) | <4.7 (15) | 6.41 (99) |
| 3-12 mixture of isomers | 6.81 (116) | <4.7 (5) | <4.7 (3) | 5.97 (48) |
| 3-16 mixture of isomers | 8.18 (103) | <4.7 (10) | <4.7 (39) | 6.90 (90) |
| 3-17 Isomer 1 | 8.52 (92) | <4.7 (0) | <4.7 (0) | 7.14 (80) |
| 3-19 Isomer 2 | 7.52 (101) | <4.7 (5) | <4.7 (6) | 5.76 (39) |
| 3-20 Isomer 2 | 7.94 (139) | <4.7 (27) | <4.7 (2) | <4.7 (7) |
| 3-21 mixture of isomers | 6.14 (90) | <4.7 (3) | <4.7 (2) | <4.7 (53) |
| 3-26 mixture of isomers | 7.39 (85) | NT | NT | NT |
| 3-28 mixture of isomers | 6.11 (116) | <4.7 (15) | <4.7 (7) | 6.61 (91) |
| 3-29 mixture of isomers | 6.27 (75) | <4.7 (3) | <4.7 (3) | 6.70 (68) |
| 3-30 Isomer 1 | 6.53 (104) | <4.7 (6) | <4.7 (0) | 6.64 (72) |
| 3-31 Isomer 1 | 7.71 (91) | <4.7 (8) | <4.7 (0) | 5.59 (52) |
| 3-32 Isomer 1 | 7.65 (106) | <4.7 (2) | <4.7 (0) | 6.12 (30) |
| 4-3 isomer 2 | 6.10 (57) | <4.7(3) | <4.7 (2) | <4.7 (20) |
| 4-4 isomer 2 | 6.59 (48) | NT | NT | <4.7 (12) |
| 4-6 isomer 1 | 6.24 (85) | NT | NT | 5.49 (26) |
| 4-6 isomer 2 | 7.44 (130) | <4.8 (39) | <4.8 (17) | 7.12 (116) |
| 4-7 isomer 1 | 7.35 (115) | <4.7 (16) | <4.7 (20) | 5.27 (100) |
| 4-8 isomer 1 | 5.96 (67) | NT | NT | 6.42 (52) |
| 4-8 isomer 2 | 6.69 (97) | <4.7 (17) | <4.7 (9) | 7.01 (95) |
| 4-11 isomer 2 | 6.88 (107) | <4.7 (9) | <4.7 (2) | 6.51 (55) |
| 4-12 isomer 1 | 7.05 (107) | <4.7 (3) | <4.7 (34) | <4.7 (10) |
| 4-13 isomer 2 | 6.02 (38) | NT | NT | 6.46 (39) |
| 4-14 isomer 1 | 6.01 (76) | NT | NT | <4.7 (24) |
| 4-16 isomer 1 | 6.05 (60) | NT | NT | <4.7 (5) |
| 4-17 isomer 2 | 6.36 (89) | NT | NT | <4.7 (19) |
| 4-19 isomer 1 | 5.17 (104) | NT | NT | 6.49 (97) |
| 4-24 isomer 2 | 6.09 (75) | NT | NT | 6.50 (61) |
| 5-1 Isomer 2 | 7.18 (115) | <4.7 (8) | <4.7 (7) | 6.29 (26) |
| 6-2-Isomer 2 | 7.23 (129) | <4.7 (0) | <4.7 (12) | 7.27 (49) |
| 7-1 isomer 1 | 6.59 (112) | NT | NT | 6.80 (26) |
| 7-1 isomer 2 | 6.31 (68) | NT | NT | 6.55 (20) |
| 7-2 isomer 1 | 7.12 (122) | <4.7 (37) | <4.7 (3) | 6.77 (32) |
| 7-2 isomer 2 | 6.41 (66) | NT | NT | <4.7 (10) |
| 9-1 Isomer 1 | 6.67 (84) | <4.7 (7) | <4.7 (0) | <4.7 (14) |
| 10-1 mixture of isomers | 7.41 (39) | NT | NT | <4.7 (8) |
| 11-1 Isomer 2 | 6.56 (105) | <4.7 (1) | <4.7 (3) | <4.7 (19) |
| 12-1 isomer 1 | 7.86 (109) | <4.7 (18) | <4.7 (1) | 8.32 (82) |
| 12-2 isomer 1 | 7.59 (65) | <4.7 (27) | <4.7 (0) | 7.97 (48) |
| 13-1 Isomer 2 | 9.35 (121) | <4.7 (21) | <4.7 (7) | 9.84 (121) |
| 14-1 Isomer 2 | 7.05 (106) | <4.7 (0) | <4.7 (1) | 6.45 (63) |
| 15-1 Isomer 2 | 6.81 (117) | <4.7 (14) | <4.7 (6) | 6.84 (21) |
| 17-1 Isomer 2 | 7.01 (111) | <4.7 (7) | <4.7 (9) | 6.60 (61) |
| 19-1 Isomer 2 | 5.76 (45) | <4.7 (21) | <4.7 (8) | 6.65 (83) |
| 19-2 Isomer 2 | 6.72 (118) | 5.62 (35) | <4.7 (5) | 6.86 (96) |
| 20-1 Isomer 2 | 6.66 (78) | <4.7 (61) | <4.7 (30) | 6.90 (58) |
| 21-2 Isomer 3 | 7.14 (77) | <4.7 (16) | <4.7 (15) | 7.21 (58) |
| 21-3 Isomer 3 | 6.25 (51) | NT | NT | <4.7 (15) |
| 21-3 Isomer 4 | 6.79 (80) | NT | NT | 7.16 (75) |
| 21-4 Isomer 4 | 5.67 (47) | NT | NT | 6.51 (68) |
| 21-5 Isomer 1 | <4.7 (18) | NT | NT | 5.97 (55) |
| 21-5 Isomer 2 | 4.84 (82) | NT | NT | 5.90 (51) |
| 22-1 Isomer 1 | 6.64 (83) | <4.7 (11) | <4.7 (11) | 6.40 (47) |
| 22-2 Isomer 1 | 7.15 (55) | <4.7 (12) | <4.7 (21) | 6.27 (42) |
| 22-3 Isomer 1 | 6.91 (51) | <4.7 (17) | <4.7 (59) | 6.85 (40) |
| 22-4 Isomer 1 | 7.10 (76) | <4.7 (20) | <4.7 (17) | 6.66 (39) |
| 23-1 Isomer 1 | 6.46 (113) | NT | <4.7 (8) | 6.60 (78) |
| 24-1 Isomer 1 | 6.66 (89) | <4.7 (16) | <4.7 (23) | 6.98 (62) |
| 24-2 Isomer 1 | 7.20 (62) | 5.12 (38) | 4.80 (100) | 5.36 (85) |
| 24-3 Isomer 1 | 6.45 (81) | NT | NT | 6.38 (39) |
| 25-1 Isomer 1 | 6.21 (43) | <4.7 (13) | <4.7 (6) | 6.81 (70) |
| 26-1 Isomer 2 | 7.82 (74) | <4.7 (22) | <4.7 (7) | 7.39 (50) |
| 26-2 Isomer 1 | 7.79 (38) | <4.7 (6) | <4.7 (4) | 7.09 (35) |
| 26-2 Isomer 3 | 6.65 (51) | NT | NT | <4.7 (14) |
| 26-3 Isomer 1 | 7.03 (31) | <4.7 (11) | <4.7 (19) | 7.54 (72) |
| 27-1 Isomer 2 | 6.27 (92) | NT | NT | 6.75 (84) |
| 28-1 Isomer 2 | 6.01 (59) | NT | NT | 6.08 (45) |
| 28-2 Isomer 2 | 5.46 (40) | NT | NT | 6.02 (55) |

NT - Not tested

Example B

Pharmaceutical Formulations (i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) with 100 mg lactose and optionally 1% by weight of magnesium stearate and filling the resulting mixture into standard opaque hard gelatin capsules.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:
1. A compound of formula (1a):

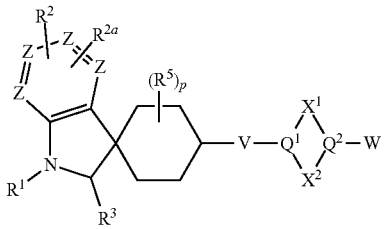

or a pharmaceutically acceptable salt thereof,
wherein:

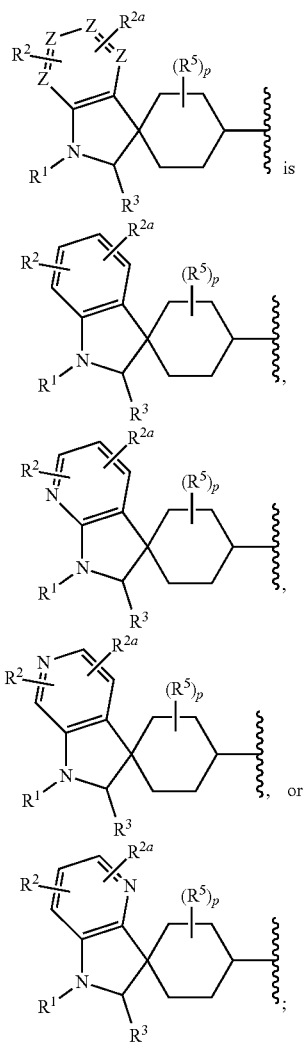

is p is 0, 1 or 2;
R$^1$ is H, (CH$_2$)$_{0-2}$C(O)OR$^7$, (CH$_2$)$_{0-2}$C(O)NR$^7$R$^8$, (CH$_2$)$_{0-2}$S(O)$_2$R$^7$, or a C$_{1-6}$ non-aromatic hydrocarbon group, wherein 1 or 2 carbon atoms of the C$_{1-6}$ non-aromatic hydrocarbon group may optionally be replaced by a heteroatom selected from the group consisting of O, N and S;

R$^2$ is H, halogen, CN, OH, NH$_2$, or a C$_{1-4}$ non-aromatic hydrocarbon group, wherein the C$_{1-4}$ non-aromatic hydrocarbon group is optionally substituted with 1, 2, 3, 4, 5 or 6 F and 1 or 2 carbon atoms of the C$_{1-4}$ non-aromatic hydrocarbon group may optionally be replaced by a heteroatom selected from the group consisting of O, N and S;

R$^{2a}$ is H, halogen, CN, OH, NH$_2$, or a C$_{1-4}$ non-aromatic hydrocarbon group, wherein the C$_{1-4}$ non-aromatic hydrocarbon group is optionally substituted with 1, 2, 3, 4, 5 or 6 F and 1 or 2 carbon atoms of the C$_{1-4}$ non-aromatic hydrocarbon group may optionally be replaced by a heteroatom selected from the group consisting of O, N and S;

R$^3$ is H or oxo;
each R$^5$ is independently F or a C$_{1-4}$ hydrocarbon group;
R$^7$ is H or a C$_{1-4}$ hydrocarbon group;
R$^8$ is H or a C$_{1-4}$ hydrocarbon group;
V is a bond, —NH—, —N(C$_{1-3}$ alkyl)-, —NHCH$_2$—, or —N(C$_{1-3}$ alkyl)CH$_2$—;

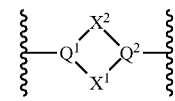

is a monocyclic or bicyclic ring;
Q$^1$ is —CH— or —N—;
Q$^2$ is —CH— or —N—;
X$^1$ is a saturated hydrocarbon group, optionally substituted with 1, 2 or 3 substituents independently selected from the group consisting of F, Cl, Br, I, CN, OH, NH$_2$, and a C$_{1-6}$ alkyl, wherein the C$_{1-6}$ alkyl is optionally substituted with 1, 2, 3, 4, 5 or 6 F;
X$^2$ is a saturated hydrocarbon group, optionally substituted with 1, 2 or 3 substituents independently selected from the group consisting of F, Cl, Br, I, CN, OH, NH$_2$, and a C$_{1-6}$ alkyl, wherein the C$_{1-6}$ alkyl is optionally substituted with 1, 2, 3, 4, 5 or 6 F;
W is a 5- or 6-membered heterocyclic aromatic ring containing 1, 2 or 3 heteroatoms selected from the group consisting of O, N and S, optionally substituted with 1 or more substituents independently selected from the group consisting of F, Cl, Br, I, CN, OH, NH$_2$, and a C$_{1-10}$ non-aromatic hydrocarbon group, wherein the C$_{1-10}$ non-aromatic hydrocarbon group is optionally substituted with 1, 2, 3, 4, 5 or 6 F and 1, 2 or 3 carbon atoms of the C$_{1-10}$ non-aromatic hydrocarbon group may optionally be replaced by a heteroatom selected from the group consisting of O, N and S; or
W is -Q$^3$C(O)YCH$_2$R$^4$;
Q$^3$ is a bond or -(Alk)$_q$-NR$^6$, wherein Alk is C$_{1-4}$ alkyl;
q is 0 or 1;
Y is —CH$_2$— or —O—;
R$^4$ is H or a C$_{1-6}$ non-aromatic hydrocarbon group, wherein the C$_{1-6}$ non-aromatic hydrocarbon group is optionally substituted with 1, 2, 3, 4, 5 or 6 F and 1 or 2 carbon atoms of the C$_{1-6}$ non-aromatic hydrocarbon group may optionally be replaced by a heteroatom selected from the group consisting of O, N and S; and
R$^6$ is H or a saturated C$_{1-4}$ hydrocarbon group;
with the provisos that:
(1) at least one of Q$^1$ or V has a nitrogen atom;
(2) when W is an optionally substituted 5- or 6-membered heterocyclic aromatic ring, Q$^2$ is —CH—;

(3) when $Q^2$ is —N— and $Q^3$ is -(Alk)$_q$-NR$^6$, there are at least 2 carbons between $Q^2$ and NR$^6$;
(4) when $Q^3$ is a bond, $Q^2$ is —N—; and
(5) $X^1$ and $X^2$ together contain a total of 1, 2, 3, 4, 5, 6, 7, 8 or 9 carbons.

2. The compound according to claim 1, or a pharmaceutically acceptable salt thereof, wherein:

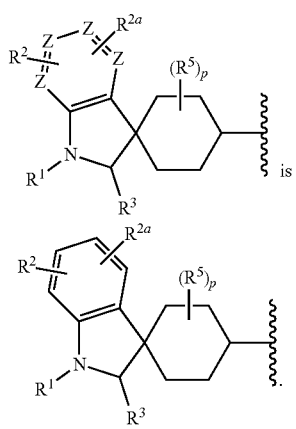

is

3. The compound according to claim 1, or a pharmaceutically acceptable salt thereof, wherein:
(a) p is 0; or
(b) p is 1; and
    $R^5$ is F or CH$_3$.

4. The compound according to claim 1, or a pharmaceutically acceptable salt thereof, wherein $R^1$ is H, C(O)OCH$_2$CH$_3$, CH$_2$C(O)NH$_2$, S(O)$_2$CH$_3$, or CH$_3$.

5. The compound according to claim 4, or a pharmaceutically acceptable salt thereof, wherein $R^1$ is H.

6. The compound according to claim 1, or a pharmaceutically acceptable salt thereof, wherein:
$R^2$ is H, F, Cl, CN, CH$_3$, or OCH$_3$; and
$R^2$ is H, F, Cl, CN, CH$_3$, or OCH$_3$.

7. The compound according to claim 1, or a pharmaceutically acceptable salt thereof, wherein $R^3$ is oxo.

8. The compound according to claim 1, or a pharmaceutically acceptable salt thereof, wherein:
V is a bond; and
$Q^1$ is —N—.

9. The compound according to claim 1, or a pharmaceutically acceptable salt thereof, wherein

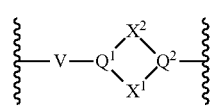

is A, F, L, M, Q, S, T, CC, or DD:

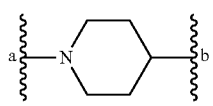

A

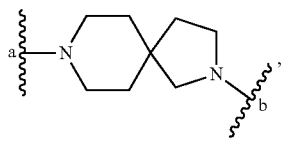

F

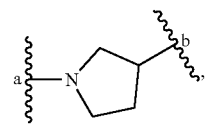

L

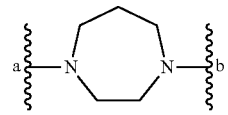

M

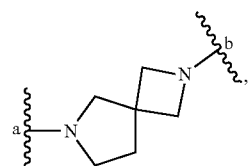

Q

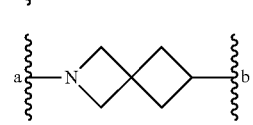

S

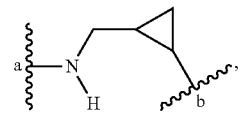

T

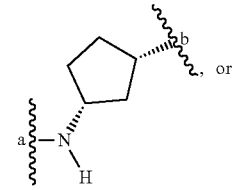

CC

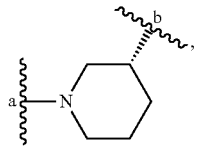

DD where "a" indicates the point of attachment to the cyclohexane ring and "b" indicates the point of attachment to the W group.

10. The compound according to claim 1, or a pharmaceutically acceptable salt thereof, wherein W is optionally substituted 1,2,4-oxadiazolyl.

11. The compound according to claim 1, or a pharmaceutically acceptable salt thereof, wherein:
W is -Q$^3$C(O)YCH$_2$R$^4$;
$Q^3$ is a bond, —NH—, or —NCH$_3$—;
Y is —O—; and
$R^4$ is H, CH$_3$, or CH$_2$CH$_3$.

12. The compound according to claim 1, wherein the compound is selected from the group consisting of:

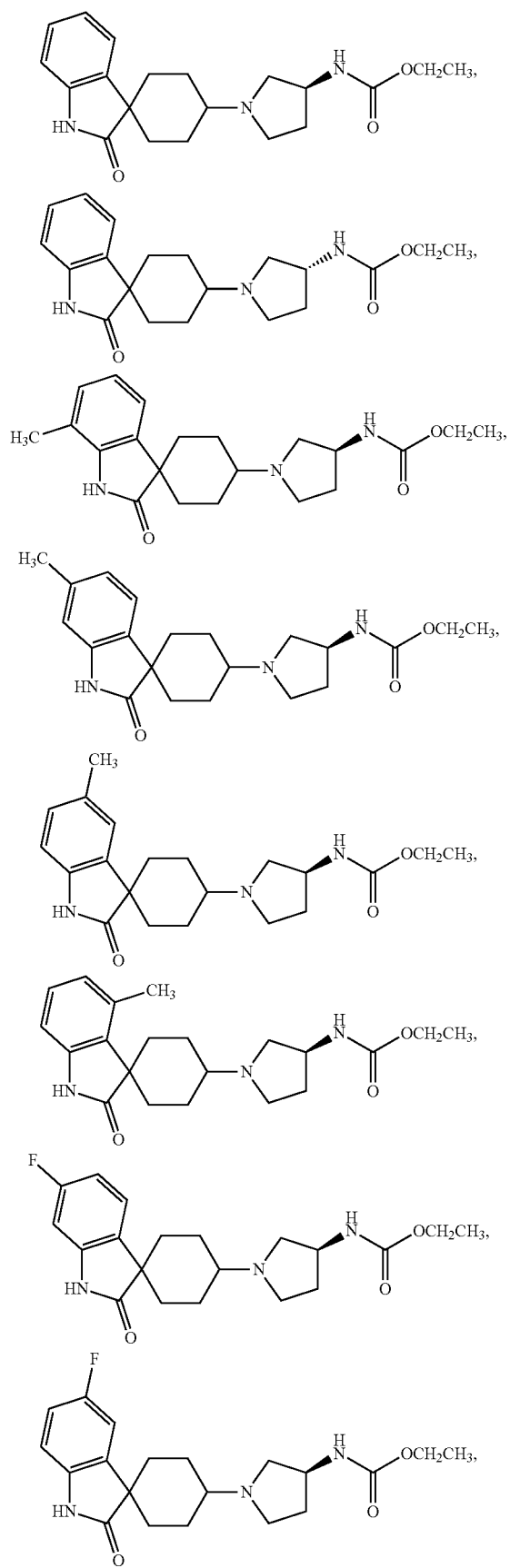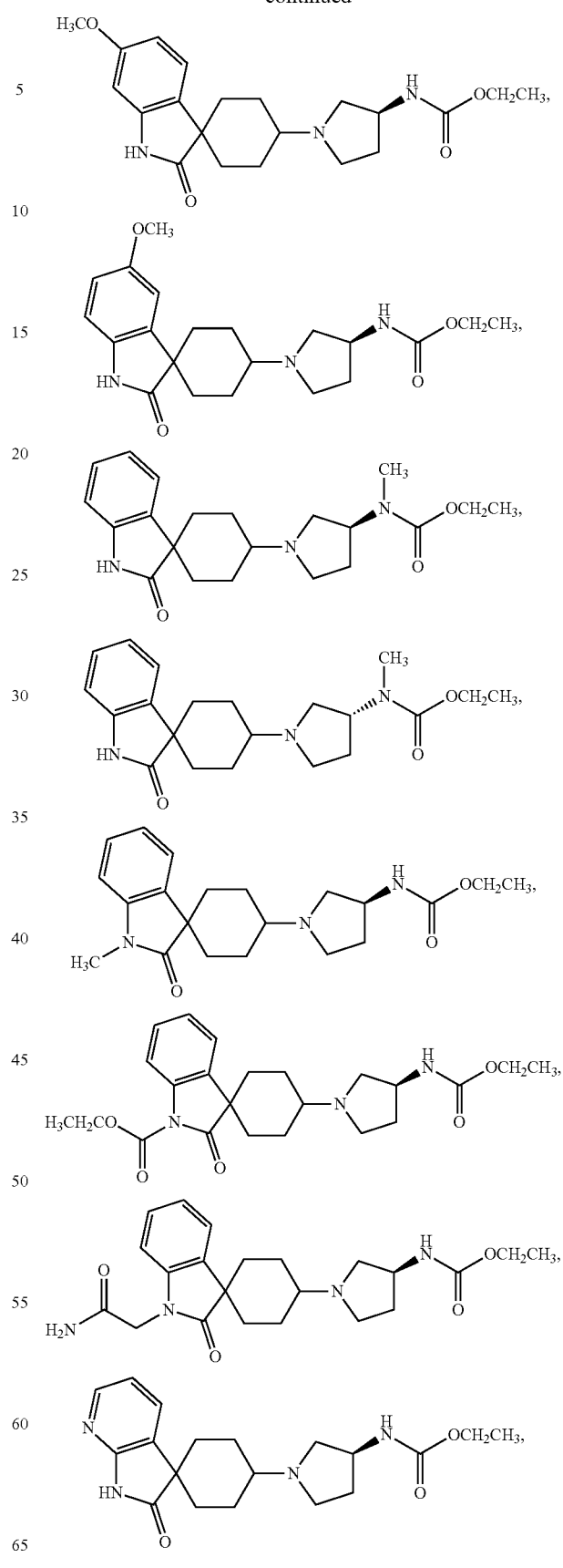

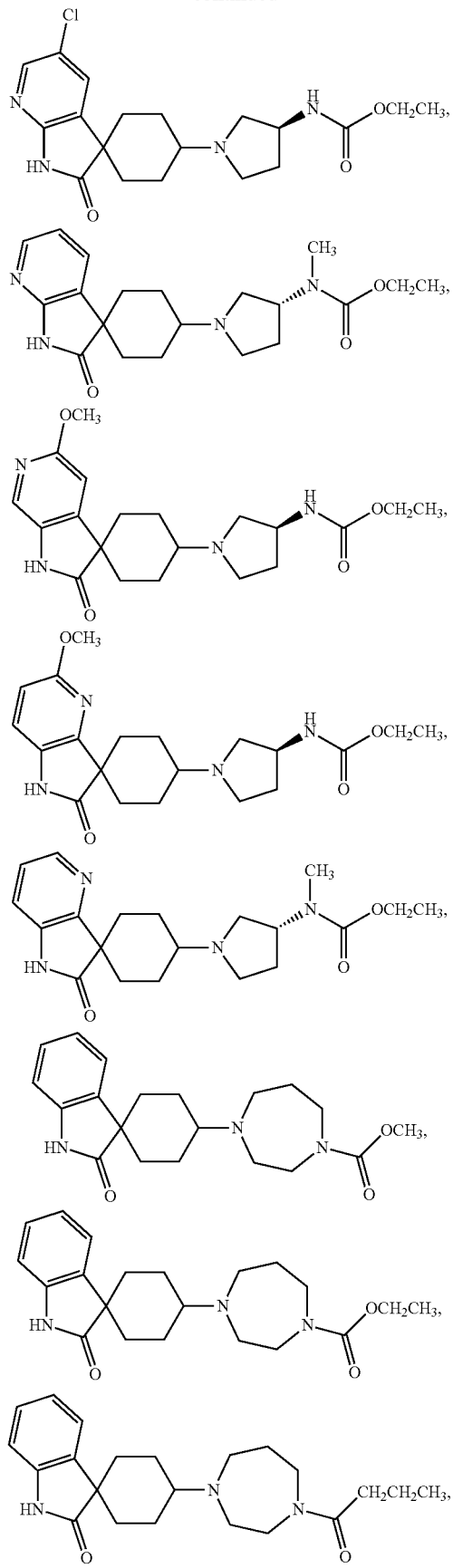
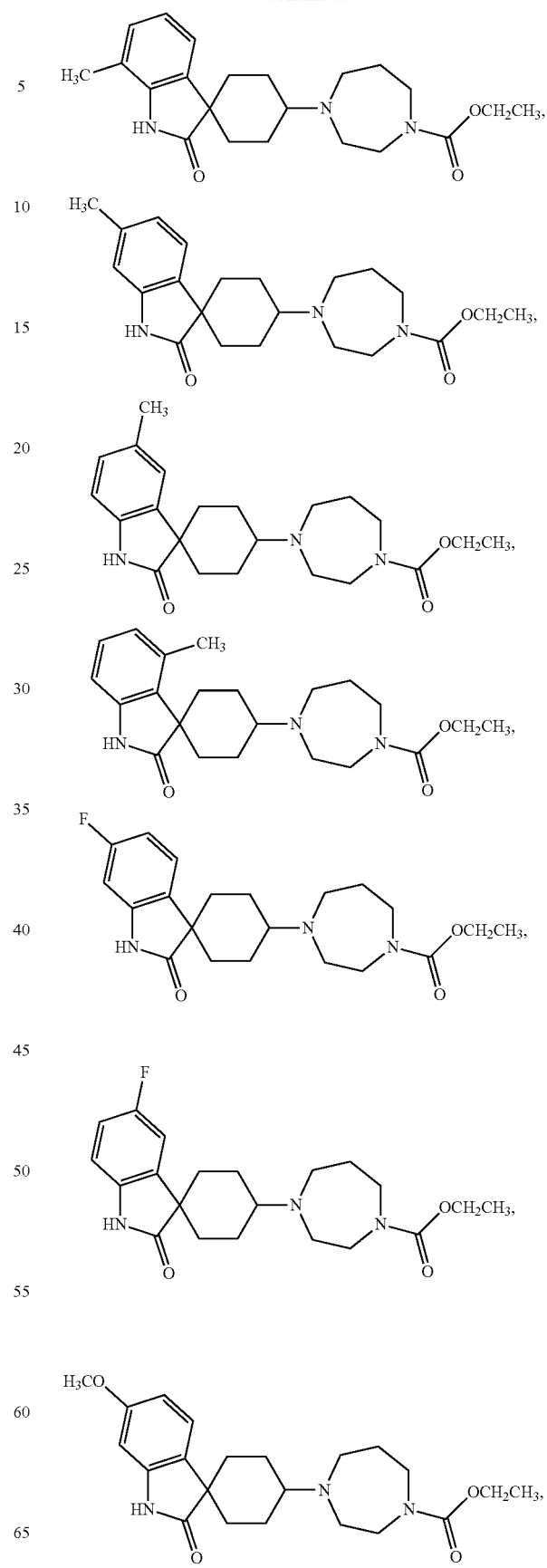

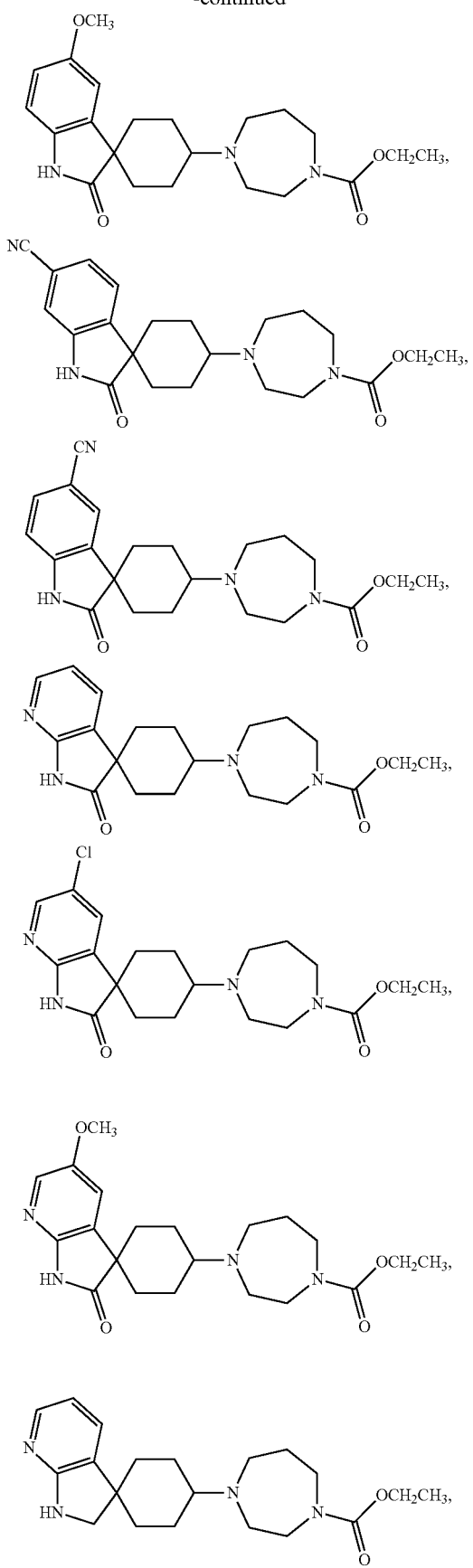
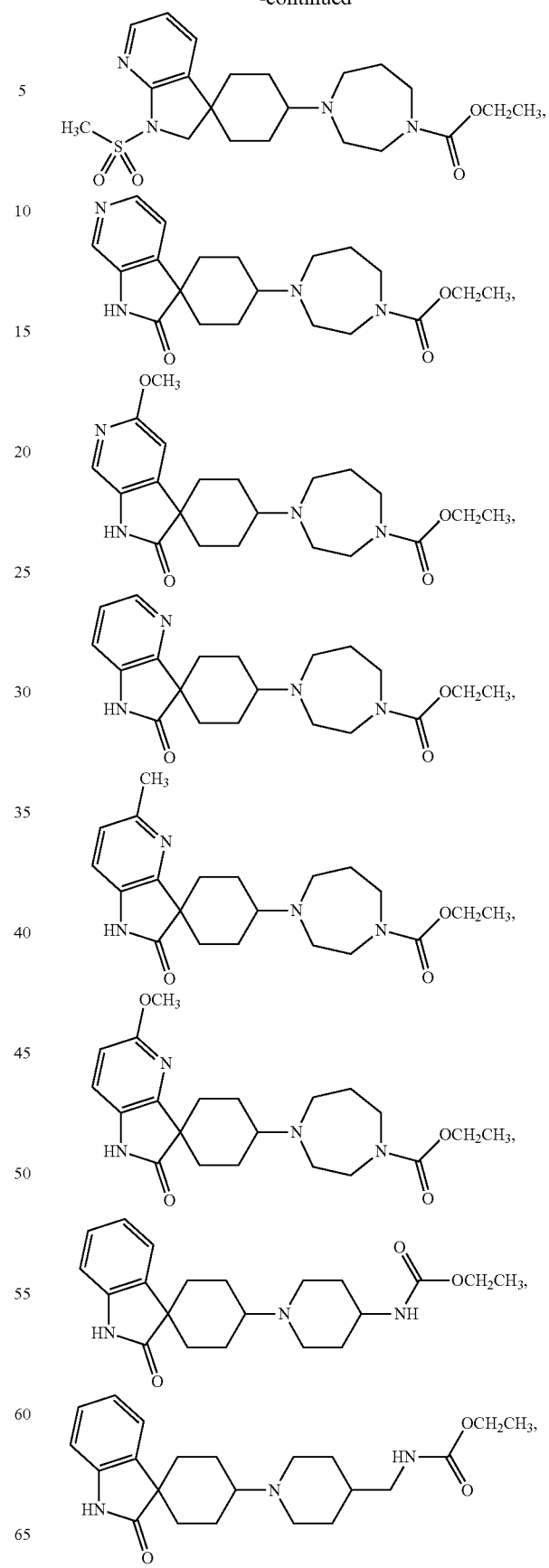

197
-continued
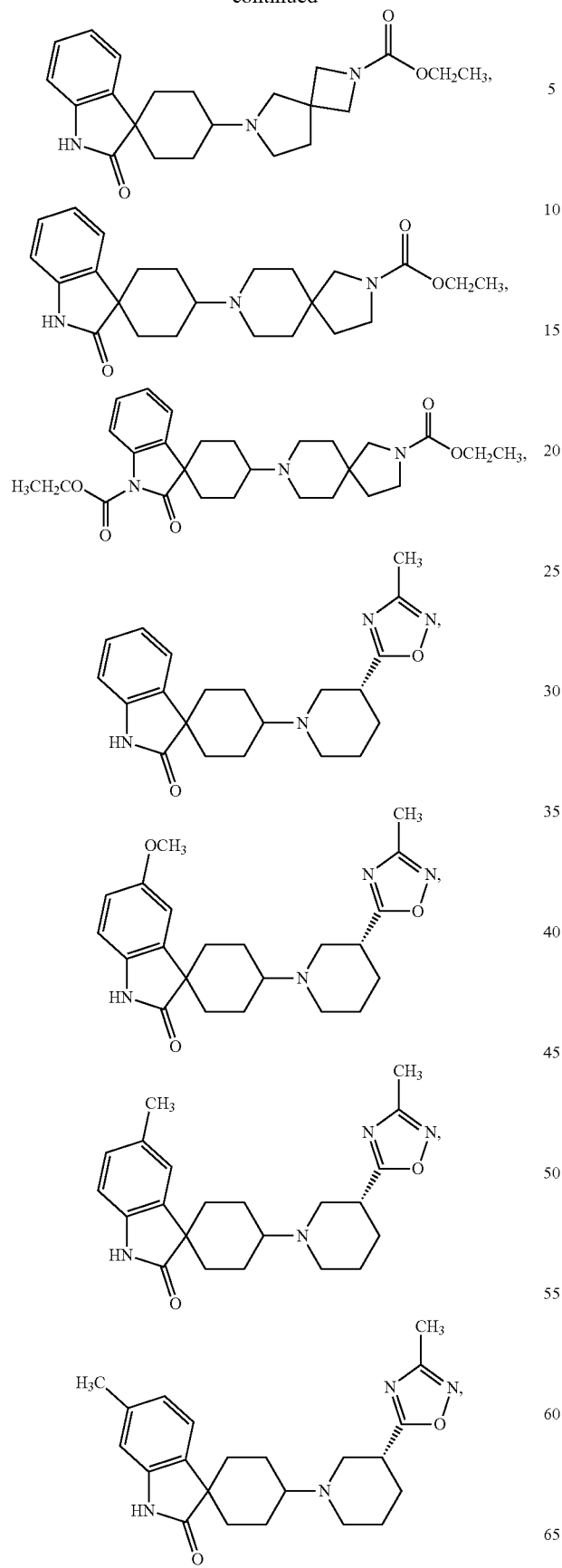
198
-continued
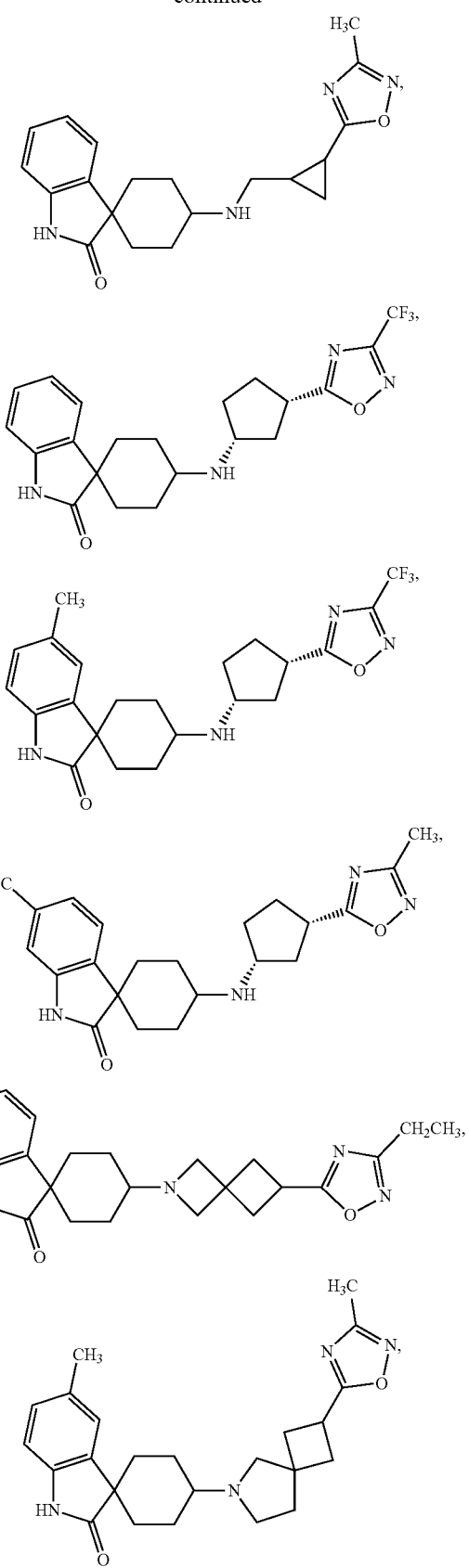

-continued

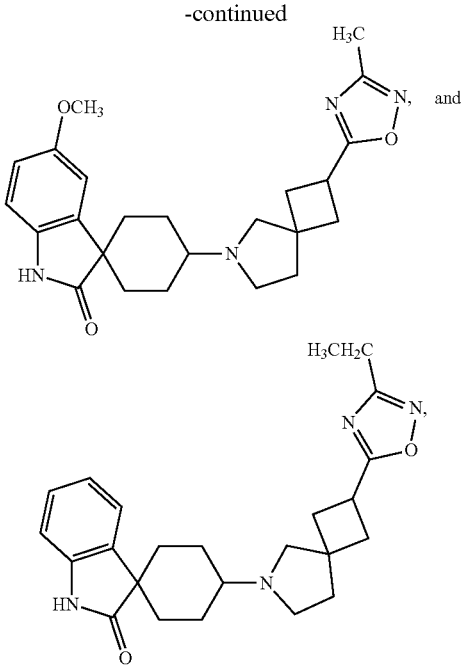 and

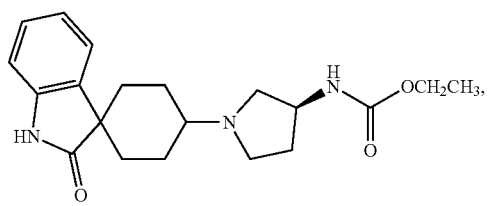 [SMILES: CCOC(=O)N[C@H]1CCN(C2CCC3(CC2)C(=O)Nc2ccccc23)C1]

or a pharmaceutically acceptable salt thereof.

13. The compound according to claim 12, wherein the compound is:

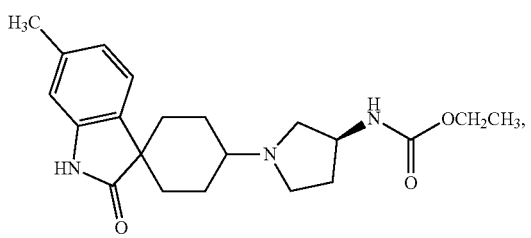 [SMILES: CCOC(=O)N[C@H]1CCN(C2CCC3(CC2)C(=O)Nc2cc(C)ccc23)C1]

or a pharmaceutically acceptable salt thereof.

14. The compound according to claim 12, wherein the compound is:

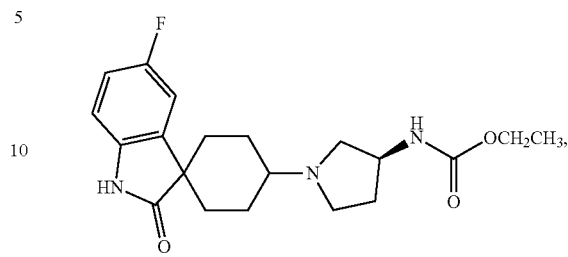

or a pharmaceutically acceptable salt thereof.

15. The compound according to claim 12, wherein the compound is:

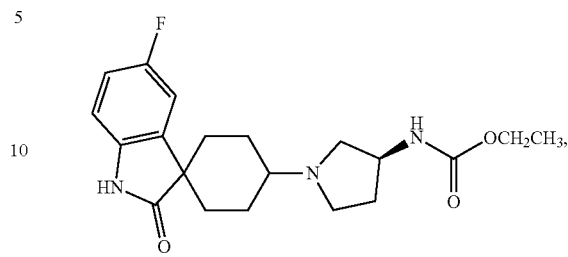

or a pharmaceutically acceptable salt thereof.

16. The compound according to claim 12, wherein the compound is:

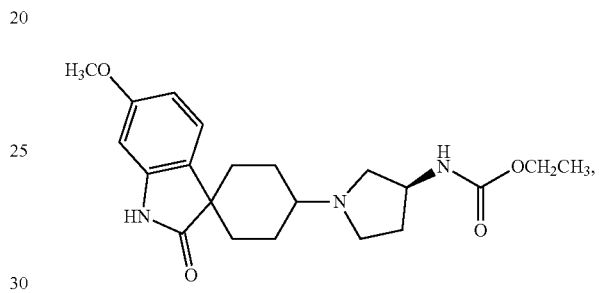

or a pharmaceutically acceptable salt thereof.

17. The compound according to claim 12, wherein the compound is:

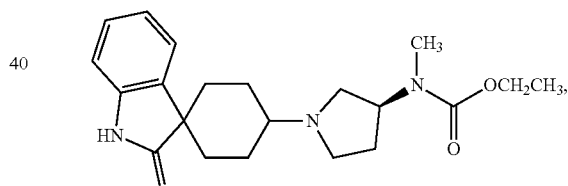

or a pharmaceutically acceptable salt thereof.

18. A pharmaceutical composition comprising a compound according to claim 1, or a pharmaceutically acceptable salt thereof, and a pharmaceutically acceptable excipient.

* * * * *

UNITED STATES PATENT AND TRADEMARK OFFICE
CERTIFICATE OF CORRECTION

PATENT NO. : 10,759,751 B2
APPLICATION NO. : 16/295364
DATED : September 1, 2020
INVENTOR(S) : Giles Albert Brown et al.

Page 1 of 1

It is certified that error appears in the above-identified patent and that said Letters Patent is hereby corrected as shown below:

In the Claims

At Column 188, Claim number 1, Line number 8, delete "$R^2$" and replace with -- $R^{2a}$ --.

At Column 189, Claim number 6, Line number 42, delete "$R^2$" and replace with -- $R^{2a}$ --.

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*